(12) United States Patent
Lee

(10) Patent No.: US 10,519,471 B2
(45) Date of Patent: Dec. 31, 2019

(54) ORGANISMS FOR PHOTOBIOLOGICAL BUTANOL PRODUCTION FROM CARBON DIOXIDE AND WATER

(71) Applicant: James Weifu Lee, Chesapeake, VA (US)

(72) Inventor: James Weifu Lee, Chesapeake, VA (US)

(*) Notice: Subject to any disclaimer, the term of this patent is extended or adjusted under 35 U.S.C. 154(b) by 0 days.

(21) Appl. No.: 15/613,166

(22) Filed: Jun. 3, 2017

(65) Prior Publication Data
US 2017/0268025 A1    Sep. 21, 2017

Related U.S. Application Data

(63) Continuation of application No. 14/245,848, filed on Apr. 4, 2014, now Pat. No. 9,695,448, which is a continuation of application No. 12/918,784, filed as application No. PCT/US2009/093480 on Feb. 21, 2009, now Pat. No. 8,735,651.

(60) Provisional application No. 61/066,845, filed on Feb. 23, 2008, provisional application No. 61/066,835, filed on Feb. 23, 2008.

(51) Int. Cl.
| C12P 7/16 | (2006.01) |
| A01H 5/10 | (2018.01) |
| C10L 1/02 | (2006.01) |

(52) U.S. Cl.
CPC ............... *C12P 7/16* (2013.01); *A01H 5/10* (2013.01); *C10L 1/02* (2013.01); *C10G 2300/1014* (2013.01); *Y02E 50/10* (2013.01); *Y02P 30/20* (2015.11); *Y02P 60/247* (2015.11)

(58) Field of Classification Search
None
See application file for complete search history.

(56) References Cited

U.S. PATENT DOCUMENTS

| 6,699,696 | B2 * | 3/2004 | Woods .................... A01H 13/00 435/155 |
| 7,682,821 | B2 * | 3/2010 | Woods .................... C12M 21/02 126/569 |
| 7,973,214 | B2 | 7/2011 | Lee |
| 8,986,963 | B2 * | 3/2015 | Lee .......................... C12P 7/04 435/160 |
| 9,695,448 | B2 | 7/2017 | Lee |
| 2002/0042111 | A1 | 4/2002 | Woods et al. |
| 2006/0119066 | A1 | 6/2006 | Chuang |
| 2007/0037196 | A1 | 2/2007 | Gibson et al. |
| 2007/0037197 | A1 | 2/2007 | Young et al. |
| 2007/0065035 | A1 | 3/2007 | Chi |
| 2007/0092957 | A1 | 4/2007 | Donaldson et al. |
| 2007/0122826 | A1 | 5/2007 | Glass et al. |
| 2007/0128648 | A1 | 6/2007 | Li et al. |
| 2007/0128649 | A1 | 6/2007 | Young |
| 2007/0264688 | A1 | 11/2007 | Venter et al. |
| 2007/0269862 | A1 | 11/2007 | Glass et al. |
| 2008/0176304 | A1 | 7/2008 | Lee |
| 2009/0081746 | A1 | 3/2009 | Liao et al. |
| 2009/0111154 | A1 | 4/2009 | Liao et al. |
| 2009/0130734 | A1 | 5/2009 | Mets |
| 2009/0176280 | A1 | 7/2009 | Ill et al. |
| 2009/0203070 | A1 | 8/2009 | Devroe et al. |
| 2010/0105103 | A1 | 4/2010 | Juan et al. |
| 2010/0151545 | A1 | 6/2010 | Roessler et al. |
| 2010/0209986 | A1 | 8/2010 | Liao et al. |
| 2010/0221800 | A1 | 9/2010 | Liao et al. |
| 2010/0279390 | A1 | 11/2010 | Saphire |
| 2010/0330637 | A1 | 12/2010 | Lee |
| 2013/0344553 | A1 | 12/2013 | Lee |
| 2015/0353961 | A1 | 12/2015 | Lee |

FOREIGN PATENT DOCUMENTS

| CN | 101748069 A | 6/2010 |
| WO | 2005100582 A2 | 10/2005 |
| WO | 2006119066 A2 | 11/2006 |

(Continued)

OTHER PUBLICATIONS

Knowles et al, 2003, Plant Cell Physiol., 44:758-763.*
Sanderson, 2006, Nature, 444:673-676.*
Brigham et al., "Engineering Ralstonia eutropha for Production of Isobutanol from CO2, H2, and O2", Chapter 39: Advanced Biofules and Bioproducts, J.W. Lee (ed.), pp. 1065-1090, Springer (2013).
Rawat et al., "Biodiesel from Microalgae: A Critical Evaluation from Laboratory to Large Scale Production", Applied Energy 103, pp. 444-467 (2013).
Steinbusch et al., "Alcohol Production Through Volatile Fatty Acids Reduction with Hydrogen as Electron Donor by Mixed Culture", Water Research 42, pp. 4059-4066 (2008).
Ramesh V. Nair et al., Regulation of the sol Locus Genes for Butanol and Acetone Formation in Clostridium acetobutylicum ATCC 824 by a Putative Transcriptional Repressor, Journal of Bacteriology, Jan. 1999, vol. 181, N. 1, p. 319-300.

(Continued)

*Primary Examiner* — Jason Deveau Rosen

(57) ABSTRACT

The present invention provides a biosafety-guarded photobiological butanol production technology based on designer transgenic plants, designer algae, designer blue-green algae (cyanobacteria and oxychlorobacteria), or designer plant cells. The designer photosynthetic organisms are created such that the endogenous photobiological regulation mechanism is tamed, and the reducing power (NADPH) and energy (ATP) acquired from the photosynthetic process are used for synthesis of butanol ($CH_3CH_2CH_2CH_2OH$) directly from carbon dioxide ($CO_2$) and water ($H_2O$). The butanol production methods of the present invention completely eliminate the problem of recalcitrant lignocellulosics by bypassing the bottleneck problem of the biomass technology. The photobiological butanol-production technology of the present invention is expected to have a much higher solar-to-butanol energy-conversion efficiency than the current technology and could also help protect the Earth's environment from the dangerous accumulation of $CO_2$ in the atmosphere.

10 Claims, 5 Drawing Sheets

Specification includes a Sequence Listing.

(56) References Cited

FOREIGN PATENT DOCUMENTS

| WO | 2007032837 A2 | 3/2007 |
|---|---|---|
| WO | 2007047148 A1 | 4/2007 |
| WO | 2007065035 A2 | 6/2007 |
| WO | 2008006038 A2 | 1/2008 |
| WO | 2008039450 A2 | 4/2008 |
| WO | 2007134340 | 7/2009 |
| WO | 2009105714 A2 | 8/2009 |
| WO | 2009105733 A9 | 12/2009 |
| WO | 2010044960 A1 | 4/2010 |
| WO | 2010068821 A1 | 6/2010 |

OTHER PUBLICATIONS

Ramesh V. Nair et al., Regulation of the sol Locus Genes for Butanol and Acetone Formulation in Clostridium acetobutyllicum ATCC 824 by a Putative Transcriptional Repressor:, Journal of Bacteriology, Jan 1999; vol. 181, N. 1, pp. 319-330.
The Eurasian Patent Office, Search Report.
Shen et al., "Metabolic Engineering of *Escherichia coli* for 1-butanol and 1-propanol production via the keto-acid pathways", 2008, Metabolic Engineering 10:312-320.
ISR from International Application PCT/US2011/066090.
(Casey and Grossman (1994) "In vivo and in vitro characterization of the light-regulated cpcB2A2 promoter of Fremyella diplosiphont" Journal of Bacteriology, 176(20):6362-6374).
(Deng and Coleman (1999) "Ethanol synthesis by genetic engineering in cyanobacteria," Applied and Environmental Microbiology, 65(2):523-528).
(Domain, Houot, Chauvat, and Cassier-Chauvat (2004) "Function and regulation of the cyanobacterial genes lexA, recA and ruvB: LexA is critical to the survival of cells facing inorganic carbon starvation," Molecular Microbiology, 53 (1):65-80).
(Durre, P. 1998 Appl Microbiol Biotechnol 49: 639-648.
(Fang and Barnum (2004) "Expression of the heat shock gene hsp16.6 and promoter analysis in the Cyanobacterium, *Synechocystis sp.* PCC 6803," Current Microbiology 49:192-198).
(Fire, Xu, Montgomery, Kostas, Driver, Mello (1998) "Potent and specific genetic interference by double-stranded RNA in Caenorhabditis elegans". Nature 391(6669):806-11.
(Fuhrmann, Stahlberg, Govorunova, Rank and Hegemann (2001) Journal of Cell Science 114:3857-3863).
(Gfeller and Gibbs (1984) "Fermentative metabolism of Chlamydomonas reinhardtii," Plant Physiol. 75:212-218).
(Griffin, Adams, and Tsien (1998), "Specific covalent labeling of recombinant protein molecules inside live cells", Science, 281:269-272).
(Hirano, Ueda, Hirayama, and Ogushi (1997) "CO2 fixation and ethanol production with microalgal photosynthesis and intracellular anaerobic fermentation" Energy 22(2/3):137-142).
(Keppetipola, Coffman, and et al (2003). Rapid detection of in vitro expressed proteins using LumioTM technology, Gene Expression, 25.3: 7-11).
(Lee, Blankinship and Greenbaum (1995), "Temperature effect on production of hydrogen and oxygen by Chlamydomonas cold strain CCMP1619 and wild type 137c," Applied Biochemistry and Biotechnology 51/52:379-386).
(Lee, Mets, and Greenbaum (2002). "Improvement of photosynthetic efficiency at high light intensity through reduction of chlorophyll antenna size," Applied Biochemistry and Biotechnology, 98-100: 37-48).
(Liszewski (Jun. 1, 2003) Progress in RNA interference, Genetic Engineering News, vol. 23, No. 11, pp. 1-59).
(Loppes and Radoux (2002) "Two short regions of the promoter are essential for activation and repression of the nitrate reductase gene in Chlamydomonas reinhardtii," Mol Genet Genomics 268: 42-48).
(Michel, Pistorius, and Golden (2001) "Unusual regulatory elements for iron deficiency induction of the idiA gene of Synechococcus elongatus PCC 7942" Journal of Bacteriology, 183(17):5015-5024).

(Muto, Miyachi, Usuda, Edwards and Bassham (1981) "Light-induced conversion of nicotinamide adenine dinucleotide to nicotinamide adenine dinucleotide phosphate in higher plant leaves," Plant Physiology 68(2):324-328.
(Nakajima, Tsuzuki, and Ueda (1999) "Reduced photoinhibition of a phycocyanin-deficient mutant of Synechocystis PCC 6714", Journal of Applied Phycology 10: 447-452).
(Nakamoto, Suzuki, and Roy (2000) "Constitutive expression of a small heat-shock protein confers cellular thermotolerance and thermal protection to the photosynthetic apparatus in cyanobacteria," FEBS Letters 483:169-174).
(Pattanayak and Chatterjee (1998) "Nicotinamide adenine dinucleotide phosphate phosphatase facilitates dark reduction of nitrate: regulation by nitrate and ammonia," Biologia Plantarium 41(1):75-84).
(Patterson-Fortin, Colvin and Owttrim (2006) "A LexA-related protein regulates redox-sensitive expression of the cyanobacterial RNA helicase, crhR", Nucleic Acids Research, 34(12):3446-3454).
(Qi, Hao, Ng, Slater, Baszis, Weiss, and Valentin (2005) "Application of the Synechococcus nirA promoter to establish an inducible expression system for engineering the Synechocystis tocopherol pathway," Applied and Environmental Microbiology, 71(10): 5678-5684.
(Quinn, Barraco, Ericksson and Merchant (2000). "Coordinate copper- and oxygen-responsive Cyc6 and Cpx1 expression in Chlamydomonas is mediated by the same element." J Biol Chem 275: 6080-6089).
(Sjoholm, Oliveira, and Lindblad (2007) "Transcription and regulation of the bidirectional hydrogenase in the *Cyanobacterium Nostoc* sp. strain PCC 7120," Applied and Environmental Microbiology, 73(17): 5435-5446).
(Kojima and Nakamoto (2007) "A novel light- and heat-responsive regulation of the groE transcription in the absence of HrcA or CIRCE in cyanobacteria," FEBS Letters 581:1871-1880).
7942 (Erbe, Adams, Taylor and Hall (1996) "Cyanobacteria carrying an smt-lux transcriptional fusion as biosensors for the detection of heavy metal cations," Journal of Industrial Microbiology, 17:80-83).
Atsumi et al.; "Diret Photosynthetic Recycling of Carbon Dioxide to Isobutyraldehyde", Nature Biotechnology 27 (12):1177-1180 (2009).
Atsumi, S. et al., "Non-fermentative Pathways for Synthesis of Branched-Chain Higher Alcohols as Biofuels", Nature, Jan. 2008, vol. 451, pp. 86-90.
B. Wu et al., "Alternative Isoleucine Synthesis Pathway in Cyanobacterial Species", Microbiology, vol. 156, No. 2, Oct. 29, 2009, pp. 596-602.
Chen et al., Photo Res., 2005, 86:165-173.
Deng et al., "Ethanol Synthesis by Genetic Engineering in Cyanobacteria", Applied and Environmental Microbiology, 65 (2):523-528(1999).
Deng M. and Coleman, J.R., "Ethanol Synthesis by Genetic Engineering in Cyanobateria", Applied and Environmental Microbiology, 1999, vol. 65, No. 2, pp. 523-528.
Dykxhoom, Novina, Sharp (2003) "Killing the messenger: short RNAs that silence gene expression", Nat Rev Mol Cell Biol. 4(6):457-67).
E.I. Lan and J. Liao; "Metabolic engineering of Cyanobacteria for 1-Butanol Production from Carbon Dioxide", Metabolic Engineering, vol. 13, No. 4, Jul. 1, 2011, pp. 353-363.
Extended European Search Report from corresponding European Patent Application No. 09712906.8-2405 (dated Nov. 8, 2011).
Fischer et al., "Selection and Optimization of Microbial Hosts for Biofuels Production", Metabolic Engineering 10 pp. 295-304 (2008).
Habibollah Younesi, "Ethanol and Acetate Production from Synthesis Gas via Fermentation Processes Using Anaerobic Bacterium, *Clostridium ljungdahiii*", In: Biochemical Engineering Journal, Dec. 15, 2005, vol. 27(2), pp. 110-119.
Jones et al., 1986, Microbiol. Rev., 50:484-524.
Kaneko Takakazu et al., "Complete Genomic Sequence of the Filamentous Nitrogen Fixing Cyanobacterium *Anabaena* sp. Strain PCC 7120"; DNA Research 8, 205-213 (2001).

(56) References Cited

OTHER PUBLICATIONS

Keneko Takakazu et al., Complete Genomic Sequence of the Filamentous Nitrogen-fixing Cyanobacterium *Anabaena* sp. Strain PCC 7120, DNA Research 8, 205-213 (2001).

Lee et al., "Discovery of an Alternative Oxygen Sensitivity in Algal Photosynthetic H2 Production", Proceedings of the 2000 U.S. DOE Hydrogen Program Review, NREL/CP-570-28890.

Maeda, Kawaguchi, Ohe, and Omata (1998) "cis-Acting sequences required for NtcB-dependent, nitrite-responsive positive regulation of the nitrate assimilation operon in the Cyanobacterium *Synechococcus* sp. strain PCC 7942," Journal of Bacteriology, 180(16):4080-4088).

Matsumura-Kadota, Muto, Miyachi (1982) "Light-induced conversion of NAD+ to NADP+ in Chlorella cells," Biochimica Biophysica Acta 679(2):300-300).

Palligama T. Vasudevan et aL, "Biodiesel production: current state of the art and challenges", Journal of Industrial Microbiology & Technology, Official Journal of the Society for Industrial Microbiology, Springer, Berlin, DE, vol. 35, No. 5, Jan. 18, 2008, pp. 421-430.

Palligarnai T. Vasudevan et al., "Biodiesel Production: Current State of the Art and Challenges", Journal of Industrial Microbiology & Biotechnology' Springer, Berlin, DE, vol. 35, No. 5, Jan. 18, 2008.

Pickett-Heap et al, 1999, Am J. of Botany, 86:153-172.

Qureshi, Hughes, Maddox, and Cotta 2005 Bioprocess Biosyst Eng 27: 215-222).

R. Radakovits et al., "Genetic Engineering of Algae for Enhanced Biofuel Production", Eukaryotic Cell, vol. 9, No. 4, Apr. 1, 2010, pp. 486-501.

Raines, 2003, Photosynthesis Res., 75:1-10.

T. Morton et al., "Paired-End Analysis of Transcription Start Sites in Arabidopsis Reveals Plant-Specific Promoter Signatures", The Plant Cell, vol. 26, pp. 2746-2760, Jul. (2014).

Benfey and Chua, "The Cauliflower Mosaic Virus 35S Promoter: Combinatorial Regulation of Transcription in Plants", Science 250, pp. 959-966 (1990).

Blumenthal et al., "A Global Analysis of Caenorhabditis elogans operons", Nature 417, pp. 851-854 (2002).

* cited by examiner

5'- | PCR FD Primer | Inducible Promoter | Targeting Seq | Butanol-Production-Pathway Gene(s) | PCR RE Primer | -3'

FIG. 2A

5'- | PCR FD Primer | Inducible Promoter | Targeting Seq | NADPH/NADH-Conversion Gene(s) | PCR RE Primer | -3'

FIG. 2B

5'- | PCR FD Primer | Inducible Promoter | iRNA Starch/Glycogen-Synthesis Inhibitor(s) | PCR RE Primer | -3'

FIG. 2C

5'- | PCR FD Primer | Inducible Promoter | Starch-Degradation-Glycolysis Gene(s) | PCR RE Primer | -3'

FIG. 2D

5'- | PCR FD Primer | Inducible Promoter | Butanol-Production-Pathway Gene(s) | PCR RE Primer | -3'

FIG. 2E

5'- | Recombination Site 1 | Designer Butanol-Production-Pathway Gene(s) | Recombination Site 2 | -3'

FIG. 2F

5'- | PCR FD Primer | Inducible Promoter | Biosafety-Control Gene(s) | PCR RE Primer | -3'

FIG. 2G

5'- | PCR FD Primer | Inducible Promoter | Designer Proton-Channel Gene(s) | PCR RE Primer | -3'

FIG. 2H

ORGANISMS FOR PHOTOBIOLOGICAL BUTANOL PRODUCTION FROM CARBON DIOXIDE AND WATER

CROSS-REFERENCE TO RELATED APPLICATIONS

This Application is a continuation of co-pending U.S. patent application Ser. No. 14/245,848, filed Apr. 4, 2014, which is a continuation of U.S. patent application Ser. No. 12/918,784, filed Aug. 20, 2010, which is a U.S. National Stage Application of International Patent Application No. PCT/US2009/034801, filed Feb. 21, 2009, which claimed the benefit of U.S. Provisional Application Numbers U.S. 61/066,845 and U.S. 61/066,835 filed on Feb. 23, 2008. The entire disclosures of all of these applications are incorporated herein by reference.

FIELD OF THE INVENTION

The present invention generally relates to biosafety-guarded biofuel energy production technology. More specifically, the present invention provides a photobiological butanol production methodology based on designer transgenic plants, such as transgenic algae, blue-green algae (cyanobacteria and oxychlorobacteria), or plant cells that are created to use the reducing power (NADPH) and energy (ATP) acquired from the photosynthetic process for immediate synthesis of butanol ($CH_3CH_2CH_2CH_2OH$) directly from carbon dioxide ($CO_2$) and water ($H_2O$).

REFERENCE TO SEQUENCE LISTING

The present invention contains references to amino acid sequences and/or nucleic acid sequences which have been submitted concurrently herewith as the sequence listing text file "2009_03_26_JWL_002_PCT_ST25.txt" created Mar. 26, 2009, file size 148 KB, which was previously submitted in U.S. patent application Ser. No. 14/245,848, submitted in International Application No. PCT/US2009/034801 on Mar. 26, 2009 and contained in U.S. patent application Ser. No. 12/918,784, filed Aug. 20, 2010, which is a U.S. National Stage Application of International Patent Application No. PCT/US2009/034801. The aforementioned sequence listing was prepared in electronic format and complies with all format requirements and is incorporated herein by reference in its entirety including pursuant to 37 C.F.R. § 1.52(e)(5) where applicable. The amino acid sequences and/or nucleic acid sequences were also previously submitted in International Application No. PCT/US2009/034801 Feb. 21, 2009 as the sequence listing .pdf file "JWL_002_PCT_SequenceListing.pdf" and listed on the PCT Request as part of the International Application. The entire contents of all of these files are incorporated herein by reference.

BACKGROUND OF THE INVENTION

Butanol ($CH_3CH_2CH_2CH_2OH$), a four-carbon alcohol, can be used as a liquid fuel to run engines such as cars. Butanol can replace gasoline and the energy contents of the two fuels are nearly the same (110,000 Btu per gallon for butanol; 115,000 Btu per gallon for gasoline). Butanol has many superior properties as an alternative fuel when compared to ethanol as well. These include: 1) Butanol has higher energy content (110,000 Btu per gallon butanol) than ethanol (84,000 Btu per gallon ethanol); 2) Butanol is six times less "evaporative" than ethanol and 13.5 times less evaporative than gasoline, making it safer to use as an oxygenate and thereby eliminating the need for very special blends during the summer and winter seasons; 3) Butanol can be transported through the existing fuel infrastructure including the gasoline pipelines whereas ethanol must be shipped via rail, barge or truck; and 4) Butanol can be used as replacement for gasoline gallon for gallon e.g. 100% or any other percentage, whereas ethanol can only be used as an additive to gasoline up to about 85% (E-85) and then only after significant modification to the engine (while butanol can work as a 100% replacement fuel without having to modify the current car engine).

A significant potential market for butanol as a liquid fuel already exists in the current transportation and energy systems. Butanol is also used as an industrial solvent. In the United States, currently, butanol is manufactured primarily from petroleum. Historically (1900s-1950s), biobutanol was manufactured from corn and molasses in a fermentation process that also produced acetone and ethanol and was known as an ABE (acetone, butanol, ethanol) fermentation typically with certain butanol-producing bacteria such as *Clostridium acetobutylicum* and *Clostridium beijerinckii*. When the USA lost its low-cost sugar supply from Cuba around 1954, however, butanol production by fermentation declined mainly because the price of petroleum dropped below that of sugar. Recently, there is renewed R&D interest in producing butanol and/or ethanol from biomass such as corn starch using Clostridia- and/or yeast-fermentation process. However, similarly to the situation of "cornstarch ethanol production," the "cornstarch butanol production" process also requires a number of energy-consuming steps including agricultural corn-crop cultivation, corn-grain harvesting, corn-grain starch processing, and starch-to-sugar-to-butanol fermentation. The "cornstarch butanol production" process could also probably cost nearly as much energy as the energy value of its product butanol. This is not surprising, understandably because the cornstarch that the current technology can use represents only a small fraction of the corn crop biomass that includes the corn stalks, leaves and roots. The cornstovers are commonly discarded in the agricultural fields where they slowly decompose back to $CO_2$, because they represent largely lignocellulosic biomass materials that the current biorefinery industry cannot efficiently use for ethanol or butanol production. There are research efforts in trying to make ethanol or butanol from lignocellulosic plant biomass materials—a concept called "cellulosic ethanol" or "cellulosic butanol". However, plant biomass has evolved effective mechanisms for resisting assault on its cell-wall structural sugars from the microbial and animal kingdoms. This property underlies a natural recalcitrance, creating roadblocks to the cost-effective transformation of lignocellulosic biomass to fermentable sugars. Therefore, one of its problems known as the "lignocellulosic recalcitrance" represents a formidable technical barrier to the cost-effective conversion of plant biomass to fermentable sugars. That is, because of the recalcitrance problem, lignocellulosic biomasses (such as cornstover, switchgrass, and woody plant materials) could not be readily converted to fermentable sugars to make ethanol or butanol without certain pretreatment, which is often associated with high processing cost. Despite more than 50 years of R&D efforts in lignocellulosic biomass pretreatment and fermentative butanol-production processing, the problem of recalcitrant lignocellulosics still remains as a formidable technical barrier that has not yet been eliminated so far. Furthermore, the steps of lignocellulosic biomass cultivation, harvesting, pretreatment processing, and cellulose-to-sugar-to-butanol fermentation all cost energy. Therefore, any new technology that could bypass these bottleneck problems of the biomass technology would be useful.

Oxyphotobacteria (also known as blue-green algae including cyanobacteria and oxychlorobacteria) and algae (such as *Chlamydomonas reinhardtii, Platymonas subcordiformis, Chlorella fusca, Dunaliella salina, Ankistrodesmus braunii*, and *Scenedesmus obliquus*), which can perform photosynthetic assimilation of $CO_2$ with $O_2$ evolution from water in a liquid culture medium with a maximal theoretical solar-to-biomass energy conversion of about 10%, have tremendous potential to be a clean and renewable energy resource. However, the wild-type oxygenic photosynthetic green plants, such as blue-green algae and eukaryotic algae, do not possess the ability to produce butanol directly from $CO_2$ and $H_2O$. The wild-type photosynthesis uses the reducing power (NADPH) and energy (ATP) from the photosynthetic water splitting and proton gradient-coupled electron transport process through the algal thylakoid membrane system to reduce $CO_2$ into carbohydrates $(CH_2O)_n$ such as starch with a series of enzymes collectively called the "Calvin cycle" at the stroma region in an algal or green-plant chloroplast. The net result of the wild-type photosynthetic process is the conversion of $CO_2$ and $H_2O$ into carbohydrates $(CH_2O)_n$ and $O_2$ using sunlight energy according to the following process reaction:

$$nCO_2 + nH_2O \rightarrow (CH_2O)n + nO_2 \quad [1]$$

The carbohydrates $(CH_2O)_n$ are then further converted to all kinds of complicated cellular (biomass) materials including proteins, lipids, and cellulose and other cell-wall materials during cell metabolism and growth.

In certain alga such as *Chlamydomonas reinhardtii*, some of the organic reserves such as starch could be slowly metabolized to ethanol (but not to butanol) through a secondary fermentative metabolic pathway. The algal fermentative metabolic pathway is similar to the yeast-fermentation process, by which starch is breakdown to smaller sugars such as glucose that is, in turn, transformed into pyruvate by a glycolysis process. Pyruvate may then be converted to formate, acetate, and ethanol by a number of additional metabolic steps (Gfeller and Gibbs (1984) "Fermentative metabolism of *Chlamydomonas reinhardtii*," *Plant Physiol*. 75:212-218). The efficiency of this secondary metabolic process is quite limited, probably because it could use only a small fraction of the limited organic reserve such as starch in an algal cell. Furthermore, the native algal secondary metabolic process could not produce any butanol. As mentioned above, butanol has many superior physical properties to serve as a replacement for gasoline as a fuel. Therefore, a new photobiological butanol-producing mechanism with a high solar-to-butanol energy efficiency is needed.

The present invention provides revolutionary designer photosynthetic organisms, which are capable of directly synthesizing butanol from $CO_2$ and $H_2O$ using sunlight. The photobiological butanol-production system provided by the present invention could bypass all the bottleneck problems of the biomass technology mentioned above.

SUMMARY OF THE INVENTION

The present invention provides photobiological butanol production methods based on designer transgenic plants (such as algae and oxyphotobacteria) or plant cells. The designer photosynthetic organisms are created through genetic engineering such that the endogenous photosynthesis regulation mechanism is tamed, and the reducing power (NADPH) and energy (ATP) acquired from the photosynthetic water splitting and proton gradient-coupled electron transport process are used for synthesis of butanol $(CH_3CH_2CH_2CH_2OH)$ directly from carbon dioxide $(CO_2)$ and water $(H_2O)$. The photobiological butanol-production methods of the present invention completely eliminate the problem of recalcitrant lignocellulosics by bypassing the bottleneck problem of the biomass technology. The photosynthetic butanol-production technology of the present invention is expected to have a much higher solar-to-butanol energy-conversion efficiency than the current technology.

A fundamental feature of the present photosynthetic butanol production methodology is to create designer plants (such as algae) or plant cells that contain transgenes coding for a set of enzymes that can act on an intermediate product of the Calvin cycle and convert the intermediate product immediately into butanol, instead of making starch and other complex biomass materials. Accordingly, the present invention provides, inter alia, methods for producing butanol based on a designer plant or plant cells, DNA constructs encoding genes of a designer butanol-production pathway, as well as the designer plants and designer plant cells created.

In one aspect, the present invention provides a method for photosynthetic production of butanol by growing a designer plant (such as a designer alga or designer blue-green alga) or plant cells in a liquid culture medium, wherein the plant or plant cells are genetically engineered to express a set of enzymes that act on an intermediate product of the Calvin cycle and convert the intermediate product into butanol.

According to the present invention, a designer plant, such as a designer alga, or designer plant cell for use in the photosynthetic butanol production can be created utilizing essentially any plant, plant tissue, or plant cells as host, so long as such plant, plant tissue and cells have a photosynthetic capability and can be cultured in a liquid medium. In a preferred embodiment, an aquatic plant (hydrophytes) is utilized to create a designer plant, which includes, but not limited to, submersed aquatic herbs (such as *Hydrilla verticillata, Elodea densa, Aponogeton boivinianus, Hygrophila difformmis*), duckweeds (such as *Spirodela polyrrhiza, Wolffia globosa, Landoltia punctata*), water cabbage (*Pistia stratiotes*), buttercups (*Ranunculus*), water caltrop (*Trapa natans* and *Trapa bicornis*), water lily (such as *Nymphaea lotus*), water hyacinth (*Eichhornia crassipes*), seagrasses (such as *Heteranthera Zosterifolia*), and algae.

In an especially preferred embodiment, algae are used as host to create designer algae for photosynthetic butanol production. Algae suitable for use in the present invention can be either unicellular or multicellular algae (the latter including, but not limited to, seaweeds such as *Ulva latissima* (sea lettuce), *Ascophyllum nodosum*, and *Porphyra tenera*), and include green algae (Chlorophyta), red algae (Rhodophyta), brown algae (Phaeophyta), diatoms (Bacillariophyta), and blue-green algae (Oxyphotobacteria including Cyanophyta (cyanobacteria) and Prochlorophytes (oxychlorobacteria)). Both the prokaryotic blue-green algae (oxyphotobacteria) and the eukaryotic algae are highly suitable for use in this invention. A particularly preferred species of algae for use in the present invention is a species of green algae, *Chlamydomonas reinhardtii*, of which the genome has recently been sequenced.

The selection of the enzymes appropriate for use to create a designer butanol-production pathway in a host depends on from which intermediate product of the Calvin cycle the designer pathway branches off from the Calvin cycle. In one embodiment, the designer pathway branches off from the point of glyceraldehydes 3-phosphate and converts it into butanol by using, for example, the set of enzymes consisting of glyceraldehyde-3-phosphate dehydrogenase, phosphoglycerate kinase, phosphoglycerate mutase, enolase, pyruvate kinase, pyruvate-ferredoxin oxidoreductase (or pyruvate-NADP$^+$ oxidoreductase), thiolase, 3-hydroxybutyryl-CoA dehydrogenase, crotonase, butyryl-CoA dehydrogenase, butyraldehyde dehydrogenase, and butanol dehydrogenase. In this designer pathway, for conversion of two molecules of glyceraldehyde-3-phosphate to butanol, two NADH molecules are generated from NAD$^+$ at the step from glyceraldehyde-3-phosphate to 1,3-diphosphoglycerate catalyzed by glyceraldehyde-3-phosphate dehydrogenase; meanwhile two molecules of NADH are converted to NAD$^+$: one at the step catalyzed by 3-hydroxybutyryl-CoA dehydrogenase to reduce acetoacetyl-CoA to 3-hydroxybutyryl-CoA and another at the step catalyzed by butyryl-CoA dehydrogenase to reduce crotonyl-CoA to butyryl-CoA. Consequently, in this designer pathway, the number of NADH molecules consumed is balanced with the number of NADH molecules generated. Furthermore, both the step catalyzed by butyraldehyde dehydrogenase in reducing butyryl-CoA to butyraldehyde and the terminal step catalyzed by butanol dehydrogenase in reducing butyraldehyde to butanol can use NADPH, which can be regenerated by the photosynthetic water splitting and proton gradient-coupled electron transport process. Therefore, this designer butanol-production pathway can operate continuously.

In another example, a designer pathway is created that takes the intermediate product, 3-phosphoglycerate, and converts it into butanol by using, for example, a set of enzymes consisting of phosphoglycerate mutase, enolase, pyruvate kinase, pyruvate-ferredoxin oxidoreductase, thiolase, 3-hydroxybutyryl-CoA dehydrogenase, crotonase, butyryl-CoA dehydrogenase, butyraldehyde dehydrogenase, and butanol dehydrogenase.

In order for this 3-phosphoglycerate-branched butanol-production pathway to operate, it is important to use a 3-hydroxybutyryl-CoA dehydrogenase and a butyryl-CoA dehydrogenase that can use NADPH which can be supplied by the photo-driven electron transport process. Alternatively, when a 3-hydroxybutyryl-CoA dehydrogenase and a butyryl-CoA dehydrogenase that can use only NADH are employed, it is preferably here to use an additional embodiment that can confer an NADPH/NADH conversion mechanism to supply NADH by converting NADPH to NADH to facilitate photosynthetic production of butanol through the 3-phosphoglycerate-branched designer pathway.

In still another example, a designer pathway is created that takes fructose-1,6-diphosphate and converts it into butanol by using, for example, a set of enzymes consisting of aldolase, triose phosphate isomerase, glyceraldehyde-3-phosphate dehydrogenase, phosphoglycerate kinase, phosphoglycerate mutase, enolase, pyruvate kinase, pyruvate-NADP$^+$ oxidoreductase (or pyruvate-ferredoxin oxidoreductase), thiolase, 3-hydroxybutyryl-CoA dehydrogenase, crotonase, butyryl-CoA dehydrogenase, butyraldehyde dehydrogenase, and butanol dehydrogenase. The addition of yet one more enzyme in the designer organism, phosphofructose kinase, permits the creation of another designer pathway which branches off from the point of fructose-6-phosphate for the production of butanol. Like the glyceraldehyde-3-phosphate-branched butanol-production pathway, both the fructose-1,6-diphosphate-branched pathway and the fructose-6-phosphate-branched pathway can themselves generate NADH for use in the pathway at the step catalyzed by 3-hydroxybutyryl-CoA dehydrogenase to reduce acetoacetyl-CoA to 3-hydroxybutyryl-CoA and another at the step catalyzed by butyryl-CoA dehydrogenase to reduce crotonyl-CoA to butyryl-CoA. In each of these designer butanol-production pathways, the numbers of NADH molecules consumed are balanced with the numbers of NADH molecules generated; and both the butyraldehyde dehydrogenase (catalyzing the step in reducing butyryl-CoA to butyraldehyde) and the butanol dehydrogenase (catalyzing the terminal step in reducing butyraldehyde to butanol) can all use NADPH, which can be regenerated by the photosynthetic water splitting and proton gradient-coupled electron transport process. Therefore, these designer butanol-production pathways can operate continuously. It can be noted that certain sets of designer enzymes may permit two or more designer pathways, i.e., pathways that branches off from two or more points of the Calvin cycle for the production of butanol.

According to the present invention, nucleic acids encoding for these enzymes are genetically engineered such that the enzymes expressed are inserted into the chloroplasts of the host to achieve targeted cellular localization. The targeted insertion of designer butanol-production-pathway enzymes can be accomplished through use of a nucleotide sequence that encodes for a stroma "signal" peptide, placed in an operable linkage to the nucleotide sequence encoding for a designer enzyme. A number of transit peptide sequences are suitable for use for the targeted insertion of the designer butanol-production enzymes into chloroplast, including but not limited to the transit peptide sequences of the hydrogenase apoproteins (such as Hydl), ferredoxin apoprotein (Frx1), thioredoxin m apoprotein (Trx2), glutamine synthase apoprotein (Gs2), LhcII apoproteins, PSII-T apoprotein (PsbT), PSII-S apoprotein (PsbS), PSII-W apoprotein (PsbW), $CF_0CF_1$ subunit-□ apoprotein (AtpC), $CF_0CF_1$ subunit-□ apoprotein (AtpD), $CF_0CF_1$ subunit-II apoprotein (AtpG), photosystem I (PSI) apoproteins (such as, of genes PsaD, PsaE, PsaF, PsaG, PsaH, and PsaK), and Rubisco small-subunit (SSU) apoproteins (such as RbcS2). Preferred transit peptide sequences include the Hyd1 transit peptide, the Frx1 transit peptide, and the Rubisco SSU transit peptides (such as RbcS2).

Further in accordance with the present invention, the expression of the designer butanol-producing pathway is controlled through the use of an externally inducible promoter so that the designer transgenes are inducibly expressed under certain specific conditions. In one embodiment, the inducible promoter used to control the expression of designer genes is a promoter that is inducible by anaerobiosis, including, for example, the promoters of the hydrogenase gene (Hyd1), the Cyc6 gene encoding the apoprotein of Cytochrome $C_6$, and the Cpx1 gene encoding coprogen oxidase. Additional inducible promoters suitable for use in the present invention include the nitrate reductase (Nia1) promoter, heat-shock protein promoter HSP70A, CabII-1 promoter, Ca1 promoter, Ca2 promoter, nitrite-reductase-gene (nirA) promoters, bidirectional-hydrogenase-gene hox promoters, light- and heat-responsive groE promoters, Rubisco-operon rbcL promoters, metal (zinc)-inducible smt promoter, iron-responsive idiA promoter, redox-responsive crhR promoter, heat-shock-gene hsp16.6 promoter, small heat-shock protein (Hsp) promoter, $CO_2$-responsive carbonic-anhydrase-gene promoters, green/red light responsive cpcB2A2 promoter, UV-light responsive lexA, recA and ruvB promoters, nitrate-reductase-gene (narB) promoters, and combinations thereof.

In another aspect of the present invention, designer DNA constructs are provided, which contain one or more nucleotide sequences encoding one or more designer butanol-production-pathway enzymes, each of which is placed in an operable linkage to an inducible promoter, and to a nucleotide sequence encoding for an appropriate chloroplast-targeting transit peptide. The constructs may contain additional appropriate sequences, such as a selection marker gene to facilitate the screening and identification of transformants. Nucleic acid constructs carrying designer genes can be delivered into a host alga, plant organism or plant tissue or cells using the available gene-transformation techniques, such as electroporation, natural transformation, conjugation, PEG induced uptake, and ballistic delivery of DNA, and Agrobacterium-mediated transformation.

The designer plants (e.g., designer algae), plant tissues, and plant cells that have been created to contain one or more designer construct, form another embodiment of the present invention. In a further aspect, the present invention provides additional methods for enhanced photosynthetic butanol production, the related designer constructs and designer plants, plant tissues and cells.

In a specific embodiment, a photosynthetic butanol-producing designer plant (for example, a designer alga), plant tissue or cell(s), as described above, has been further modified to contain additional designer transgenes to inducibly express one or more enzymes to facilitate the NADPH/NADH conversion, such as the NAD$^+$-dependent glyceraldehyde-3-phosphate dehydrogenase, NADPH phosphatase and NAD kinase. Alternatively, the 3-hydroxybutyryl-CoA dehydrogenase, butyryl-CoA dehydrogenase, butyraldehyde dehydrogenase, and butanol dehydrogenase of the designer plant, plant tissue or cell(s) can be selected and modified so that they can use NADPH as well.

In another embodiment, a photosynthetic butanol-producing designer plant or plant tissue, or cell(s) has been further modified to inactivate starch-synthesis activity. In a specific embodiment, such further modification includes introduction of a designer DNA construct that encodes and inducibly expresses an interfering RNA (iRNA) molecule that specifically inhibits the synthesis of a starch-synthesis-pathway enzyme, for example, starch synthase, glucose-1-phosphate adenylyltransferase, glucose-phosphate-isomerase and/or phosphoglucomutase for enhanced photobiological production of butanol.

In still another embodiment, a photosynthetic butanol-producing designer plant or plant tissue or cell(s) has been further modified to contain an additional set of designer genes that facilitate starch degradation and glycolysis in the stroma. Such additional designer genes include, for example, genes coding for amylase, starch phosphorylase, hexokinase, phosphoglucomutase, and glucose-phosphate-isomerase.

In yet another embodiment, a photobiological butanol-production pathway(s) is distributed in parts in both chloroplast and cytoplasm. The distribution of the designer butanol-production-pathway enzymes between chloroplast and cytoplasm is controlled by the use and/or deletion of the transit peptide sequences in the designer DNA constructs.

In still another embodiment, a photobiological butanol-production pathway(s) is distributed entirely in cytoplasm as in the case of designer oxyphotobacteria (blue-green algae) including designer cyanobacteria and designer oxychlorobacteria.

This invention also provides a biosafety-guarded photobiological biofuel-production technology based on cell-division-controllable designer transgenic plants, algae, blue-green algae (cyanobacteria and oxychlorobacteria), or plant cells. The cell-division-controllable designer photosynthetic organisms contain two key functions: a designer biosafety mechanism(s) and a designer biofuel-production pathway(s). The designer biosafety feature(s) is conferred by a number of mechanisms including: (1) the inducible insertion of designer proton-channels into cytoplasm membrane to permanently disable any cell division and/or mating capability, (2) the selective application of designer cell-division-cycle regulatory protein or interference RNA (iRNA) to permanently inhibit the cell division cycle and preferably keep the cell at the $G_1$ phase or $G_0$ state, and (3) the innovative use of a high-$CO_2$-requiring host photosynthetic organism for expression of the designer biofuel-production pathway(s). The designer cell-division-control technology can help ensure biosafety in using the designer organisms for photosynthetic biofuel production.

The present invention further provides a process of using a designer photosynthetic organism (such as a designer cyanobacterium or alga), in combination with a photobiological reactor system and a butanol separation/harvesting process for photobiological production of butanol and $O_2$ directly from $CO_2$ and $H_2O$ using sunlight. Both industrial $CO_2$ sources and/or atmospheric $CO_2$ from the environment may be used in the photobiological butanol-production process.

BRIEF DESCRIPTION OF THE DRAWINGS

FIG. 2A presents a DNA construct for designer butanol-production-pathway gene(s).

FIG. 2B presents a DNA construct for NADPH/NADH-conversion designer gene for NADPH/NADH inter-conversion.

FIG. 2C presents a DNA construct for a designer iRNA starch/glycogen-synthesis inhibitor(s) gene.

FIG. 2D presents a DNA construct for a designer starch-degradation-glycolysis gene(s).

FIG. 2E presents a DNA construct of a designer butanol-production-pathway gene(s) for cytosolic expression.

FIG. 2F presents a DNA construct of a designer butanol-production-pathway gene(s) with two recombination sites for integrative genetic transformation in oxyphotobacteria.

FIG. 2G presents a DNA construct of a designer biosafety-control gene(s).

FIG. 2H presents a DNA construct of a designer proton-channel gene(s).

DETAILED DESCRIPTION OF THE INVENTION

The present invention is directed to a photobiological butanol production technology based on designer photosynthetic organisms such as designer transgenic plants (e.g., algae and oxyphotobacteria) or plant cells. The designer plants and plant cells are created using genetic engineering techniques such that the endogenous photosynthesis regulation mechanism is tamed, and the reducing power (NADPH) and energy (ATP) acquired from the photosynthetic water splitting and proton gradient-coupled electron transport process can be used for immediate synthesis of butanol ($CH_3CH_2CH_2CH_2OH$) directly from carbon dioxide ($CO_2$) and water ($H_2O$) according to the following process reaction:

$$4CO_2 + 5H_2O \rightarrow CH_3CH_2CH_2CH_2OH + 6O_2 \quad [2]$$

Figure 1:
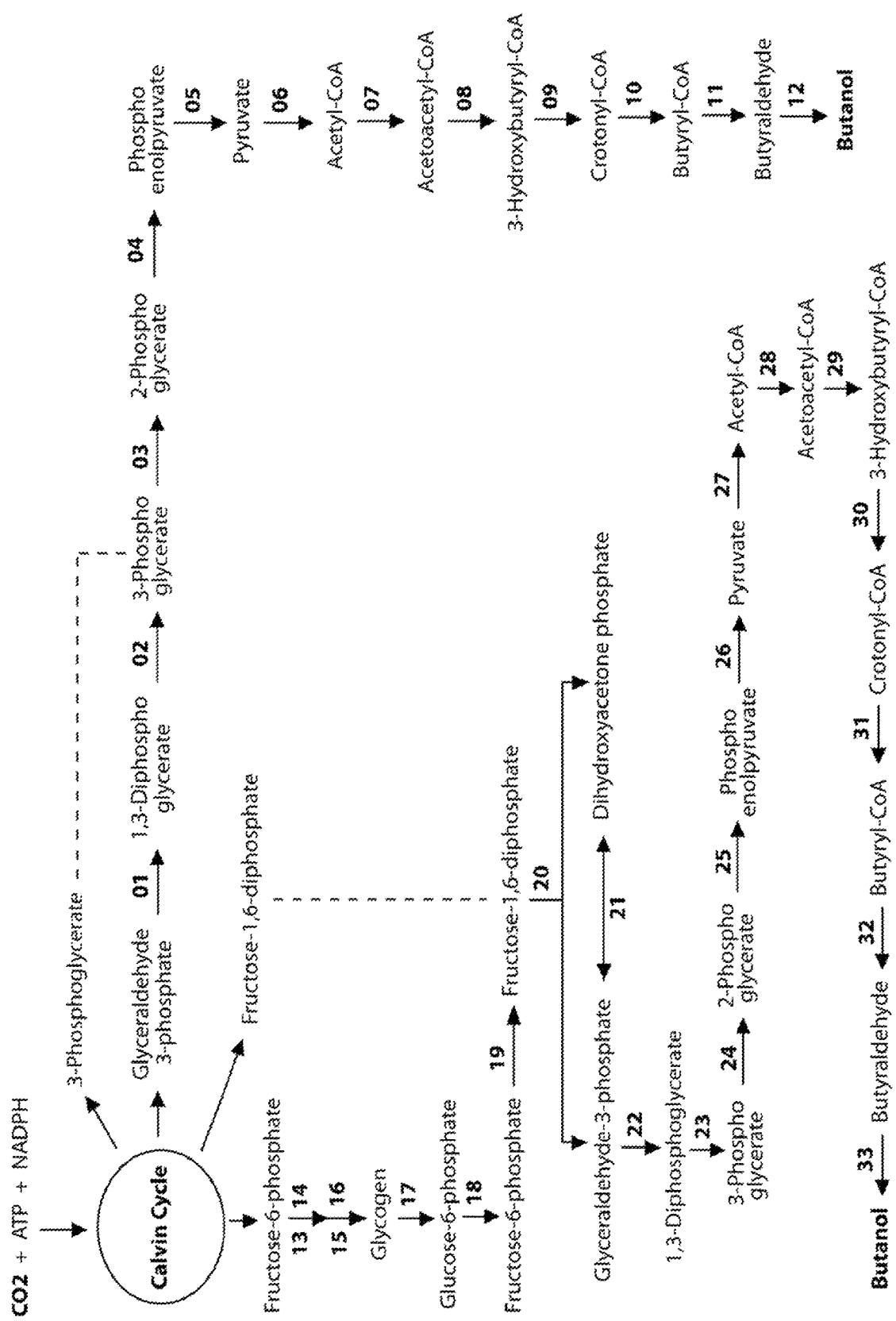
FIG. 1 presents designer butanol-production pathways branched from the Calvin cycle using the reducing power (NADPH) and energy (ATP) from the photosynthetic water splitting and proton gradient-coupled electron transport process to reduce carbon dioxide ($CO_2$) into butanol $CH_3CH_2CH_2CH_2OH$ with a series of enzymatic reactions.

The photobiological butanol-production methods of the present invention completely eliminate the problem of recalcitrant lignocellulosics by bypassing the bottleneck problem of the biomass technology. As shown in FIG. 1, the photosynthetic process in a designer organism effectively uses the reducing power (NADPH) and energy (ATP) from the photosynthetic water splitting and proton gradient-coupled electron transport process for immediate synthesis of butanol ($CH_3CH_2CH_2CH_2OH$) directly from carbon dioxide ($CO_2$) and water ($H_2O$) without being drained into the other pathway for synthesis of the undesirable lignocellulosic materials that are very hard and often inefficient for the biorefinery industry to use. This approach is also different from the existing "cornstarch butanol production" process. In accordance with this invention, butanol can be produced directly from carbon dioxide ($CO_2$) and water ($H_2O$) without having to go through many of the energy consuming steps that the cornstarch butanol-production process has to go through, including corn crop cultivation, corn-grain harvesting, corn-grain cornstarch processing, and starch-to-sugar-to-butanol fermentation. As a result, the photosynthetic butanol-production technology of the present invention is expected to have a much (more than 10-times) higher solar-to-butanol energy-conversion efficiency than the current technology. Assuming a 10% solar energy conversion efficiency for the proposed photosynthetic butanol production process, the maximal theoretical productivity (yield) could be about 72,700 kg of butanol per acre per year, which could support about 70 cars (per year per acre). Therefore, this invention could bring a significant capability to the society in helping to ensure energy security. The present invention could also help protect the Earth's environment from the dangerous accumulation of $CO_2$ in the atmosphere, because the present methods convert $CO_2$ directly into clean butanol energy.

A fundamental feature of the present methodology is utilizing a plant (e.g., an alga or oxyphotobacterium) or plant cells, introducing into the plant or plant cells nucleic acid molecules encoding for a set of enzymes that can act on an intermediate product of the Calvin cycle and convert the intermediate product into butanol as illustrated in FIG. 1, instead of making starch and other complicated cellular (biomass) materials as the end products by the wild-type photosynthetic pathway. Accordingly, the present invention provides, inter alia, methods for producing butanol based on a designer plant (such as a designer alga and a designer oxyphotobacterium), designer plant tissue, or designer plant cells, DNA constructs encoding genes of a designer butanol-production pathway, as well as the designer algae, designer oxyphotobacteria (including designer cyanobacteria), designer plants, designer plant tissues, and designer plant cells created. The various aspects of the present invention are described in further detail hereinbelow.

Host Photosynthetic Organisms

According to the present invention, a designer organism or cell for the photosynthetic butanol production of the invention can be created utilizing as host, any plant (including alga and oxyphotobacterium), plant tissue, or plant cells that have a photosynthetic capability, i.e., an active photosynthetic apparatus and enzymatic pathway that captures light energy through photosynthesis, using this energy to convert inorganic substances into organic matter. Preferably, the host organism should have an adequate photosynthetic $CO_2$ fixation rate, for example, to support photosynthetic butanol production from $CO_2$ and $H_2O$ at least about 1,450 kg butanol per acre per year, more preferably, 7,270 kg butanol per acre per year, or even more preferably, 72,700 kg butanol per acre per year.

In a preferred embodiment, an aquatic plant is utilized to create a designer plant. Aquatic plants, also called hydrophytic plants, are plants that live in or on aquatic environments, such as in water (including on or under the water surface) or permanently saturated soil. As used herein, aquatic plants include, for example, algae, blue-green algae (cyanobacteria and oxychlorobacteria), submersed aquatic herbs (*Hydrilla verticillata, Elodea densa, Hippuris vulgaris, Aponogeton Boivinianus Aponogeton Rigidifolius, Aponogeton Longiplumulosus, Didiplis Diandra, Vesicularia Dubyana, Hygrophilia Augustifolia, Micranthemum Umbrosum, Eichhornia Azurea, Saururus Cernuus, Cryptocoryne Lingua, Hydrotriche Hottoniiflora Eustralis Stellata, Vallisneria Rubra, Hygrophila Salicifolia, Cyperus Helferi, Cryptocoryne Petchii, Vallisneria americana, Vallisneria Torta, Hydrotriche Hottoniiflora, Crassula Helmsii, Limnophila Sessiliflora, Potamogeton Perfoliatus, Rotala Wallichii, Cryptocoryne Becketii, Blyxa Aubertii, Hygrophila Difformmis*), duckweeds (*Spirodela polyrrhiza, Wollfia globosa, Lemna trisulca, Lemna gibba, Lemna minor, Landoltia punctata*), water cabbage (*Pistia stratiotes*), buttercups (*Ranunculus*), water caltrop (*Trapa natans* and *Trapa bicornis*), water lily (*Nymphaea lotus*, Nymphaeaceae and Nelumbonaceae), water hyacinth (*Eichhornia crassipes*), *Bolbitis heudelotii, Cabomba* sp., seagrasses (*Heteranthera Zosterifolia*, Posidoniaceae, Zosteraceae, Hydrocharitaceae, and Cymodoceaceae). Butanol produced from an aquatic plant can diffuse into water, permitting normal growth of the plants and more robust production of butanol from the plants. Liquid cultures of aquatic plant tissues (including, but not limited to, multicellular algae) or cells (including, but not limited to, unicellular algae) are also highly preferred for use, since the butanol molecules produced from a designer butanol-production pathway can readily diffuse out of the cells or tissues into the liquid water medium, which can serve as a large pool to store the product butanol that can be subsequently harvested by filtration and/or distillation/evaporation techniques.

Although aquatic plants or cells are preferred host organisms for use in the methods of the present invention, tissue and cells of non-aquatic plants, which are photosynthetic and can be cultured in a liquid culture medium, can also be used to create designer tissue or cells for photosynthetic butanol production. For example, the following tissue or cells of non-aquatic plants can also be selected for use as a host organism in this invention: the photoautotrophic shoot tissue culture of wood apple tree *Feronia limonia*, the chlorophyllous callus-cultures of corn plant *Zea mays*, the green root cultures of Asteraceae and Solanaceae species, the tissue culture of sugarcane stalk parenchyma, the tissue culture of bryophyte *Physcomitrella patens*, the photosynthetic cell suspension cultures of soybean plant (*Glycine max*), the photoautotrophic and photomixotrophic culture of green Tobacco (*Nicotiana tabacum* L.) cells, the cell suspension culture of *Gisekia pharnaceoides* (a C₄ plant), the photosynthetic suspension cultured lines of *Amaranthus powellii* Wats., *Datura innoxia* Mill., *Gossypium hirsutum* L., and *Nicotiana tabacum*×*Nicotiana glutinosa* L. fusion hybrid.

By "liquid medium" is meant liquid water plus relatively small amounts of inorganic nutrients (e.g., N, P, K etc, commonly in their salt forms) for photoautotrophic cultures; and sometimes also including certain organic substrates (e.g., sucrose, glucose, or acetate) for photomixotrophic and/or photoheterotrophic cultures.

In an especially preferred embodiment, the plant utilized in the butanol production method of the present invention is an alga or a blue-green alga. The use of algae and/or blue-green algae has several advantages. They can be grown in an open pond at large amounts and low costs. Harvest and purification of butanol from the water phase is also easily accomplished by distillation/evaporation or membrane separation.

Algae suitable for use in the present invention include both unicellular algae and multi-unicellular algae. Multicellular algae that can be selected for use in this invention include, but are not limited to, seaweeds such as *Ulva latissima* (sea lettuce), *Ascophyllum nodosum, Codium fragile, Fucus vesiculosus, Eucheuma denticulatum, Gracilaria gracilis, Hydrodictyon reticulatum, Laminaria japonica, Undaria pinntifida, Saccharina japonica, Porphyra yezoensis*, and *Porphyra tenera*. Suitable algae can also be chosen from the following divisions of algae: green algae (Chlorophyta), red algae (Rhodophyta), brown algae (Phaeophyta), diatoms (Bacillariophyta), and blue-green algae (Oxyphotobacteria including Cyanophyta and Prochlorophytes). Suitable orders of green algae include Ulvales, Ulotrichales, Volvocales, Chlorellales, Schizogoniales, Oedogoniales, Zygnematales, Cladophorales, Siphonales, and Dasycladales. Suitable genera of Rhodophyta are *Porphyra, Chondrus, Cyanidioschyzon, Porphyridium, Gracilaria, Kappaphycus, Gelidium* and *Agardhiella*. Suitable genera of Phaeophyta are *Laminaria, Undaria, Macrocystis, Sargassum* and *Dictyosiphon*. Suitable genera of Cyanophyta (also known as Cyanobacteria) include (but not limited to) *Phoridium, Synechocystis, Syncechococcus, Oscillatoria*, and *Anabaena*. Suitable genera of Prochlorophytes (also known as oxychlorobacteria) include (but not limited to) *Prochloron, Prochlorothrix*, and *Prochlorococcus*. Suitable genera of Bacillariophyta are *Cyclotella, Cylindrotheca, Navicula, Thalassiosira*, and *Phaeodactylum*. Preferred species of algae for use in the present invention include *Chlamydomonas reinhardtii, Platymonas subcordiformis, Chlorella fusca, Chlorella sorokiniana, Chlorella vulgaris, 'Chlorella' ellipsoidea, Chlorella* spp., *Dunaliella salina, Dunaliella viridis, Dunaliella bardowil, Haematococcus pluvialis; Parachlorella kessleri, Betaphycus gelatinum, Chondrus crispus, Cyanidioschyzon merolae, Cyanidium caldarium, Galdieria sulphuraria, Gelidiella acerosa, Gracilaria changii, Kappaphycus alvarezii, Porphyra miniata, Ostreococcus tauri, Porphyra yezoensis, Porphyridium* sp., *Palmaria palmata, Gracilaria* spp., *Isochrysis galbana, Kappaphycus* spp., *Laminaria japonica, Laminaria* spp., *Monostroma* spp., *Nannochloropsis oculata, Porphyra* spp., *Porphyridium* spp., *Undaria pinnatifida, Ulva lactuca, Ulva* spp., *Undaria* spp., *Phaeodactylum Tricornutum, Navicula saprophila, Crypthecodinium cohnii, Cylindrotheca fusiformis, Cyclotella cryptica, Euglena gracilis, Amphidinium* sp., *Symbiodinium microadriaticum, Macrocystis pyrifera, Ankistrodesmus braunii*, and *Scenedesmus obliquus*.

Preferred species of blue-green algae (oxyphotobacteria including cyanobacteria and oxychlorobacteria) for use in the present invention include *Thermosynechococcus elongatus* BP-1, *Nostoc* sp. PCC 7120, *Synechococcus elongatus* PCC 6301, *Syncechococcus* sp. strain PCC 7942, *Syncechococcus* sp. strain PCC 7002, *Syncechocystis* sp. strain PCC 6803, *Prochlorococcus marinus* MED4, *Prochlorococcus marinus* MIT 9313, *Prochlorococcus marinus* NATL1A, *Prochlorococcus* SS120, *Spirulina platensis* (*Arthrospira platensis*), *Spirulina pacifica, Lyngbya majuscule, Anabaena* sp., *Synechocystis* sp., *Synechococcus elongates, Synechococcus* (MC-A), *Trichodesmium* sp., *Richelia intracellularis, Synechococcus* WH7803, *Synechococcus* WH8102, *Nostoc punctiforme, Syncechococcus* sp. strain PCC 7943, *Synechocyitis* PCC 6714 phycocyanin-deficient mutant PD-1, *Cyanothece* strain 51142, *Cyanothece* sp. CCY0110, *Oscillatoria limosa, Lyngbya majuscula, Symploca muscorum, Gloeobacter violaceus, Prochloron didemni, Prochlorothrix hollandica, Synechococcus* (MC-A), *Trichodesmium* sp., *Richelia intracellularis, Prochlorococcus marinus, Prochlorococcus* SS120, *Synechococcus* WH8102, *Lyngbya majuscula, Symploca muscorum, Synechococcus bigranulatus, cryophilic Oscillatoria* sp., *Phormidium* sp., *Nostoc* sp.-1, *Calothrix parietina*, thermophilic *Synechococcus bigranulatus, Synechococcus lividus*, thermophilic *Mastigocladus laminosus, Chlorogloeopsis fritschii* PCC 6912, *Synechococcus vulcanus, Synechococcus* sp. strain MA4, *Synechococcus* sp. strain MA19, and *Thermosynechococcus elongatus*.

Proper selection of host photosynthetic organisms for their genetic backgrounds and certain special features is also beneficial. For example, a photosynthetic-butanol-producing designer alga created from cryophilic algae (psychrophiles) that can grow in snow and ice, and/or from cold-tolerant host strains such as *Chlamydomonas* cold strain CCMG1619, which has been characterized as capable of performing photosynthetic water splitting as cold as 4° C. (Lee, Blankinship and Greenbaum (1995), "Temperature effect on production of hydrogen and oxygen by *Chlamydomonas* cold strain CCMP1619 and wild type 137c," *Applied Biochemistry and Biotechnology* 51/52:379-386), permits photobiological butanol production even in cold seasons or regions such as Canada. Meanwhile, a designer alga created from a thermophilic/thermotolerant photosynthetic organism such as thermophilic algae *Cyanidium caldarium* and *Galdieria sulphuraria* and/or thermophilic cyanobacteria (blue-green algae) such as *Thermosynechococcus elongatus* BP-1 and *Synechococcus bigranulatus* may permit the practice of this invention to be well extended into the hot seasons or areas such as Mexico and the Southwestern region of the United States including Nevada, California, Arizona, New Mexico and Texas, where the weather can often be hot. Furthermore, a photosynthetic-butanol-producing designer alga created from a marine alga, such as *Platymonas subcordiformis*, permits the practice of this invention using seawater, while the designer alga created from a freshwater alga such as *Chlamydomonas reinhardtii* can use freshwater. Additional optional features of a photosynthetic butanol-producing designer alga include the benefits of reduced chlorophyll-antenna size, which has been demonstrated to provide higher photosynthetic productivity (Lee, Mets, and Greenbaum (2002). "Improvement of photosynthetic efficiency at high light intensity through reduction of chlorophyll antenna size," *Applied Biochemistry and Biotechnology*, 98-100: 37-48) and butanol-tolerance that allows for more robust and efficient photosynthetic production of butanol from $CO_2$ and $H_2O$. By use of a phycocyanin-deficient mutant of *Synechocystis* PCC 6714, it has been experimentally demonstrated that photoinhibition can be reduced also by reducing the content of light-harvesting pigments (Nakajima, Tsuzuki, and Ueda (1999) "Reduced photoinhibition of a phycocyanin-deficient mutant of *Synechocystis* PCC 6714", *Journal of Applied Phycology* 10: 447-452). These optional features can be incorporated into a designer alga, for example, by use of a butanol-tolerant and/or chlorophyll antenna-deficient mutant (e.g., *Chlamydomonas reinhardtii* strain DS521) as a host organism, for gene transformation with the designer butanol-production-pathway genes. Therefore, in one of the various embodiments, a host alga is selected from the group consisting of green algae, red algae, brown algae, blue-green algae (oxyphotobacteria including cyanobacteria and prochlorophytes), diatoms, marine algae, freshwater algae, unicellular algae, multicellular algae, seaweeds, cold-tolerant algal strains, heat-tolerant algal strains, light-harvesting-antenna-pigment-deficient mutants, butanol-tolerant algal strains, and combinations thereof.

Creating a Designer Butanol-Production Pathway in a Host
Selecting Appropriate Designer Enzymes One of the key features in the present invention is the creation of a designer butanol-production pathway to tame and work with the natural photosynthetic mechanisms to achieve the desirable synthesis of butanol directly from $CO_2$ and $H_2O$. The natural photosynthetic mechanisms include (1) the process of photosynthetic water splitting and proton gradient-coupled electron transport through the thylakoid membrane, which produces the reducing power (NADPH) and energy (ATP), and (2) the Calvin cycle, which reduces $CO_2$ by consumption of the reducing power (NADPH) and energy (ATP).

In accordance with the present invention, a series of enzymes are used to create a designer butanol-production pathway that takes an intermediate product of the Calvin cycle and converts the intermediate product into butanol as illustrated in FIG. 1. A "designer butanol-production-pathway enzyme" is hereby defined as an enzyme that serves as a catalyst for at least one of the steps in a designer butanol-production pathway. According to the present invention, a number of intermediate products of the Calvin cycle can be utilized to create designer butanol-production pathway(s); and the enzymes required for a designer butanol-production pathway are selected depending upon from which intermediate product of the Calvin cycle the designer butanol-production pathway branches off from the Calvin cycle.

In one example, a designer pathway is created that takes glyceraldehydes-3-phosphate and converts it into butanol by using, for example, a set of enzymes consisting of, as shown with the numerical labels 01-12 in FIG. 1, glyceraldehyde-3-phosphate dehydrogenase 01, phosphoglycerate kinase 02, phosphoglycerate mutase 03, enolase 04, pyruvate kinase 05, pyruvate-ferredoxin oxidoreductase 06, thiolase 07, 3-hydroxybutyryl-CoA dehydrogenase 08, crotonase 09, butyryl-CoA dehydrogenase 10, butyraldehyde dehydrogenase 11, and butanol dehydrogenase 12. In this glyceraldehydes-3-phosphate-branched designer pathway, for conversion of two molecules of glyceraldehyde-3-phosphate to butanol, two NADH molecules are generated from $NAD^+$ at the step from glyceraldehyde-3-phosphate to 1,3-diphosphoglycerate catalyzed by glyceraldehyde-3-phosphate dehydrogenase 01; meanwhile two molecules of NADH are converted to $NAD^+$: one at the step catalyzed by 3-hydroxybutyryl-CoA dehydrogenase 08 in reducing acetoacetyl-CoA to 3-hydroxybutyryl-CoA and another at the step catalyzed by butyryl-CoA dehydrogenase 10 in reducing crotonyl-CoA to butyryl-CoA. Consequently, in this glyceraldehydes-3-phosphate-branched designer pathway (01-12), the number of NADH molecules consumed is balanced with the number of NADH molecules generated. Furthermore, both the pathway step catalyzed by butyraldehyde dehydrogenase 11 (in reducing butyryl-CoA to butyraldehyde) and the terminal step catalyzed by butanol dehydrogenase 12 (in reducing butyraldehyde to butanol) can use NADPH, which can be regenerated by the photosynthetic water splitting and proton gradient-coupled electron transport process. Therefore, this glyceraldehydes-3-phosphate-branched designer butanol-production pathway can operate continuously.

In another example, a designer pathway is created that takes the intermediate product, 3-phosphoglycerate, and converts it into butanol by using, for example, a set of enzymes consisting of (as shown with the numerical labels 03-12 in FIG. 1) phosphoglycerate mutase 03, enolase 04, pyruvate kinase 05, pyruvate-ferredoxin oxidoreductase 06, thiolase 07, 3-hydroxybutyryl-CoA dehydrogenase 08, crotonase 09, butyryl-CoA dehydrogenase 10, butyraldehyde dehydrogenase 11, and butanol dehydrogenase 12. It is worthwhile to note that the last ten enzymes (03-12) of the glyceraldehydes-3-phosphate-branched designer butanol-producing pathway (01-12) are identical with those utilized in the 3-phosphoglycerate-branched designer pathway (03-12). In other words, the designer enzymes (01-12) of the glyceraldehydes-3-phosphate-branched pathway permit butanol production from both the point of 3-phosphoglycerate and the point glyceraldehydes 3-phosphate in the Calvin cycle. These two pathways, however, have different characteristics. Unlike the glyceraldehyde-3-phosphate-branched butanol-production pathway, the 3-phosphoglycerate-branched pathway which consists of the activities of only ten enzymes (03-12) could not itself generate any NADH that is required for use at two places: one at the step catalyzed by 3-hydroxybutyryl-CoA dehydrogenase 08 in reducing acetoacetyl-CoA to 3-hydroxybutyryl-CoA, and another at the step catalyzed by butyryl-CoA dehydrogenase 10 in reducing crotonyl-CoA to butyryl-CoA. That is, if (or when) a 3-hydroxybutyryl-CoA dehydrogenase and/or a butyryl-CoA dehydrogenase that can use strictly only NADH but not NADPH is employed, it would require a supply of NADH for the 3-phosphoglycerate-branched pathway (03-12) to operate. Consequently, in order for the 3-phosphoglycerate-branched butanol-production pathway to operate, it is important to use a 3-hydroxybutyryl-CoA dehydrogenase 08 and a butyryl-CoA dehydrogenase 10 that can use NADPH which can be supplied by the photo-driven electron transport process. Therefore, it is a preferred practice to use a 3-hydroxybutyryl-CoA dehydrogenase and a butyryl-CoA dehydrogenase that can use NADPH or both NADPH and NADH (i.e., NAD(P)H) for this 3-phosphoglycerate-branched designer butanol-production pathway (03-12 in FIG. 1). Alternatively, when a 3-hydroxybutyryl-CoA dehydrogenase and a butyryl-CoA dehydrogenase that can use only NADH are employed, it is preferably here to use an additional embodiment that can confer an NADPH/NADH conversion mechanism (to supply NADH by converting NADPH to NADH, see more detail later in the text) in the designer organism to facilitate photosynthetic production of butanol through the 3-phosphoglycerate-branched designer pathway.

In still another example, a designer pathway is created that takes fructose-1,6-diphosphate and converts it into butanol by using, as shown with the numerical labels 20-33 in FIG. 1, a set of enzymes consisting of aldolase 20, triose phosphate isomerase 21, glyceraldehyde-3-phosphate dehydrogenase 22, phosphoglycerate kinase 23, phosphoglycerate mutase 24, enolase 25, pyruvate kinase 26, pyruvate-NADP$^+$ oxidoreductase (or pyruvate-ferredoxin oxidoreductase) 27, thiolase 28, 3-hydroxybutyryl-CoA dehydrogenase 29, crotonase 30, butyryl-CoA dehydrogenase 31, butyraldehyde dehydrogenase 32, and butanol dehydrogenase 33, with aldolase 20 and triose phosphate isomerase 21 being the only two additional enzymes relative to the glyceraldehydes-3-phosphate-branched designer pathway. The use of a pyruvate-NADP$^+$ oxidoreductase 27 (instead of pyruvate-ferredoxin oxidoreductase) in catalyzing the conversion of a pyruvate molecule to acetyl-CoA enables production of an NADPH, which can be used in some other steps of the butanol-production pathway. The addition of yet one more enzyme in the designer organism, phosphofructose kinase 19, permits the creation of another designer pathway which branches off from the point of fructose-6-phosphate of the Calvin cycle for the production of butanol. Like the glyceraldehyde-3-phosphate-branched butanol-production pathway, both the fructose-1,6-diphosphate-branched pathway (20-33) and the fructose-6-phosphate-branched pathway (19-33) can themselves generate NADH for use in the pathway at the step catalyzed by 3-hydroxybutyryl-CoA dehydrogenase 29 to reduce acetoacetyl-CoA to 3-hydroxybutyryl-CoA and at the step catalyzed by butyryl-CoA dehydrogenase 31 to reduce crotonyl-CoA to butyryl-CoA. In each of these designer butanol-production pathways, the numbers of NADH molecules consumed are balanced with the numbers of NADH molecules generated; and both the butyraldehyde dehydrogenase 32 (catalyzing the step in reducing butyryl-CoA to butyraldehyde) and the butanol dehydrogenase 33 (catalyzing the terminal step in reducing butyraldehyde to butanol) can all use NADPH, which can be regenerated by the photosynthetic water splitting and proton gradient-coupled electron transport process. Therefore, these designer butanol-production pathways can operate continuously.

Table 1 lists examples of the enzymes including those identified above for construction of the designer butanol-production pathways. Throughout this specification, when reference is made to an enzyme, such as, for example, any of the enzymes listed in Table 1, it includes their isozymes, functional analogs, and designer modified enzymes and combinations thereof. These enzymes can be selected for use in construction of the designer butanol-production pathways (such as those illustrated in FIG. 1). The "isozymes or functional analogs" refer to certain enzymes that have the same catalytic function but may or may not have exactly the same protein structures. The most essential feature of an enzyme is its active site that catalyzes the enzymatic reaction. Therefore, certain enzyme-protein fragment(s) or subunit(s) that contains such an active catalytic site may also be selected for use in this invention. For various reasons, some of the natural enzymes contain not only the essential catalytic structure but also other structure components that may or may not be desirable for a given application. With techniques of bioinformatics-assisted molecular designing, it is possible to select the essential catalytic structure(s) for use in construction of a designer DNA construct encoding a desirable designer enzyme. Therefore, in one of the various embodiments, a designer enzyme gene is created by artificial synthesis of a DNA construct according to bioinformatics-assisted molecular sequence design. With the computer-assisted synthetic biology approach, any DNA sequence (thus its protein structure) of a designer enzyme may be selectively modified to achieve more desirable results by design. Therefore, the terms "designer modified sequences" and "designer modified enzymes" are hereby defined as the DNA sequences and the enzyme proteins that are modified with bioinformatics-assisted molecular design. For example, when a DNA construct for a designer chloroplast-targeted enzyme is designed from the sequence of a mitochondrial enzyme, it is a preferred practice to modify some of the protein structures, for example, by selectively cutting out certain structure component(s) such as its mitochondrial transit-peptide sequence that is not suitable for the given application, and/or by adding certain peptide structures such as an exogenous chloroplast transit-peptide sequence (e.g., a 135-bp Rubisco small-subunit transit peptide (RbcS2)) that is needed to confer the ability in the chloroplast-targeted insertion of the designer protein. Therefore, one of the various embodiments flexibly employs the enzymes, their isozymes, functional analogs, designer modified enzymes, and/or the combinations thereof in construction of the designer butanol-production pathway(s).

As shown in Table 1, many genes of the enzymes identified above have been cloned and/or sequenced from various organisms. Both genomic DNA and/or mRNA sequence data can be used in designing and synthesizing the designer DNA constructs for transformation of a host alga, oxyphotobacterium, plant, plant tissue or cells to create a designer organism for photobiological butanol production (FIG. 1). However, because of possible variations often associated with various source organisms and cellular compartments with respect to a specific host organism and its chloroplast/thylakoid environment where the butanol-production pathway(s) is designed to work with the Calvin cycle, certain molecular engineering art work in DNA construct design including codon-usage optimization and sequence modification is often necessary for a designer DNA construct (FIG. 2) to work well. For example, in creating a butanol-producing designer eukaryotic alga, if the source sequences are from cytosolic enzymes (sequences), a functional chloroplast-targeting sequence may be added to provide the capability for a designer unclear gene-encoded enzyme to insert into a host chloroplast to confer its function for a designer butanol-production pathway. Furthermore, to provide the switchability for a designer butanol-production pathway, it is also important to include a functional inducible promoter sequence such as the promoter of a hydrogenase (Hyd1) or nitrate reductase (Nia1) gene, or nitrite reductase (nirA) gene in certain designer DNA construct(s) as illustrated in FIG. 2A to control the expression of designer gene(s). In addition, as mentioned before, certain functional derivatives or fragments of these enzymes (sequences), chloroplast-targeting transit peptide sequences, and inducible promoter sequences can also be selected for use in full, in part or in combinations thereof, to create the designer organisms according to various embodiments of this invention. The arts in creating and using the designer organisms are further described hereinbelow.

Table 1 lists examples of enzymes for construction of designer butanol-production pathways.

| Enzyme | Source (Organism) | GenBank Accession Number, JGI Protein ID or Citation |
|---|---|---|
| Butanol dehydrogenase | Clostridium saccharoperbutylacetonicum; Propionibacterium freudenreichii; Trichomonas vaginalis; Aeromonas hydrophila; Clostridium beijerinckii; Clostridium acetobutylicum | GenBank: AB257439; AJ508920; AF112135; AF388671; AF157307; M96946, M96945 |
| Butyraldehyde dehydrogenase | Clostridium saccharoperbutylacetonicum | GenBank: AY251646 |
| Butyryl-CoA dehydrogenase | Clostridium beijerinckii; Butyrivibrio fibrisolvens; Butyrate-producing bacterium L2-50; Thermoanaerobacterium thermosaccharolyticum; | GenBank: AF494018; AB190764; DQ987697; Z92974 |
| Crotonase | Clostridium beijerinckii; Butyrivibrio fibrisolvens; Butyrate-producing bacterium L2-50; Thermoanaerobacterium thermosaccharolyticum; | GenBank: AF494018; AB190764; DQ987697; Z92974 |
| 3-Hydroxybutyryl-CoA dehydrogenase | Clostridium beijerinckii; Butyrivibrio fibrisolvens; Ajellomyces capsulatus; Aspergillus fumigatus; Aspergillus clavatus; Neosartorya fischeri; Butyrate-producing bacterium L2-50; Arabidopsis thaliana; Thermoanaerobacterium thermosaccharolyticum; | GenBank: AF494018; AB190764; XM_001537366; XM_741533; XM_001274776; XM_001262361; DQ987697; BT001208; Z92974 |
| Thiolase | Butyrivibrio fibrisolvens; butyrate-producing bacterium L2-50; Thermoanaerobacterium thermosaccharolyticum; | GenBank: AB190764; DQ987697; Z92974 |
| Glyceraldehyde-3-phosphate dehydrogenase | Mesostigma viride cytosol; Triticum aestivum cytosol; Chlamydomonas reinhardtii chloroplast; Botryotinia fuckeliana; Saccharomyces cerevisiae; Zymomonas mobilis; Karenia brevis; Ajellomyces capsulatus; Pichia stipitis; Pichia guilliermondii; Kluyveromyces marxianus, Triticum aestivum; Arabidopsis thaliana; Zea mays cytosolic | GenBank: DQ873404; EF592180; L27668; XM_001549497; J01324; M18802; EU078558; XM_001539393; XM_001386423, XM_001386568; XM_001485596; DQ681075; EF592180; NM_101214; U45857, ZMU45856, U45855 |
| Phosphoglycerate kinase | Chlamydomonas reinhardtii chloroplast; Plasmodium vivax; Babesia bovis; Botryotinia fuckeliana; Monocercomonoides sp.; Lodderomyces elongisporus; Pichia guilliermondii; Arabidopsis thaliana; Helianthus annuus; Oryza sativa; Dictyostelium discoideum; Euglena gracilis; Chondrus crispus; Phaeodactylum tricornutum; Solanum tuberosum | GenBank: U14912, AF244144; XM_001614707; XM_001610679; XM_001548271; DQ665858; XM_001523843; XM_001484377; NM_179576; DQ835564; EF122488; AF316577; AY647236; AY029776; AF108452; AF073473 |
| Phosphoglycerate mutase (phosphoglyceromutase) | Chlamydomonas reinhardtii cytoplasm; Aspergillus fumigatus; Coccidioides immitis; Leishmania braziliensis; Ajellomyces capsulatus; Monocercomonoides sp.; Aspergillus clavatus; Arabidopsis thaliana; Zea mays | JGI Chlre2 protein ID 161689, GenBank: AF268078; XM_747847; XM_749597; XM_001248115; XM_001569263; XM_001539892; DQ665859; XM_001270940; NM_117020; M80912 |
| Enolase | Chlamydomonas reinhardtii cytoplasm; Arabidopsis thaliana; Leishmania Mexicana; Lodderomyces elongisporus; Babesia bovis; Sclerotinia sclerotiorum; Pichia guilliermondii; Spirotrichonympha leidyi; Oryza sativa; Trimastix pyriformis; Leuconostoc mesenteroides; Davidiella tassiana; Aspergillus oryzae; Schizosaccharomyces pombe; Brassica napus; Zea mays | GenBank: X66412, P31683; AK222035; DQ221745; XM_001528071; XM_001611873; XM_001594215; XM_001483612; AB221057; EF122486, U09450; DQ845796; AB088633; U82438; D64113; U13799; AY307449; U17973 |
| Pyruvate kinase | Chlamydomonas reinhardtii cytoplasm; Arabidopsis thaliana; Saccharomyces cerevisiae; Babesia bovis; Sclerotinia sclerotiorum; Trichomonas vaginalis; Pichia guilliermondii; Pichia stipitis; Lodderomyces elongisporus; Coccidioides immitis; Trimastix pyriformis; Glycine max (soybean) | JGI Chlre3 protein ID 138105; GenBank: AK229638; AY949876, AY949890, AY949888; XM_001612087; XM_001594710; XM_001329865; XM_001487289; XM_001384591; XM_001528210; XM_001240868; DQ845797; L08632 |
| Phosphofructose kinase | Chlamydomonas reinhardtii; Arabidopsis thaliana; Ajellomyces capsulatus; Yarrowia lipolytica; Pichia stipitis; Dictyostelium | JGI Chlre2 protein ID 159495; GenBank: NM_001037043, NM_179694, NM_119066, |

| Enzyme | Source (Organism) | GenBank Accession Number, JGI Protein ID or Citation |
|---|---|---|
| | discoideum; Tetrahymena thermophila; Trypanosoma brucei; Plasmodium falciparum; Spinacia oleracea; | NM_125551; XM_001537193; AY142710; XM_001382359, XM_001383014; XM_639070; XM_001017610; XM_838827; XM_001347929; DQ437575; |
| Fructose-diphosphate aldolase | Chlamydomonas reinhardtii chloroplast; Fragaria × ananassa cytoplasm; Homo sapiens; Babesia bovis; Trichomonas vaginalis; Pichia stipitis; Arabidopsis thaliana | GenBank: X69969; AF308587; NM_005165; XM_001609195; XM_001312327, XM_001312338; XM_001387466; NM_120057, NM_001036644 |
| Triose phosphate isomerase | Arabidopsis thaliana; Chlamydomonas reinhardtii; Sclerotinia sclerotiorum; Chlorella pyrenoidosa; Pichia guilliermondii; Euglena intermedia; Euglena longa; Spinacia oleracea; Solanum chacoense; Hordeum vulgare; Oryza sativa | GenBank: NM_127687, AF247559; AY742323; XM_001587391; AB240149; XM_001485684; DQ459379; AY742325; L36387; AY438596; U83414; EF575877; |
| Glucose-1-phosphate adenylyltransferase | Arabidopsis thaliana; Zea mays; Chlamydia trachomatis; Solanum tuberosum (potato); Shigella flexneri; Lycopersicon esculentum | GenBank: NM_127730, NM_124205, NM_121927, AY059862; EF694839, EF694838; AF087165; P55242; NP_709206; T07674 |
| Starch synthase | Chlamydomonas reinhardtii; Phaseolus vulgaris; Oryza sativa; Arabidopsis thaliana; Colocasia esculenta; Amaranthus cruentus; Parachlorella kessleri; Triticum aestivum; Sorghum bicolor; Astragalus membranaceus; Perilla frutescens; Zea mays; Ipomoea batatas | GenBank: AF026422, AF026421, DQ019314, AF433156; AB293998; D16202, AB115917, AY299404; AF121673, AK226881; NM_101044; AY225862, AY142712; DQ178026; AB232549; Y16340; AF168786; AF097922; AF210699; AF019297; AF068834 |
| Alpha-amylase | Hordeum vulgare aleurone cells; Trichomonas vaginalis; Phanerochaete chrysosporium; Chlamydomonas reinhardtii; Arabidopsis thaliana; Dictyoglomus thermophilum heat-stable amylase gene; | GenBank: J04202; XM_001319100; EF143986; AY324649; NM_129551; X07896 |
| Beta-amylase | Arabidopsis thaliana; Hordeum vulgare; Musa acuminata | GenBank: NM_113297; D21349; DQ166026 |
| Starch phosphorylase | Citrus hybrid cultivar root; Solanum tuberosum chloroplast; Arabidopsis thaliana; Triticum aestivum; Ipomoea batatas | Genbank: AY098895; P53535; NM_113857, NM_114564; AF275551; M64362 |
| Phosphoglucomutase | Oryza sativa plastid; Ajellomyces capsulatus; Pichia stipitis; Lodderomyces elongisporus; Aspergillus fumigatus; Arabidopsis thaliana; Populus tomentosa; Oryza sativa; Zea mays | GenBank: AC105932, AF455812; XM_001536436; XM_001383281; XM_001527445; XM_749345; NM_124561, NM_180508, AY128901; AY479974; AF455812; U89342, U89341 |
| Glucosephosphate (glucose-6-phosphate) isomerase | Chlamydomonas reinhardtii; Saccharomyces cerevisiae; Pichia stipitis; Ajellomyces capsulatus; Spinacia oleracea cytosol; Oryza sativa cytoplasm; Arabidopsis thaliana; Zea mays | JGI Chlre3 protein ID 135202; GenBank: M21696; XM_001385873; XM_001537043; T09154; P42862; NM_123638, NM_118595; U17225 |
| Hexokinase (glucokinase) | Ajellomyces capsulatus; Pichia stipitis; Pichia angusta; Thermosynechococcus elongates; Babesia bovis; Solanum chacoense; Oryza sativa; Arabidopsis thaliana | GenBank: XM_001541513; XM_001386652, AY278027; XM_001386035; NC_004113; XM_001608698; DQ177440; DQ116383; NM_112895 |
| NADP(H) phosphatase | Methanococcus jannaschii | The Journal Of Biological Chemistry 280 (47): 39200-39207 (2005) |
| NAD kinase | Babesia bovis; Trichomonas vaginalis | GenBank: XM_001609395; XM_001324239 |

| Enzyme | Source (Organism) | GenBank Accession Number, JGI Protein ID or Citation |
|---|---|---|
| Pyruvate-NADP$^+$ oxidoreductase | Peranema trichophorum; Euglena gracilis | GenBank: EF114757; AB021127, AJ278425 |
| Pyruvate-ferredoxin oxidoreductase | Mastigamoeba balamuthi; Desulfovibrio africanus; Entamoeba histolytica; Trichomonas vaginalis; Cryptosporidium parvum; Cryptosporidium baileyi; Giardia lamblia; Entamoeba histolytica; Hydrogenobacter thermophilus; Clostridium pasteurianum; | GenBank: AY101767; Y09702; U30149; XM_001582310, XM_001313670, XM_001321286, XM_001307087, XM_001311860, XM_001314776, XM_001307250; EF030517; EF030516; XM_764947; XM_651927; AB042412; Y17727 |

Targeting the Designer Enzymes to the Stroma Region of Chloroplasts

Some of the designer enzymes discussed above, such as, pyruvate-ferredoxin oxidoreductase, thiolase, 3-hydroxybutyryl-CoA dehydrogenase, crotonase, butyryl-CoA dehydrogenase, butyraldehyde dehydrogenase, and butanol dehydrogenase are known to function in certain special bacteria such as Clostridium; but wild-type plant chloroplasts generally do not possess these enzymes to function with the Calvin cycle. Therefore, in one of the various embodiments in creating a butanol-producing eukaryotic designer organism, designer nucleic acids encoding for these enzymes are expressed in the chloroplast(s) of a host cell. This can be accomplished by delivery of designer butanol-production-pathway gene(s) into the chloroplast genome of the eukaryotic host cell typically using a genegun. In certain extent, the molecular genetics of chloroplasts are similar to that of cyanobacteria. After being delivered into the chloroplast, a designer DNA construct that contains a pair of proper recombination sites as illustrated in FIG. 2F can be incorporated into the chloroplast genome through a natural process of homologous DNA double recombination.

In another embodiment, nucleic acids encoding for these enzymes are genetically engineered such that the enzymes expressed are inserted into the chloroplasts to operate with the Calvin cycle there. Depending on the genetic background of a particular host organism, some of the designer enzymes discussed above such as phosphoglycerate mutase and enolase may exist at some background levels in its native form in a wild-type chloroplast. For various reasons including often the lack of their controllability, however, some of the chloroplast background enzymes may or may not be sufficient to serve as a significant part of the designer butanol-production pathway(s). Furthermore, a number of useful inducible promoters happen to function in the nuclear genome. For example, both the hydrogenase (Hyd1) promoter and the nitrate reductase (Nia1) promoter that can be used to control the expression of the designer butanol-production pathways are located in the nuclear genome of Chlamydomonas reinhardtii, of which the genome has recently been sequenced. Therefore, in one of the various embodiments, it is preferred to use nuclear-genome-encodable designer genes to confer a switchable butanol-production pathway. Consequently, nucleic acids encoding for these enzymes also need to be genetically engineered with proper sequence modification such that the enzymes are controllably expressed and are inserted into the chloroplasts to create a designer butanol-production pathway.

According to one of the various embodiments, it is best to express the designer butanol-producing-pathway enzymes only into chloroplasts (at the stroma region), exactly where the action of the enzymes is needed to enable photosynthetic production of butanol. If expressed without a chloroplast-targeted insertion mechanism, the enzymes would just stay in the cytosol and not be able to directly interact with the Calvin cycle for butanol production. Therefore, in addition to the obvious distinctive features in pathway designs and associated approaches, another significant distinction is that one of the various embodiments innovatively employs a chloroplast-targeted mechanism for genetic insertion of many designer butanol-production-pathway enzymes into chloroplast to directly interact with the Calvin cycle for photobiological butanol production.

With a chloroplast stroma-targeted mechanism, the cells will not only be able to produce butanol but also to grow and regenerate themselves when they are returned to certain conditions under which the designer pathway is turned off, such as under aerobic conditions when designer hydrogenase promoter-controlled butanol-production-pathway genes are used. Designer algae, plants, or plant cells that contain normal mitochondria should be able to use the reducing power (NADH) from organic reserves (and/or some exogenous organic substrate such as acetate or sugar) to power the cells immediately after returning to aerobic conditions. Consequently, when the designer algae, plants, or plant cells are returned to aerobic conditions after use under anaerobic conditions for photosynthetic butanol production, the cells will stop making the butanol-producing-pathway enzymes and start to restore the normal photoautotrophic capability by synthesizing new and functional chloroplasts. Therefore, it is possible to use such genetically engineered designer alga/plant organisms for repeated cycles of photoautotrophic growth under normal aerobic conditions and efficient production of butanol directly from $CO_2$ and $H_2O$ under certain specific designer butanol-producing conditions such as under anaerobic conditions and/or in the presence of nitrate when a Nia1 promoter-controlled butanol-production pathway is used.

The targeted insertion of designer butanol-production-pathway enzymes can be accomplished through use of a DNA sequence that encodes for a stroma "signal" peptide. A stroma-protein signal (transit) peptide directs the transport and insertion of a newly synthesized protein into stroma. In accordance with one of the various embodiments, a specific targeting DNA sequence is preferably placed in between the promoter and a designer butanol-production-pathway enzyme sequence, as shown in a designer DNA construct (FIG. 2A). This targeting sequence encodes for a signal (transit) peptide that is synthesized as part of the apoprotein of an enzyme in the cytosol. The transit peptide guides the insertion of an apoprotein of a designer butanol-production-pathway enzyme from cytosol into the chloroplast. After the apoprotein is inserted into the chloroplast, the transit peptide is cleaved off from the apoprotein, which then becomes an active enzyme.

A number of transit peptide sequences are suitable for use for the targeted insertion of the designer butanol-production-pathway enzymes into chloroplast, including but not limited to the transit peptide sequences of: the hydrogenase apoproteins (such as HydA1 (Hyd1) and HydA2, GenBank accession number AJ308413, AF289201, AY090770), ferredoxin apoprotein (Frx1, accession numbers L10349, P07839), thioredoxin m apoprotein (Trx2, X62335), glutamine synthase apoprotein (Gs2, Q42689), LhcII apoproteins (AB051210, AB051208, AB051205), PSII-T apoprotein (PsbT), PSII-S apoprotein (PsbS), PSII-W apoprotein (PsbW), $CF_0CF_1$ subunit-□ apoprotein (AtpC), $CF_0CF_1$ subunit-□ apoprotein (AtpD, U41442), $CF_0CF_1$ subunit-II apoprotein (AtpG), photosystem I (PSI) apoproteins (such as, of genes PsaD, PsaE, PsaF, PsaG, PsaH, and PsaK), Rubisco SSU apoproteins (such as RbcS2, X04472). Throughout this specification, when reference is made to a transit peptide sequence, such as, for example, any of the transit peptide sequence described above, it includes their functional analogs, modified designer sequences, and combinations thereof. A "functional analog" or "modified designer sequence" in this context refers to a peptide sequence derived or modified (by, e.g., conservative substitution, moderate deletion or addition of amino acids, or modification of side chains of amino acids) based on a native transit peptide sequence, such as those identified above, that has the same function as the native transit peptide sequence, i.e., effecting targeted insertion of a desired enzyme.

In certain specific embodiments, the following transit peptide sequences are used to guide the insertion of the designer butanol-production-pathway enzymes into the stroma region of the chloroplast: the Hyd1 transit peptide (having the amino acid sequence: msalvlkpca aysirgsscr arqvaprapl aastvrvala tleaparrlg nvacaa (SEQ ID NO: 54)), the RbcS2 transit peptides (having the amino acid sequence: maaviakssv saavarpars svrpmaalkp avkaapvaap aqanq (SEQ ID NO: 55)), ferredoxin transit peptide (having the amino acid sequence: mamamrs (SEQ ID NO: 56)), the $CF_0CF_1$ subunit-δ transit peptide (having the amino acid sequence: mlaaksiagp rafkasavra apkagrrtvv vma (SEQ ID NO: 57)), their analogs, functional derivatives, designer sequences, and combinations thereof.

Use of a Genetic Switch to Control the Expression of a Designer Butanol-Producing Pathway.

Another key feature of the invention is the application of a genetic switch to control the expression of the designer butanol-producing pathway(s), as illustrated in FIG. 1. This switchability is accomplished through the use of an externally inducible promoter so that the designer transgenes are inducibly expressed under certain specific inducing conditions. Preferably, the promoter employed to control the expression of designer genes in a host is originated from the host itself or a closely related organism. The activities and inducibility of a promoter in a host cell can be tested by placing the promoter in front of a reporting gene, introducing this reporter construct into the host tissue or cells by any of the known DNA delivery techniques, and assessing the expression of the reporter gene.

In a preferred embodiment, the inducible promoter used to control the expression of designer genes is a promoter that is inducible by anaerobiosis, i.e., active under anaerobic conditions but inactive under aerobic conditions. A designer alga/plant organism can perform autotrophic photosynthesis using $CO_2$ as the carbon source under aerobic conditions, and when the designer organism culture is grown and ready for photosynthetic butanol production, anaerobic conditions will be applied to turn on the promoter and the designer genes that encode a designer butanol-production pathway(s).

A number of promoters that become active under anaerobic conditions are suitable for use in the present invention. For example, the promoters of the hydrogenase genes (HydA1 (Hyd1) and HydA2, GenBank accession number: AJ308413, AF289201, AY090770) of *Chlamydomonas reinhardtii*, which is active under anaerobic conditions but inactive under aerobic conditions, can be used as an effective genetic switch to control the expression of the designer genes in a host alga, such as *Chlamydomonas reinhardtii*. In fact, *Chlamydomonas* cells contain several nuclear genes that are coordinately induced under anaerobic conditions. These include the hydrogenase structural gene itself (Hyd1), the Cyc6 gene encoding the apoprotein of Cytochrome $C_6$, and the Cpx1 gene encoding coprogen oxidase. The regulatory regions for the latter two have been well characterized, and a region of about 100 bp proves sufficient to confer regulation by anaerobiosis in synthetic gene constructs (Quinn, Barraco, Ericksson and Merchant (2000). "Coordinate copper- and oxygen-responsive Cyc6 and Cpx1 expression in *Chlamydomonas* is mediated by the same element." *J Biol Chem* 275: 6080-6089). Although the above inducible algal promoters may be suitable for use in other plant hosts, especially in plants closely related to algae, the promoters of the homologous genes from these other plants, including higher plants, can be obtained and employed to control the expression of designer genes in those plants.

In another embodiment, the inducible promoter used in the present invention is an algal nitrate reductase (Nia1) promoter, which is inducible by growth in a medium containing nitrate and repressed in a nitrate-deficient but ammonium-containing medium (Loppes and Radoux (2002) "Two short regions of the promoter are essential for activation and repression of the nitrate reductase gene in *Chlamydomonas reinhardtii*," *Mol Genet Genomics* 268: 42-48). Therefore, the Nia1 (gene accession number AF203033) promoter can be selected for use to control the expression of the designer genes in an alga according to the concentration levels of nitrate and ammonium in a culture medium. Additional inducible promoters that can also be selected for use in the present invention include, for example, the heat-shock protein promoter HSP70A (accession number: DQ059999, AY456093, M98823; Schroda, Blocker, Beek (2000) The HSP70A promoter as a tool for the improved expression of transgenes in *Chlamydomonas*. *Plant Journal* 21:121-131), the promoter of CabII-1 gene (accession number M24072), the promoter of Ca1 gene (accession number P20507), and the promoter of Ca2 gene (accession number P24258).

In the case of blue-green algae (oxyphotobacteria including cyanobacteria and oxychlorobacteria), there are also a number of inducible promoters that can be selected for use in the present invention. For example, the promoters of the anaerobic-responsive bidirectional hydrogenase hox genes of *Nostoc* sp. PCC 7120 (GenBank: BA000019), *Prochlorothrix hollandica* (GenBank: U88400; hoxUYH operon promoter), *Synechocystis* sp. strain PCC 6803 (CyanoBase: sll1220 and sll1223), *Synechococcus elongatus* PCC 6301 (CyanoBase: syc1235_c), *Arthrospira platensis* (GenBank:

ABC26906), *Cyanothece* sp. CCY0110 (GenBank: ZP_01727419) and *Synechococcus* sp. PCC 7002 (GenBank: AAN03566), which are active under anaerobic conditions but inactive under aerobic conditions (Sjoholm, Oliveira, and Lindblad (2007) "Transcription and regulation of the bidirectional hydrogenase in the Cyanobacterium *Nostoc* sp. strain PCC 7120," *Applied and Environmental Microbiology,* 73(17): 5435-5446), can be used as an effective genetic switch to control the expression of the designer genes in a host oxyphotobacterium, such as *Nostoc* sp. PCC 7120, *Synechocystis* sp. strain PCC 6803, *Synechococcus elongatus* PCC 6301, *Cyanothece* sp. CCY0110, *Arthrospira platensis*, or *Synechococcus* sp. PCC 7002.

In another embodiment in creating switchable butanol-production designer organisms such as switchable designer oxyphotobacteria, the inducible promoter selected for use is a nitrite reductase (nirA) promoter, which is inducible by growth in a medium containing nitrate and repressed in a nitrate-deficient but ammonium-containing medium (Qi, Hao, Ng, Slater, Baszis, Weiss, and Valentin (2005) "Application of the *Synechococcus* nirA promoter to establish an inducible expression system for engineering the *Synechocystis* tocopherol pathway,"*Applied and Environmental Microbiology,* 71(10): 5678-5684; Maeda, Kawaguchi, Ohe, and Omata (1998) "cis-Acting sequences required for NtcB-dependent, nitrite-responsive positive regulation of the nitrate assimilation operon in the Cyanobacterium *Synechococcus* sp. strain PCC 7942," *Journal of Bacteriology,* 180(16):4080-4088). Therefore, the nirA promoter sequences can be selected for use to control the expression of the designer genes in a number of oxyphotobacteria according to the concentration levels of nitrate and ammonium in a culture medium. The nirA promoter sequences that can be selected and modified for use include (but not limited to) the nirA promoters of the following oxyphotobacteria: *Synechococcus elongatus* PCC 6301 (GenBank: AP008231, region 355890-255950), *Synechococcus* sp. (GenBank: X67680.1, D16303.1, D12723.1, and D00677), *Synechocystis* sp. PCC 6803 (GenBank: NP 442378, BA000022, AB001339, D63999-D64006, D90899-D90917), *Anabaena* sp. (GenBank: X99708.1), *Nostoc* sp. PCC 7120 (GenBank: BA000019.2 and AJ319648), *Plectonema boryanum* (GenBank: D31732.1), *Synechococcus elongatus* PCC 7942 (GenBank: P39661, CP000100.1), *Thermosynechococcus elongatus* BP-1 (GenBank: BAC08901, NP_682139), *Phormidium laminosum* (GenBank: CAA79655, Q51879), *Mastigocladus laminosus* (GenBank: ABD49353, ABD49351, ABD49349, ABD49347), *Anabaena variabilis* ATCC 29413 (GenBank: YP 325032), *Prochlorococcus marinus* str. MIT 9303 (GenBank: YP 001018981), *Synechococcus* sp. WH 8103 (GenBank: AAC17122), *Synechococcus* sp. WH 7805 (GenBank: ZP_01124915), and *Cyanothece* sp. CCY0110 (GenBank: ZP_01727861).

In yet another embodiment, an inducible promoter selected for use is the light- and heat-responsive chaperone gene groE promoter, which can be induced by heat and/or light [Kojima and Nakamoto (2007) "A novel light- and heat-responsive regulation of the groE transcription in the absence of HrcA or CIRCE in cyanobacteria," FEBS Letters 581:1871-1880). A number of groE promoters such as the groES and groEL (chaperones) promoters are available for use as an inducible promoter in controlling the expression of the designer butanol-production-pathway enzymes. The groE promoter sequences that can be selected and modified for use in one of the various embodiments include (but not limited to) the groES and/or groEL promoters of the following oxyphotobacteria: *Synechocystis* sp. (GenBank: D12677.1), *Synechocystis* sp. PCC 6803 (GenBank: BA000022.2), *Synechococcus elongatus* PCC 6301 (GenBank: AP008231.1), *Synechococcus* sp (GenBank: M58751.1), *Synechococcus elongatus* PCC 7942 (GenBank: CP000100.1), *Nostoc* sp. PCC 7120 (GenBank: BA000019.2), *Anabaena variabilis* ATCC 29413 (GenBank: CP000117.1), *Anabaena* sp. L-31 (GenBank: AF324500); *Thermosynechococcus elongatus* BP-1 (CyanoBase: tl10185, tl10186), *Synechococcus vulcanus* (GenBank: D78139), *Oscillatoria* sp. NKBG091600 (GenBank: AF054630), *Prochlorococcus marinus* MIT9313 (GenBank: BX572099), *Prochlorococcus marinus* str. MIT 9303 (GenBank: CP000554), *Prochlorococcus marinus* str. MIT 9211 (GenBank: ZP_01006613), *Synechococcus* sp. WH8102 (GenBank: BX569690), *Synechococcus* sp. CC9605 (GenBank: CP000110), *Prochlorococcus marinus* subsp. *marinus* str. CCMP1375 (GenBank: AE017126), and *Prochlorococcus marinus* MED4 (GenBank: BX548174).

Additional inducible promoters that can also be selected for use in the present invention include: for example, the metal (zinc)-inducible smt promoter of *Synechococcus* PCC 7942 (Erbe, Adams, Taylor and Hall (1996) "Cyanobacteria carrying an smt-lux transcriptional fusion as biosensors for the detection of heavy metal cations," *Journal of Industrial Microbiology,* 17:80-83); the iron-responsive idiA promoter of *Synechococcus elongatus* PCC 7942 (Michel, Pistorius, and Golden (2001) "Unusual regulatory elements for iron deficiency induction of the idiA gene of *Synechococcus elongatus* PCC 7942" *Journal of Bacteriology,* 183(17): 5015-5024); the redox-responsive cyanobacterial crhR promoter (Patterson-Fortin, Colvin and Owttrim (2006) "A LexA-related protein regulates redox-sensitive expression of the cyanobacterial RNA helicase, crhR", Nucleic Acids Research, 34(12):3446-3454); the heat-shock gene hsp16.6 promoter of *Synechocystis* sp. PCC 6803 (Fang and Barnum (2004) "Expression of the heat shock gene hsp16.6 and promoter analysis in the Cyanobacterium, *Synechocystis* sp. PCC 6803," Current Microbiology 49:192-198); the small heat-shock protein (Hsp) promoter such as *Synechococcus vulcanus* gene hspA promoter (Nakamoto, Suzuki, and Roy (2000) "Constitutive expression of a small heat-shock protein confers cellular thermotolerance and thermal protection to the photosynthetic apparatus in cyanobacteria," FEBS Letters 483:169-174); the $CO_2$-responsive promoters of oxyphotobacterial carbonic-anhydrase genes (GenBank: EAZ90903, EAZ90685, ZP_01624337, EAW33650, ABB17341, AAT41924, CA089711, ZP_00111671, YP 400464, AAC44830; and CyanoBase: al12929, PMT1568 slr0051, slr1347, and syc0167_c); the nitrate-reductase-gene (narB) promoters (such as GenBank accession numbers: BAC08907, NP_682145, AAO25121; ABI46326, YP_732075, BAB72570, NP_484656); the green/red light-responsive promoters such as the light-regulated cpcB2A2 promoter of *Fremyella diplosiphon* (Casey and Grossman (1994) "In vivo and in vitro characterization of the light-regulated cpcB2A2 promoter of *Fremyella diplosiphont*" *Journal of Bacteriology,* 176(20):6362-6374); and the UV-light responsive promoters of cyanobacterial genes lexA, recA and ruvB (Domain, Houot, Chauvat, and Cassier-Chauvat (2004) "Function and regulation of the cyanobacterial genes lexA, recA and ruvB: LexA is critical to the survival of cells facing inorganic carbon starvation," *Molecular Microbiology,* 53(1):65-80).

Furthermore, in one of the various embodiments, certain "semi-inducible" or constitutive promoters can also be selected for use in combination of an inducible promoter(s) for construction of a designer butanol-production pathway (s) as well. For example, the promoters of oxyphotobacterial Rubisco operon such as the rbcL genes (GenBank: X65960, ZP_01728542, Q3M674, BAF48766, NP_895035, 0907262A; CyanoBase: PMT1205, PMM0550, Pro0551, t111506, SYNW1718, glr2156, a1r1524, s1r0009), which have certain light-dependence but could be regarded almost as constitutive promoters, can also be selected for use in combination of an inducible promoter(s) such as the nirA, hox, and/or groE promoters for construction of the designer butanol-production pathway(s) as well.

Throughout this specification, when reference is made to inducible promoter, such as, for example, any of the inducible promoters described above, it includes their analogs, functional derivatives, designer sequences, and combinations thereof. A "functional analog" or "modified designer sequence" in this context refers to a promoter sequence derived or modified (by, e.g., substitution, moderate deletion or addition or modification of nucleotides) based on a native promoter sequence, such as those identified hereinabove, that retains the function of the native promoter sequence.

DNA Constructs and Transformation into Host Organisms

DNA constructs are generated in order to introduce designer butanol-production-pathway genes to a host alga, plant, plant tissue or plant cells. That is, a nucleotide sequence encoding a designer butanol-production-pathway enzyme is placed in a vector, in an operable linkage to a promoter, preferably an inducible promoter, and in an operable linkage to a nucleotide sequence coding for an appropriate chloroplast-targeting transit-peptide sequence. In a preferred embodiment, nucleic acid constructs are made to have the elements placed in the following 5' (upstream) to 3' (downstream) orientation: an externally inducible promoter, a transit targeting sequence, and a nucleic acid encoding a designer butanol-production-pathway enzyme, and preferably an appropriate transcription termination sequence. One or more designer genes (DNA constructs) can be placed into one genetic vector. An example of such a construct is depicted in FIG. 2A. As shown in the embodiment illustrated in FIG. 2A, a designer butanol-production-pathway transgene is a nucleic acid construct comprising: a) a PCR forward primer; b) an externally inducible promoter; c) a transit targeting sequence; d) a designer butanol-production-pathway-enzyme-encoding sequence with an appropriate transcription termination sequence; and e) a PCR reverse primer.

In accordance with various embodiments, any of the components a) through e) of this DNA construct are adjusted to suit for certain specific conditions. In practice, any of the components a) through e) of this DNA construct are applied in full or in part, and/or in any adjusted combination to achieve more desirable results. For example, when an algal hydrogenase promoter is used as an inducible promoter in the designer butanol-production-pathway DNA construct, a transgenic designer alga that contains this DNA construct will be able to perform autotrophic photosynthesis using ambient-air $CO_2$ as the carbon source and grows normally under aerobic conditions, such as in an open pond. When the algal culture is grown and ready for butanol production, the designer transgene(s) can then be expressed by induction under anaerobic conditions because of the use of the hydrogenase promoter. The expression of designer gene(s) produces a set of designer butanol-production-pathway enzymes to work with the Calvin cycle for photobiological butanol production (FIG. 1).

The two PCR primers are a PCR forward primer (PCR FD primer) located at the beginning (the 5' end) of the DNA construct and a PCR reverse primer (PCR RE primer) located at the other end (the 3' end) as shown in FIG. 2A. This pair of PCR primers is designed to provide certain convenience when needed for relatively easy PCR amplification of the designer DNA construct, which is helpful not only during and after the designer DNA construct is synthesized in preparation for gene transformation, but also after the designer DNA construct is delivered into the genome of a host alga for verification of the designer gene in the transformants. For example, after the transformation of the designer gene is accomplished in a *Chlamydomonas reinhardtii*-arg7 host cell using the techniques of electroporation and argininosuccinate lyase (arg7) complementation screening, the resulted transformants can be then analyzed by a PCR DNA assay of their nuclear DNA using this pair of PCR primers to verify whether the entire designer butanol-production-pathway gene (the DNA construct) is successfully incorporated into the genome of a given transformant. When the nuclear DNA PCR assay of a transformant can generate a PCR product that matches with the predicted DNA size and sequence according to the designer DNA construct, the successful incorporation of the designer gene (s) into the genome of the transformant is verified.

Therefore, the various embodiments also teach the associated method to effectively create the designer transgenic algae, plants, or plant cells for photobiological butanol production. This method, in one of embodiments, includes the following steps: a) Selecting an appropriate host alga, plant, plant tissue, or plant cells with respect to their genetic backgrounds and special features in relation to butanol production; b) Introducing the nucleic acid constructs of the designer genes into the genome of said host alga, plant, plant tissue, or plant cells; c) Verifying the incorporation of the designer genes in the transformed alga, plant, plant tissue, or plant cells with DNA PCR assays using the said PCR primers of the designer DNA construct; d) Measuring and verifying the designer organism features such as the inducible expression of the designer butanol-pathway genes for photosynthetic butanol production from carbon dioxide and water by assays of mRNA, protein, and butanol-production characteristics according to the specific designer features of the DNA construct(s) (FIG. 2A).

The above embodiment of the method for creating the designer transgenic organism for photobiological butanol production can also be repeatedly applied for a plurality of operational cycles to achieve more desirable results. In various embodiments, any of the steps a) through d) of this method described above are adjusted to suit for certain specific conditions. In various embodiments, any of the steps a) through d) of the method are applied in full or in part, and/or in any adjusted combination.

Examples of designer butanol-production-pathway genes (DNA constructs) are shown in the sequence listings. SEQ ID NO: 1 presents a detailed DNA construct of a designer Butanol Dehydrogenase gene (1809 bp) that includes a PCR FD primer (sequence 1-20), a 262-bp nitrate reductase Nia1 promoter (21-282), a 135-bp RbcS2 transit peptide (283-417), an enzyme-encoding sequence (418-1566) selected and modified from a *Clostridium saccharoperbutylacetonicum* Butanol Dehydrogenase sequence (AB257439), a 223-bp RbcS2 terminator (1567-1789), and a PCR RE primer (1790-1809). The 262-bp Nia1 promoter (DNA sequence 21-282) is used as an example of an inducible promoter to control the expression of a designer butanol-production-pathway Butanol Dehydrogenase gene (DNA sequence 418-1566). The 135-bp RbcS2 transit peptide (DNA sequence 283-417) is used as an example to guide the insertion of the designer enzyme (DNA sequence 418-1566) into the chloroplast of the host organism. The RbcS2 terminator (DNA sequence 1567-1789) is employed so that the transcription and translation of the designer gene is properly terminated to produce the designer apoprotein (RbcS2 transit peptide-Butanol Dehydrogenase) as desired. Because the Nia1 promoter is a nuclear DNA that can control the expression only for nuclear genes, the synthetic butanol-production-pathway gene in this example is designed according to the codon usage of *Chlamydomonas* nuclear genome. Therefore, in this case, the designer enzyme gene is transcribed in nucleus. Its mRNA is naturally translocated into cytosol, where the mRNA is translated to an apoprotein that consists of the RbcS2 transit peptide (corresponding to DNA sequence 283-417) with its C-terminal end linked together with the N-terminal end of the Butanol Dehydrogenase protein (corresponding to DNA sequence 418-1566). The transit peptide of the apoprotein guides its transportation across the chloroplast membranes and into the stroma area, where the transit peptide is cut off from the apoprotein. The resulting Butanol Dehydrogenase then resumes its function as an enzyme for the designer butanol-production pathway in chloroplast. The two PCR primers (sequences 1-20 and 1790-1809) are selected and modified from the sequence of a Human actin gene and can be paired with each other. Blasting the sequences against *Chlamydomonas* GenBank found no homologous sequences of them. Therefore, they can be used as appropriate PCR primers in DNA PCR assays for verification of the designer gene in the transformed alga.

SEQ ID NO: 2 presents example 2 for a designer Butyraldehyde Dehydrogenase DNA construct (2067 bp) that includes a PCR FD primer (sequence 1-20), a 262-bp nitrate reductase Nia1 promoter (21-282), a 135-bp RbcS2 transit peptide (283-417), a Butyraldehyde Dehydrogenase-encoding sequence (418-1824) selected and modified from a *Clostridium saccharoperbutylacetonicum* Butyraldehyde Dehydrogenase sequence (AY251646), a 223-bp RbcS2 terminator (1825-2047), and a PCR RE primer (2048-2067). This DNA construct is similar to example 1, SEQ ID NO: 1, except that a Butyraldehyde Dehydrogenase-encoding sequence (418-1824) selected and modified from a *Clostridium saccharoperbutylacetonicum* Butyraldehyde Dehydrogenase sequence (AY251646) is used.

SEQ ID NO: 3 presents example 3 for a designer Butyryl-CoA Dehydrogenase construct (1815 bp) that includes a PCR FD primer (sequence 1-20), a 262-bp nitrate reductase promoter (21-282), a 9-bp Xho I NdeI site (283-291), a 135-bp RbcS2 transit peptide (292-426), a Butyryl-CoA Dehydrogenase encoding sequence (427-1563) selected/modified from the sequences of a *Clostridium beijerinckii* Butyryl-CoA Dehydrogenase (AF494018), a 9-bp XbaI site (1564-1572), a 223-bp RbcS2 terminator (1573-1795), and a PCR RE primer (1796-1815) at the 3' end. This DNA construct is similar to example 1, SEQ ID NO: 1, except that a Butyryl-CoA Dehydrogenase encoding sequence (427-1563) selected/modified from the sequences of a *Clostridium beijerinckii* Butyryl-CoA Dehydrogenase (AF494018) is used and restriction sites of Xho I NdeI and XbaI are added to make the key components such as the targeting sequence (292-426) and the designer enzyme sequence (427-1563) as a modular unit that can be flexible replaced when necessary to save cost of gene synthesis and enhance work productivity. Please note, the enzyme does not have to be *Clostridium beijerinckii* Butyryl-CoA Dehydrogenase; a number of butyryl-CoA dehydrogenase enzymes (such as those listed in Table 1) including their isozymes, designer modified enzymes, and functional analogs from other sources such as *Butyrivibrio fibrisolvens*, Butyrate producing bacterium L2-50, *Thermoanaerobacterium thermosaccharolyticum*, can also be selected for use.

SEQ ID NO: 4 presents example 4 for a designer Crotonase DNA construct (1482 bp) that includes a PCR FD primer (sequence 1-20), a 262-bp nitrate reductase promoter (21-282), a 9-bp Xho I NdeI site (283-291) a 135-bp RbcS2 transit peptide (292-426), a Crotonase-encoding sequence (427-1209) selected/modified from the sequences of a *Clostridium beijerinckii* Crotonase (Genbank: AF494018), a 21-bp Lumio-tag-encoding sequence (1210-1230), a 9-bp XbaI site (1231-1239) containing a stop codon, a 223-bp RbcS2 terminator (1240-1462), and a PCR RE primer (1463-1482) at the 3' end. This DNA construct is similar to example 3, SEQ ID NO: 3, except that a Crotonase-encoding sequence (427-1209) selected/modified from the sequences of a *Clostridium beijerinckii* Crotonase (Genbank: AF494018) is used and a 21-bp Lumio-tag-encoding sequence (1210-1230) is added at the C-terminal end of the enolase sequence. The 21-bp Lumio-tag sequence (1210-1230) is employed here to encode a Lumio peptide sequence Gly-Cys-Cys-Pro-Gly-Cys-Cys (SEQ ID NO: 58), which can become fluorescent when treated with a Lumio reagent that is now commercially available from Invitrogen. Lumio molecular tagging technology is based on an EDT (1,2-ethanedithiol) coupled biarsenical derivative (the Lumio reagent) of fluorescein that binds to an engineered tetracysteine sequence (Keppetipola, Coffman, and et al (2003). Rapid detection of in vitro expressed proteins using Lumio technology, *Gene Expression*, 25.3: 7-11). The tetracysteine sequence consists of Cys-Cys-Xaa-Xaa-Cys-Cys (SEQ ID NO: 59), where Xaa is any non-cysteine amino acid such as Pro or Gly in this example. The EDT-linked Lumio reagent allows free rotation of the arsenic atoms that quenches the fluorescence of fluorescein. Covalent bond formation between the thiols of the Lumio's arsenic groups and the tetracysteines prevents free rotation of arsenic atoms that releases the fluorescence of fluorescein (Griffin, Adams, and Tsien (1998), "Specific covalent labeling of recombinant protein molecules inside live cells", *Science*, 281:269-272). This also permits the visualization of the tetracysteine-tagged proteins by fluorescent molecular imaging. Therefore, use of the Lumio tag in this manner enables monitoring and/or tracking of the designer Crotonase when expressed to verify whether the designer butanol-production pathway enzyme is indeed delivered into the chloroplast of a host organism as designed. The Lumio tag (a short 7 amino acid peptide) that is linked to the C-terminal end of the Crotonase protein in this example should have minimal effect on the function of the designer enzyme, but enable the designer enzyme molecule to be visualized when treated with the Lumio reagent. Use of the Lumio tag is entirely optional. If the Lumio tag somehow affects the designer enzyme function, this tag can be deleted in the DNA sequence design.

SEQ ID NO: 5 presents example 5 for a designer 3-Hydroxybutyryl-CoA Dehydrogenase DNA construct (1367 bp) that includes a PCR FD primer (sequence 1-20), a 84-bp nitrate reductase promoter (21-104), a 9-bp Xho I NdeI site (105-113) a 135-bp RbcS2 transit peptide (114-248), a 3-Hydroxybutyryl-CoA Dehydrogenase-encoding sequence (249-1094) selected/modified from a *Clostridium beijerinckii* 3-Hydroxybutyryl-CoA Dehydrogenase sequence (Genbank: AF494018), a 21-bp Lumio-tag sequence (1095-1115), a 9-bp XbaI site (1116-1124), a 223-bp RbcS2 terminator (1125-1347), and a PCR RE primer (1348-1367). This DNA construct is similar to example 4, SEQ ID NO: 4, except that an 84-bp nitrate reductase promoter (21-104) and a 3-Hydroxybutyryl-CoA Dehydrogenase-encoding sequence (249-1094) selected/modified from a *Clostridium beijerinckii* 3-Hydroxybutyryl-CoA Dehydrogenase sequence (Genbank: AF494018) are used. The 84-bp nitrate-reductase promoter is artificially created by joining two partially homologous sequence regions (−231 to −201 and −77 to −25 with respect to the start site of transcription) of the native *Chlamydomonas reinhardtii* Nia1 promoter. Experimental studies have demonstrated that the 84-bp sequence is more active than the native Nia1 promoter (Loppes and Radoux (2002) "Two short regions of the promoter are essential for activation and repression of the nitrate reductase gene in *Chlamydomonas reinhardtii," Mol Genet Genomics* 268: 42-48). Therefore, this is also an example where functional synthetic sequences, analogs, functional derivatives and/or designer modified sequences such as the synthetic 84-bp sequence can be selected for use according to various embodiments in this invention.

SEQ ID NO: 6 presents example 6 for a designer Thiolase DNA construct (1721 bp) that includes a PCR FD primer (sequence 1-20), a 84-bp nitrate reductase promoter (21-104), a 9-bp Xho I NdeI site (105-113) a 135-bp RbcS2 transit peptide (114-248), a Thiolase-encoding sequence (248-1448) selected/modified from a *Butyrivibrio fibrisolvens* Thiolase sequence (AB190764), a 21-bp Lumio-tag sequence (1449-1469), a 9-bp XbaI site (1470-1478), a 223-bp RbcS2 terminator (1479-1701), and a PCR RE primer (1702-1721). This DNA construct is also similar to example 4, SEQ ID NO: 4, except that a Thiolase-encoding-encoding sequence (249-1448) and an 84-bp synthetic Nia1 promoter (21-104) are used. This is another example that functional synthetic sequences can also be selected for use in designer DNA constructs.

SEQ ID NO: 7 presents example 7 for a designer Pyruvate-Ferredoxin Oxidoreductase DNA construct (4211 bp) that includes a PCR FD primer (sequence 1-20), a 2×84-bp nitrate reductase promoter (21-188), a 9-bp Xho I NdeI site (189-197) a 135-bp RbcS2 transit peptide (198-332), a Pyruvate-Ferredoxin Oxidoreductase-encoding sequence (333-3938) selected/modified from the sequences of a *Mastigamoeba balamuthi* Pyruvate-ferredoxin oxidoreductase (GenBank: AY101767), a 21-bp Lumio-tag sequence (3939-3959), a 9-bp XbaI site (3960-3968), a 223-bp RbcS2 terminator (3969-4191), and a PCR RE primer (4192-4211). This DNA construct is also similar to example 4, SEQ ID NO: 4, except a designer 2×84-bp Nia1 promoter and a Pyruvate-Ferredoxin Oxidoreductase-encoding sequence (333-3938) selected/modified from the sequences of a *Mastigamoeba balamuthi* Pyruvate-ferredoxin oxidoreductase (GenBank: AY101767) are used. The 2×84-bp Nia1 promoter is constructed as a tandem duplication of the 84-bp synthetic Nia1 promoter sequence presented in SEQ ID NO: 6 above. Experimental tests have shown that the 2×84-bp synthetic Nia1 promoter is even more powerful than the 84-bp sequence which is more active than the native Nia1 promoter (Loppes and Radoux (2002) "Two short regions of the promoter are essential for activation and repression of the nitrate reductase gene in *Chlamydomonas reinhardtii," Mol Genet Genomics* 268: 42-48). Use of this type of inducible promoter sequences with various promoter strengths can also help in adjusting the expression levels of the designer enzymes for the butanol-production pathway(s).

SEQ ID NO: 8 presents example 8 for a designer Pyruvate Kinase DNA construct (2021 bp) that includes a PCR FD primer (sequence 1-20), a 84-bp nitrate reductase promoter (21-104), a 9-bp Xho I NdeI site (105-113) a 135-bp RbcS2 transit peptide (114-248), a pyruvate kinase-encoding sequence (249-1748) selected/modified from a *Saccharomyces cerevisiae* Pyruvate Kinase sequence (GenBank: AY949876), a 21-bp Lumio-tag sequence (1749-1769), a 9-bp XbaI site (1770-1778), a 223-bp RbcS2 terminator (1779-2001), and a PCR RE primer (2002-2021). This DNA construct is similar to example 6, SEQ ID NO: 6, except that a pyruvate kinase-encoding sequence (249-1748) is used.

SEQ ID NO: 9 presents example 9 for a designer Enolase gene (1815 bp) consisting of a PCR FD primer (sequence 1-20), a 262-bp nitrate reductase promoter (21-282), a 9-bp Xho I NdeI site (283-291) a 135-bp RbcS2 transit peptide (292-426), a enolase-encoding sequence (427-1542) selected/modified from the sequences of a *Chlamydomonas reinhardtii* cytosolic enolase (Genbank: X66412, P31683), a 21-bp Lumio-tag-encoding sequence (1507-1527), a 9-bp XbaI site (1543-1551) containing a stop codon, a 223-bp RbcS2 terminator (1552-1795), and a PCR RE primer (1796-1815) at the 3' end. This DNA construct is similar to example 3, SEQ ID NO: 3, except that an enolase-encoding sequence (427-1542) selected/modified from the sequences of a *Chlamydomonas reinhardtii* cytosolic enolase is used.

SEQ ID NO: 10 presents example 10 for a designer Phosphoglycerate-Mutase DNA construct (2349 bp) that includes a PCR FD primer (sequence 1-20), a 262-bp nitrate reductase promoter (21-282), a 9-bp Xho I NdeI site (283-291), a 135-bp RbcS2 transit peptide (292-426), a phosphoglycerate-mutase encoding sequence (427-2097) selected/modified from the sequences of a *Chlamydomonas reinhardtii* cytosolic phosphoglycerate mutase (JGI Chlre2 protein ID 161689, Genbank: AF268078), a 9-bp XbaI site (2098-2106), a 223-bp RbcS2 terminator (2107-2329), and a PCR RE primer (2330-2349) at the 3' end. This DNA construct is similar to example 3, SEQ ID NO: 3, except that a phosphoglycerate-mutase encoding sequence (427-2097) selected/modified from the sequences of a *Chlamydomonas reinhardtii* cytosolic phosphoglycerate mutase is used.

SEQ ID NO: 11 presents example 11 for a designer Phosphoglycerate Kinase DNA construct (1908 bp) that includes a PCR FD primer (sequence 1-20), a 262-bp nitrate reductase Nia1 promoter (21-282), a phosphoglycerate-kinase-encoding sequence (283-1665) selected from a *Chlamydomonas reinhardtii* chloroplast phosphoglycerate-kinase sequence including its chloroplast signal peptide and mature enzyme sequence (GenBank: U14912), a 223-bp RbcS2 terminator (1666-1888), and a PCR RE primer (1889-1908). This DNA construct is similar to example 1, SEQ ID NO: 1, except a phosphoglycerate-kinase-encoding sequence (283-1665) selected from a *Chlamydomonas reinhardtii* chloroplast phosphoglycerate-kinase sequence including its chloroplast signal peptide and mature enzyme sequence is used. Therefore, this is also an example where the sequence of a nuclear-encoded chloroplast enzyme such as the *Chlamydomonas reinhardtii* chloroplast phosphoglycerate kinase can also be used in design and construction of a designer butanol-production pathway gene when appropriate with a proper inducible promoter such as the Nia1 promoter (DNA sequence 21-282).

SEQ ID NO: 12 presents example 12 for a designer Glyceraldehyde-3-Phosphate Dehydrogenase gene (1677 bp) that includes a PCR FD primer (sequence 1-20), a 262-bp nitrate reductase Nia1 promoter (21-282), a 135-bp RbcS2 transit peptide (283-417), an enzyme-encoding sequence (418-1434) selected and modified from a *Mesostigma viride* cytosolic glyceraldehyde-3-phosphate dehydrogenase (mRNA) sequence (GenBank accession number DQ873404), a 223-bp RbcS2 terminator (1435-1657), and a PCR RE primer (1658-1677). This DNA construct is similar to example 1, SEQ ID NO: 1, except that an enzyme-encoding sequence (418-1434) selected and modified from a *Mesostigma viride* cytosolic glyceraldehyde-3-phosphate dehydrogenase (mRNA) sequence (GenBank accession number DQ873404) is used.

SEQ ID NO: 13 presents example 13 for a designer HydA1-promoter-linked Phosphoglycerate Mutase DNA construct (2351 bp) that includes a PCR FD primer (sequence 1-20), a 282-bp HydA1 promoter (21-302), a 135-bp RbcS2 transit peptide (303-437), a phosphoglycerate-mutase encoding sequence (438-2108) selected/modified from the sequences of a *Chlamydomonas reinhardtii* cytosolic phosphoglycerate mutase (JGI Chlre2 protein ID 161689, Genbank: AF268078), a 223-bp RbcS2 terminator (2109-2331), and a PCR RE primer (2332-2351). This designer DNA construct is quite similar to example 1, SEQ ID NO:1, except that a 282-bp HydA1 promoter (21-302) and a phosphoglycerate-mutase encoding sequence (438-2108) selected/modified from the sequences of a *Chlamydomonas reinhardtii* cytosolic phosphoglycerate mutase are used. The 282-bp HydA1 promoter (21-302) has been proven active by experimental assays at the inventor's laboratory. Use of the HydA1 promoter (21-302) enables activation of designer enzyme expression by using anaerobic culture-medium conditions.

With the same principle of using an inducible anaerobic promoter and a chloroplast-targeting sequence as that shown in SEQ ID NO: 13 (example 13), SEQ ID NOS: 14-23 show designer-gene examples 14-23. Briefly, SEQ ID NO: 14 presents example 14 for a designer HydA1-promoter-linked Enolase DNA construct (1796 bp) that includes a PCR FD primer (sequence 1-20), a 282-bp HydA1 promoter (21-302), a 135-bp RbcS2 transit peptide (303-437), a Enolase-encoding sequence (438-1553) selected/modified from the sequences of a *Chlamydomonas reinhardtii* cytosolic enolase (Genbank: X66412, P31683), a 223-bp RbcS2 terminator (1554-1776), and a PCR RE primer (1777-1796).

SEQ ID NO: 15 presents example 15 for a designer HydA1-promoter-controlled Pyruvate-Kinase DNA construct that includes a PCR FD primer (sequence 1-20), a 282-bp HydA1 promoter (21-302), a 135-bp RbcS2 transit peptide (303-437), a Pyruvate Kinase-encoding sequence (438-1589) selected/modified from a *Chlamydomonas reinhardtii* cytosolic pyruvate kinase sequence (JGI Chlre3 protein ID 138105), a 223-bp RbcS2 terminator (1590-1812), and a PCR RE primer (1813-1832).

SEQ ID NO:16 presents example 16 for a designer HydA1-promoter-linked Pyruvate-ferredoxin oxidoreductase DNA construct (4376 bp) that includes a PCR FD primer (sequence 1-20), a 282-bp HydA1 promoter (21-302), a 135-bp RbcS2 transit peptide (303-437), a Pyruvate-ferredoxin oxidoreductase-encoding sequence (438-4133) selected/modified from a *Desulfovibrio africanus* Pyruvate-ferredoxin oxidoreductase sequence (GenBank Accession Number Y09702), a 223-bp RbcS2 terminator (4134-4356), and a PCR RE primer (4357-4376).

SEQ ID NO:17 presents example 17 for a designer HydA1-promoter-linked Pyruvate-NADP$^+$ oxidoreductase DNA construct (6092 bp) that includes a PCR FD primer (sequence 1-20), a 282-bp HydA1 promoter (21-302), a 135-bp RbcS2 transit peptide (303-437), a Pyruvate-NADP$^+$ oxidoreductase-encoding sequence (438-5849) selected/modified from a *Euglena gracilis* Pyruvate-NADP$^+$ oxidoreductase sequence (GenBank Accession Number AB021127), a 223-bp RbcS2 terminator (5850-6072), and a PCR RE primer (6073-6092).

SEQ ID NO:18 presents example 18 for a designer HydA1-promoter-linked Thiolase DNA construct (1856 bp) that includes a PCR FD primer (sequence 1-20), a 282-bp HydA1 promoter (21-302), a 135-bp RbcS2 transit peptide (303-437), a Thiolase-encoding sequence (438-1613) selected/modified from the sequences of a *Thermoanaerobacterium thermosaccharolyticum* Thiolase (GenBank Z92974), a 223-bp RbcS2 terminator (1614-1836), and a PCR RE primer (1837-1856).

SEQ ID NO:19 presents example 19 for a designer HydA1-promoter-linked 3-Hydroxybutyryl-CoA dehydrogenase DNA construct (1550 bp) that includes a PCR FD primer (sequence 1-20), a 282-bp HydA1 promoter (21-302), a 135-bp RbcS2 transit peptide (303-437), a 3-Hydroxybutyryl-CoA dehydrogenase-encoding sequence (438-1307) selected/modified from the sequences of a *Thermoanaerobacterium thermosaccharolyticum* 3-Hydroxybutyryl-CoA dehydrogenase (GenBank Z92974), a 223-bp RbcS2 terminator (1308-1530), and a PCR RE primer (1531-1550).

SEQ ID NO:20 presents example 20 for a designer HydA1-promoter-linked Crotonase DNA construct (1457 bp) that includes a PCR FD primer (sequence 1-20), a 282-bp HydA1 promoter (21-302), a 135-bp RbcS2 transit peptide (303-437), a Crotonase-encoding sequence (438-1214) selected/modified from the sequences of a *Thermoanaerobacterium thermosaccharolyticum* Crotonase (GenBank Z92974), a 223-bpRbcS2 terminator (1215-1437), and a PCR RE primer (1438-1457).

SEQ ID NO:21 presents example 21 for a designer HydA1-promoter-linked Butyryl-CoA dehydrogenase DNA construct (1817 bp) that includes a PCR FD primer (sequence 1-20), a 282-bp HydA1 promoter (21-302), a 135-bp RbcS2 transit peptide (303-437), a Butyryl-CoA dehydrogenase-encoding sequence (438-1574) selected/modified from the sequences of a *Thermoanaerobacterium thermosaccharolyticum* Butyryl-CoA dehydrogenase (GenBank Z92974), a 223-bp RbcS2 terminator (1575-1797), and a PCR RE primer (1798-1817).

SEQ ID NO: 22 presents example 22 for a designer HydA1-promoter-linked Butyraldehyde dehydrogenase DNA construct (2084 bp) that includes a PCR FD primer (sequence 1-20), a 282-bp HydA1 promoter (21-302), a 135-bp RbcS2 transit peptide (303-437), a Butyraldehyde dehydrogenase-encoding sequence (438-1841) selected/modified from the sequences of a *Clostridium saccharoperbutylacetonicum* Butyraldehyde dehydrogenase (GenBank AY251646), a 223-bp RbcS2 terminator (1842-2064), and a PCR RE primer (2065-2084).

SEQ ID NO: 23 presents example 23 for a designer HydA1-promoter-linked Butanol dehydrogenase DNA construct (1733 bp) that includes a PCR FD primer (sequence 1-20), a 282-bp HydA1 promoter (21-302), a 135-bp RbcS2 transit peptide (303-437), a Butanol dehydrogenase-encoding sequence (438-1490) selected/modified from the sequences of a *Clostridium beijerinckii* Butanol dehydrogenase (GenBank AF157307), a 223-bp RbcS2 terminator (1491-1713), and a PCR RE primer (1714-1733).

With the same principle of using a 2×84 synthetic Nia1 promoter and a chloroplast-targeting mechanism as mentioned previously, SEQ ID NOS:24-26 show more examples of designer-enzyme DNA-constructs. Briefly, SEQ ID NO: 24 presents example 24 for a designer Fructose-Diphosphate-Aldolase DNA construct that includes a PCR FD primer (sequence 1-20), a 2×84-bp NR promoter (21-188), a Fructose-Diphosphate Aldolase-encoding sequence (189-1313) selected/modified from a *C. reinhardtii* chloroplast fructose-1,6-bisphosphate aldolase sequence (GenBank: X69969), a 223-bpRbcS2 terminator (1314-1536), and a PCR RE primer (1537-1556).

SEQ ID NO: 25 presents example 24 for a designer Triose-Phosphate-Isomerase DNA construct that includes a PCR FD primer (sequence 1-20), a 2×84-bp NR promoter (21-188), a Triose-Phosphate Isomerase-encoding sequence (189-1136) selected and modified from a *Arabidopsis thaliana* chloroplast triosephosphate-isomerase sequence (GenBank: AF247559), a 223-bp RbcS2 terminator (1137-1359), and a PCR RE primer (1360-1379).

SEQ ID NO: 26 presents example 26 for a designer Phosphofructose-Kinase DNA construct that includes a PCR FD primer (sequence 1-20), a 2×84-bp NR promoter (21-188), a 135-bp RbcS2 transit peptide (189-323), a Phosphofructose Kinase-encoding sequence (324-1913) selected/modified from *Arabidopsis thaliana* 6-phosphofructokinase sequence (GenBank: NM 001037043), a 223-bp RbcS2 terminator (1914-2136), and a PCR RE primer (2137-2156).

The nucleic acid constructs, such as those presented in the examples above, may include additional appropriate sequences, for example, a selection marker gene, and an optional biomolecular tag sequence (such as the Lumio tag described in example 4, SEQ ID NO: 4). Selectable markers that can be selected for use in the constructs include markers conferring resistances to kanamycin, hygromycin, spectinomycin, streptomycin, sulfonyl urea, gentamycin, chloramphenicol, among others, all of which have been cloned and are available to those skilled in the art. Alternatively, the selective marker is a nutrition marker gene that can complement a deficiency in the host organism. For example, the gene encoding argininosuccinate lyase (arg7) can be used as a selection marker gene in the designer construct, which permits identification of transformants when *Chlamydomonas reinhardtii* arg7– (minus) cells are used as host cells.

Nucleic acid constructs carrying designer genes can be delivered into a host alga, blue-green alga, plant, or plant tissue or cells using the available gene-transformation techniques, such as electroporation, PEG induced uptake, and ballistic delivery of DNA, and *Agrobacterium*-mediated transformation. For the purpose of delivering a designer construct into algal cells, the techniques of electroporation, glass bead, and biolistic genegun can be selected for use as preferred methods; and an alga with single cells or simple thallus structure is preferred for use in transformation. Transformants can be identified and tested based on routine techniques.

The various designer genes can be introduced into host cells sequentially in a step-wise manner, or simultaneously using one construct or in one transformation. For example, the ten DNA constructs shown in SEQ ID NO: 13-16 (or 17) and 18-23 for the ten-enzyme 3-phosphoglycerate-branched butanol-production pathway can be placed into a genetic vector such as p389-Arg7 with a single selection marker (Arg7). Therefore, by use of a plasmid in this manner, it is possible to deliver all the ten DNA constructs (designer genes) into an arginine-requiring *Chlamydomonas reinhardtii*-arg7 host (CC-48) in one transformation for expression of the 3-phosphoglycerate-branched butanol-production pathway (03-12 in FIG. 1). When necessary, a transformant containing the ten DNA constructs can be further transformed to get more designer genes into its genomic DNA with an additional selection marker such as streptomycin. By using combinations of various designer-enzymes DNA constructs such as those presented in SEQ ID NO: 1-26 in genetic transformation with an appropriate host organism, various butanol-production pathways such as those illustrated in FIG. 1 can be constructed. For example, the designer DNA constructs of SEQ ID NO: 1-12 can be selected for construction of the glyceraldehydes-3-phosphate-branched butanol-production pathway (01-12 in FIG. 1); The designer DNA constructs of SEQ ID NO: 1-12, 24, and 25 can be selected for construction of the fructose-1,6-diphosphate-branched butanol-production pathway (20-33); and the designer DNA constructs of SEQ ID NO: 1-12 and 24-26 can be selected for construction of the fructose-6-phosphate-branched butanol-production pathway (19-33).

Additional Host Modifications to Enhance Photosynthetic Butanol Production

An NADPH/NADH Conversion Mechanism

According to the photosynthetic butanol production pathway(s), to produce one molecule of butanol from $4CO_2$ and $5H_2O$ is likely to require 14 ATP and 12 NADPH, both of which are generated by photosynthetic water splitting and photophosphorylation across the thylakoid membrane. In order for the 3-phosphoglycerate-branched butanol-production pathway (03-12 in FIG. 1) to operate, it is a preferred practice to use a butanol-production-pathway enzyme(s) that can use NADPH that is generated by the photo-driven electron transport process. *Clostridium saccharoperbutylacetonicum* butanol dehydrogenase (GenBank accession number: AB257439) and butyaldehyde dehydrogenase (GenBank: AY251646) are examples of a butanol-production-pathway enzyme that is capable of accepting either NADP (H) or NAD(H). Such a butanol-production-pathway enzyme that can use both NADPH and NADH (i.e., NAD(P)H) can also be selected for use in this 3-phosphoglycerate-branched and any of the other designer butanol-production pathway(s) (FIG. 1) as well. *Clostridium beijerinckii* Butyryl-CoA dehydrogenase (GenBank: AF494018) and 3-Hydroxybutyryl-CoA dehydrogenase (GenBank: AF494018) are examples of a butanol-production-pathway enzyme that can accept only NAD(H). When a butanol-production-pathway enzyme that can only use NADH is employed, it may require an NADPH/NADH conversion mechanism in order for this 3-phosphoglycerate-branched butanol-production pathway to operate well. However, depending on the genetic backgrounds of a host organism, a conversion mechanism between NADPH and NADH may exist in the host so that NADPH and NADH may be interchangeably used in the organism. In addition, it is known that NADPH could be converted into NADH by a NADPH-phosphatase activity (Pattanayak and Chatterjee (1998) "Nicotinamide adenine dinucleotide phosphate phosphatase facilitates dark reduction of nitrate: regulation by nitrate and ammonia," *Biologia Plantarium* 41(1):75-84) and that NAD can be converted to NADP by a NAD kinase activity (Muto, Miyachi, Usuda, Edwards and Bassham (1981) "Light-induced conversion of nicotinamide adenine dinucleotide to nicotinamide adenine dinucleotide phosphate in higher plant leaves," *Plant Physiology* 68(2):324-328; Matsumura-Kadota, Muto, Miyachi (1982) "Light-induced conversion of $NAD^+$ to $NADP^+$ in *Chlorella* cells," *Biochimica Biophysica Acta* 679(2):300-300). Therefore, when enhanced NADPH/NADH conversion is desirable, the host may be genetically modified to enhance the NADPH phosphatase and NAD kinase activities. Thus, in one of the various embodiments, the photosynthetic butanol-producing designer plant, designer alga or plant cell further contains additional designer transgenes (FIG. 2B) to inducibly express one or more enzymes to facilitate the NADPH/NADH inter-conversion, such as the NADPH phosphatase and NAD kinase (GenBank: XM_001609395, XM_001324239), in the stroma region of the algal chloroplast.

Another embodiment that can provide an NADPH/NADH conversion mechanism is by properly selecting an appropriate branching point at the Calvin cycle for a designer butanol-production pathway to branch from. To confer this NADPH/NADH conversion mechanism by pathway design according to this embodiment, it is a preferred practice to branch a designer butanol-production pathway at or after the point of glyceraldehydes-3-phosphate of the Calvin cycle as shown in FIG. 1. In these pathway designs, the NADPH/NADH conversion is achieved essentially by a two-step mechanism: 1) Use of the step with the Calvin-cycle's glyceraldehyde-3-phosphate dehydrogenase, which uses NADPH in reducing 1,3-diphosphoglycerate to glyceraldehydes-3-phosphate; and 2) use of the step with the designer pathway's NAD$^+$-dependent glyceraldehyde-3-phosphate dehydrogenase 01, which produces NADH in oxidizing glyceraldehyde-3-phosphate to 1,3-diphosphoglycerate. The net result of the two steps described above is the conversion of NADPH to NADH, which can supply the needed reducing power in the form of NADH for the designer butanol-production pathway(s). For step 1), use of the Calvin-cycle's NADPH-dependent glyceraldehyde-3-phosphate dehydrogenase naturally in the host organism is usually sufficient. Consequently, introduction of a designer NAD$^+$-dependent glyceraldehyde-3-phosphate dehydrogenase 01 to work with the Calvin-cycle's NADPH-dependent glyceraldehyde-3-phosphate dehydrogenase may confer the function of an NADPH/NADH conversion mechanism, which is needed for the 3-phosphoglycerate-branched butanol-production pathway (03-12 in FIG. 1) to operate well. For this reason, the designer NAD$^+$-dependent glyceraldehyde-3-phosphate-dehydrogenase DNA construct (example 12, SEQ ID NO:12) is used also as an NADPH/NADH-conversion designer gene (FIG. 2B) to support the 3-phosphoglycerate-branched butanol-production pathway (03-12 in FIG. 1) in one of the various embodiments. This also explains why it is important to use a NAD$^+$-dependent glyceraldehyde-3-phosphate dehydrogenase 01 to confer this two-step NADPH/NADH conversion mechanism for the designer butanol-production pathway(s). Therefore, in one of the various embodiments, it is also a preferred practice to use a NAD$^+$-dependent glyceraldehyde-3-phosphate dehydrogenase, its isozymes, functional derivatives, analogs, designer modified enzymes and/or combinations thereof in the designer butanol-production pathway(s) as illustrated in FIG. 1.

iRNA Techniques to Further Tame Photosynthesis Regulation Mechanism

In another embodiment of the present invention, the host plant or cell is further modified to tame the Calvin cycle so that the host can directly produce liquid fuel butanol instead of synthesizing starch (glycogen in the case of oxyphotobacteria), celluloses and lignocelluloses that are often inefficient and hard for the biorefinery industry to use. According to the one of the various embodiments, inactivation of starch-synthesis activity is achieved by suppressing the expression of any of the key enzymes, such as, starch synthase (glycogen synthase in the case of oxyphotobacteria) 13, glucose-1-phosphate (G-1-P) adenylyltransferase 14, phosphoglucomutase 15, and hexose-phosphate-isomerase 16 of the starch-synthesis pathway which connects with the Calvin cycle (FIG. 1).

Introduction of a genetically transmittable factor that can inhibit the starch-synthesis activity that is in competition with designer butanol-production pathway(s) for the Calvin-cycle products can further enhance photosynthetic butanol production. In a specific embodiment, a genetically encoded-able inhibitor (FIG. 2C) to the competitive starch-synthesis pathway is an interfering RNA (iRNA) molecule that specifically inhibits the synthesis of a starch-synthesis-pathway enzyme, for example, starch synthase 16, glucose-1-phosphate (G-1-P) adenylyltransferase 15, phosphoglucomutase 14, and/or hexose-phosphate-isomerase 13 as shown with numerical labels 13-16 in FIG. 1. The DNA sequences encoding starch synthase iRNA, glucose-1-phosphate (G-1-P) adenylyltransferase iRNA, a phosphoglucomutase iRNA and/or a G-P-isomerase iRNA, respectively, can be designed and synthesized based on RNA interference techniques known to those skilled in the art (Liszewski (Jun. 1, 2003) Progress in RNA interference, *Genetic Engineering News*, Vol. 23, number 11, pp. 1-59). Generally speaking, an interfering RNA (iRNA) molecule is anti-sense but complementary to a normal mRNA of a particular protein (gene) so that such iRNA molecule can specifically bind with the normal mRNA of the particular gene, thus inhibiting (blocking) the translation of the gene-specific mRNA to protein (Fire, Xu, Montgomery, Kostas, Driver, Mello (1998) "Potent and specific genetic interference by double-stranded RNA in *Caenorhabditis elegans*". *Nature* 391(6669):806-11; Dykxhoorn, Novina, Sharp (2003) "Killing the messenger: short RNAs that silence gene expression", *Nat Rev Mol Cell Biol.* 4(6):457-67).

Examples of a designer starch-synthesis iRNA DNA construct (FIG. 2C) are shown in SEQ ID NO: 27 and 28 listed. Briefly, SEQ ID NO: 27 presents example 27 for a designer Nia1-promoter-controlled Starch-Synthase-iRNA DNA construct (860 bp) that includes a PCR FD primer (sequence 1-20), a 262-bp Nia1 promoter (21-282), a Starch-Synthase iRNA sequence (283-617) consisting of start codon atg and a reverse complement sequence of two unique sequence fragments of a *Chlamydomonas reinhardtii* starch-synthase-mRNA sequence (GenBank: AF026422), a 223-bp RbcS2 terminator (618-850), and a PCR RE primer (851-860). Because of the use of a Nia1 promoter (21-282), this designer starch-synthesis iRNA gene is designed to be expressed only when needed to enhance photobiological butanol production in the presence of its specific inducer, nitrate (NO$_3^-$), which can be added into the culture medium as a fertilizer for induction of the designer organisms. The Starch-Synthase iRNA sequence (283-617) is designed to bind with the normal mRNA of the starch synthase gene, thus blocking its translation into a functional starch synthase. The inhibition of the starch/glycogen synthase activity at 16 in this manner is to channel more photosynthetic products of the Calvin cycle into the Calvin-cycle-branched butanol-production pathway(s) such as the glyceraldehydes-3-phosphate-branched butanol-production pathway 01-12 as illustrated in FIG. 1.

SEQ ID NO: 28 presents example 28 for a designer HydA1-promoter-controlled Starch-Synthase-iRNA DNA construct (1328 bp) that includes a PCR FD primer (sequence 1-20), a 282-bp HydA1 promoter (21-302), a designer Starch-Synthase iRNA sequence (303-1085), a 223-bp RbcS2 terminator (1086-1308), and a PCR RE primer (1309-1328). The designer Starch-Synthase-iRNA sequence (303-1085) comprises of: a 300-bp sense fragment (303-602) selected from the first 300-bp unique coding sequence of a *Chlamydomonas reinhardtii* starch synthase mRNA sequence (GenBank: AF026422), a 183-bp designer intron-like loop (603-785), and a 300-bp antisense sequence (786-1085) complement to the first 300-bp coding sequence of a *Chlamydomonas reinhardtii* starch-synthase-mRNA sequence (GenBank: AF026422). This designer Starch-Synthase-iRNA sequence (303-1085) is designed to inhibit the synthesis of starch synthase by the following two mechanisms. First, the 300-bp antisense complement iRNA sequence (corresponding to DNA sequence 786-1085) binds with the normal mRNA of the starch synthase gene, thus blocking its translation into a functional starch synthase. Second, the 300-bp antisense complement iRNA sequence (corresponding to DNA sequence 786-1085) can also bind with the 300-bp sense counterpart (corresponding to DNA sequence 303-602) in the same designer iRNA molecule, forming a hairpin-like double-stranded RNA structure with the 183-bp designer intron-like sequence (603-785) as a loop. Experimental studies have shown that this type of hairpin-like double-stranded RNA can also trigger post-transcriptional gene silencing (Fuhrmann, Stahlberg, Govorunova, Rank and Hegemann (2001) *Journal of Cell Science* 114:3857-3863). Because of the use of a HydA1 promoter (21-302), this designer starch-synthesis-iRNA gene is designed to be expressed only under anaerobic conditions when needed to enhance photobiological butanol production by channeling more photosynthetic products of the Calvin cycle into the butanol-production pathway(s) such as 01-12, 03-12, and/or 20-33 as illustrated in FIG. 1.

Designer Starch-Degradation and Glycolysis Genes

In yet another embodiment of the present invention, the photobiological butanol production is enhanced by incorporating an additional set of designer genes (FIG. 2D) that can facilitate starch/glycogen degradation and glycolysis in combination with the designer butanol-production gene(s) (FIG. 2A). Such additional designer genes for starch degradation include, for example, genes coding for 17: amylase, starch phosphorylase, hexokinase, phosphoglucomutase, and for 18: glucose-phosphate-isomerase (G-P-isomerase) as illustrated in FIG. 1. The designer glycolysis genes encode chloroplast-targeted glycolysis enzymes: glucose-phosphate isomerase 18, phosphofructose kinase 19, aldolase 20, triose phosphate isomerase 21, glyceraldehyde-3-phosphate dehydrogenase 22, phosphoglycerate kinase 23, phosphoglycerate mutase 24, enolase 25, and pyruvate kinase 26. The designer starch-degradation and glycolysis genes in combination with any of the butanol-production pathways shown in FIG. 1 can form additional pathway(s) from starch/glycogen to butanol (17-33). Consequently, co-expression of the designer starch-degradation and glycolysis genes with the butanol-production-pathway genes can enhance photobiological production of butanol as well. Therefore, this embodiment represents another approach to tame the Calvin cycle for enhanced photobiological production of butanol. In this case, some of the Calvin-cycle products flow through the starch synthesis pathway (13-16) followed by the starch/glycogen-to-butanol pathway (17-33) as shown in FIG. 1. In this case, starch/glycogen acts as a transient storage pool of the Calvin-cycle products before they can be converted to butanol. This mechanism can be quite useful in maximizing the butanol-production yield in certain cases. For example, at high sunlight intensity such as around noon, the rate of Calvin-cycle photosynthetic $CO_2$ fixation can be so high that may exceed the maximal rate capacity of a butanol-production pathway(s); use of the starch-synthesis mechanism allows temporary storage of the excess photosynthetic products to be used later for butanol production as well.

FIG. 1 also illustrates the use of a designer starch/glycogen-to-butanol pathway with designer enzymes (as labeled from 17 to 33) in combination with a Calvin-cycle-branched designer butanol-production pathway(s) such as the glyceraldehydes-3-phosphate-branched butanol-production pathway 01-12 for enhanced photobiological butanol production. Similar to the benefits of using the Calvin-cycle-branched designer butanol-production pathways, the use of the designer starch/glycogen-to-butanol pathway (17-33) can also help to convert the photosynthetic products to butanol before the sugars could be converted into other complicated biomolecules such as lignocellulosic biomasses which cannot be readily used by the biorefinery industries. Therefore, appropriate use of the Calvin-cycle-branched designer butanol-production pathway(s) (such as 01-12, 03-12, and/or 20-33) and/or the designer starch/glycogen-to-butanol pathway (17-33) may represent revolutionary inter alia technologies that can effectively bypass the bottleneck problems of the current biomass technology including the "lignocellulosic recalcitrance" problem.

Another feature is that a Calvin-cycle-branched designer butanol-production pathway activity (such as 01-12, 03-12, and/or 20-33) can occur predominantly during the days when there is light because it uses an intermediate product of the Calvin cycle which requires supplies of reducing power (NADPH) and energy (ATP) generated by the photosynthetic water splitting and the light-driven proton-translocation-coupled electron transport process through the thylakoid membrane system. The designer starch/glycogen-to-butanol pathway (17-33) which can use the surplus sugar that has been stored as starch/glycogen during photosynthesis can operate not only during the days, but also at nights. Consequently, the use of a Calvin-cycle-branched designer butanol-production pathway (such as 01-12, 03-12, and/or 20-33) together with a designer starch/glycogen-to-butanol pathway(s) (17-33) as illustrated in FIG. 1 enables production of butanol both during the days and at nights.

Because the expression for both the designer starch/glycogen-to-butanol pathway(s) and the Calvin-cycle-branched designer butanol-production pathway(s) is controlled by the use of an inducible promoter such as an anaerobic hydrogenase promoter, this type of designer organisms is also able to grow photoautotrophically under aerobic (normal) conditions. When the designer photosynthetic organisms are grown and ready for photobiological butanol production, the cells are then placed under the specific inducing conditions such as under anaerobic conditions [or an ammonium-to-nitrate fertilizer use shift, if designer Nia1/nirA promoter-controlled butanol-production pathway(s) is used] for enhanced butanol production, as shown in FIGS. 1 and 3.

Examples of designer starch (glycogen)-degradation genes are shown in SEQ ID NO: 29-33 listed. Briefly, SEQ ID NO:29 presents example 29 for a designer Amylase DNA construct (1889 bp) that includes a PCR FD primer (sequence 1-20), a 2×84-bp NR promoter (21-188), a 9-bp Xho I NdeI site (189-197), a 135-bp RbcS2 transit peptide (198-332), an Amylase-encoding sequence (333-1616) selected and modified from a *Barley alpha-amylase* (GenBank: J04202A my46 expression tested in aleurone cells), a 21-bp Lumio-tag sequence (1617-1637), a 9-bp XbaI site (1638-1646), a 223-bp RbcS2 terminator (1647-1869), and a PCR RE primer (1870-1889).

SEQ ID NO: 30 presents example 30 for a designer Starch-Phosphorylase DNA construct (3089 bp) that includes a PCR FD primer (sequence 1-20), a 2×84-bp NR promoter (21-188), a 135-bp RbcS2 transit peptide (189-323), a Starch Phosphorylase-encoding sequence (324-2846) selected and modified from a Citrus root starch-phosphorylase sequence (GenBank: AY098895, expression tested in citrus root), a 223-bp RbcS2 terminator (2847-3069), and a PCR RE primer (3070-3089).

SEQ ID NO: 31 presents example 31 for a designer Hexose-Kinase DNA construct (1949 bp) that includes a PCR FD primer (sequence 1-20), a 2×84-bp NR promoter (21-188), a 135-bp RbcS2 transit peptide (189-323), a Hexose Kinase-encoding sequence (324-1706) selected and modified from *Ajellomyces capsulatus* hexokinase mRNA sequence (Genbank: XM_001541513), a 223-bp RbcS2 terminator (1707-1929), and a PCR RE primer (1930-1949).

SEQ ID NO: 32 presents example 32 for a designer Phosphoglucomutase DNA construct (2249 bp) that includes a PCR FD primer (sequence 1-20), a 2×84-bp NR promoter (21-188), a 135-bp RbcS2 transit peptide (189-323), a Phosphoglucomutase-encoding sequence (324-2006) selected and modified from *Pichia stipitis* phosphoglucomutase sequence (Genbank: XM_001383281), a 223-bp RbcS2 terminator (2007-2229), and a PCR RE primer (2230-2249).

SEQ ID NO: 33 presents example 33 for a designer Glucosephosphate-Isomerase DNA construct (2231 bp) that includes a PCR FD primer (sequence 1-20), a 2×84-bp NR promoter (21-188), a 135-bp RbcS2 transit peptide (189-323), a Glucosephosphate Isomerase-encoding sequence (324-1988) selected and modified from a *S cerevisiae* phosphoglucoisomerase sequence (GenBank: M21696), a 223-bp RbcS2 terminator (1989-2211), and a PCR RE primer (2212-2231).

The designer starch-degradation genes such as those shown in SEQ ID NO: 29-33 can be selected for use in combination with various designer butanol-production-pathway genes for construction of various designer starch-degradation butanol-production pathways such as the pathways shown in FIG. 1. For example, the designer genes shown in SEQ ID NOS: 1-12, 24-26, and 29-33 can be selected for construction of a Nia1 promoter-controlled starch-to-butanol production pathway that comprises of the following designer enzymes: amylase, starch phosphorylase, hexokinase, phosphoglucomutase, glucosephosphate isomerase, phosphofructose kinase, fructose diphosphate aldolase, those phosphate isomerase, glyceraldehyde-3-phosphate dehydrogenase, phosphoglycerate kinase, phosphoglycerate mutase, enolase, pyruvate kinase, pyruvate-NADP$^+$ oxidoreductase (or pyruvate-ferredoxin oxidoreductase), thiolase, 3-hydroxybutyryl-CoA dehydrogenase, crotonase, butyryl-CoA dehydrogenase, butyraldehyde dehydrogenase, and butanol dehydrogenase. This starch/glycogen-to-butanol pathway 17-33 may be used alone and/or in combinations with other butanol-production pathway(s) such as the 3-phosphoglycerate-branched butanol-production pathway 03-12 as illustrated in FIG. 1.

Distribution of Designer Butanol-Production Pathways Between Chloroplast and Cytoplasm In yet another embodiment of the present invention, photobiological butanol productivity is enhanced by a selected distribution of the designer butanol-production pathway(s) between chloroplast and cytoplasm in a eukaryotic plant cell. That is, not all the designer butanol-production pathway(s) (FIG. 1) have to operate in the chloroplast; when needed, part of the designer butanol-production pathway(s) can operate in cytoplasm as well. For example, in one of the various embodiments, a significant part of the designer starch-to-butanol pathway activity from dihydroxyacetone phosphate to butanol (21-33) is designed to occur at the cytoplasm while the steps from starch to dihydroxyacetone phosphate (17-20) are in the chloroplast. In this example, the linkage between the chloroplast and cytoplasm parts of the designer pathway is accomplished by use of the triose phosphate-phosphate translocator, which facilitates translocation of dihydroxyacetone across the chloroplast membrane. By use of the triose phosphate-phosphate translocator, it also enables the glyceraldehyde-3-phospahte-branched designer butanol-production pathway to operate not only in chloroplast, but also in cytoplasm as well. The cytoplasm part of the designer butanol-production pathway can be constructed by use of designer butanol-production pathway genes (DNA constructs of FIG. 2A) with their chloroplast-targeting sequence omitted as shown in FIG. 2E.

Designer Oxyphotobacteria with Designer Butanol-Production Pathways in Cytoplasm In prokaryotic photosynthetic organisms such as blue-green algae (oxyphotobacteria including cyanobacteria and oxychlorobacteria), which typically contain photosynthetic thylakoid membrane but no chloroplast structure, the Calvin cycle is located in the cytoplasm. In this special case, the entire designer butanol-production pathway(s) (FIG. 1) including (but not limited to) the glyceraldehyde-3-phosphate branched butanol-production pathway (01-12), the 3-phosphpglycerate-branched butanol-production pathway (03-12), the fructose-1,6-diphosphate-branched pathway (20-33), the fructose-6-phosphate-branched pathway (19-33), and the starch (or glycogen)-to-butanol pathways (17-33) are adjusted in design to operate with the Calvin cycle in the cytoplasm of a blue-green alga. The construction of the cytoplasm designer butanol-production pathways can be accomplished by use of designer butanol-production pathway genes (DNA construct of FIG. 2A) with their chloroplast-targeting sequence all omitted. When the chloroplast-targeting sequence is omitted in the designer DNA construct (s) as illustrated in FIG. 2E, the designer gene(s) is transcribed and translated into designer enzymes in the cytoplasm whereby conferring the designer butanol-production pathway(s). The designer gene(s) can be incorporated into the chromosomal and/or plasmid DNA in host blue-green algae (oxyphotobacteria including cyanobacteria and oxychlorobacteria) by using the techniques of gene transformation known to those skilled in the art. It is a preferred practice to integrate the designer genes through an integrative transformation into the chromosomal DNA that can usually provide better genetic stability for the designer genes. In oxyphotobacteria such as cyanobacteria, integrative transformation can be achieved through a process of homologous DNA double recombination into the host's chromosomal DNA using a designer DNA construct as illustrated in FIG. 2F, which typically, from the 5' upstream to the 3' downstream, consists of: recombination site 1, a designer butanol-production-pathway gene(s), and recombination site 2. This type of DNA constructs (FIG. 2F) can be delivered into oxyphotobacteria (blue-green algae) with a number of available genetic transformation techniques including electroporation, natural transformation, and/or conjugation. The transgenic designer organisms created from blue-green algae are also called designer blue-green algae (designer oxyphotobacteria including designer cyanobacteria and designer oxychlorobacteria).

Examples of designer oxyphotobacterial butanol-production-pathway genes are shown in SEQ ID NO: 34-45 listed. Briefly, SEQ ID NO:34 presents example 34 for a designer oxyphotobacterial Butanol Dehydrogenase DNA construct (1709 bp) that includes a PCR FD primer (sequence 1-20), a 400-bp nitrite reductase (nirA) promoter from *Thermosynechococcus elongatus* BP-1 (21-420), an enzyme-encoding sequence (421-1569) selected and modified from a *Clostridium saccharoperbutylacetonicum* Butanol Dehydrogenase sequence (AB257439), a 120-bp rbcS terminator from *Thermosynechococcus elongatus* BP-1 (1570-1689), and a PCR RE primer (1690-1709) at the 3' end.

SEQ ID NO:35 presents example 35 for a designer oxyphotobacterial Butyraldehyde Dehydrogenase DNA construct (1967 bp) that includes a PCR FD primer (sequence 1-20), a 400-bp *Thermosynechococcus elongatus* BP-1 nitrite reductase nirA promoter (21-420), an enzyme-encoding sequence (421-1827) selected and modified from a *Clostridium saccharoperbutylacetonicum* Butyraldehyde Dehydrogenase sequence (AY251646), a 120-bp rbcS terminator from *Thermosynechococcus elongatus* BP-1 (1828-1947), and a PCR RE primer (1948-1967) at the 3' end.

SEQ ID NO:36 presents example 36 for a designer oxyphotobacterial Butyryl-CoA Dehydrogenase DNA construct (1602 bp) that includes a PCR FD primer (sequence 1-20), a 305-bp *Thermosynechococcus elongatus* BP-1 nitrate reductase promoter (21-325), a Butyryl-CoA Dehydrogenase encoding sequence (326-1422) selected/modified from the sequences of a *Clostridium beijerinckii* Butyryl-CoA Dehydrogenase (AF494018), a 120-bp *Thermosynechococcus elongatus* BP-1 rbcS terminator (1423-1582), and a PCR RE primer (1583-1602) at the 3' end.

SEQ ID NO:37 presents example 37 for a designer oxyphotobacterial Crotonase DNA construct (1248 bp) that includes a PCR FD primer (sequence 1-20), a 305-bp *Thermosynechococcus elongatus* BP-1 nitrate reductase promoter (21-325), a Crotonase-encoding sequence (326-1108) selected/modified from the sequences of a *Clostridium beijerinckii* Crotonase (GenBank: AF494018), 120-bp *Thermosynechococcus elongatus* BP-1 rbcS terminator (1109-1228), and a PCR RE primer (1229-1248).

SEQ ID NO:38 presents example 38 for a designer oxyphotobacterial 3-Hydroxybutyryl-CoA Dehydrogenase DNA construct (1311 bp) that include of a PCR FD primer (sequence 1-20), a 305-bp nirA promoter from (21-325), a 3-Hydroxybutyryl-CoA Dehydrogenase-encoding sequence (326-1171) selected/modified from a *Clostridium beijerinckii* 3-Hydroxybutyryl-CoA Dehydrogenase sequence Crotonase (GenBank: AF494018), a 120-bp *Thermosynechococcus elongatus* BP-1 rbcS terminator (1172-1291), and a PCR RE primer (1292-1311).

SEQ ID NO:39 presents example 39 for a designer oxyphotobacterial Thiolase DNA construct (1665 bp) that includes a PCR FD primer (sequence 1-20), a 305-bp nirA promoter from *Thermosynechococcus elongatus* BP-1 (21-325), a Thiolase-encoding sequence (326-1525) selected/modified from a *Butyrivibrio fibrisolvens* Thiolase sequence (AB190764), a 120-bp rbcS terminator from *Thermosynechococcus elongatus* BP-1 (1526-1645), and a PCR RE primer (1646-1665).

SEQ ID NO:40 presents example 40 for a designer oxyphotobacterial Pyruvate-Ferredoxin Oxidoreductase DNA construct (4071 bp) that includes a PCR FD primer (sequence 1-20), a 305-bp nirA promoter from *Thermosynechococcus elongatus* BP-1 (21-325), a Pyruvate-Ferredoxin Oxidoreductase-encoding sequence (326-3931) selected/modified from the sequences of a *Mastigamoeba balamuthi* Pyruvate-ferredoxin oxidoreductase (GenBank: AY101767), a 120-bp rbcS terminator from *Thermosynechococcus elongatus* BP-1 (3932-4051), and a PCR RE primer (4052-4071).

SEQ ID NO:41 presents example 41 for a designer oxyphotobacterial Pyruvate Kinase DNA construct (1806 bp) that includes a PCR FD primer (sequence 1-20), a 305-bp nirA promoter from *Thermosynechococcus elongatus* BP-1 (21-325), a pyruvate kinase-encoding sequence (326-1666) selected/modified from a *Thermoproteus tenax* pyruvate kinase (GenBank: AF065890), a 120-bp *Thermosynechococcus elongatus* BP-1 rbcS terminator (1667-1786), and a PCR RE primer (1787-1806) at the 3' end.

SEQ ID NO:42 presents example 42 for a designer oxyphotobacterial Enolase DNA construct (1696 bp) that includes a PCR FD primer (sequence 1-20), a 231-bp nirA promoter from *Thermosynechococcus elongatus* BP-1 (21-251), a enolase-encoding sequence (252-1556) selected/modified from the sequences of a *Chlamydomonas reinhardtii* cytosolic enolase (GenBank: X66412, P31683), a 120-bp rbcS terminator from *Thermosynechococcus elongatus* BP-1 (1557-1676), and a PCR RE primer (1677-1696) at the 3' end.

SEQ ID NO:43 presents example 43 for a designer oxyphotobacterial Phosphoglycerate-Mutase DNA construct (2029 bp) that includes a PCR FD primer (sequence 1-20), a 231-bp nirA promoter from *Thermosynechococcus elongatus* BP-1 (21-251), a phosphoglycerate-mutase encoding sequence (252-1889) selected/modified from the sequences of a *Pelotomaculum thermopropionicum* SI phosphoglycerate mutase (GenBank: YP_001213270), a 120-bp *Thermosynechococcus elongatus* BP-1 rbcS terminator (1890-2009), and a PCR RE primer (2010-2029) at the 3' end.

SEQ ID NO:44 presents example 44 for a designer oxyphotobacterial Phosphoglycerate Kinase DNA construct (1687 bp) that includes a PCR FD primer (sequence 1-20), a 231-bp nirA promoter from *Thermosynechococcus elongatus* BP-1 (21-251), a phosphoglycerate-kinase-encoding sequence (252-1433) selected from *Pelotomaculum thermopropionicum* SI phosphoglycerate kinase (BAF60903), a 234-bp *Thermosynechococcus elongatus* BP-1 rbcS terminator (1434-1667), and a PCR RE primer (1668-1687).

SEQ ID NO:45 presents example 45 for a designer oxyphotobacterial Glyceraldehyde-3-Phosphate Dehydrogenase DNA construct (1514 bp) that includes a PCR FD primer (sequence 1-20), a 305-bp *Thermosynechococcus elongatus* BP-1 nirA promoter (21-325), an enzyme-encoding sequence (326-1260) selected and modified from *Blastochloris viridis* NAD-dependent Glyceraldehyde-3-phosphate dehydrogenase (CAC80993), a 234-bp rbcS terminator from *Thermosynechococcus elongatus* BP-1 (1261-1494), and a PCR RE primer (1495-1514).

The designer oxyphotobacterial genes such as those shown in SEQ ID NO: 34-45 can be selected for use in full or in part, and/or in combination with various other designer butanol-production-pathway genes for construction of various designer oxyphotobacterial butanol-production pathways such as the pathways shown in FIG. 1. For example, the designer genes shown in SEQ ID NOS: 34-45 can be selected for construction of an oxyphotobacterial nirA promoter-controlled and glyceraldehyde-3-phosphate-branched butanol-production pathway (01-12) that comprises of the following designer enzymes: NAD-dependent glyceraldehyde-3-phosphate dehydrogenase 01, phosphoglycerate kinase 02, phosphoglycerate mutase 03, enolase 04, pyruvate kinase 05, pyruvate-ferredoxin oxidoreductase (or pyruvate-NADP$^+$ oxidoreductase) 06, thiolase 07, 3-hydroxybutyryl-CoA dehydrogenase 08, crotonase 09, butyryl-CoA dehydrogenase 10, butyraldehyde dehydrogenase 11, and butanol dehydrogenase 12. Use of these designer oxyphotobacterial butanol-production-pathway genes (SEQ ID NOS: 34-45) in a thermophilic and/or thermotolerant cyanobacterium may represent a thermophilic and/or thermotolerant butanol-producing oxyphotobacterium. Fox example, use of these designer genes (SEQ ID NOS: 34-45) in a thermophilic/thermotolerant cyanobacterium such as

*Thermosynechococcus elongatus* BP-1 may represent a designer thermophilic/thermotolerant butanol-producing cyanobacterium such as a designer butanol-producing *Thermosynechococcus*.

Further Host Modifications to Help Ensure Biosafety

The present invention also provides biosafety-guarded photosynthetic biofuel production methods based on cell-division-controllable designer transgenic plants (such as algae and oxyphotobacteria) or plant cells. The cell-division-controllable designer photosynthetic organism (FIG. 3) are created through use of a designer biosafety-control gene(s) (FIG. 2G) in conjunction with the designer butanol-production-pathway gene(s) (FIGS. 2A-2F) such that its cell division and mating function can be controllably stopped to provide better biosafety features.

In one of the various embodiments, a fundamental feature is that a designer cell-division-controllable photosynthetic organism (such as an alga, plant cell, or oxyphotobacterium) contains two key functions (FIG. 3A): a designer biosafety mechanism(s) and a designer biofuel-production pathway(s). As shown in FIG. 3B, the designer biosafety feature(s) is conferred by a number of mechanisms including: (1) the inducible insertion of designer proton-channels into cytoplasm membrane to permanently disable any cell division and mating capability, (2) the selective application of designer cell-division-cycle regulatory protein or interference RNA (iRNA) to permanently inhibit the cell division cycle and preferably keep the cell at the $G_1$ phase or $G_0$ state, and (3) the innovative use of a high-$CO_2$-requiring host photosynthetic organism for expression of the designer biofuel-production pathway(s). Examples of the designer biofuel-production pathway(s) include the designer butanol-production pathway(s), which work with the Calvin cycle to synthesize biofuel such as butanol directly from carbon dioxide ($CO_2$) and water ($H_2O$). The designer cell-division-control technology can help ensure biosafety in using the designer organisms for photosynthetic biofuel production. Accordingly, this embodiment provides, inter alia, biosafety-guarded methods for producing biofuel based on a cell-division-controllable designer biofuel-producing alga, cyanobacterium, oxychlorobacterium, plant or plant cells.

In one of the various embodiments, a cell-division-controllable designer butanol-producing eukaryotic alga or plant cell is created by introducing a designer proton-channel gene (FIG. 2H) into a host alga or plant cell (FIG. 3B). SEQ ID NO: 46 presents example 46 for a detailed DNA construct of a designer Nia1-promoter-controlled proton-channel gene (609 bp) that includes a PCR FD primer (sequence 1-20), a 262-bp nitrate reductase Nia1 promoter (21-282), a Melittin proton-channel encoding sequence (283-366), a 223-bp RbcS2 terminator (367-589), and a PCR RE primer (590-609).

The expression of the designer proton-channel gene (FIG. 2H) is controlled by an inducible promoter such as the nitrate reductase (Nia1) promoter, which can also be used to control the expression of a designer biofuel-production-pathway gene(s). Therefore, before the expression of the designer gene(s) is induced, the designer organism can grow photoautotrophically using $CO_2$ as the carbon source and $H_2O$ as the source of electrons just like wild-type organism. When the designer organism culture is grown and ready for photobiological production of biofuels, the cell culture is then placed under a specific inducing condition (such as by adding nitrate into the culture medium if the nitrate reductase (Nia1) promoter is used as an inducible promoter) to induce the expression of both the designer proton-channel gene and the designer biofuel-production-pathway gene(s).

The expression of the proton-channel gene is designed to occur through its transcription in the nucleus and its translation in the cytosol. Because of the specific molecular design, the expressed proton channels are automatically inserted into the cytoplasm membrane, but leave the photosynthetic thylakoid membrane intact. The insertion of the designer proton channels into cytoplasm membrane collapses the proton gradient across the cytoplasm membrane so that the cell division and mating function are permanently disabled. However, the photosynthetic thylakoid membrane inside the chloroplast is kept intact (functional) so that the designer biofuel-production-pathway enzymes expressed into the stroma region can work with the Calvin cycle for photobiological production of biofuels from $CO_2$ and $H_2O$. That is, when both the designer proton-channel gene and the designer biofuel-production-pathway gene(s) are turned on, the designer organism becomes a non-reproducible cell for dedicated photosynthetic production of biofuels. Because the cell division and mating function are permanently disabled (killed) at this stage, the designer-organism culture is no longer a living matter except its catalytic function for photochemical conversion of $CO_2$ and $H_2O$ into a biofuel. It will no longer be able to mate or exchange any genetic materials with any other cells, even if it somehow comes in contact with a wild-type cell as it would be the case of an accidental release into the environments.

According to one of the various embodiments, the nitrate reductase (Nia1) promoter or nitrite reductase (nirA) promoter is a preferred inducible promoter for use to control the expression of the designer genes. In the presence of ammonium (but not nitrate) in culture medium, for example, a designer organism with Nia1-promoter-controlled designer proton-channel gene and biofuel-production-pathway gene(s) can grow photoauotrophically using $CO_2$ as the carbon source and $H_2O$ as the source of electrons just like a wild-type organism. When the designer organism culture is grown and ready for photobiological production of biofuels, the expression of both the designer proton-channel gene and the designer biofuel-production-pathway gene(s) can then be induced by adding some nitrate fertilizer into the culture medium. Nitrate is widely present in soils and nearly all surface water on Earth. Therefore, even if a Nia1-promoter-controlled designer organism is accidentally released into the natural environment, it will soon die since the nitrate in the environment will trig the expression of a Nia1-promoter-controlled designer proton-channel gene which inserts proton-channels into the cytoplasm membrane thereby killing the cell. That is, a designer photosynthetic organism with Nia1-promoter-controlled proton-channel gene is programmed to die as soon as it sees nitrate in the environment. This characteristic of cell-division-controllable designer organisms with Nia1-promoter-controlled proton-channel gene provides an added biosafety feature.

The art in constructing proton-channel gene (FIG. 2H) with a thylakoid-membrane targeting sequence has recently been disclosed [James W. Lee (2007). Designer proton-channel transgenic algae for photobiological hydrogen production, PCT International Publication Number: WO 2007/134340 A2]. In the present invention of creating a cell-division-controllable designer organism, the thylakoid-membrane-targeting sequence must be omitted in the proton-channel gene design. For example, the essential components of a Nia1-promoter-controlled designer proton-channel gene can simply be a Nia1 promoter linked with a proton-channel-encoding sequence (without any thylakoid-membrane-targeting sequence) so that the proton channel will insert into the cytoplasm membrane but not into the photosynthetic thylakoid membrane.

According to one of the various embodiments, it is a preferred practice to use the same inducible promoter such as the Nia1 promoter to control the expression of both the designer proton-channel gene and the designer biofuel-production pathway genes. In this way, the designer biofuel-production pathway(s) can be inducibly expressed simultaneously with the expression of the designer proton-channel gene that terminates certain cellular functions including cell division and mating.

In one of the various embodiments, an inducible promoter that can be used in this designer biosafety embodiment is selected from the group consisting of the hydrogenase promoters [HydA1 (Hyd1) and HydA2, accession number: AJ308413, AF289201, AY090770], the Cyc6 gene promoter, the Cpx1 gene promoter, the heat-shock protein promoter HSP70A, the CabII-1 gene (accession number M24072) promoter, the Ca1 gene (accession number P20507) promoter, the Ca2 gene (accession number P24258) promoter, the nitrate reductase (Nia1) promoter, the nitrite-reductase-gene (nirA) promoters, the bidirectional-hydrogenase-gene hox promoters, the light- and heat-responsive groE promoters, the Rubisco-operon rbcL promoters, the metal (zinc)-inducible smt promoter, the iron-responsive idiA promoter, the redox-responsive crhR promoter, the heat-shock-gene hsp16.6 promoter, the small heat-shock protein (Hsp) promoter, the $CO_2$-responsive carbonic-anhydrase-gene promoters, the green/red light responsive cpcB2A2 promoter, the UV-light responsive lexA, recA and ruvB promoters, the nitrate-reductase-gene (narB) promoters, and combinations thereof.

In another embodiment, a cell-division-controllable designer photosynthetic organism is created by use of a carbonic anhydrase deficient mutant or a high-$CO_2$-requiring mutant as a host organism to create the designer biofuel-production organism. High-$CO_2$-requiring mutants that can be selected for use in this invention include (but not limited to): *Chlamydomonas reinhardtii* carbonic-anhydrase-deficient mutant12-1C (CC-1219 cal mt-), *Chlamydomonas reinhardtii* cia3 mutant (*Plant Physiology* 2003, 132:2267-2275), the high-$CO_2$-requiring mutant M3 of *Synechococcus* sp. Strain PCC 7942, or the carboxysome-deficient cells of *Synechocystis* sp. PCC 6803 (*Plant biol* (Stuttg) 2005, 7:342-347) that lacks the $CO_2$-concentrating mechanism can grow photoautotrophically only under elevated $CO_2$ concentration level such as 0.2-3% $CO_2$.

Under atmospheric $CO_2$ concentration level (380 ppm), the carbonic anhydrase deficient or high-$CO_2$-requiring mutants commonly can not survive. Therefore, the key concept here is that a high-$CO_2$-requiring designer biofuel-production organism that lacks the $CO_2$ concentrating mechanism will be grown and used for photobiological production of biofuels always under an elevated $CO_2$ concentration level (0.2-5% $CO_2$) in a sealed bioreactor with $CO_2$ feeding. Such a designer transgenic organism can not survive when it is exposed to an atmospheric $CO_2$ concentration level (380 ppm=0.038% $CO_2$) because its $CO_2$-concentrating mechanism (CCM) for effective photosynthetic $CO_2$ fixation has been impaired by the mutation. Even if such a designer organism is accidentally released into the natural environment, its cell will soon not be able to divide or mate, but die quickly of carbon starvation since it can not effectively perform photosynthetic $CO_2$ fixation at the atmospheric $CO_2$ concentration (380 ppm). Therefore, use of such a high-$CO_2$-requiring mutant as a host organism for the gene transformation of the designer biofuel-production-pathway gene(s) represents another way in creating the envisioned cell-division-controllable designer organisms for biosafety-guarded photobiological production of biofuels from $CO_2$ and $H_2O$. No designer proton-channel gene is required here.

In another embodiment, a cell-division-controllable designer organism (FIG. 3B) is created by use of a designer cell-division-cycle regulatory gene as a biosafety-control gene (FIG. 2G) that can control the expression of the cell-division-cycle (cdc) genes in the host organism so that it can inducibly turn off its reproductive functions such as permanently shutting off the cell division and mating capability upon specific induction of the designer gene.

Biologically, it is the expression of the natural cdc genes that controls the cell growth and cell division cycle in cyanobacteria, algae, and higher plant cells. The most basic function of the cell cycle is to duplicate accurately the vast amount of DNA in the chromosomes during the S phase (S for synthesis) and then segregate the copies precisely into two genetically identical daughter cells during the M phase (M for mitosis). Mitosis begins typically with chromosome condensation: the duplicated DNA strands, packaged into elongated chromosomes, condense into the much-more compact chromosomes required for their segregation. The nuclear envelope then breaks down, and the replicated chromosomes, each consisting of a pair of sister chromatids, become attached to the microtubules of the mitotic spindle. As mitosis proceeds, the cell pauses briefly in a state called metaphase, when the chromosomes are aligned at the equator of the mitotic spindle, poised for segregation. The sudden segregation of sister chromatids marks the beginning of anaphase during which the chromosomes move to opposite poles of the spindle, where they decondense and reform intact nuclei. The cell is then pinched into two by cytoplasmic division (cytokinesis) and the cell division is then complete. Note, most cells require much more time to grow and double their mass of proteins and organelles than they require to replicate their DNA (the S phase) and divide (the M phase). Therefore, there are two gap phases: a $G_1$ phase between M phase and S phase, and a G2 phase between S phase and mitosis. As a result, the eukaryotic cell cycle is traditionally divided into four sequential phases: $G_1$, S, $G_2$, and M. Physiologically, the two gap phases also provide time for the cell to monitor the internal and external environment to ensure that conditions are suitable and preparation are complete before the cell commits itself to the major upheavals of S phase and mitosis. The $G_1$ phase is especially important in this aspect. Its length can vary greatly depending on external conditions and extracellular signals from other cells. If extracellular conditions are unfavorable, for example, cells delay progress through $G_1$ and may even enter a specialized resting state known as $G_0$ (G zero), in which they remain for days, weeks, or even for years before resuming proliferation. Indeed, many cells remain permanently in $G_0$ state until they die.

In one of the various embodiments, a designer gene(s) that encodes a designer cdc-regulatory protein or a specific cdc-iRNA is used to inducibly inhibit the expression of certain cdc gene(s) to stop cell division and disable the mating capability when the designer gene(s) is trigged by a specific inducing condition. When the cell-division-controllable designer culture is grown and ready for photosynthetic production of biofuels, for example, it is a preferred practice to induce the expression of a specific designer cdc-iRNA gene(s) along with induction of the designer biofuel-production-pathway gene(s) so that the cells will permanently halt at the $G_1$ phase or $G_0$ state. In this way, the grown designer-organism cells become perfect catalysts for photosynthetic production of biofuels from $CO_2$ and $H_2O$ while their functions of cell division and mating are permanently shut off at the $G_1$ phase or $G_0$ state to help ensure biosafety.

Figure 3A:
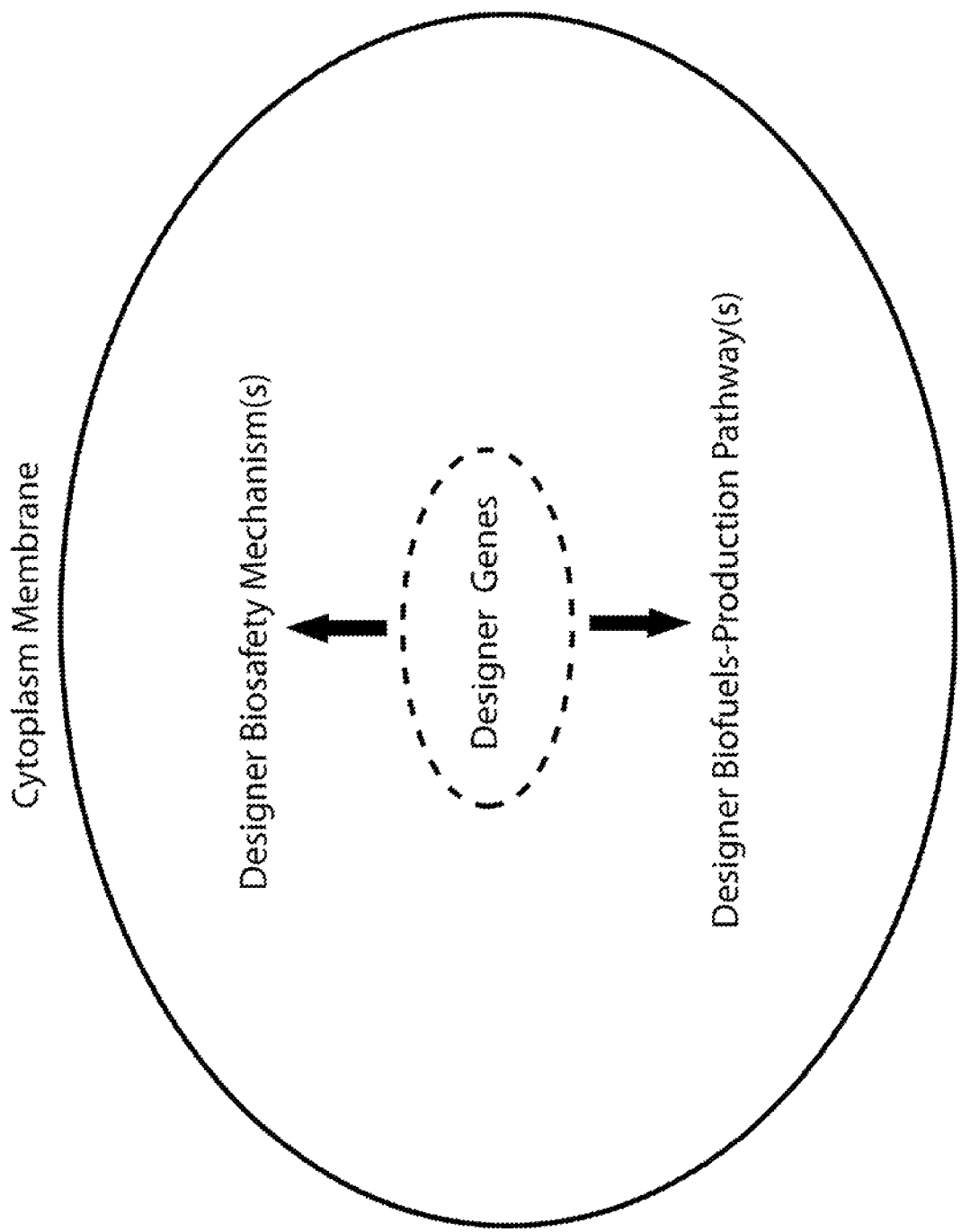
FIG. 3A illustrates a cell-division-controllable designer organism that contains two key functions: designer biosafety mechanism(s) and designer biofuel-production pathway(s).
Figure 3B:
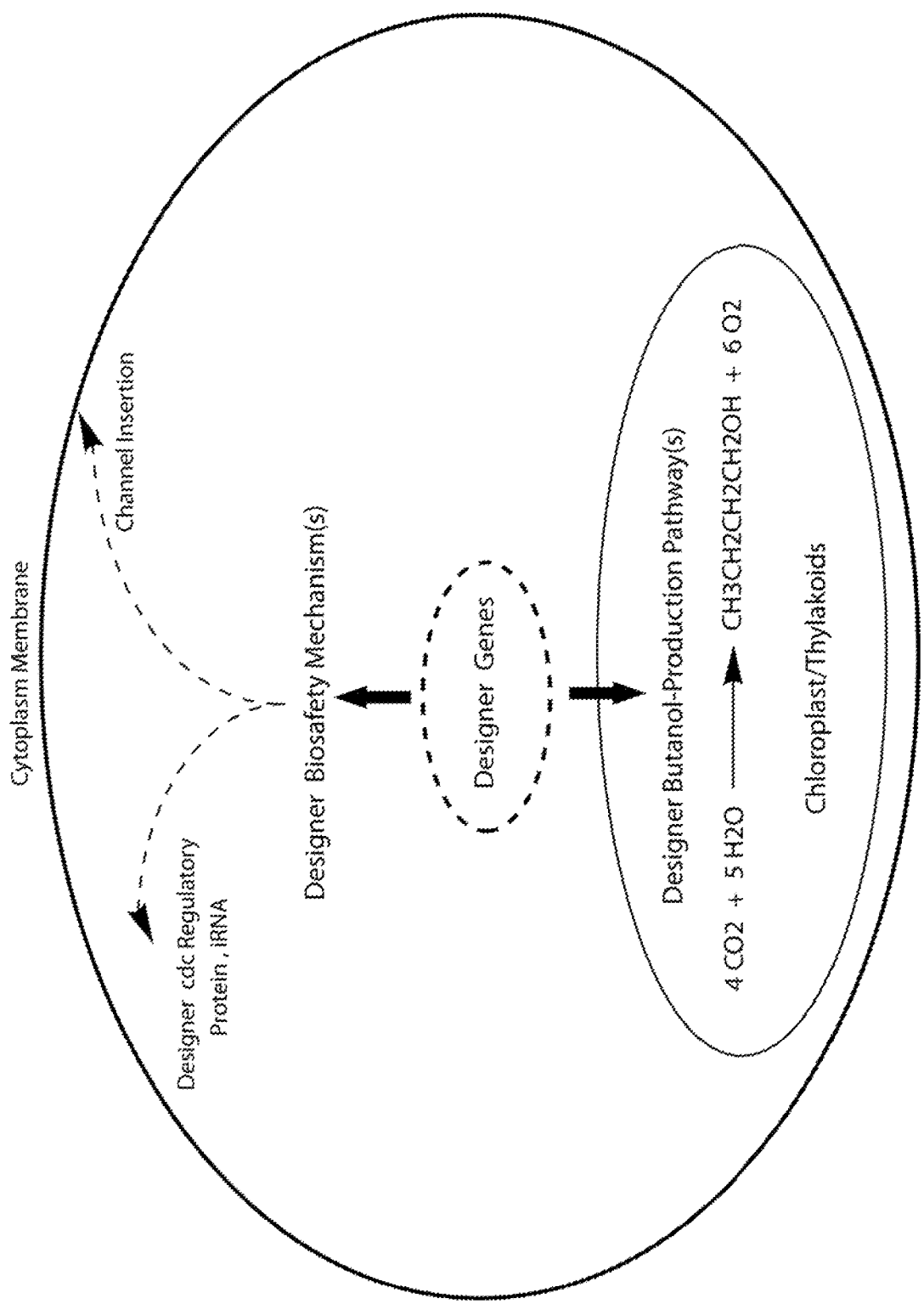
FIG. 3B illustrates a cell-division-controllable designer organism for photobiological production of butanol ($CH_3CH_2CH_2CH_2OH$) from carbon dioxide ($CO_2$) and water ($H_2O$) with designer biosafety mechanism(s).
Figure 3C:
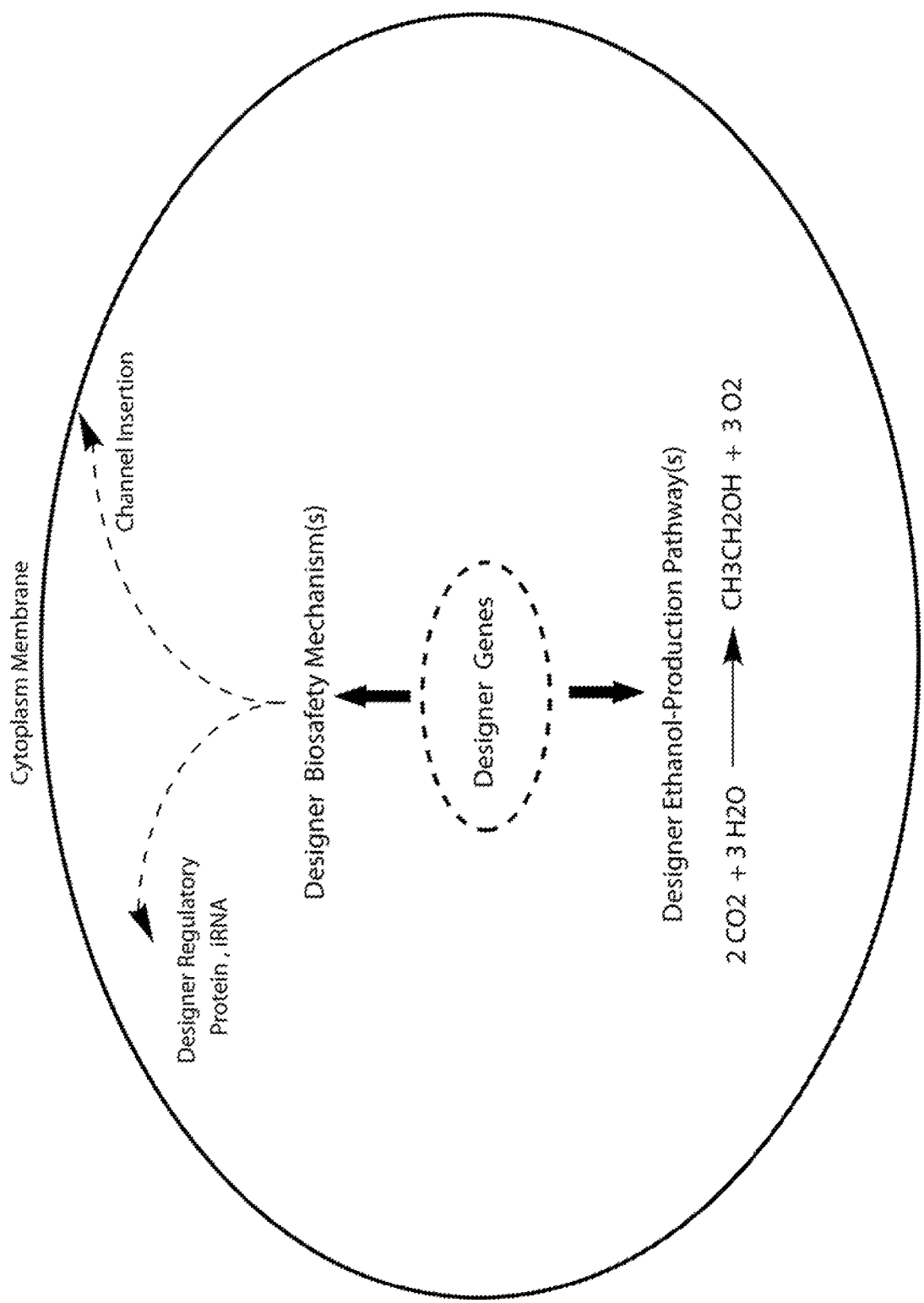
FIG. 3C illustrates a cell-division-controllable designer organism for biosafety-guarded photobiological production of other biofuels such as ethanol ($CH_3CH_2OH$) from carbon dioxide ($CO_2$) and water ($H_2O$).

Use of the biosafety embodiments with various designer biofuel-production-pathways genes listed in SEQ ID: 1-45 can create various biosafety-guarded photobiological biofuel producers (FIGS. 3A, 3B, and 3C). Note, SEQ ID NO: 46 and 1-12 (examples 1-12) represent an example for a cell-division-controllable designer eukaryotic organism such as a cell-division-controllable designer alga (e.g., *Chlamydomonas*) that contains a designer Nia1-promoter-controlled proton-channel gene (SEQ ID NO: 46) and a set of designer Nia1-promoter-controlled butanol-production-pathway genes (SEQ ID NO: 1-12). Because the designer proton-channel gene and the designer biofuel-production-pathway gene(s) are all controlled by the same Nia1-promoter sequences, they can be simultaneously expressed upon induction by adding nitrate fertilizer into the culture medium to provide the biosafety-guarded photosynthetic biofuel-producing capability as illustrated in FIG. 3B. Use of the designer Nia1-promoter-controlled butanol-production-pathway genes (SEQ ID NO: 1-12) in a high-$CO_2$-requiring host photosynthetic organism, such as *Chlamydomonas reinhardtii* carbonic-anhydrase-deficient mutant12-1C (CC-1219 cal mt-) or *Chlamydomonas reinhardtii* cia3 mutant, represents another example in creating a designer cell-division-controllable photosynthetic organism to help ensure biosafety.

This designer biosafety feature may be useful to the production of other biofuels such as biooils, biohydrogen, ethanol, and intermediate products as well. For example, this biosafety embodiment in combination with a set of designer ethanol-production-pathway genes such as those shown SEQ ID NO: 47-53 can represent a cell-division-controllable ethanol producer (FIG. 3C). Briefly, SEQ ID NO: 47 presents example 47 for a detailed DNA construct (1360 base pairs (bp)) of a nirA-promoter-controlled designer NAD-dependent Glyceraldehyde-3-Phosphate-Dehydrogenase gene including: a PCR FD primer (sequence 1-20), a 88-bp nirA promoter (21-108) selected from the *Synechococcus* sp. strain PCC 7942 (freshwater cyanobacterium) nitrite-reductase-gene promoter sequence, an enzyme-encoding sequence (109-1032) selected and modified from a *Cyanidium caldarium* cytosolic NAD-dependent glyceraldehyde-3-phosphate-dehydrogenase sequence (GenBank accession number: CAC85917), a 308-bp *Synechococcus* sp. strain PCC 7942 rbcS terminator (1033-1340), and a PCR RE primer (1341-1360) at the 3' end.

SEQ ID NO: 48 presents example 48 for a designer nirA-promoter-controlled Phosphoglycerate Kinase DNA construct (1621 bp) that includes a PCR FD primer (sequence 1-20), a 88-bp *Synechococcus* sp. strain PCC 7942 nitrite-reductase nirA promoter (21-108), a phosphoglycerate-kinase-encoding sequence (109-1293) selected from a *Geobacillus kaustophilus* HTA426 phosphoglycerate-kinase sequence (GenBank: BAD77342), a 308-bp *Synechococcus* sp. strain PCC 7942 rbcS terminator (1294-1601), and a PCR RE primer (1602-1621).

SEQ ID NO: 49 presents example 49 for a designer nirA-promoter-controlled Phosphoglycerate-Mutase DNA construct (1990 bp) that includes a PCR FD primer (sequence 1-20), a 88-bp *Synechococcus* sp. strain PCC 7942 nitrite-reductase nirA promoter (21-108), a 9-bp Xho I NdeI site (109-117), a phosphoglycerate-mutase encoding sequence (118-1653) selected from the sequences of a *Caldicellulosiruptor saccharolyticus* DSM 8903 phosphoglycerate mutase (GenBank: ABP67536), a 9-bp XbaI site (1654-1662), a 308-bp *Synechococcus* sp. strain PCC 7942 rbcS terminator (1663-1970), and a PCR RE primer (1971-1990).

SEQ ID NO: 50 presents example 50 for a designer nirA-promoter-controlled Enolase DNA construct (1765 bp) that includes a PCR FD primer (sequence 1-20), a 88-bp *Synechococcus* sp. strain PCC 7942 nitrite reductase nirA promoter (21-108), a 9-bp Xho I NdeI site (109-117), an enolase-encoding sequence (118-1407) selected from the sequence of a *Cyanothece* sp. CCY0110 enolase (GenBank: ZP_01727912), a 21-bp Lumio-tag-encoding sequence (1408-1428), a 9-bp XbaI site (1429-1437) containing a stop codon, a 308-bp *Synechococcus* sp. strain PCC 7942 rbcS terminator (1438-1745), and a PCR RE primer (1746-1765) at the 3' end.

SEQ ID NO: 51 presents example 51 for a designer nirA-promoter-controlled Pyruvate Kinase DNA construct (1888 bp) that includes a PCR FD primer (sequence 1-20), a 88-bp *Synechococcus* sp. strain PCC 7942 nitrite reductase nirA promoter (21-108), a 9-bp Xho I NdeI site (109-117), a Pyruvate-Kinase-encoding sequence (118-1530) selected from a *Selenomonas ruminantium* Pyruvate Kinase sequence (GenBank: AB037182), a 21-bp Lumio-tag sequence (1531-1551), a 9-bp XbaI site (1552-1560), a 308-bp *Synechococcus* sp. strain PCC 7942 rbcS terminator (1561-1868), and a PCR RE primer (1869-1888).

SEQ ID NO: 52 presents example 52 for a designer nirA-promoter-controlled Pyruvate Decarboxylase DNA construct (2188 bp) that includes a PCR FD primer (sequence 1-20), a 88-bp *Synechococcus* sp. strain PCC 7942 nitrite reductase nirA promoter (21-108), a 9-bp Xho I NdeI site (109-117), a Pyruvate-Decarboxylase-encoding sequence (118-1830) selected from the sequences of a *Pichia stipitis* pyruvate-decarboxylase sequence (GenBank: XM_001387668), a 21-bp Lumio-tag sequence (1831-1851), a 9-bp XbaI site (1852-1860), a 308-bp *Synechococcus* sp. strain PCC 7942 rbcS terminator (1861-2168), and a PCR RE primer (2169-2188) at the 3' end.

SEQ ID NO: 53 presents example 53 for a nirA-promoter-controlled designer NAD(P)H-dependent Alcohol Dehydrogenase DNA construct (1510 bp) that includes a PCR FD primer (sequence 1-20), a 88-bp *Synechococcus* sp. strain PCC 7942 nitrite-reductase nirA promoter (21-108), a NAD(P)H dependent Alcohol-Dehydrogenase-encoding sequence (109-1161) selected/modified (its mitochondrial signal peptide sequence removed) from the sequence of a *Kluyveromyces lactis* alcohol dehydrogenase (ADH3) gene (GenBank: X62766), a 21-bp Lumio-tag sequence (1162-1182), a 308-bp *Synechococcus* sp. strain PCC 7942 rbcS terminator (1183-1490), and a PCR RE primer (1491-1510) at the 3' end.

Note, SEQ ID NO: 47-53 (DNA-construct examples 47-53) represent a set of designer nirA-promoter-controlled ethanol-production-pathway genes that can be used in oxyphotobacteria such as *Synechococcus* sp. strain PCC 7942. Use of this set of designer ethanol-production-pathway genes in a high-$CO_2$-requiring cyanobacterium such as the *Synechococcus* sp. Strain PCC 7942 mutant M3 represents another example of cell-division-controllable designer cyanobacterium for biosafety-guarded photosynthetic production of biofuels from $CO_2$ and $H_2O$.

Use of Designer Butanol-Producing Organisms with Photobioreactor-Butanol-Harvesting Processes The various embodiments further teach how the designer organisms including the designer cell-division-controllable organisms (FIG. 3) may be used with a photobioreactor and a butanol-separation-harvesting process for photosynthetic production of butanol ($CH_3CH_2CH_2CH_2OH$) and $O_2$ directly from $CO_2$ and $H_2O$ using sunlight. There are a number of embodiments on how the designer organisms may be used for photobiological butanol production. One of the preferred embodiments is to use the designer organisms for direct photosynthetic butanol production from $CO_2$ and $H_2O$ with a photobiological reactor and butanol-harvesting (filtration and distillation/evaporation) system, which includes a specific operational process described as a series of the following steps: a) Growing a designer transgenic organism photoautotrophically in minimal culture medium using air $CO_2$ as the carbon source under aerobic (normal) conditions before inducing the expression of the designer butanol-production-pathway genes; b) When the designer organism culture is grown and ready for butanol production, sealing or placing the culture into a specific condition, such as an anaerobic condition that can be generated by removal of $O_2$ from the photobiological reactor, to induce the expression of designer butanol-production genes; c) When the designer butanol-production-pathway enzymes are expressed, supplying visible light energy such as sunlight for the designer-genes-expressed cells to work as the catalysts for photosynthetic butanol production from $CO_2$ and $H_2O$; d) Harvesting the product butanol by any method known to those skilled in the art. For example, harvesting the butanol product from the photobiological reactor by a combination of membrane filtration and distillation/evaporation butanol-harvesting techniques and flexibly collecting the $O_2$ gas product from the reactor.

The above process to use the designer organisms for photosynthetic $CH_3CH_2CH_2CH_2OH$ and $O_2$ production from $CO_2$ and $H_2O$ with a biological reactor and butanol-harvesting and gas product separation and collection system can be repeated for a plurality of operational cycles to achieve more desirable results. Any of the steps a) through d) of this process described above can also be adjusted in accordance of the invention to suit for certain specific conditions. In practice, any of the steps a) through d) of the process can be applied in full or in part, and/or in any adjusted combination as well for enhanced photobiological butanol production in accordance of this invention.

The sources of $CO_2$ that can be used in this process include, but not limited to, industrial $CO_2$, (bi)carbonates, and atmospheric $CO_2$. For an example, flue-gas $CO_2$ from fossil fuel-fired and/or biomass-fired industrial facilities can be fed through a pipeline into a photobiological reactor in this process. The industrial facilities that can generate $CO_2$ supplies for the designer photosynthetic butanol-production process include (but not limited to): coal-fired power plants, iron and steelmaking industries, cement-manufacturing plants, petroleum refinery facilities, chemical fertilizer production factories, biomass-fired and/or fossil fuel-fired biofuels (or intermediate products) distillation/separation facilities, biomass-pyrolysis processes, smokestacks, fermentation bioreactors, biofuel-refinery facilities, and combinations thereof.

Alternatively, this designer photobiological butanol-production process can also use the $CO_2$ in the environment and from the atmosphere as well. Gaseous $CO_2$, dissolved $CO_2$, bicarbonate, and carbonates can all be used by the designer-organism photobiological butanol-production technology.

This embodiment is illustrated in more details here using designer algae as an example. As described above, designer algae of the present invention, such as the one that contains a set of designer HydA1 promoter-controlled designer butanol-production-pathway genes (for examples, the DNA constructs of SEQ ID NO: 13-16 (or 17) and 18-23), can grow normally under aerobic conditions by autotrophic photosynthesis using air $CO_2$ in a manner similar to that of a wild-type alga. The designer algae can grow also photoheterotrophically using an organic substrate as well.

In a preferred embodiment, a designer alga is grown photoautotrophically using air $CO_2$ as the carbon source under the aerobic conditions in a minimal medium that contains the essential mineral (inorganic) nutrients. No organic substrate such as acetate is required to grow a designer alga under the normal conditions before the designer photosynthetic butanol-production-pathway genes are expressed. Most of the algae can grow rapidly in water through autotrophic photosynthesis using air $CO_2$ as long as there are sufficient mineral nutrients. The nutrient elements that are commonly required for algal growth are: N, P, and K at the concentrations of about 1-10 mM, and Mg, Ca, S, and Cl at the concentrations of about 0.5 to 1.0 mM, plus some trace elements Mn, Fe, Cu, Zn, B, Co, Mo among others at μM concentration levels. All of the mineral nutrients can be supplied in an aqueous minimal medium that can be made with well-established recipes of algal culture media using water (freshwater for the designer freshwater algae; seawater for the salt-tolerant designer marine algae) and relatively small of inexpensive fertilizers and mineral salts such as ammonium bicarbonate ($NH_4HCO_3$) (or ammonium nitrate, urea, ammonium chloride), potassium phosphates ($K_2HPO_4$ and $KH_2PO_4$), magnesium sulfate heptahydrate ($MgSO_4.7H_2O$), calcium chloride ($CaCl_2$), zinc sulfate heptahydrate ($ZnSO_4.7H_2O$), iron (II) sulfate heptahydrate ($FeSO_4.7 H_2O$), and boric acid ($H_3BO_3$), among others. That is, large amounts of designer algae cells can be inexpensively grown in a short period of time because, under aerobic conditions such as in an open pond, the designer algae can photoautotrophically grow by themselves using air $CO_2$ as rapidly as their wild-type parental strains. This is a significant feature (benefit) of the invention that could provide a cost-effective solution in generation of photoactive biocatalysts (the designer photosynthetic butanol-producing algae) for renewable solar energy production.

When the algal culture is grown and ready for butanol production, the grown algal culture is sealed or placed into certain specific conditions, such as anaerobic conditions that can be generated by removal of $O_2$ from the sealed photobiological reactor, to induce the expression of the designer HydA1-promoter-controlled butanol-production-pathway genes. When the designer butanol-production-pathway enzymes are expressed, visible light energy such as sunlight is supplied for the designer-genes-expressing algal cells to work as the catalysts for photosynthetic butanol production from $CO_2$ and $H_2O$. When the designer genes are expressed, the algal cells can essentially become efficient and robust "green machines" that are perfect for photosynthetic production of butanol ($CH_3CH_2CH_2CH_2OH$) and $O_2$ from $CO_2$ and $H_2O$. The product butanol from the algal photobiological rector can be harvested by a combination of membrane filtration and distillation/evaporation butanol-harvesting techniques including (but not limited to) liquid/liquid extraction, gas stripping, membrane evaporation, pervaporation, and adsorption techniques (Durre, P. 1998 *Appl Microbiol Biotechnol* 49: 639-648; Qureshi, Hughes, Maddox, and Cotta 2005 *Bioprocess Biosyst Eng* 27: 215-222).

Photosynthetic production of $CH_3CH_2CH_2CH_2OH$ and $O_2$ directly from $CO_2$ and $H_2O$ in accordance with the present invention can, in principle, have high quantum yield. Theoretically, it requires only 48 photons to produce a $CH_3CH_2CH_2CH_2OH$ and $6O_2$ from water and carbon dioxide by this mechanism. The maximal theoretical sunlight-to-butanol energy efficiency by the process of direct photosynthetic butanol production from $CO_2$ and $H_2O$ is about 10%, which is the highest possible among all the biological approaches. Consequently, this approach has great potential when implemented properly with an algal reactor and butanol-oxygen-harvesting process.

The above process to use the designer algae for photosynthetic production of $CH_3CH_2CH_2CH_2OH$ and $O_2$ from $CO_2$ and $H_2O$ with an algal reactor and a butanol-harvesting and gas product separation and collection system can be repeated for a plurality of operational cycles to achieve more desirable results.

Another feature is that the designer switchable butanol-production organism provides the capability for repeated cycles of photoautotrophic culture growth under normal aerobic conditions with a manner similar to that of a wild type and efficient photobiological production of butanol (FIGS. 1 and 3) when the designer butanol-production pathway is switched on by an inducible promoter (such as hydrogenase promoter) at certain specific inducing conditions (such as under anaerobic conditions) in a bioreactor. For example, the switchable designer alga with designer hydrogenase promoter-controlled butanol-production genes contains normal mitochondria, which uses the reducing power (NADH) from organic reserves (and/or exogenous substrates, such as acetate) to power the cell immediately after its return to aerobic conditions. Therefore, when the algal cell is returned to aerobic conditions after its use under anaerobic conditions for production of butanol, the cell will stop producing butanol-production-pathway enzymes and start to restore its normal photoautotrophic capability by synthesizing normal functional chloroplast. Consequently, it is possible to use this type of genetically transformed organism for repeated cycles of photoautotrophic culture growth under normal aerobic conditions and efficient production of butanol under anaerobic conditions in an anaerobic reactor. That is, this photobiological butanol-production technology can be operated for a plurality of operational cycles by rejuvenating the used culture under aerobic conditions and recyclably using the rejuvenated algal culture under butanol-producing conditions to achieve more desirable results. Optionally, this photobiological butanol-production technology is operated continuously by circulating rejuvenated algal culture from an aerobic reactor into the anaerobic reactor while circulating the used algal culture from the anaerobic reactor (after its use for butanol production) into the aerobic reactor for rejuvenation by synthesizing normal functional chloroplasts through photosynthetic $CO_2$ fixation and photoautotrophic growth.

Some of the designer organisms could grow photoautotrophically even with the butanol-production pathway(s) switched on. Whether or how fast a designer organism could grow under the butanol-producing conditions may depend on its genetic background and how much of the Calvin cycle products are still available for cell growth after use by the designer butanol-production pathway(s). Designer organisms that can, under the butanol-producing conditions, maintain essential cellular functions with an appropriate growth rate can also be used for continuous photobiological production of $CH_3CH_2CH_2CH_2OH$ and $O_2$ from $CO_2$ and $H_2O$ with a bioreactor and butanol-harvesting process.

There are additional ways that the switchable designer organisms including the cell-division-controllable designer organisms (FIG. 3) can be used for biosafety-guarded photobiological production of biofuels. With use of the designer biosafety features described previously, for example, the used designer algal culture from a photobiological butanol-production reactor does not have to be circulated back to a culture-growth reactor. Instead, the used algal culture is taken out to be used as fertilizers or biomass feed stocks for other processing because the photoautotrophic growth of the switchable designer alga in a culture-growth reactor is capable of continuously supplying algal cells to a photobiological butanol-production reactor for the biofuel production. This embodiment is, especially, helpful to using some of the designer organisms that can grow photoautotrophically only before but not after the butanol-production-pathway(s) is switched on. For example, by keeping a continuously growing culture of a designer alga (that can grow photoautotrophically only before the butanol-production-pathway(s) is switched on) in a culture-growth reactor, it can provide continuous supplies of grown algal cells for use in a photobiological butanol-production reactor. This approach makes it possible to use those designer organisms that can grow only before the butanol-production-pathway(s) is switched on for photobiological butanol production as well.

Because of various reasons, some of the designer butanol-production organisms could grow only photohetrotrophically or photomixotrophically but not photoautotrophically. Use of a culture-growth reactor can also grow this type of designer butanol-production organisms photohetrotrophically or photomixotrophically using organic substrates including, but not limited to, sucrose, glucose, acetate, ethanol, methanol, propanol, butanol, acetone, starch, hemicellulose, cellulose, lipids, proteins, organic acids, biomass materials and combination thereof. The so-grown culture can also be supplied to a photobiological butanol-production reactor for induction of the designer pathways for butanol production. This modified embodiment on culture growth makes it possible to use those designer organisms that can grow only photohetrotrophically, or photomixotrophically also for photobiological butanol production as well.

For certain specific designer organisms with designer nitrate reductase (Nia1) promoter-controlled butanol-production-pathway genes, the above photobiological reactor process may be further adjusted to achieve more beneficial results. For example, both a designer alga that contains Nia1 (or nirA) promoter-controlled butanol-production-pathway genes such as the ones shown in DNA sequence design examples 1-12 (SEQ ID NO: 1-12) and a designer oxyphotobacterium that carries designer nirA promoter-controlled butanol-production-pathway genes shown in SEQ ID NO: 34-45, can grow normally in a culture medium with ammonium (but no nitrate) by autotrophic photosynthesis using air $CO_2$ in a manner similar to that of a wild-type alga. This is because the expression of the butanol-production-pathway genes in the designer organism will be turned on only in the presence of nitrate as desired owning to the use of a nitrate reductase (Nia1) promoter or a nitrite reductase (nirA) promoter in controlling the designer pathway(s) expression. A significant feature of the designer organisms with nirA or Nia1 promoter-controlled butanol-production-pathway genes is that the expression of the designer butanol-production pathways can be induced by manipulating the concentration levels of nitrate ($NO_3^-$) relative to that of ammonium ($NH_4^+$) in the culture medium without requiring any anaerobic conditions. That is, the expression of the designer butanol-production pathway(s) can be induced under both aerobic and anaerobic conditions. This enables the designer photobiological butanol-production process to operate even under aerobic conditions using atmospheric $CO_2$. Likewise, this type of designer organisms with Nia1 promoter-controlled butanol-production-pathway genes can grow photoautotrophically both under aerobic and anaerobic conditions as well. Therefore, as a further embodiment, the operational process of using designer organism with nitrate reductase (Nia1) promoter-controlled butanol-production-pathway genes is adjusted to the following: a) Growing a designer transgenic organism photoautotrophically in minimal culture medium in the presence of ammonium ($NH_4^+$) but no nitrate ($NO_3^-$) before inducing the expression of the designer butanol-production-pathway genes; b) When the designer organism culture is grown and ready for butanol production, adding nitrate ($NO_3^-$) fertilizer into the culture medium to raise the concentration of nitrate ($NO_3^-$) relative to that of ammonium ($NH_4^+$) to induce the expression of designer butanol-production-pathway genes; c) When the designer butanol-production-pathway enzymes are expressed, supplying visible light energy such as sunlight for the designer-genes-expressed cells to work as the catalysts for photosynthetic butanol production from $CO_2$ and $H_2O$; d) Harvesting the butanol product from the photobiological reactor by a combination of membrane filtration and butanol-harvesting techniques.

In addition to butanol production, it is also possible to use a designer organism or part of its designer butanol-production pathway(s) to produce certain intermediate products including: butyraldehyde, butyryl-CoA, crotonyl-CoA, 3-hydroxybutyryl-CoA, acetoacetyl-CoA, acetyl-CoA, pyruvate, phosphoenolpyruvate, 2-phosphoglycerate, 1,3-diphosphoglycerate, glyceraldehye-3-phosphate, dihydroxyacetone phosphate, fructose-1,6-diphosphate, fructose-6-phosphate, glucose-6-phosphate, glucose, and glucose-1-phosphate. Therefore, a further embodiment comprises an additional step of harvesting the intermediate products that can be produced also from an induced transgenic designer organism. The production of an intermediate product can be selectively enhanced by switching off a designer-enzyme activity that catalyzes its consumption in the designer pathways. The production of a said intermediate product can be enhanced also by using a designer organism with one or some of designer enzymes omitted from the designer butanol-production pathways. For example, a designer organism with the butanol dehydrogenase or butyraldehyde dehydrogenase omitted from the designer pathway(s) of FIG. 1 may be used to produce butyraldehyde or butyryl-CoA, respectively.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A method for photobiological production of butanol comprising:
    obtaining a transgenic photosynthetic organism comprising transgenes coding for a set of enzymes that operate within the Calvin cycle and in conjunction with Calvin cycle enzymes to convert a certain intermediate product of the Calvin cycle selected from the group consisting of glyceraldehyde 3-phosphate, 3-phosphoglycerate, fructose-1,6-diphosphate, and fructose-6-phosphate, into butanol;
    using reducing power and energy associated with the transgenic photosynthetic organism acquired from photosynthetic water splitting and proton gradient coupled electron transport process to synthesize butanol; and
    using a butanol separation process to harvest the synthesized butanol.

2. The method of claim 1, wherein the transgenic photosynthetic organism comprises a transgenic photosynthetic plant or cell.

3. The method of claim 1, wherein the transgenic photosynthetic organism comprises *Chlamydomonas reinhardtii*.

4. The method of claim 1, wherein the intermediate product of the Calvin cycle comprises glyceraldehyde 3-phosphate and the set of enzymes comprises at least one of the enzymes selected from the group consisting of glyceraldehyde-3-phosphate dehydrogenase, phosphoglycerate kinase, phosphoglycerate mutase, enolase, pyruvate kinase, pyruvate-ferredoxin oxidoreductase (or pyruvate-NADP+ oxidoreductase), thiolase, 3-hydroxybutyryl-CoA dehydrogenase, crotonase, butyryl-CoA dehydrogenase, butyraldehyde dehydrogenase, butanol dehydrogenase, and combinations thereof.

5. The method of claim 1, wherein the intermediate product of the Calvin cycle comprises fructose-1,6-diphosphate and the set of enzymes comprises at least one of the enzymes selected from the group consisting of aldolase, triose phosphate isomerase, glyceraldehyde-3-phosphate dehydrogenase, phosphoglycerate kinase, phosphoglycerate mutase, enolase, pyruvate kinase, pyruvate-NADP+ oxidoreductase (or pyruvate-ferredoxin oxidoreductase), thiolase, 3-hydroxybutyryl-CoA dehydrogenase, crotonase, butyryl-CoA dehydrogenase, butyraldehyde dehydrogenase, butanol dehydrogenase, and combinations thereof.

6. The method of claim 1, wherein the intermediate product of the Calvin cycle comprises fructose-6-phosphate and the set of enzymes comprises phosphofructose kinase and at least one of the enzymes selected from the group consisting of aldolase, triose phosphate isomerase, glyceraldehyde-3-phosphate dehydrogenase, phosphoglycerate kinase, phosphoglycerate mutase, enolase, pyruvate kinase, pyruvate-NADP+ oxidoreductase (or pyruvate-ferredoxin oxidoreductase), thiolase, 3-hydroxybutyryl-CoA dehydrogenase, crotonase, butyryl-CoA dehydrogenase, butyraldehyde dehydrogenase, butanol dehydrogenase, and combinations thereof.

7. The method of claim 1, wherein the intermediate product of the Calvin cycle comprises 3-phosphoglycerate and the set of enzymes comprises at least one of the enzymes selected from the group consisting of phosphoglycerate mutase, enolase, pyruvate kinase, pyruvate-ferredoxin oxidoreductase, thiolase, 3-hydroxybutyryl-CoA dehydrogenase, crotonase, butyryl-CoA dehydrogenase, butyraldehyde dehydrogenase, butanol dehydrogenase and combinations thereof.

8. The method of claim 1, wherein:
    the method further comprises introducing the transgenic photosynthetic organism into a photobiological reactor system;
    using the butanol separation process further comprises using the butanol separation process to harvest the synthesized butanol from the photobiological reactor.

9. The method of claim 1, wherein the transgenic photosynthetic organism comprises *Synechococcus elongatus*.

10. The method of claim 1, wherein the transgenic photosynthetic organism comprises marine cyanobacteria or freshwater cyanobacteria.

* * * * *

SEQUENCE LISTING

<160> NUMBER OF SEQ ID NOS: 57

<210> SEQ ID NO 1
<211> LENGTH: 1809
<212> TYPE: DNA
<213> ORGANISM: Artificial Sequence
<220> FEATURE:
<223> OTHER INFORMATION: Synthetic Construct- Example 1: designer
      Butanol-Dehydrogenase DNA construct

<400> SEQUENCE: 1

```
agaaaatctg gcaccacacc tatatggtag ggtgcgagtg accccgcgcg acttggagct      60
cgatggcccc gggttgtttg gggcgtccgc ctctcgcgct attctgagct ggagaccgag     120
gcgcatgaaa atgcattcgc ttccatagga cgctgcattg tggcttgaag gttcaaggga     180
agggttcaaa cgaccccgcc gtacgaactt ttgtcggggg gcgctcccgg ccccgggctc     240
ttgtgcgcgc attagggctt cgggtcgcaa gcaagacgat acatggccgc cgtcattgcc     300
aagtcctccg tctccgcggc cgtggctcgc ccggcccgct ccagcgtgcg ccccatggcc     360
gcgctgaagc ccgccgtcaa ggctgccccc gtggctgccc cggctcaggc caaccagatg     420 gagaattta gatttaatgc atatacagag atgctttttg gaaagggaca aatagagaag     480
cttccagagg ttttaaaaag atatggtaaa aatatattac ttgcatatgg tggtggaagt     540 ataaaaaga atggactcta tgatactatc caaaagctat tgaaagattt taatattgtt     600
gaattaagtg gtattgaacc aaatccaaga attgaaactg taagacgtgg agttgaactt     660
tgcagaaaaa ataaagtaga tgttatttta gctgttggtg gagggagtac aatagactgc     720
tcaaaggtta taggggcagg ttattattat gctggagatg catgggacct tgtaaaaaat     780
ccagctaaaa taggtgaggt tttaccaata gtgacagttt taacaatggc agctactggt     840
tctgaaatga atagaaatgc tgttattttca aagatggata caaatgaaaa gcttggaaca     900
```

```
ggatcaccta agatgatccc tcaaacttct attttagatc cagaatattt gtatacattg      960
ccagcaattc aaacagctgc aggttgtgct gatattatgt cacacatatt tgaacaatat     1020
tttaataaaa ctacagatgc ttttgtacaa gataaatttg cggaaggttt gttgcaaact     1080
tgtataaaat attgccctgt tgctttaaag gaaccaaaga attatgaagc tagagcaaat     1140
ataatgtggg ctagttcaat ggctcttaac ggacttttag gaagtgggaa agctggagct     1200
tggacttgtc atccaataga acatgaatta agtgcatttt atgatataac tcatggagta     1260
ggtcttgcaa ttttaactcc aagttggatg agatatatct taagtgatgt aacagttgat     1320
aagtttgtta acgtatggca tttagaacaa aaagaagata aatttgctct tgcaaatgaa     1380
gcaatagatg caacagaaaa attctttaaa gcttgtggta ttccaatgac tttaactgaa     1440
cttggaatag ataaagcaaa ctttgaaaag atggcaaaag ctgcagtaga acatggtgct     1500
ttagaatatg catatgtttc attaaatgcc gaggatgtat ataaaatttt agaaatgtcc     1560
ctttaataaa tggaggcgct cgttgatctg agccttgccc cctgacgaac ggcggtggat     1620
ggaagatact gctctcaagt gctgaagcgg tagcttagct ccccgtttcg tgctgatcag     1680 tcttttcaa cacgtaaaaa gcggaggagt tttgcaattt tgttggttgt aacgatcctc      1740
cgttgatttt ggcctctttc tccatgggcg ggctgggcgt atttgaagcg ttctctcttc     1800
ctgccgtta                                                             1809

<210> SEQ ID NO 2
<211> LENGTH: 2067
<212> TYPE: DNA
<213> ORGANISM: Artificial Sequence
<220> FEATURE:
<223> OTHER INFORMATION: Synthetic Construct- Example 2: designer
      Butyraldehyde-Dehydrogenase DNA construct

<400> SEQUENCE: 2
agaaaatctg gcaccacacc tatatggtag ggtgcgagtg accccgcgcg acttggagct       60
cgatggcccc gggttgtttg gggcgtccgc ctctcgcgct attctgagct ggagaccgag      120
gcgcatgaaa atgcattcgc ttccatagga cgctgcattg tggcttgaag gttcaaggga      180
agggttcaaa cgaccccgcc gtacgaactt ttgtcggggg gcgctcccgg ccccgggctc      240
ttgtgcgcgc attagggctt cgggtcgcaa gcaagacgat acatggccgc cgtcattgcc      300
aagtcctccg tctccgcggc cgtggctcgc ccggcccgct ccagcgtgcg ccccatggcc      360
gcgctgaagc ccgccgtcaa ggctgccccc gtggctgccc cggctcaggc caaccagatg      420
attaaagaca cgctagtttc tataacaaaa gatttaaaat taaaaacaaa tgttgaaaat      480
gccaatctaa agaactacaa ggatgattct tcatgtttcg gagttttcga aaatgttgaa      540
aatgctataa gcaatgccgt acacgcacaa aagatattat cccttcatta tacaaaagaa      600
caaagagaaa aaatcataac tgagataaga aaggccgcat tagaaaataa agagattcta      660
gctacaatga ttcttgaaga acacacatat ggaagatatg aagataaaat attaaagcat      720
gaattagtag ctaaatacac tcctgggaca gaagatttaa ctactactgc ttggtcagga      780
gataacgggc ttcagttgt agaaatgtct ccatatggcg ttataggtgc ataactcct      840 tctacgaatc caactgaaac tgtaatatgt aatagtatag gcatgatagc tgctggaaat      900
actgtggtat taacggaca tccaggcgct aaaaaatgtg ttgcttttgc tgtcgaaatg      960
ataaataaag ctattatttc atgtggtggt cctgagaatt tagtaacaac tataaaaaat     1020
ccaactatgg actctctaga tgcaattatt aagcaccctt caataaaaact actttgcgga     1080
```

```
actggagggc caggaatggt aaaaaccctc ttaaattctg gtaagaaagc tataggtgct      1140
ggtgctggaa atccaccagt tattgtagat gatactgctg atatagaaaa ggctggtaag      1200
agtatcattg aaggctgttc ttttgataat aatttacctt gtattgcaga aaaagaagta      1260
tttgtttttg agaacgttgc agatgattta atatctaaca tgctaaaaaa taatgctgta      1320
attataaatg aagatcaagt atcaaagtta atagatttag tattacaaaa aaataatgaa      1380
actcaagaat actctataaa taagaaatgg gtcggaaaag atgcaaaatt attcttagat      1440
gaaatagatg ttgagtctcc ttcaagtgtt aaatgcataa tctgcgaagt aagtgcaagg      1500
catccatttg ttatgacaga actcatgatg ccaatattac caattgtaag agttaaagat      1560
atagatgaag ctattgaata tgcaaaaata gcagaacaaa atagaaaaca tagtgcctat      1620
atttattcaa aaaatataga caacctaaat aggtttgaaa gagaaatcga tactactatc      1680
tttgtaaaga atgctaaatc ttttgccggt gttggttatg aagcagaagg ctttacaact      1740
ttcactattg ctggatccac tggtgaagga ataacttctg caagaaattt tacaagacaa      1800
agaagatgtg tactcgccgg ttaataaatg gaggcgctcg ttgatctgag ccttgcccc       1860 tgacgaacgg cggtggatgg aagatactgc tctcaagtgc tgaagcggta gcttagctcc      1920
ccgtttcgtg ctgatcagtc ttttcaaca cgtaaaaagc ggaggagttt tgcaattttg       1980
ttggttgtaa cgatcctccg ttgattttgg cctctttctc catgggcggg ctgggcgtat      2040
ttgaagcggt tctctcttct gccgtta                                         2067

<210> SEQ ID NO 3
<211> LENGTH: 1815
<212> TYPE: DNA
<213> ORGANISM: Artificial Sequence
<220> FEATURE:
<223> OTHER INFORMATION: Synthetic Construct- Example 3: designer
      Butyryl-CoA-Dehydrogenase DNA construct

<400> SEQUENCE: 3
agaaaatctg gcaccacacc tatatggtag ggtgcgagtg accccgcgcg acttggagct        60
cgatggcccc gggttgtttg gggcgtccgc ctctcgcgct attctgagct ggagaccgag       120
gcgcatgaaa atgcattcgc ttccatagga cgctgcattg tggcttgaag gttcaaggga       180
agggttcaaa cgaccccgcc gtacgaactt ttgtcggggg gcgctcccgg ccccgggctc       240
ttgtgcgcgc attagggctt cgggtcgcaa gcaagacgat acctcgagca tatggccgcc       300
gtcattgcca gtcctccgt ctccgcggcc gtggctcgcc cggcccgctc cagcgtgcgc        360
cccatggccg cgctgaagcc cgccgtcaag gctgccccg tggctgcccc ggctcaggcc        420
aaccagatga atttccaatt aactagagaa caacaattag tacaacaaat ggttagagaa       480
ttcgcagtaa atgaagttaa gccaatagct gctgaaatcg acgaaacaga aagattccct       540
atggaaaacg ttgaaaaaat ggctaagctt aaaatgatgg gtatcccatt ttctaaagaa       600
tttggtggag caggcggaga tgttcttttca tatataatag ctgtggaaga attatcaaaa       660
gtttgtggta ctacaggagt tattctttca gcgcatacat cattatgtgc atcagtaatt       720
aatgaaaatg gaactaacga acaaagagca aaatatttac ctgatctttg cagcggtaaa       780
aagatcggtg ctttcggatt aactgaacca ggtgctggta cagatgctgc aggacaacaa       840
acaactgctg tattagaagg ggatcattat gtattaaatg gttcaaaaat cttcataaca       900
aatggtggag ttgctgaaac tttcataata tttgctatga cagataagag tcaaggaaca       960
aaaggaattt ctgcattcat agtagaaaag tcattcccag gattctcaat aggaaaatta      1020
```

```
gaaaataaga tgggatcag agcatcttca actactgagt tagttatgga aaactgcata      1080
gtaccaaaag aaaacctact tagcaaagaa ggtaagggat ttggtatagc aatgaaaact      1140
cttgatggag gaagaattgg tatagctgct caagctttag gtattgcaga aggagctttt      1200
gaagaagctg ttaactatat gaagaaaaga aaacaatttg gtaaaccatt atcagcattc      1260
caaggattac aatggtatat agctgaaatg gatgttaaaa tccaagctgc taaatactta      1320
gtatacctag ctgcaacaaa gaagcaagct ggtgagcctt actcagtaga tgctgcaaga      1380
gctaaattat ttgctgcaga tgttgcaatg gaagttacaa ctaaagcagt tcaaatcttt      1440
ggtggatatg gttacactaa agaatacccca gtagaaagaa tgatgagaga tgctaaaata      1500
tgcgaaatct acgaaggaac ttcagaagtt caaaagatgg ttatcgcagg aagcatttta      1560
agataatcta gataaatgga ggcgctcgtt gatctgagcc ttgcccccctg acgaacggcg      1620 gtggatggaa gatactgctc tcaagtgctg aagcggtagc ttagctcccc gtttcgtgct      1680
gatcagtctt tttcaacacg taaaagcgg aggagttttg caattttgtt ggttgtaacg      1740
atcctccgtt gattttggcc tctttctcca tgggcgggct gggcgtattt gaagcggttc      1800
tctcttctgc cgtta                                                       1815

<210> SEQ ID NO 4
<211> LENGTH: 1482
<212> TYPE: DNA
<213> ORGANISM: Artificial Sequence
<220> FEATURE:
<223> OTHER INFORMATION: Synthetic Construct- Example 4: designer
      Crotonase DNA construct

<400> SEQUENCE: 4
agaaaatctg gcaccacacc tatatggtag ggtgcgagtg accccgcgcg acttggagct        60
cgatggcccc gggttgtttg gggcgtccgc ctctcgcgct attctgagct ggagaccgag       120
gcgcatgaaa atgcattcgc ttccatagga cgctgcattg tggcttgaag gttcaaggga       180
agggttcaaa cgaccccgcc gtacgaactt ttgtcggggg gcgctcccgg ccccgggctc       240
ttgtgcgcgc attagggctt cgggtcgcaa gcaagacgat acctcgagca tatggccgcc       300
gtcattgcca agtcctccgt ctccgcggcc gtggctcgcc cggcccgctc cagcgtgcgc       360
cccatggccg cgctgaagcc cgccgtcaag gctgcccccg tggctgcccc ggctcaggcc       420
aaccagatgg aattaaaaaa tgttattctt gaaaagaag gcatttagc tattgttaca       480 atcaatagac caaaggcatt aaatgcattg aattcagaaa cactaaaaga tttaaatgtt       540
gttttagatg atttagaagc agacaacaat gtgtatgcag ttatagttac tggtgctggt       600
gagaaatctt tgttgctgg agcagatatt tcagaaatga agatcttaa tgaagaacaa       660 ggtaaagaat ttggtatttt taggaaataat gtcttcagaa gattagaaaa attggataag       720
ccagttatcg cagctatatc aggatttgct cttggtggtg atgtgaact tgctatgtca       780 tgtgacataa gaatagcttc agttaaagct aaatttggtc aaccagaagc aggacttgga       840
ataactccag gatttggtgg aactcaaaga ttagcaagaa tagttggacc aggaaaagct       900
aaagaattaa tttatacttg tgaccttata atgcagaaga agcttatag aataggctta       960 gttaataaag tagttgaatt agaaaaattg atggaagaag caaaagcaat ggctaacaag      1020
attgcagcta atgctccaaa agcagttgca tattgtaaag atgctataga cagaggaatg      1080
caagttgata tagatgcagc tatattaata gaagcagaag actttgggaa gtgctttgca      1140
acagaagatc aaacagaagg aatgactgcg ttcttagaaa gaagagcaga aaagaatttt      1200
```

```
caaaataaag gctgctgccc cggctgctgc taatctagat aaatggaggc gctcgttgat    1260
ctgagccttg ccccctgacg aacggcggtg gatggaagat actgctctca agtgctgaag    1320
cggtagctta gctccccgtt tcgtgctgat cagtcttttt caacacgtaa aaagcggagg    1380
agttttgcaa ttttgttggt tgtaacgatc ctccgttgat tttggcctct ttctccatgg    1440
gcgggctggg cgtatttgaa gcggttctct cttctgccgt ta                      1482
```

<210> SEQ ID NO 5
<211> LENGTH: 1367
<212> TYPE: DNA
<213> ORGANISM: Artificial Sequence
<220> FEATURE:
<223> OTHER INFORMATION: Synthetic Construct- Example 5: designer
      3-Hydroxybutyryl-CoA-Dehydrogenase DNA construct

<400> SEQUENCE: 5

```
agaaaatctg gcaccacacc atggtagggt gcgagtgacc ccgcgcgact tggaagggtt     60
caaacgaccc cgccgtacga acttttgtcg ggggcgctc ccggctcgag catatggccg    120
ccgtcattgc caagtcctcc gtctccgcgg ccgtggctcg cccggcccgc tccagcgtgc    180
gccccatggc cgcgctgaag cccgccgtca aggctgcccc cgtggctgcc ccggctcagg    240
ccaaccagat gaaaaagatt tttgtacttg gagcaggaac tatgggtgct ggtatcgttc    300
aagcattcgc tcaaaaaggt tgtgaggtaa ttgtaagaga cataaaggaa gaatttgttg    360
acagaggaat agctggaatc actaaaggat tagaaaagca agttgctaaa ggaaaaatgt    420
ctgaagaaga taaagaagct atactttcaa gaatttcagg aacaactgat atgaagttag    480
ctgctgactg tgatttagta gttgaagctg caatcgaaaa catgaaaatt aagaaggaaa    540
tctttgctga gttagatgga atttgtaagc cagaagcgat tttagcttca aacacttcat    600
ctttatcaat tactgaagtt gcttcagcta caaagagacc tgataaagtt atcggaatgc    660
atttctttaa tccagctcca gtaatgaagc ttgttgaaat tattaaagga atagctactt    720
ctcaagaaac ttttgatgct gttaaggaat tatcagttgc tattggaaaa gaaccagtag    780
aagttgcaga agctccagga ttcgttgtaa acggaatctt aatcccaatg attaacgaag    840
cttcattcat ccttcaagaa ggaatagctt cagttgaaga tattgataca gctatgaaat    900
atggtgctaa ccatccaatg ggaccttag ctttaggaga tcttattgga ttagatgttt    960
gcttagctat catggatgtt ttattcactg aaacaggtga taacaagtac agagctagca   1020
gcatattaag aaaatatgtt agagctggat ggcttggaag aaaatcagga aaaggattct   1080
atgattattc taaaggctgc tgccccggct gctgctaatc tagataaatg gaggcgctcg   1140
ttgatctgag ccttgccccc tgacgaacg cggtggatgg aagatactgc tctcaagtgc   1200
tgaagcggta gcttagctcc ccgtttcgtg ctgatcagtc tttttcaaca cgtaaaaagc   1260
ggaggagttt tgcaattttg ttggttgtaa cgatcctccg ttgatttggg cctctttctc   1320
catgggcggg ctgggcgtat ttgaagcggt tctctcttct gccgtta              1367
```

<210> SEQ ID NO 6
<211> LENGTH: 1721
<212> TYPE: DNA
<213> ORGANISM: Artificial Sequence
<220> FEATURE:
<223> OTHER INFORMATION: Synthetic Construct- Example 6: designer
      Thiolase DNA construct

<400> SEQUENCE: 6

```
agaaaatctg gcaccacacc atggtagggt gcgagtgacc ccgcgcgact tggaagggtt      60
caaacgaccc cgccgtacga acttttgtcg ggggcgctc ccggctcgag catatggccg      120
ccgtcattgc caagtcctcc gtctccgcgg ccgtggctcg cccggcccgc tccagcgtgc     180
gccccatggc cgcgctgaag cccgccgtca aggctgcccc cgtggctgcc ccggctcagg     240
ccaaccagat gggcaaagaa agtagtttta gctgtgcatg tcgtacagcc atcggaacaa     300
tgggtggatc tcttagcaca attcctgcag tagatttagg tgctatcgtt atcaaagagg     360
ctcttaaccg cgcaggtgtt aaacctgaag atgttgatca cgtatacatg ggatgcgtta     420
ttcaggcagg acagggacag aacgttgctc gtcaggcttc tatcaaggct ggtcttcctg     480
tagaagtacc tgcagttaca actaacgttg tatgtggttc aggtcttaac tgtgttaacc     540
aggcagctca gatgatcatg gctggagatg ctgatatcgt tgttgccggt ggtatggaaa     600
acatgtcact tgcaccattt gcacttccta atggccgtta cggatatcgt atgatgtggc     660
caagccagag ccagggtggt cttgtagaca ctatggttaa ggatgctctt tgggatgctt     720
tcaatgatta tcatatgatc cagacagcag acaacatctg cacagagtgg ggtcttacac     780
gtgaagagct cgatgagttt gcagctaaga gccagaacaa ggcttgtgca gcaatcgaag     840
ctggcgcatt caaggatgag atcgttcctg tagagatcaa gaagaagaaa gagacagtta     900
tcttcgatac agatgaaggc ccaagacagg gtgttacacc tgaatctctt tcaaagcttc     960
gtcctatcaa caaggatgga ttcgttacag ctggtaacgc ttcaggtatc aacgacggtg    1020
ctgcagcact cgtagttatg tctgaagaga aggctaagga gctcggcgtt aagcctatgg    1080
ctacattcgt agctggagca cttgctggtg ttcgtcctga agttatgggt atcggtcctg    1140
tagcagctac tcagaaggct atgaagaagg ctggtatcga aacgtatct gagttcgata    1200
tcatcgaggc taacgaagca ttcgcagctc agtctgtagc agttggtaag gatcttggaa    1260
tcgacgtcca caagcagctc aatcctaacg gtggtgctat cgctcttgga caccagttg     1320
gagcttcagg tgctcgtatc cttgttacac ttcttcacga gatgcagaag aaagacgcta    1380
agaagggtct tgctacactt tgcatcggtg gcggtatggg atgcgctact atcgttgaga    1440
agtacgaagg ctgctgcccc ggctgctgct aatctagata aatggaggcg ctcgttgatc    1500
tgagccttgc cccctgacga acggcggtgg atggaagata ctgctctcaa gtgctgaagc    1560
ggtagcttag ctccccgttt cgtgctgatc agtcttttc aacacgtaaa aagcggagga    1620
gttttgcaat tttgttggtt gtaacgatcc tccgttgatt ttggcctctt tctccatggg    1680
cgggctgggc gtatttgaag cggttctctc ttctgccgtt a                        1721
```

<210> SEQ ID NO 7  
<211> LENGTH: 4211  
<212> TYPE: DNA  
<213> ORGANISM: Artificial Sequence  
<220> FEATURE:  
<223> OTHER INFORMATION: Synthetic Construct- Example 7: designer  
Pyruvate-Ferredoxin-Oxidoreductase DNA construct

<400> SEQUENCE: 7

```
agaaaatctg gcaccacacc atggtagggt gcgagtgacc ccgcgcgact tggaagggtt      60
caaacgaccc cgccgtacga acttttgtcg ggggcgctc ccggatggta gggtgcgagt     120
gaccccgcgc gacttggaag ggttcaaacg accccgccgt acgaactttt gtcgggggc     180
gctcccggct cgagcatatg gccgccgtca ttgccaagtc ctccgtctcc gcggccgtgg    240
ctcgcccggc ccgctccagc gtgcgcccca tggccgcgct gaagcccgcc gtcaaggctg    300
```

```
ccccgtggc tgccccggct caggccaacc agatggcgca gaggtgcaag gagcccgtcg      360
acggaacgac agccacgacg cacgtggcct acttcatgag cgacagcgcg ttcatcttcc     420
ccatcacgcc cagctcggtc atgtccgagg tcgcccacga gtggtccatg aacggccgca     480
agaacgcctt cggccagccc acgatggtcc gccagatgca gagcgaggct gggtctgccg     540
gcgccctgca cggcgcgctc agcgagggag cgctggcgac gacgttcacg agcagccagg     600
gcctgctgct catgatcccc aacatgtaca agatcgccgg cgagctcctg ccctgcgtca     660
tgcacatcgc cgcccgcacc gtcgccaccg aggccctctc tatcttcggc gaccacacgg     720
atgtctacgc ggtgaggtcg acggggttcg cgttcctgtg ctccgcgacc gtccaggagt     780
gcatccacat gtccgccgcc gcgcacgccg ccaccctgtc cagcgaggtc ccgttcgccc     840
acttcttcga cggcttccgc acgtcccacg agatccagaa gatcgacttc ccctcggacg     900
ccgacctgct ggcctgcatg aactttgacg acgtccgcag gttccgtggc cgctcgctgt     960
gctgcgagcg cccgctgctg cgcgggacgg cgcagaaccc cgacgtcttc atgcaggcgt     1020
ccgagtcgaa cctggcgacg ctggccaggg tccccgcggc catcgacgag gcgctggctc     1080
gtgtgaacaa ggtgttcggg accaactaca ggacctacga gtactatggc caccccgagg     1140
ccacggacgt gatcgtggcc atgggaagcg gcaccgaagt ggccatctcg actgccaact     1200
tcctcaactc gcgcgacgcg aactcgaggg tcggcgtcgt gagggtgcgg ctgttccggc     1260
cgtttgtgtc ggcggcgttt gtggctgcgc tgcccaagac cgtcaagagg atctgcgttc     1320
tggaccgcgg gagggacggg caggcggccg cggaccccct gcaccaggac gtcctgtcgg     1380
cgctgggtct ggcagcgccc ggagggttc aggtgtgcgt gggaggcgtg tacggtctgt     1440
cgtccaagga cttcaaccc gaccacgtga tcgccgtgta caggaacctc gcgtcggcga     1500
gccccaagaa caggttcagc gtcggcatcg tcgacgacgt gacgcacaac agcctggaca     1560
tgggagagca cgtggacgcg ctgccgcagg ggacgaagca gtgcctgctg tggggcatcg     1620
gcggagacgg gaccatcggg gcgaacaaga cggccatcaa gctgatcgcg gaccacacgg     1680
agctgcacgc gcaggggtac tttgcgtacg acgccaacaa ggccggcggc ctgacagtct     1740
cgcacctgcg gttcggcccg acgcggttcg aggcgccgta cctggtgaac gacagcaact     1800
acgtggcgtg ccacaacttc tcgtacgtgc acaggttcaa cctgctgtcg tcgctgcgca     1860 ccggggcac gttcgtgctc aactgcccgt gccggaccgt ggaggagctg acacggcac     1920 tcccggtgcg cctgaggcgc gagatcgcca ggcggcaggc caagttctat gtgatcgacg     1980
cgaccaagat cgccaaggac aacgggatgg ccccgttcat caacatggtc ctccaggccg     2040
tgttcttcta tctgtcccac gtgctcgatg tgaacgaggc agtggcactc ctgaagaaga     2100
gcatccagaa gatgtacgcg cgcaagggcg aggaggttgt caggaagaac gtggcatcgg     2160
tcgacgcgtc gctggatccc aaggcgttgc tgcacatcga gtaccccgca gacaggtggc     2220
ttgcgctggc cgacgagcac gtgccccgca tgggtctgct cactgtcccc gagcgcctgc     2280
agaagttcaa cgccgagctg tacgagccga ccctcgcgta cgatgggag agcatcccgg     2340 tcagcaggtt ccctcgcggc ggcgagacgc cgacgggcac gactcagctg ggcaagcgtg     2400
gcatcgccga gagcgtgccg cactggaacc acgagaagtg cgtgcagtgc aaccagtgct     2460
cgttcgtgtg cccgcacgcc gtcatccggt cgtaccagat cagcgaggag gagatgaaga     2520
acgcccctgc cggcttcgac actcttaagt cgcgcaagcc cgggtatcgt ttccgcatca     2580
acgtcagcgc cctggactgc actggctgca gcgtgtgcgt ggagcagtgc ccagtcaagt     2640
gcctggagat gaagcctctc gagtccgagt tcgagatgca gaaggacgcc atcaggttcg     2700
```

```
tccgcgagat ggtcgcgccc aagcccgagc tgggagaccg caagactccc gtcggcatcg    2760
cgtctcacac gccgctgttc gagttcccgg gagcctgcgc cgggtgcggt gagacccccgc   2820 tggtgcgcct cgtgacgcag atgttcggtg agcgcatggt catcgccgcg gccactgggt    2880
gcaactcgat ctggggagcg tcgttcccga acgtgccgta cacaaccaac gcccgcgggg    2940
agggccccgc gtggcacaac tcgctgttcg aggacgcggc ggagctcggg tatggcatta    3000
cgtgtgcgta tcgccagcgc cgcgagcgcc tcatcggcat cgtgcggagc gtcgtcgacg    3060
atgcgggatc cgtgcagggt ctgtctgctg agctgaaggc tctgctggtc gagtggctcg    3120
cgcacgtcag ggacttcgag aagacccgcg agctccgcga caggatgaac cccctgatcg    3180
acgcaatccc agcgaacgcg gactgcaggg ttctggagct cagggagaag cacaaccgcg    3240
agctgatcgc gcgcacgagt ttctggatcc tcggtggcga cgggtgggcg tacgacatcg    3300
gcttcggtgg actggaccac gtgatcgcca acaacgagga cgtcaacatc cttgttctcg    3360
acacggaggt ctactccaac actggtggcc agcgctccaa gtcgacgccg ctcggcgccc    3420
gcgccaagta cgctgtgctg ggcaaggaca ctgggaagaa ggacctgggg cgcatcgcga    3480
tgacctacga gaccgcgtac gtggccagca tcgcgcaggg agccaaccag cagcagtgca    3540
tggacgcgct gagggaggcc gaggcctacc agggcccctc gatcgtcatt gcgtacactc    3600
cgtgcatgga gcaccagatg gtccgcggga tgaaggagag ccagaagaac cagaagctgg    3660
ctgtggagac gggctactgg ctgctgtacc gcttcaaccc cgacctcatc cacgagggca    3720
agaaccccct caccctcgac tcgaagcctc cctcgaagcc tcccaaggag ttcctggaca    3780
cgcagggccg tttcattact ctgcagcgcg agcaccccga gcaggccac ctccttcacg     3840 aggcactcac ccgctctctg gccacccgct tcgtgcgcta ccagcgcctc gtgcagctgt    3900
acgagcccgc tgcccctgcc gcagctcctg ccacgcatgg ctgctgcccc ggctgctgct    3960
aatctagata aatggaggcg ctcgttgatc tgagccttgc cccctgacga acggcggtgg    4020
atggaagata ctgctctcaa gtgctgaagc ggtagcttag ctccccgttt cgtgctgatc    4080
agtctttttc aacacgtaaa aagcggagga gttttgcaat tttgttggtt gtaacgatcc    4140
tccgttgatt ttggcctctt tctccatggg cgggctgggc gtatttgaag cggttctctc    4200
ttctgccgtt a                                                          4211
```

<210> SEQ ID NO 8
<211> LENGTH: 2021
<212> TYPE: DNA
<213> ORGANISM: Artificial Sequence
<220> FEATURE:
<223> OTHER INFORMATION: Synthetic Construct- Example 8: designer
      Pyruvate-Kinase DNA construct

<400> SEQUENCE: 8

```
agaaaatctg gcaccacacc atggtagggt gcgagtgacc ccgcgcgact tggaagggtt      60
caaacgaccc cgccgtacga actttttgtcg ggggcgctc ccggctcgag catatggccg    120
ccgtcattgc caagtcctcc gtctccgcgg ccgtggctcg cccggcccgc tccagcgtgc    180
gccccatggc cgcgctgaag cccgccgtca aggctgcccc cgtggctgcc ccggctcagg    240
ccaaccagat gtctagatta gaaagattga cctcattaaa cgttgttgct ggttctgact    300
tgagaagaac ctccatcatt ggtaccatcg gtccaaagac caacaaccca gaaaccttgg    360
ttgctttgag aaaggctggt ttgaacattg tccgtatgaa cttctctcac ggttcttacg    420
aataccacaa gtctgtcatt gacaacgcca gaaagtccga agaattgtac ccaggtagac    480
```

```
cattggccat tgctttggac accaagggtc cagaaatcag aactggtacc accaccaacg      540
atgttgacta cccaatccca ccaaaccacg aaatgatctt caccaccgat gacaagtacg      600
ctaaggcttg tgacgacaag atcatgtacg ttgactacaa gaacatcacc aaggtcatct      660
ccgctggtag aatcatctac gttgatgatg gtgttttgtc tttccaagtt ttggaagtcg      720
ttgacgacaa gactttgaag gtcaaggctt gaacgccgg taagatctgt tcccacaagg      780
gtgtcaactt accaggtacc gatgtcgatt gccagctttt gtctgaaaag acaaggaag      840 atttgagatt cggtgtcaag aacggtgtcc acatggtctt cgcttctttc atcagaaccg      900
ccaacgatgt tttgaccatc agagaagtct gggtgaaca aggtaaggac gtcaagatca      960
ttgtcaagat tgaaaaccaa caaggtgtta acaacttcga cgaaatcttg aaggtcactg     1020
acggtgttat ggttgccaga ggtgacttgg gtattgaaat cccagcccca gaagtcttgg     1080
ctgtccaaaa gaaattgatt gctaagtcta acttggctgg taagccagtt atctgtgcta     1140
cccaaatgtt ggaatccatg acttacaacc aagaccaaac cagagctgaa gtttccgatg     1200
tcggtaacgc tatcttggat ggtgctgact gtgttatgtt gtctggtgaa accgccaagg     1260
gtaactaccc aatcaacgcc gttaccacta tggctgaaac cgctgtcatt gctgaacaag     1320
ctatcgctta cttgccaaac tacgatgaca tgagaaactg tactccaaag ccaacctcca     1380
ccaccgaaac cgtcgctgcc tccgctgtcg ctgctgtttt cgaacaaaag gccaaggcta     1440
tcattgtctt gtccacttcc ggtaccaccc caagattggt ttccaagtac agaccaaact     1500
gtccaatcat cttggttacc agatgcccaa gagctgctag attctctcac ttgtacagag     1560
gtgtcttccc attcgttttc gaaaaggaac ctgtctctga ctggactgat gatgttgaag     1620
cccgtatcaa cttcggtatt gaaaaggcta aggaattcgg tatcttgaag aagggtgaca     1680
cttacgtttc catccaaggt ttcaaggccg gtgctggtca ctccaacact tgcaagtct      1740 ctaccgttgg ctgctgcccc ggctgctgct aatctagata aatggaggcg ctcgttgatc     1800
tgagccttgc cccctgacga acggcggtgg atggaagata ctgctctcaa gtgctgaagc     1860
ggtagcttag ctccccgttt cgtgctgatc agtcttttc aacacgtaaa agcggagga      1920 gttttgcaat tttgttggtt gtaacgatcc tccgttgatt ttggcctctt tctccatggg     1980
cgggctgggc gtatttgaag cggttctctc ttctgccgtt a                         2021
```

<210> SEQ ID NO 9  
<211> LENGTH: 1815  
<212> TYPE: DNA  
<213> ORGANISM: Artificial Sequence  
<220> FEATURE:  
<223> OTHER INFORMATION: Synthetic Construct- Example 9: designer Enolase DNA construct

<400> SEQUENCE: 9

```
agaaaatctg gcaccacacc tatatggtag ggtgcgagtg accccgcgcg acttggagct       60
cgatggcccc gggttgtttg gggcgtccgc ctctcgcgct attctgagct ggagaccgag      120
gcgcatgaaa atgcattcgc ttccatagga cgctgcattg tggcttgaag gttcaaggga     180
agggttcaaa cgaccccgcc gtacgaactt ttgtcggggg cgctcccgg ccccgggctc       240 ttgtgcgcgc attagggctt cgggtcgcaa gcaagacgat acctcgagca tatggccgcc      300
gtcattgcca agtcctccgt ctccgcggcc gtggctcgcc cggcccgctc cagcgtgcgc      360
cccatggccg cgctgaagcc cgccgtcaag gctgcccccg tggctgcccc ggctcaggcc     420
aaccaggtga ccaaggctgt tgagaacatc aacgctatta ttgccccccgc cctgaagggc    480
```

```
atggacccog tcaagcaggc ggagattgac cagaagatga aggacctgga cggcactgac    540
aacaagggca agctgggtgc caacgccatc ctggccgtct ccatggccgt gtgcaaggcc    600
ggtgccgctg agaagggcgt gccoctgtac aagcacattg cggacctggc cggcaacagc    660
aagctgatcc tgcccgtgcc ctcgttcaac atcatcaacg cggcagcca cgccggcaac    720 gccctggcta tgcaggagtt catgatcctg cccgttggcg cctcgagctt ctctgaggcc    780
atgcgcatgg gctgcgaggt gtaccacgcc ctgaagggcc tgatcaaggc caagtacggc    840
caggacgcct gcaacgtggg tgatgagggt ggcttcgccc ccaacatcgg ctccaacgat    900
gagggcctga acttggtgaa cgaggccatc gagaaggccg gctacaccgg caaggtgaag    960
atcggcatgg acgtggcctc gtcggagttc tacaccgagg acggcatgta cgacctggac   1020
ttcaagaacc agcccaacga tggctcgcag aagaagacca aggagcagat gctggagctg   1080
tacaacgagt tctgcaagaa gtacccggtc atctccatcg aggacccctt cgagcaggac   1140
gactgggagc cctgcgccaa gctgaccacc gagaacatct gccaggtggt cggcgacgac   1200
atcctggtga ccaaccccgt gcgcgtgaag aaggccatcg acgccaaggc cgtcaacgct   1260
ctgctgctca aggtcaacca gatcggtacc attaccgagt ccattgaggc cgtgcgcatg   1320
gccaaggagg ccggctgggg tgtcatgacc agccaccgct cgggtgagac tgaggactct   1380
ttcatcgccg acctggcggt gggcctggcc tccggccaga tcaagaccgg cgcccoctgc   1440 cgctcggagc gcaatgccaa gtacaaccag ctgctgcgca tcgaggagga gctgggcgag   1500
aacgctgtgt acgctggcga gagctggcgc cacatcggct ggggctgctg ccccggctgc   1560
tgctaatcta gataaatgga ggcgctcgtt gatctgagcc ttgcccotg acgaacggcg   1620 gtggatggaa gatactgctc tcaagtgctg aagcggtagc ttagctcccc gtttcgtgct   1680
gatcagtctt tttcaacacg taaaaagcgg aggagttttg caattttgtt ggttgtaacg   1740
atcctccgtt gattttggcc tctttctcca tgggcgggct gggcgtattt gaagcggttc   1800
tctcttctgc cgtta                                                    1815
```

<210> SEQ ID NO 10  
<211> LENGTH: 2349  
<212> TYPE: DNA  
<213> ORGANISM: Artificial Sequence  
<220> FEATURE:  
<223> OTHER INFORMATION: Synthetic Construct- Example 10: designer Phosphoglycerate-Mutase DNA construct

<400> SEQUENCE: 10

```
agaaaatctg gcaccacacc tatatggtag ggtgcgagtg accccgcgcg acttggagct     60
cgatggcccc gggttgtttg gggcgtccgc ctctcgcgct attctgagct ggagaccgag    120
gcgcatgaaa atgcattcgc ttccatagga cgctgcattg tggcttgaag gttcaaggga    180
agggttcaaa cgaccccgcc gtacgaactt ttgtcgggg cgctcccgg ccccgggctc    240 ttgtgcgcgc attagggctt cgggtcgcaa gcaagacgat acctcgagca tatgccgcc    300 gtcattgcca agtcctccgt ctccgcggcc gtggctcgcc cggcccgctc cagcgtgcgc    360
cccatggccg cgctgaagcc cgccgtcaag gctgcccccg tggctgcccc ggctcaggcc    420
aaccagatgg cgcacgacta caagctgaag gcccacccgg cgattcctgc gcccgagggc    480
ccgctgctgg tctgcattct ggacggcttc ggcgagaacg agtacaagga tgagttcaac    540
gccgtgcacg tggctaagac gcccactgtg acgcgctgc gcgtgtgcc ccatcgcttc    600 cgttccatca aggcgcacgg aaaggctgtg ggcctgccca gcgatgccga catgggcaac    660
```

```
agcgaggtgg ggcacaacgc cctgggctcg ggccaggtgg tggaccaagg cgcgcgcctg      720
gtggacctgg cgctggagac cggccgtatg ttctcggacc ccggctggaa gctcatcagc      780
gaggccttcc cctcccacac cgtccacttc atcggcctgc tgtccgacgg cggcgtgcac      840
tcgcgcgccg atcagctgca cggctgcctg cgcggcgccg tggagcgcgg cgccaagcgc      900
gtgcgcgtgc acatcctgac tgacggccgc gacgtgccgg acggcagcag catccggttc      960
gtggaggagc tggaggcggt gctggcggag ctgcgcggca agggctgcga catcgccatc     1020
gcctcgggcg gcggccgcat gcaggtcacc atggaccgct acgaggcgga ctggagcatg     1080
gtgaagcgcg gctgggacgc gcacgtgctg ggcaaggcgc cccactactt caaggacgcc     1140
aagaccgcgg tcaccaccct gcgcggctcc gaggacgcgc cggtgtctga ccagtacgtg     1200 gcccccttg tgattgtgga cgaggcggac aagccggtgg gcaccattga ggacggcgac     1260
gcggtggtgc tgttcaactt ccgcgcggac cgcatggtgg agatcagcaa ggccttcgag     1320
tacgaggacg gcttcaccgc ctttgagcgc gagcgcttcc ccaagggcct gcgcttcgtg     1380
ggcatgatgc agtacgacgg cgacctgaag ctgcccgcca acttcctggt gccgccgccc     1440
ctgattgagc acgtgtcggg cgagtacctg tgcaagaacg ggctgagcac cttcgcctgc     1500
tccgagactc agaagttcgg gcacgtgacg ttcttctgga acggcaaccg ctccggctac     1560
ctggacgcca gcaggagca gtacctggag atcccgtcgg acaagatcga gttcaacaag     1620
gctccggaca tgaaggcgcg cgagatcacc gccgccggca ttgaggcgct caagagcggc     1680
aagtacaagg tggtgcgcat caactacgcc aacccggaca tggtcggcca caccggcgac     1740
atggctgcca ccgtccgcgc ctgcgagacc gtggacgggt gcgtgaagga gctgctggag     1800
gtggtggaca gcctgaacgg ccgctggatc gtcacgtccg accacggcaa cgccgacgac     1860
atggtgcagc gcgacaagaa gggcaagccc ctgctgggcg aggacggcaa gccgctgccc     1920
ctgaccagcc acacgctggc gcccgtgccg ttcttcatcg gcggcaaggg cctgccggac     1980
ggcgtggtgc tgcgcgacga cctgccggac gccgggctgg ccaacgtggc cgccaccacc     2040
ttcaacctgc tgggcttcga ggcgcccggc atctacaagc ccagcatggt caaggcgtaa     2100
tctagataaa tggaggcgct cgttgatctg agccttgccc cctgacgaac ggcggtggat     2160
ggaagatact gctctcaagt gctgaagcgg tagcttagct ccccgtttcg tgctgatcag     2220 tcttttttcaa cacgtaaaaa gcggaggagt tttgcaattt tgttggttgt aacgatcctc     2280
cgttgatttt ggcctctttc tccatgggcg ggctgggcgt atttgaagcg gttctctctt     2340
ctgccgtta                                                              2349
```

<210> SEQ ID NO 11
<211> LENGTH: 1908
<212> TYPE: DNA
<213> ORGANISM: Artificial Sequence
<220> FEATURE:
<223> OTHER INFORMATION: Synthetic Construct- Example 11: designer
      Phosphoglycerate-Kinase DNA construct

<400> SEQUENCE: 11

```
agaaaatctg gcaccacacc tatatggtag ggtgcgagtg accccgcgcg acttggagct       60
cgatggcccc gggttgtttg gggcgtccgc ctctcgcgct attctgagct ggagaccgag      120
gcgcatgaaa atgcattcgc ttccatagga cgctgcattg tggcttgaag gttcaaggga      180
agggttcaaa cgacccgcc gtacgaactt ttgtcggggg gcgctcccgg ccccgggctc       240
ttgtgcgcgc attagggctt cgggtcgcaa gcaagacgat acatggccct ctctatgaag      300
```

```
atgcgcgcca acgcgcgcgt gtccggtcgc cgcgtcgccg ctgtggcccc ccgcgtggtg    360
cccttctcgt cggcctccag ctccgtgctg cgctctggct tcgcgctgag gtgtctgtgg    420
acatccgccg cgtgggccgc tctcgcatcc gtcgtcgagg cggtgaagaa gtcggttggc    480
gacctgcaca aggctgacct ggagggcaag cgcgtgttcg tccgcgcgga cctgaacgtg    540
cctcttgaca aggccaccct ggccatcacc gacgacaccc gcattcgcgc ggccgtcccc    600
accctgaagt acctgctgga caacggtgct aaggtcctgc tgacctcgca cctgggtcgc    660
ccgaagggcg gtcccgagga caagtaccgc ctgaccccg tggtggcccg cctgtcggag    720
ctgctgggca gcccgtgac caaggtcgat gactgcatcg ccccgaggt ggagaaggcg    780 gtgggcgcca tgaagaacgg cgagctgctg ctgctggaga actgccgctt ctacaaggag    840
gaggagaaga cgagcccga gttcgccaag aagctggccg ccaacgccga cctgtacgtg    900
aacgacgcgt tcggcactgc ccaccgcgcc cacgcctcca ccgagggtgt gaccaagttc    960
ctgaagccct ccgtggccgg cttcctgctg cagaaggagc tggactacct tgatggcgcc    1020
gtgtccaacc ccaagcgccc cttcgtggcc attgtgggcg gctccaaggt gtcctccaag    1080
atcaccgtca ttgaggcgct gatggagaag tgcgacaaga tcatcatcgg cggtggcatg    1140
atcttcacct tctacaaggc ccgcgcgctg aaggtgggct cctcgctggt tgaggacgac    1200
aagatcgagc tggccaagaa gctggaggag atggccaagg ccaagggtgt gcagctgctg    1260
ctgcccaccg acgtggtggt ggccgacaag ttcgacgcca cgccaacac ccagaccgtg    1320 cccatcaccg ccatccccga tgctggatg ggtctggaca ttggcccgga ctccgtcaag    1380
accttcaacg acgccctggc cgacgccaag accgttgtgt ggaacggccc catgggtgtg    1440
ttcgagtttc cccaagttcg ccaacgcacc gtgtcgatcg ccaacaccct ggccggcctg    1500
acgcccaagg gctgcatcac catcattggt ggcggtgact ccgtggctgc cgtcgagcag    1560
gccggcgttg ccgagaagat gagccacatc tccaccggcg gcggtgcctc cctggagctg    1620
ctggagggca aggtcctgcc cggcgtggcc gccctggacg agaagtaaat ggaggcgctc    1680
gttgatctga gccttgcccc ctgacgaacg gcggtggatg gaagatactg ctctcaagtg    1740
ctgaagcggt agcttagctc cccgtttcgt gctgatcagt cttttcaac acgtaaaaag    1800 cggaggagtt ttgcaatttt gttggttgta acgatcctcc gttgattttg gcctctttct    1860
ccatgggcgg gctgggcgta tttgaagcgg ttctctcttc tgccgtta              1908
```

<210> SEQ ID NO 12
<211> LENGTH: 1677
<212> TYPE: DNA
<213> ORGANISM: Artificial Sequence
<220> FEATURE:
<223> OTHER INFORMATION: Synthetic Construct- Example 12: designer NAD-dependent Glyceraldehyde-3-Phosphate-Dehydrogenase DNA construct

<400> SEQUENCE: 12

```
agaaaatctg gcaccacacc tatatggtag ggtgcgagtg accccgcgcg acttggagct     60
cgatggcccc gggttgtttg gggcgtccgc ctctcgcgct attctgagct ggagaccgag    120
gcgcatgaaa atgcattcgc ttccatagga cgctgcattg tggcttgaag gttcaaggga    180
agggttcaaa cgaccccgcc gtacgaactt tgtcggggg gcgctccgg ccccgggctc    240 ttgtgcgcgc attagggctt cgggtcgcaa gcaagacgat acatgccgc cgtcattgcc    300 aagtcctccg tctccgcggc cgtggctcgc ccggcccgct ccagcgtgcg ccccatggcc    360
```

```
gcgctgaagc cgccgtcaa ggctgccccc gtggctgccc cggctcaggc caaccagatg      420
gctcccatca agatcggcat caatggtttt ggtcgtattg ccgcctcgt gtggcgtgcc      480 actcttaacc gtgacgatgt cgaggtcgtc gccatcaatg atccattcat tgatgtgcca      540
tacatggtct acatgccaa gtatgactcg gtccacggca acctgaccca cgacgttcag      600
caaggcgacg gcaagctgat ggtcaatggc aagtcaatca ccatcttcgg caagatggat      660
gccaaggaga tcccatggaa ggaggccggc gcgaccttcg tcgttgagtc gactggtgtg      720
ttcaccaccc tggagggcgc cagctctcac ctggtcggcg gtgctgagac cgtcgtcatc      780
tccgccccat caaacgatgc ccccatgttc gtcatgggtg tcaacgagga gggctacaag      840
ccagacatga agtggtgtc caacgcgtct tgcaccacca actgcctggg cccctggcc       900 aaggtcatcc accttaagtt cggcatcctg gagggcctga tgaccaccgt ccacgcgacc      960
accgccaccc agaagaccgt cgacgggccg tccaagaagg actggcgcgg cgggcgcggc     1020
atcctggaca catcatccc ctcggcgact ggtgccgcca aggccgtcgg caaggtgctg      1080
cctgccctga cggcaagct caccggcatg gccttccgcg tgcccacccc cgatgtctcg      1140
gtcgtcgatc tgaccgtgcg cctggagaag ggtgcgtcgt acgacgccat caaggccgag     1200
atcaagcgcg cgagcgagaa cgagctcaag ggcatcctgg cctacaccga ggatgccgtg     1260
gtctccaccg acttcatcgg caacaagcac agctccatct tcgacgccga ggccggcatc     1320
gccctcaacg acaactttgt caagctggtc tcctggtacg acaacgagtg gggctactcc     1380
aaccgtgtcg tcgacctgat cgcgcacatg ccaaggtca aggccgccag ccactaaatg      1440
gaggcgctcg ttgatctgag ccttgccccc tgacgaacgg cggtggatgg aagatactgc     1500
tctcaagtgc tgaagcggta gcttagctcc ccgtttcgtg ctgatcagtc ttttttcaaca    1560 cgtaaaaagc ggaggagttt tgcaattttg ttggttgtaa cgatcctccg ttgattttgg     1620
cctctttctc catgggcggg ctgggcgtat ttgaagcggt tctctcttct gccgtta       1677
```

<210> SEQ ID NO 13
<211> LENGTH: 2351
<212> TYPE: DNA
<213> ORGANISM: Artificial Sequence
<220> FEATURE:
<223> OTHER INFORMATION: Synthetic Construct- Example 13: designer HydA1-promoter-linked Phosphoglycerate-Mutase DNA construct

<400> SEQUENCE: 13

```
agaaaatctg gcaccacacc gagctgtcat gcgttgttcc gttatgtgtc gtcaaacgcc       60
ttcgagcgct gcccggaaca atgcgtacta gtataggagc catgaggcaa gtgaacagaa      120
gcgggctgac tggtcaaggc gcacgatagg gctgacgagc gtgctgacgg ggtgtaccgc      180
cgagtgtccc ctgcattccc gccggattgg gaaatcgcga tggtcgcgca taggcaagct     240
cgcaaatgct gtcagcttat cttacatgaa cacacaaaca ctctcgcagg cactagcctc      300
aaatggccgc cgtcattgcc aagtcctccg tctccgcggc cgtggctcgc ccggcccgct     360
ccagcgtgcg cccatggcc gcgctgaagc ccgccgtcaa ggctgccccc gtggctgccc       420
cggctcaggc caaccagatg gcgcacgact acaagctgaa ggcccacccg gcgattcctg      480
cgcccgaggg cccgctgctg gtctgcattc tggacggctt cggcgagaac gagtacaagg     540
atgagttcaa cgccgtgcac gtggctaaga cgcccactgt ggacgcgctg cgcgctgtgc     600
cccatcgctt ccgttccatc aaggcgcacg gaaaggctgt gggcctgccc agcgatgccg     660
acatgggcaa cagcgaggtg gggcacaacg ccctgggctc gggccaggtg gtggaccaag      720
```

```
gcgcgcgcct ggtggacctg gcgctggaga ccggccgtat gttctcggac cccggctgga    780
agctcatcag cgaggccttc ccctcccaca ccgtccactt catcggcctg ctgtccgacg    840
gcggcgtgca ctcgcgcgcc gatcagctgc acggctgcct gcgcggcgcc gtggagcgcg    900
gcgccaagcg cgtgcgcgtg cacatcctga ctgacggccg cgacgtgccg gacggcagca    960
gcatccggtt cgtggaggag ctggaggcgg tgctggcgga gctgcgcggc aagggctgcg   1020
acatcgccat cgcctcgggc ggcggccgca tgcaggtcac catggaccgc tacgaggcgg   1080
actggagcat ggtgaagcgc ggctgggacg cgcacgtgct gggcaaggcg ccccactact   1140
tcaaggacgc caagaccgcg gtcaccaccc tgcgcggctc cgaggacgcg ccggtgtctg   1200
accagtacgt ggcccccttt gtgattgtgg acgaggcgga caagccggtg gcaccattg    1260 aggacgcga cgcggtggtg ctgttcaact cccgcgcgga ccgcatggtg gagatcagca   1320
aggccttcga gtacgaggac ggcttcaccg cctttgagcg cgagcgcttc cccaagggcc   1380
tgcgcttcgt gggcatgatg cagtacgacg gcgacctgaa gctgcccgcc aacttcctgg   1440
tgccgccgcc cctgattgag cacgtgtcgg gcgagtacct gtgcaagaac gggctgagca   1500
ccttcgcctg ctccgagact cagaagttcg ggcacgtgac gttcttctgg aacggcaacc   1560
gctccggcta cctggacgcc aagcaggagc agtacctgga gatcccgtcg acaagatcg    1620 agttcaacaa ggctccggac atgaaggcgc gcgagatcac cgccgccggc attgaggcgc   1680
tcaagagcgg caagtacaag gtggtgcgca tcaactacgc caacccggac atggtcggcc   1740
acaccggcga catggctgcc accgtccgcg cctgcgagac cgtggacggg tgcgtgaagg   1800
agctgctgga ggtggtggac agcctgaacg gccgctggat cgtcacgtcc gaccacggca   1860
acgccgacga catggtgcag cgcgacaaga agggcaagcc cctgctgggc gaggacggca   1920
agccgctgcc cctgaccagc cacacgctgg cgcccgtgcc gttcttcatc ggcggcaagg   1980
gcctgccgga cggcgtggtg ctgcgcgacg acctgccgga cgccgggctg ccaacgtgg    2040 ccgccaccac cttcaacctg ctgggcttcg aggcgcccgg catctacaag cccagcatgg   2100
tcaaggcgta aatggaggcg ctcgttgatc tgagccttgc cccctgacga acggcggtgg   2160
atggaagata ctgctctcaa gtgctgaagc ggtagcttag ctccccgttt cgtgctgatc   2220
agtctttttc aacacgtaaa aagcggagga gttttgcaat tttgttggtt gtaacgatcc   2280
tccgttgatt ttggcctctt tctccatggg cgggctgggc gtatttgaag cggttctctc   2340
ttctgccgtt a                                                        2351
```

<210> SEQ ID NO 14  
<211> LENGTH: 1796  
<212> TYPE: DNA  
<213> ORGANISM: Artificial Sequence  
<220> FEATURE:  
<223> OTHER INFORMATION: Synthetic Construct- Example 14: designer HydA1-promoter-linked Enolase DNA construct

<400> SEQUENCE: 14

```
agaaaatctg gcaccacacc gagctgtcat gcgttgttcc gttatgtgtc gtcaaacgcc     60
ttcgagcgct gcccggaaca atgcgtacta gtataggagc catgaggcaa gtgaacagaa    120
gcgggctgac tggtcaaggc gcacgatagg gctgacgagc gtgctgacgg ggtgtaccgc    180
cgagtgtccg ctgcattccc gccggattgg gaaatcgcga tggtcgcgca taggcaagct    240
cgcaaatgct gtcagcttat cttacatgaa cacacaaaca ctctcgcagg cactagcctc    300
aaatggccgc cgtcattgcc aagtcctccg tctccgcggc cgtggctcgc ccggcccgct    360
```

```
ccagcgtgcg ccccatggcc gcgctgaagc ccgccgtcaa ggctgccccc gtggctgccc    420
cggctcaggc caaccaggtg accaaggctg ttgagaacat caacgctatt attgcccccg    480
ccctgaaggg catggacccc gtcaagcagg cggagattga ccagaagatg aaggacctgg    540
acggcactga caacaagggc aagctgggtg ccaacgccat cctggccgtc tccatggccg    600
tgtgcaaggc cggtgccgct gagaagggcg tgccctgta caagcacatt gcggacctgg     660
ccggcaacag caagctgatc ctgcccgtgc cctcgttcaa catcatcaac ggcggcagcc    720
acgccggcaa cgccctggct atgcaggagt tcatgatcct gcccgttggc gcctcgagct    780
tctctgaggc catgcgcatg gctgcgagg tgtaccacgc cctgaagggc ctgatcaagg     840
ccaagtacgg ccaggacgcc tgcaacgtgg gtgatgaggg tggcttcgcc cccaacatcg    900
gctccaacga tgagggcctg aacttggtga cgaggccat cgagaaggcc ggctacaccg     960
gcaaggtgaa gatcggcatg gacgtggcct cgtcggagtt ctacaccgag gacggcatgt    1020
acgacctgga cttcaagaac cagcccaacg atggctcgca gaagaagacc aaggagcaga    1080
tgctggagct gtacaacgag ttctgcaaga gtacccggt catctccatc gaggaccccct    1140 tcgagcagga cgactgggag ccctgcgcca agctgaccac cgagaacatc tgccaggtgg    1200
tcggcgacga catcctggtg accaaccccg tgcgcgtgaa gaaggccatc gacgccaagg    1260
ccgtcaacgc tctgctgctc aaggtcaacc agatcggtac cattaccgag tccattgagg    1320
ccgtgcgcat ggccaaggag gccggctggg tgtgtcatgac cagccaccgc tcgggtgaga    1380
ctgaggactc tttcatcgcc gacctggcgg tgggcctggc ctccggccag atcaagaccg    1440 gcgcccctg ccgctcggag cgcaatgcca agtacaacca gctgctgcgc atcgaggagg     1500
agctgggcga gaacgctgtg tacgctggcg agagctggcg ccacatcggc tggtaaatgg    1560
aggcgctcgt tgatctgagc cttgcccccct gacgaacggc ggtggatgga agatactgct    1620
ctcaagtgct gaagcggtag cttagctccc cgtttcgtgc tgatcagtct tttcaacac     1680 gtaaaaagcg gaggagtttt gcaatttgt tggttgtaac gatcctccgt tgattttggc     1740
ctctttctcc atgggcgggc tgggcgtatt tgaagcggtt ctctcttctg ccgtta        1796
```

<210> SEQ ID NO 15
<211> LENGTH: 1832
<212> TYPE: DNA
<213> ORGANISM: Artificial Sequence
<220> FEATURE:
<223> OTHER INFORMATION: Synthetic Construct- Example 15: designer
      HydA1-promoter-linked Pyruvate-Kinase DNA construct

<400> SEQUENCE: 15

```
agaaaatctg gcaccacacc gagctgtcat gcgttgttcc gttatgtgtc gtcaaacgcc     60
ttcgagcgct gcccggaaca atgcgtacta gtataggagc catgaggcaa gtgaacagaa    120
gcgggctgac tggtcaaggc gcacgatagg gctgacgagc gtgctgacgg ggtgtaccgc    180
cgagtgtccg ctgcattccc gccggattgg gaaatcgcga tggtcgcgca taggcaagct    240
cgcaaatgct gtcagcttat cttacatgaa cacacaaaca ctctcgcagg cactagcctc    300
aaatggccgc cgtcattgcc aagtcctccg tctccgcggc cgtggctcgc ccggcccgct    360
ccagcgtgcg ccccatggcc gcgctgaagc ccgccgtcaa ggctgccccc gtggctgccc    420
cggctcaggc caaccagatg tgcgagatgc tggacgcggg cgtggtgggc tgccgcgtgg    480
acctgacgtg gggcccgctg gagttccacc gcaagtcgct tgccaatctg cagcaggcca    540
tgcgcaagag ccgccgcctg tgttgcacca tggtggacac gctgggccgc gagctcatga    600
```

```
tccgccgcca gagaggggca ggctggaccc agcgccagag gggtggggtg atcatcacca      660
cgcgcacgga cgtggacgcc agcagcaacg tgctgcccat cacttacagc aagttcacgg      720
agatggcggt caagggcgac accatctaca tcggccgcta cctggtgtgc ggcgcagaca      780
gcgcctcgct gtacctggag gtcatggacg tgcaggcga cgacgtgtac tgcatcgcca      840
agaacgacgc ggtgctggac ggcctgctga cggtgttcca cgcggagcgc tccgtggagg      900
ggctggccaa cgtgcagaac gacctgccgc tgctgtccga ctacgacaag gagtgcctgc      960
acatcctggc gcaggacttc gagcgcgcgc cctacatctc caagctggag tccatcgcct     1020
cctccgccgt gcgcgccgcc gaccgcgtgg gcgccagcct gattgtggtg tacacgcaca     1080
ccggcaagac ggcgcagctg gtggccaagt accggccgcc catgcccatc ctgacgctgg     1140
tggtgccgca cctggtgtct gaccagctca agtggaagct ggagggcagg tccagcgcgc     1200
gccagtgcct catcagtcgc gcgctgctgc cggtgctggc cgcgccctcg cccagcggcg     1260
accagctgct gcaggaggcg gtggccatgg cgggccgcgt caagctggtc aagccgcacg     1320
accacgtggt gtgcgtgcag cgcatccacg acgacttctg cgtcaagatc atctccgtgg     1380
acgacatggg cgcgggcatc aagcgcgacg acacggtcat gtcgcacagc gtgtttggca     1440
gcagccccat ggccgtgcag ggctcgtccg gctacgactc gccgcgcgtg cacaacaacc     1500
ccatcggcaa caagttcggc cccatgccgc ccgccatcat caccaccggc aatagcttca     1560
ccctgggcgg catgggcgtg ggcgtgctgt aaatggaggc gctcgttgat ctgagccttg     1620 cccctgacg aacggcggtg gatggaagat actgctctca agtgctgaag cggtagctta     1680 gctcccgtt tcgtgctgat cagtcttttt caacacgtaa aaagcggagg agttttgcaa     1740
ttttgttggt tgtaacgatc ctccgttgat tttggcctct ttctccatgg gcgggctggg     1800
cgtatttgaa gcggttctct cttctgccgt ta                                  1832
```

<210> SEQ ID NO 16
<211> LENGTH: 4376
<212> TYPE: DNA
<213> ORGANISM: Artificial Sequence
<220> FEATURE:
<223> OTHER INFORMATION: Synthetic Construct- Example 16: designer
      HydA1-promoter-linked Pyruvate-Ferredoxin-Oxidoreductase DNA
      construct

<400> SEQUENCE: 16

```
agaaaatctg gcaccacacc gagctgtcat gcgttgttcc gttatgtgtc gtcaaacgcc       60
ttcgagcgct gcccggaaca atgcgtacta gtataggagc catgaggcaa gtgaacagaa      120
gcgggctgac tggtcaaggc gcacgatagg gctgacgagc gtgctgacgg ggtgtaccgc      180
cgagtgtccg ctgcattccc gccggattgg gaaatcgcga tggtcgcgca taggcaagct      240
cgcaaatgct gtcagcttat cttacatgaa cacacaaaca ctctcgcagg cactagcctc      300
aaatggccgc cgtcattgcc aagtcctccg tctccgcggc cgtggctcgc ccggcccgct      360
ccagcgtgcg ccccatggcc gcgctgaagc ccgccgtcaa ggctgccccc gtggctgccc      420
cggctcaggc caaccagatg ggaaagaaaa tgatgacgac tgatggcaat acagcgacag      480
cgcacgtggc gtatgccatg agcgaagtcg ccgccatcta ccccatcacc ccttcctcga      540
ccatgggcga ggaggctgac gactgggcgg cgcaaggacg caagaacatc tttggccaga      600
ccctgaccat acgcgaaatg cagtccgagg ccggcgccgc cggcgcggtg cacggggccc      660
tggcggccgg cgccctgacc acgacctcca cggcgtcgca gggtctgctg ctgatgatcc      720
ccaacatgta caagatctcc ggcgaacttc tgcccggcgt gttccacgtc accgccgcg      780
```

```
ccatcgccgc gcacgccctg tccatcttcg gtgaccacca ggatatctac gccgcgcgcc     840
agacaggctt cgccatgctc gcctccagct cggtgcagga ggcccacgac atggccctgg     900
tggcccactt ggcggccatc gagtccaacg tgccgttcat gcacttcttc gacggattcc     960
gcacctcgca cgaaatccag aagatcgagg tcctggacta cgcggacatg gcctcgctgg    1020
tgaaccagaa ggccctggcg gaattccgcg ccaagtccat gaaccccgag caccccacg     1080
tgcgcggcac ggcccagaac cccgacatct acttccaggg tcgcgaggca gccaaccct    1140
actacctcaa ggtgcccggc atcgttgccg agtacatgca gaaggtcgcc tccctcacgg    1200
gccgcagcta caagctcttt gactacgtgg gtgctcccga cgccgagcgc gtcatcgtgt    1260
ccatgggctc ctcgtgcgag accatcgagg aggtcatcaa ccacctcgcg gccaagggcg    1320
aaaagatcgg cctgatcaag gtccgcctgt acaggccctt cgtaagcgag gccttcttcg    1380
ctgctctgcc cgcttcggcc aaggtcatca cggtcctcga ccgcaccaag gaacccggcg    1440
cgcccggcga tccgctctac ctcgacgtgt gctcggcctt cgtggagcgc ggcgaagcca    1500
tgcccaagat cctggccggc cgctacggcc tgggttccaa ggaattcagc ccggccatgg    1560
tcaagtccgt gtacgacaac atgtccgcg ctaagaagaa ccacttcacc gtgggcatcg     1620
aagacgacgt gaccggcact tcgctgccgg tggacaacgc cttcgccgac accacgccca    1680
agggcaccat ccagtgccag ttctggggcc tcggcgccga cggcactgtg ggcgccaaca    1740
agcaggccat caagatcatc ggcgacaaca cggacctgtt tgcccagggt tacttctcct    1800
acgactccaa gaaatcgggc ggcatcacca tctcgcacct gcgcttcggc gagaagccca    1860
tccagtccac ctacctggtc aacagggccg actatgtcgc ctgtcacaac ccggcctacg    1920
tgggcatata cgacatcctc gaaggcatca aggatggcgg aaccttcgtg ctcaactcgc    1980
cttggagcag cctcgaggac atggacaagc acctgccctc cggcatcaag cgcaccatcg    2040
cgaacaagaa gctcaagttc tacaacatcg acgcggtgaa aatcgccacc gatgtgggac    2100
tgggcggccg catcaacatg atcatgcaga cggccttctt caagctggcc ggagtgctgc    2160
ccttcgaaaa ggccgtggat ctgctcaaga agtccatcca aaggcctac ggcaaaaagg     2220
gcgagaagat cgtcaagatg aacaccgacg ccgtggacca ggccgtcacc tccctgcagg    2280
aattcaagta tccggattcc tggaaggacg ctcccgctga gaccaaggcc gagcccatga    2340
cgaacgagtt cttcaagaac gtcgtcaagc ccatcctgac ccagcagggc gacaagctgc    2400
cggtgagcgc cttcgaggcc gacggccgtt tcccctcgg caccagccag ttcgagaagc     2460
gcggcgtggc catcaacgtg ccgcagtggg tccccgagaa ctgcatccag tgcaaccagt    2520
gcgccttcgt ctgtccgcac agcgccatcc tgcccgtgct ggccaaggaa gaggagttgg    2580
tcggcgcgcc ggcgaacttc acggccctgg aagccaaggg caaggagctc aagggctaca    2640
agttccgcat ccagatcaac accctggact gcatgggctg cggcaactgc gccgacatct    2700
gtccgcccaa ggaaaaggct ctggtcatgc agccctgga tacccagcgc gacgcgcagg     2760
tgcccaacct ggagtacgca gcgcgcatcc cggtcaaatc cgaggtgctg ccgcgcgact    2820
cgctcaaggg cagccagttc caggagcctc tcatggaatt ctcgggcgcc tgctcgggct    2880
gcggcgagac gccctacgtg cgcgtcatca cccagctctt cggcgagcgc atgttcattg    2940
ccaacgccac gggttgctcg tccatctggg gcgcgtcggc tccttccatg ccttacaaga    3000
ccaaccgcct cggacaaggc ccggcctggg gtaactccct gttcgaagac gcggccgaat    3060
acggcttcgg catgaacatg tccatgttcg cccgccgcac gcatttggcc gatcttgccg    3120
```

```
ccaaggccct ggagagcgat gcctccggcg atgtcaagga agccctgcag ggctggcttg   3180
ccggcaagaa cgatcccatc aagtccaagg aatacggcga caagctcaag aagctgctgg   3240
ctggtcagaa ggatggtctg ctcggacaga tcgccgccat gtccgacctg tacaccaaga   3300
agagcgtgtg gatcttcggt ggcgacggct gggcctacga catcggttac ggcggcctgg   3360
accatgtgct cgcctcgggc gaggacgtga acgtcttcgt catggatacc gaggtctact   3420
ccaacaccgg cggccagtcc tccaaggcaa cgcccacggg cgccgtggcc aagttcgcgg   3480
cggccggcaa gcgtaccggc aagaaggacc tggcgcgcat ggtcatgacc tacggctacg   3540
tctacgtggc tacggtctcc atgggttaca gcaagcagca gttcctcaag gtgctcaagg   3600
aagccgaaag cttccccggc ccctcgctgg tcatcgccta tgctacctgc atcaaccagg   3660
gtctgcgcaa gggcatgggc aagagccagg acgtcatgaa caccgcgtc aagtccggtt    3720
actggccgct gttccgctac gatccgcgct tggccgccca gggcaagaac cccttccagc   3780
tcgactccaa ggctcctgac ggttccgtcg aggagttcct gatggcccag aaccgcttcg   3840
ccgtcctcga tcggtccttc cccgaggacg ccaagagact gcgcgcccag gtcgctcacg   3900
aattggacgt gcgtttcaag gagttggagc acatggccgc cacgaacatc ttcgagtcct   3960
tcgcgccagc gggcggcaag gccgatggtt cggtggattt cggcgaaggt gcggagttct   4020
gcacgcgcga cgatactccc atgatggccc gacctgattc cggtgaggcc tgcgaccaga   4080
accgcgctgg cacgagcgaa cagcagggag acctcagcaa gcggacgaag aagtaaatgg   4140
aggcgctcgt tgatctgagc cttgcccct gacgaacggc ggtggatgga agatactgct    4200
ctcaagtgct gaagcggtag cttagctccc cgtttcgtgc tgatcagtct ttttcaacac   4260
gtaaaagcg gaggagtttt gcaattttgt tggttgtaac gatcctccgt tgattttggc    4320
ctctttctcc atgggcgggc tgggcgtatt tgaagcggtt ctctcttctg ccgtta       4376
```

<210> SEQ ID NO 17
<211> LENGTH: 6092
<212> TYPE: DNA
<213> ORGANISM: Artificial Sequence
<220> FEATURE:
<223> OTHER INFORMATION: Synthetic Construct- Example 17: designer HydA1-promoter-linked Pyruvate-NADP plus-Oxidoreductase DNA construct

<400> SEQUENCE: 17

```
agaaaatctg gcaccacacc gagctgtcat gcgttgttcc gttatgtgtc gtcaaacgcc    60
ttcgagcgct gcccggaaca atgcgtacta gtataggagc catgaggcaa gtgaacagaa   120
gcgggctgac tggtcaaggc gcacgatagg gctgacgagc gtgctgacgg ggtgtaccgc   180
cgagtgtccg ctgcattccc gccggattgg gaaatcgcga tggtcgcgca taggcaagct   240
cgcaaatgct gtcagcttat cttacatgaa cacacaaaca ctctcgcagg cactagcctc   300
aaatggccgc cgtcattgcc aagtcctccg tctccgcggc cgtggctcgc ccggcccgct   360
ccagcgtgcg cccatggcc gcgctgaagc ccgccgtcaa ggctgccccc gtggctgccc    420
cggctcaggc caaccagatg aagcagtctg tccgcccaat tatttccaat gtactgcgca   480
aggaggttgc tctgtactca acaatcattg acaagacaa ggggaaggaa ccaactggtc     540
gaacatacac cagtggccca aaaccggcat ctcacattga agttccccat catgtgactg   600
tgcctgccac tgaccgcacc ccgaatcccg atgctcaatt ctttcagtct gtagatgggt   660
cacaagccac cagtcacgtt gcgtacgctc tgtctgacac agcgttcatt tacccaatta   720
cacccagttc tgtgatgggc gagctggctg atgtttggat ggctcaaggg aggaagaacg   780
```

```
cctttggtca ggttgtggat gtccgtgaga tgcaatctga ggctggagcc gcaggcgccc      840
tgcatgggc  actggctgct ggagctattg ctacaacctt cactgcctct caagggttgt      900
tgttgatgat tcccaacatg tataagattg caggtgagct gatgccctct gtcatccacg      960
ttgcagcccg agagcttgca ggccacgctc tgtccatttt tggaggacac gctgatgtca     1020
tggctgtccg ccaaacagga tgggctatgc tgtgctccca cacagtgcag cagtctcacg     1080
acatggctct catctcccac gtggccaccc tcaagtccag catcccctcc gttcacttct     1140
ttgatggttt ccgcacaagc cacgaagtga acaaaatcaa aatgctgcct tatgcagaac     1200
tgaagaaact ggtgcctcct ggcaccatgg aacagcactg gctcgttcg  ctgaacccca     1260
tgcaccccac catccgagga acaaaccagt ctgcagacat ctacttccag aatatggaaa     1320
gtgcaaacca gtactacact gatctggccg aggtcgttca ggagacaatg gacgaagttg     1380
caccatacat cggtcgccac tacaagatct ttgagtatgt tggtgcacca gatgcagaag     1440
aagtgacagt gctcatgggt tctggtgcaa ccacagtcaa cgaggcagtg gaccttcttg     1500
tgaagcgtgg aaagaaggtt ggtgcagtct tggtgcacct ctaccgacca tggtcaacaa     1560
aggcatttga aaaggtcctg cccaagacag tgaagcgcat tgctgctctg atcgctgca     1620
aggaggtgac tgcactgggt gagcctctgt atctggatgt gtcggcaact ctgaatttgt     1680
tcccggaacg ccagaatgtg aaagtcattg gaggacgtta cggattgggc tcaaaggatt     1740
tcatcccgga gcatgccctg gcaatttacg ccaacttggc cagcgagaac cccattcaaa     1800
gattcactgt gggtatcaca gatgatgtca ctggcacatc cgttcctttc gtcaacgagc     1860
gtgttgacac gttgcccgag ggcacccgcc agtgtgtctt ctggggaatt ggttcagatg     1920
gaacagtggg agccaatcgc tctgccgtga gaatcattgg agacaacagc gatttgatgg     1980
ttcaggccta cttccaattt gatgctttca agtcaggtgg tgtcacttcc tcgcatctcc     2040
gttttggacc aaagcccatc acagcgcaat accttgttac caatgctgac tacatcgcgt     2100
gccacttcca ggagtatgtc aagcgctttg acatgcttga tgccatccgt gagggggca    2160
cctttgttct caattctcgg tggaccacgg aggacatgga aaggagatt  ccggctgact     2220
tccggcgcaa gctggcacag aagaaggtcc gcttctacaa tgtggatgct cgaaagatct     2280
gtgacagttt tggtcttggg aagcgcatca atatgctgat gcaggcttgt ttcttcaagc     2340
tgtctggggt gctcccactg gccgaagctc agcggctgct gaacgagtcc attgtgcatg     2400
agtatggaaa aagggtggc aaggtggtgg agatgaacca agcagtggtg aatgctgtct     2460
ttgctggtga cctgccccag gaagttcaag tccctgccgc ctgggcaaac gcagttgata     2520
catccacccg taccccacc  gggattgagt tgttgacaa  gatcatgcgc cgctgatgg     2580
atttcaaggg tgaccagctc ccagtcagtg tgatgactcc tggtggaacc ttccctgtcg     2640
ggacaacaca gtatgccaag cgtgcaattg ctgctttcat tccccagtgg attcctgcca     2700
actgcacaca gtgcaactat tgttcgtatg tttgccccca cgccaccatc cgacctttcg     2760
tgctgacaga ccaggaggtg cagctggccc cggagagctt tgtgacacgc aaggcgaagg     2820
gtgattacca ggggatgaat ttccgcatcc aagttgctcc tgaggattgc actggctgcc     2880
aggtgtgcgt ggagacgtgc cccgatgatg ccctggagat gaccgacgct ttcaccgcca     2940
cccctgtgca acgcaccaac tgggagttcg ccatcaaggt gcccaaccgc ggcaccatga     3000
cggaccgcta ctccctgaag ggcagccagt tccagcagcc cctcctggag ttctccgggg     3060
cctgcgaggg ctgcggcgag accccatatg tcaagctgct cacccagctc ttcggcgagc     3120
```

```
ggacggtcat cgccaacgcc accggctgca gttccatctg gggtggcact gccggcctgg    3180
cgccgtacac caccaacgcc aagggccagg gcccggcctg gggcaacagc ctgttcgagg    3240
acaacgccga gttcggcttt ggcattgcag tggccaacgc cagaagagg tcccgcgtga    3300 gggactgcat cctgcaggca gtggagaaga aggtcgccga tgagggtttg accacattgt    3360
tggcgcaatg gctgcaggat tggaacacag agacaagac cttgaagtac caagaccaga    3420
tcattgcagg gctggcacag cagcgcagca aggatcccct tctggagcag atctatggca    3480
tgaaggacat gctgcctaac atcagccagt ggatcattgg tggtgatggc tgggccaacg    3540
acattggttt cggtgggctg gaccacgtgc tggcctctgg gcagaacctc aacgtcctgg    3600
tgctggacac cgagatgtac agcaacaccg gtgggcaggc ctccaagtcc acccacatgg    3660
cctctgtggc caagttttgcc ctgggaggga agcgcaccaa caagaagaac ttgacgagga    3720
tggcaatgag ctatggcaac gtctatgtgg ccaccgtctc ccatggcaac atggcccagt    3780
gcgtcaaggc gtttgtggag gctgagtctt atgatggacc ttcgctcatt gttggctatg    3840
cgccatgcat cgagcatggt ctgcgtgctg gtatggcaag gatggttcaa gagtctgagg    3900
ctgccatcgc cacgggatac tggcccctgt accgctttga ccccgcctg gcgaccgagg    3960 gcaagaaccc cttccagctg gactccaagc gcatcaaggg caacctgcag gagtacctgg    4020
accgccagaa ccggtatgtc aacctgaaga gaacaacccc gaagggtgcg gatctgctga    4080
agtctcagat ggccgacaac atcaccgccc ggttcaaccg ctaccgacgc atgttggagg    4140
gccccaatac aaaagccgcc gcccccagcg gcaaccatgt gaccatcctg tacggctccg    4200
aaactggcaa cagtgagggt ctggcaaagg agctggccac cgacttcgag cgccgggagt    4260
actccgtcgc agtgcaggct ttggatgaca tcgacgttgc tgacttggag aacatgggct    4320
tcgtggtcat tgcggtgtcc acctgtgggc agggacagtt ccccccgcaac agccagctgt    4380 tctggcggga gctgcagcgg acaagcctg agggctggct gaagaacttg aagtacactg    4440
tcttcgggct gggcgacagc acatactact tctactgcca caccgccaag cagatcgacg    4500
ctcgcctggc cgccttgggc gctcagcggg tggtgcccat tggcttcggc gacgatgggg    4560
atgaggacat gttccacacc ggcttcaaca actggatccc cagtgtgtgg aatgagctca    4620
agaccaagac tccggaggaa cgctgttca ccccgagcat cgccgtgcag ctcacccca    4680 acgccacccc gcaggatttc catttcgcca agtccacccc agtgctgtcc atcaccggtg    4740
ccgaacgcat cacgccggca gaccacaccc gcaacttcgt cactatccga tggaagaccg    4800
atttgtcgta ccaggtgggt gactctcttg gtgtcttccc tgagaacacc cggtcagtgg    4860
tggaggagtt cctgcagtat tacggcttga accccaagga cgtcatcacc atcgaaaaca    4920
agggcagccg ggagttgccc cactgcatgg ctgttgggga tctcttcacg aaggtgttgg    4980
acatcttggg caaacccaac aaccggttct acaagaccct ttcttacttt gcagtggaca    5040
aggccgagaa ggagcgcttg ttgaagatcg ccgagatggg gccggagtac agcaacatcc    5100
tgtctgagac gtaccactac gcggacatct tccacatgtt cccgtccgcc cggcccacgc    5160
tgcagtacct catcgagatg atccccaaca tcaagccccg gtactactcc atctcctccg    5220
cccccatcca caccctggc gaggtccaca gcctggtgct catcgacacc tggatcacgc    5280
tgtccggcaa gcaccgcacg gggctgacct gcaccatgct ggagcacctg caggcgggcc    5340
aggtggtgga tggctgcatc cacccacgg cgatggagtt ccccgaccac gagaagccgg    5400
tggtgatgtg cgccatgggc agtggcctgg caccgttcgt tgctttcctg cgcgacggct    5460
ccacgctgcg gaagcagggc aagaagaccg ggaacatggc attgtacttc ggcaacaggt    5520
```

```
atgagaagac ggagttcctg atgaaggagg agctgaaggg tcacatcaac gatggtttgc    5580
tgacacttcg atgcgctttc agccgagatg accccaagaa gaaggtgtat gtgcaggacc    5640
ttatcaagat ggacgaaaag atgatgtacg attacctcgt ggtgcagaag ggttctatgt    5700
attgctgtgg atcccgcagt ttcatcaagc ctgtccagga gtcattgaaa cattgcttca    5760
tgaaagctgg tgggctgact gcagagcaag ctgagaacga ggtcatcgat atgttcacga    5820
ccgggcggta caatatcgag gcatggtaat aaatggaggc gctcgttgat ctgagccttg    5880 cccccctgacg aacggcggtg gatggaagat actgctctca agtgctgaag cggtagctta    5940
gctccccgtt tcgtgctgat cagtcttttt caacacgtaa aaagcggagg agttttgcaa    6000
ttttgttggt tgtaacgatc ctccgttgat tttggcctct ttctccatgg gcgggctggg    6060
cgtatttgaa gcggttctct cttctgccgt ta                                  6092
```

<210> SEQ ID NO 18
<211> LENGTH: 1856
<212> TYPE: DNA
<213> ORGANISM: Artificial Sequence
<220> FEATURE:
<223> OTHER INFORMATION: Synthetic Construct- Example 18: designer
      HydA1-promoter-linked Thiolase DNA construct

<400> SEQUENCE: 18

```
agaaaatctg gcaccacacc gagctgtcat gcgttgttcc gttatgtgtc gtcaaacgcc      60
ttcgagcgct gcccggaaca atgcgtacta gtataggagc catgaggcaa gtgaacagaa     120
gcgggctgac tggtcaaggc gcacgatagg gctgacgagc gtgctgacgg ggtgtaccgc     180
cgagtgtccg ctgcattccc gccggattgg gaaatcgcga tggtcgcgca taggcaagct     240
cgcaaatgct gtcagcttat cttacatgaa cacacaaaca ctctcgcagg cactagcctc     300
aaatggccgc cgtcattgcc aagtcctccg tctccgcggc cgtggctcgc ccggcccgct     360
ccagcgtgcg ccccatggcc gcgctgaagc ccgccgtcaa ggctgccccc gtggctgccc     420
cggctcaggc caaccagatg aaagaagtag ttattgcaag tggtgtaagg actgctgtcg     480
ggaaatttgg tggcacgctt ctaaatgtac ctgcagtaga tttaggtgct gtgaataata     540 aagaagcat aaaaagagcc aatgtgaaac ctgaagatgt tagtgaagtg ataatgggaa     600
atgtattgca ggcaggtctt gggcagaacc ccgcaagaca agctgaaata aaagcgggca     660
taccagtaga agttccggct atgactgtaa acatggtatg tggatcaggt cttagagctg     720
tgacacttgc tgctcaggca gttatgcttg gtgatgctga cattgttgta gccggtggaa     780
tggaaaatat gtcaagagca ccatatatat taaatgatgc tcgctttggg tacaggatga     840
acaatggcca gcttgtagat gaaatggtat atgatggttt aacagatgtt tttaaccaat     900
atcacatggg aatcactgcc gaaaatcttg ctgaaaaata cggcatatca agagaagagc     960
aggatgaatt tgcatataga agccaaaaat tagcgtcaga agcgatatca tcaggaagat    1020
ttgaggatga gatagttcct gtgattgtgc cgcagaaaaa aggtgaaccg atagaattta    1080
aagttgatga acatgtgaga cctaatacga caattgaagc acttgcaaaa ttaaaaccag    1140
cattccaaaa agatggaact gtaactgctg gaaatgcatc aggaattaac gatgcagctg    1200
cagcagtagt tgtgatgtca aaagaaaagg catgtgaact tggaataaag accattgcaa    1260
cgattaaatc atttggttat gcaggtgttg accccagcat cacgggaatt ggtccagtat    1320
atgctacgag aaaggcatta gaaaaagcta atctaactgt agatgattta gatttaattg    1380
aagcaaatga agcatttgca gcacaatcac tggctgttgc aaaagaatta aaatttaata    1440
```

```
tggacagagt gaatgtaaat ggtggcgcaa ttgcgatagg tcatccaatc ggcgccagcg   1500
gatgtagaat tctagtgacg cttttatatg agatgcagaa gaggaattcg catactggac   1560
ttgcaacatt gtgcatcggc ggaggaatgg gaatagcaat ggttgtcgaa agataaatgg   1620
aggcgctcgt tgatctgagc cttgcccccct gacgaacggc ggtggatgga agatactgct   1680
ctcaagtgct gaagcggtag cttagctccc cgtttcgtgc tgatcagtct ttttcaacac   1740
gtaaaaagcg gaggagtttt gcaattttgt tggttgtaac gatcctccgt tgattttggc   1800
ctctttctcc atgggcgggc tgggcgtatt tgaagcggtt ctctcttctg ccgtta        1856
```

<210> SEQ ID NO 19
<211> LENGTH: 1550
<212> TYPE: DNA
<213> ORGANISM: Artificial Sequence
<220> FEATURE:
<223> OTHER INFORMATION: Synthetic Construct- Example 19: designer
      HydA1-promoter-linked 3-Hydroxybutyryl-CoA-Dehydrogenase DNA
      construct

<400> SEQUENCE: 19

```
agaaaatctg gcaccacacc gagctgtcat gcgttgttcc gttatgtgtc gtcaaacgcc     60
ttcgagcgct gcccggaaca atgcgtacta gtataggagc catgaggcaa gtgaacagaa    120
gcgggctgac tggtcaaggc gcacgatagg gctgacgagc gtgctgacgg ggtgtaccgc    180
cgagtgtccg ctgcattccc gccggattgg gaaatcgcga tggtcgcgca taggcaagct    240
cgcaaatgct gtcagcttat cttacatgaa cacacaaaca ctctcgcagg cactagcctc    300
aaatggccgc cgtcattgcc aagtcctccg tctccgcggc cgtggctcgc ccggcccgct    360
ccagcgtgcg ccccatggcc gcgctgaagc ccgccgtcaa ggctgccccc gtggctgccc    420
cggctcaggc caaccagatg caaaagattt gtgtaatagg tgctggaaca atgggctcag    480
gcatcgctca agtatttgca caaaatggct ttgaagtaat tttacgcgat attgatatga    540
agttcgtaga aaaggatttt ggcacaattg aaaaaattta caagaaaatg ttgacaaagg    600
gaaaattaca gcagatgaga aaacgaattt taagcagaat cagaggtaca acaaatttgg    660
aagacgcaaa agaagcagat tttgtagttg aagcggctat agaaaatatg gatctcaaga    720
aacaaatatt caaagagcta gatgaaatat gcaaaatgga aacaatcctt gcgtcaaata    780
catcatcact atccataaca gaaatagcaa gtgcgacaaa aagacctgag aaagtcatag    840
gaatgcattt cttcaaccca gttccagtaa tgaaacttgt tgaagtcata aaaggattaa    900
agacatcaga gcaaacattt aatgtcgtca gagaattggc tttaaaagta gacaaaacac    960
ctatagaggt caaagaagca cctggatttg ttgtaaatag gattttaatc ccaatgatta   1020
atgaagcaat tggaatactt gcagtggtgt tggcaactga caagagcata gatgaagcta   1080
tgaaacttgg tgcaaatcat ccaataggac ctttggcatt gtctagtttg ataggcaatg   1140
acgtcgttct tgctataatg aatgtgcttt atgaagagta cggcgattcg aaatacagac   1200
cacatccact tctaaaaaaa gtggtaagag gcggattgct gggtagaaaa actggcaaag   1260
gtttctttga atacaaaatt aatctttaa ggaggagaat atcatgataa atggaggcgc    1320
tcgttgatct gagccttgcc ccctgacgaa cggcggtgga tggaagatac tgctctcaag   1380
tgctgaagcg gtagcttagc tccccgtttc gtgctgatca gtcttttttca acacgtaaaa   1440 agcggaggag ttttgcaatt ttgttggttg taacgatcct ccgttgattt tggcctcttt   1500
ctccatgggc gggctgggcg tatttgaagc ggttctctct tctgccgtta               1550
```

<210> SEQ ID NO 20
<211> LENGTH: 1457
<212> TYPE: DNA
<213> ORGANISM: Artificial Sequence
<220> FEATURE:
<223> OTHER INFORMATION: Synthetic Construct- Example 20: designer
      HydA1-promoter-linked Crotonase DNA construct

<400> SEQUENCE: 20

| | | | | | | |
|---|---|---|---|---|---|---|
| agaaaatctg | gcaccacacc | gagctgtcat | gcgttgttcc | gttatgtgtc | gtcaaacgcc | 60 |
| ttcgagcgct | gcccggaaca | atgcgtacta | gtataggagc | catgaggcaa | gtgaacagaa | 120 |
| gcgggctgac | tggtcaaggc | gcacgatagg | gctgacgagc | gtgctgacgg | ggtgtaccgc | 180 |
| cgagtgtccg | ctgcattccc | gccggattgg | gaaatcgcga | tggtcgcgca | taggcaagct | 240 |
| cgcaaatgct | gtcagcttat | cttacatgaa | cacacaaaca | ctctcgcagg | cactagcctc | 300 |
| aaatggccgc | cgtcattgcc | aagtcctccg | tctccgcggc | cgtggctcgc | ccggcccgct | 360 |
| ccagcgtgcg | ccccatggcc | gcgctgaagc | ccgccgtcaa | ggctgccccc | gtggctgccc | 420 |
| cggctcaggc | caaccagatg | gatttttaata | atgttttatt | aaataaggat | gatgggatag | 480 |
| ctctcatcat | tataaatcgt | ccaaaggctt | taaatgcatt | aaactatgag | acactaaaag | 540 |
| agttagatag | tgtgcttgat | atagttgaaa | atgataaaga | gataaaagtt | ttaattataa | 600 |
| ctggcagcgg | tgaaaaaacc | ttcgttcag | gtgctgatat | agctgagatg | agtaatatga | 660 |
| caccacttga | agcgaagaag | ttctctcttt | atggacagaa | agtatttagg | aagatagaaa | 720 |
| tgctaagtaa | gcctgttata | gcagcggtaa | atggttttgc | acttggtggt | ggatgcgagc | 780 |
| tttctatggc | atgtgacata | cgtattgcaa | gtaaaaatgc | aaaatttggt | caacctgaag | 840 |
| taggacttgg | aataatacct | ggcttttcag | gaactcaaag | attaccacgt | cttataggca | 900 |
| cttctaaagc | taaagagctt | atttttcacag | gtgacatgat | aaattctgat | gaagcatata | 960 |
| aaataggcct | tatatctaaa | gttgttgaac | tatctgatct | cattgaagaa | gcaaaaaaac | 1020 |
| tcgcgaaaaa | aatgatgtca | aaaagtcaaa | tagcaatttc | tctagcaaag | gaagcaataa | 1080 |
| ataagggaat | ggaaacagac | ttagatacag | gcaatactat | agaagctgag | aaattttcct | 1140 |
| tatgttttac | aacagatgat | caaaaagaag | gtatgattgc | gttttctgaa | aagagggcgc | 1200 |
| ctaaatttgg | caaataaatg | gaggcgctcg | ttgatctgag | ccttgccccc | tgacgaacgg | 1260 |
| cggtggatgg | aagatactgc | tctcaagtgc | tgaagcggta | gcttagctcc | ccgtttcgtg | 1320 |
| ctgatcagtc | tttttcaaca | cgtaaaaagc | ggaggagttt | tgcaattttg | ttggttgtaa | 1380 |
| cgatcctccg | ttgattttgg | cctctttctc | catgggcggg | ctgggcgtat | ttgaagcggt | 1440 |
| tctctcttct | gccgtta | | | | | 1457 |

<210> SEQ ID NO 21
<211> LENGTH: 1817
<212> TYPE: DNA
<213> ORGANISM: Artificial Sequence
<220> FEATURE:
<223> OTHER INFORMATION: Synthetic Construct- Example 21: designer
      HydA1-promoter-linked Butyryl-CoA-Dehydrogenase DNA construct

<400> SEQUENCE: 21

| | | | | | | |
|---|---|---|---|---|---|---|
| agaaaatctg | gcaccacacc | gagctgtcat | gcgttgttcc | gttatgtgtc | gtcaaacgcc | 60 |
| ttcgagcgct | gcccggaaca | atgcgtacta | gtataggagc | catgaggcaa | gtgaacagaa | 120 |
| gcgggctgac | tggtcaaggc | gcacgatagg | gctgacgagc | gtgctgacgg | ggtgtaccgc | 180 |
| cgagtgtccg | ctgcattccc | gccggattgg | gaaatcgcga | tggtcgcgca | taggcaagct | 240 |

```
cgcaaatgct gtcagcttat cttacatgaa cacacaaaca ctctcgcagg cactagcctc      300
aaatggccgc cgtcattgcc aagtcctccg tctccgcggc cgtggctcgc ccggcccgct      360
ccagcgtgcg ccccatggcc gcgctgaagc ccgccgtcaa ggctgccccc gtggctgccc      420
cggctcaggc caaccagatg gacttttcat taacaaagga gcaagaaatg gtaaggcgtg      480
ttgtgagaga attcgctgaa aagaagttg ctcctaaagc aaaagaaata gatatcacag       540
aagagtttcc atgggataca gtaagaaaaa tggctcaaaa cgatatgatg ggtattcctt      600
atccagaaga gtatggtgga gcaggtggag attacttgag ttatatcata gctgttgaag      660
agatatcaag agcttgtgct acgactggag taatttttatc tgctcatact tcattgggaa     720
gttttccaat atatcaatgg ggaacagaag aacaaaaaag aaaatatcta gtgccacttg      780
caaaaggtga aaaattgggc gcttttggcc ttacagaacc taacgcaggt acagatgcag      840
ctggacagca gacaactgca gtattagatg gtgatcacta cgtattaaac ggctcaatat      900
ttattacaaa cggaggaaaa gctgacatat atataatctt tgcaatgaca gacaaatcaa      960
aaggcacaag aggcattagt gcatttatag ttgagaaaga ttttccgggt tttagcattg     1020
gcaaaattga agaaaaaatg ggtataagag cttcatcaac tgccgaactt gtgtttgaag     1080
attgtattgt accaaagaa atttacttg gtaaagaagg agaaggttttt aaaattgcga      1140 tggctacact agatggtgga agaataggaa tagcagcgca acgccttgga atagctcagg     1200
ctgctttaga tgaagagata aaatatgcaa aggaaagaca acagtttgga agaccaattg     1260
gaaaatttca aggcattcaa tggtatatag ctgatatggc aacgagaata aatgcttcaa     1320
gatggcttgt atacaatgcc gcttggagaa agcaggtagg tcttccgtac acaatggaag     1380
cagctatggc aaaattatat gcttccgaaa cagcaatgtt tgtaacgaca aaaacagttc     1440
agatatttgg cggctatggc tttacaaaag attatccagt ggaaagattt atgagagatg     1500
caaaaataac agaaatttat gaaggcacat cggaagtcca gaaaatggtt atttccggta     1560
acctattgaa aatgtaaatg gaggcgctcg ttgatctgag ccttgccccc tgacgaacgg     1620
cggtggatgg aagatactgc tctcaagtgc tgaagcggta gcttagctcc ccgtttcgtg     1680
ctgatcagtc tttttcaaca cgtaaaaagc ggaggagttt tgcaattttg ttggttgtaa     1740
cgatcctccg ttgattttgg cctctttctc catgggcggg ctgggcgtat tgaagcggt      1800 tctctcttct gccgtta                                                    1817
```

<210> SEQ ID NO 22
<211> LENGTH: 2084
<212> TYPE: DNA
<213> ORGANISM: Artificial Sequence
<220> FEATURE:
<223> OTHER INFORMATION: Synthetic Construct- Example 22: designer
      HydA1-promoter-linked Butyraldehyde-Dehydrogenase DNA construct

<400> SEQUENCE: 22

```
agaaaatctg gcaccacacc gagctgtcat gcgttgttcc gttatgtgtc gtcaaacgcc       60
ttcgagcgct gcccggaaca atgcgtacta gtataggagc catgaggcaa gtgaacagaa      120
gcgggctgac tggtcaaggc gcacgatagg gctgacgagc gtgctgacgg ggtgtaccgc      180
cgagtgtccg ctgcattccc gccggattgg gaaatcgcga tggtcgcgca taggcaagct      240
cgcaaatgct gtcagcttat cttacatgaa cacacaaaca ctctcgcagg cactagcctc      300
aaatggccgc cgtcattgcc aagtcctccg tctccgcggc cgtggctcgc ccggcccgct      360
ccagcgtgcg ccccatggcc gcgctgaagc ccgccgtcaa ggctgccccc gtggctgccc      420
```

```
cggctcaggc caaccagatg attaaagaca cgctagtttc tataacaaaa gatttaaaat    480
taaaaacaaa tgttgaaaat gccaatctaa agaactacaa ggatgattct tcatgtttcg    540
gagttttcga aatgttgaaa atgctataa gcaatgccgt acacgcacaa aagatattat     600
cccttcatta tacaaaagaa caaagagaaa aaatcataac tgagataaga aaggccgcat    660
tagaaaataa agagattcta gctacaatga ttcttgaaga aacacatatg ggaagatatg    720
aagataaaat attaaagcat gaattagtag ctaaatacac tcctgggaca gaagatttaa    780
ctactactgc ttggtcagga gataacgggc ttacagttgt agaaatgtct ccatatggcg    840
ttataggtgc aataactcct tctacgaatc caactgaaac tgtaatatgt aatagtatag    900
gcatgatagc tgctggaaat actgtggtat taacggaca tccaggcgct aaaaaatgtg     960
ttgcttttgc tgtcgaaatg ataaataaag ctattatttc atgtggtggt cctgagaatt    1020
tagtaacaac tataaaaaat ccaactatgg actctctaga tgcaattatt aagcacccct    1080
caataaaact actttgcgga actggagggc aggaatggg aaaaaccctc ttaaattctg     1140
gtaagaaagc tataggtgct ggtgctggaa atccaccagt tattgtagat gatactgctg    1200
atatagaaaa ggctggtaag agtatcattg aaggctgttc ttttgataat aatttacctt    1260
gtattgcaga aaaagaagta tttgtttttg agaacgttgc agatgattta atatctaaca    1320
tgctaaaaaa taatgctgta attataaatg aagatcaagt atcaaagtta atagatttag    1380
tattacaaaa aaataatgaa actcaagaat actctataaa taagaaatgg gtcggaaaag    1440
atgcaaaatt attcttagat gaaatagatg ttgagtctcc ttcaagtgtt aaatgcataa    1500
tctgcgaagt aagtgcaagg catccatttg ttatgacaga actcatgatg ccaatattac    1560
caattgtaag agttaaagat atagatgaag ctattgaata tgcaaaaata gcagaacaaa    1620
atagaaaaca tagtgcctat attttattcaa aaaatataga caacctaaat aggtttgaaa    1680
gagaaatcga tactactatc tttgtaaaga atgctaaatc ttttgccggt gttggttatg    1740
aagcagaagg ctttacaact ttcactattg ctggatccac tggtgaagga ataacttctg    1800
caagaaattt tacaagacaa agaagatgtg tactcgccgg ttaaatggag gcgctcgttg    1860
atctgagcct tgcccctga cgaacggcgg tggatggaag atactgctct caagtgctga    1920
agcggtagct tagctccccg tttcgtgctg atcagtcttt ttcaacacgt aaaaagcgga    1980
ggagttttgc aattttgttg gttgtaacga tcctccgttg attttggcct ctttctccat    2040
gggcgggctg ggcgtatttg aagcggttct ctcttctgcc gtta                    2084
```

<210> SEQ ID NO 23
<211> LENGTH: 1733
<212> TYPE: DNA
<213> ORGANISM: Artificial Sequence
<220> FEATURE:
<223> OTHER INFORMATION: Synthetic Construct- Example 23: designer HydA1-promoter-linked Butanol-Dehydrogenase DNA construct

<400> SEQUENCE: 23

```
agaaaatctg gcaccacacc gagctgtcat gcgttgttcc gttatgtgtc gtcaaacgcc    60
ttcgagcgct gcccggaaca atgcgtacta gtataggagc catgaggcaa gtgaacagaa    120
gcgggctgac tggtcaaggc gcacgatagg gctgacgagc gtgctgacgg ggtgtaccgc    180
cgagtgtccg ctgcattccc gccggattgg gaaatcgcga tggtcgcgca taggcaagct    240
cgcaaatgct gtcagcttat cttacatgaa cacacaaaca ctctcgcagg cactagcctc    300
aaatggccgc cgtcattgcc aagtcctccg tctccgcggc cgtggctcgc ccggcccgct    360
```

```
ccagcgtgcg ccccatggcc gcgctgaagc ccgccgtcaa ggctgccccc gtggctgccc      420
cggctcaggc caaccagatg aaaggttttg caatgctagg tattaataag ttaggatgga      480
tcgaaaaaga aaggccagtt gcgggttcat atgatgctat tgtacgccca ttagcagtat      540
ctccgtgtac atcagatata catactgttt ttgagggagc tcttggagat aggaagaata      600
tgattttagg gcatgaagct gtaggtgaag ttgttgaagt aggaagtgaa gtgaaggatt      660
ttaaacctgg tgacagagtt atagttcctt gtacaactcc agattggaga tctttggaag      720
ttcaagctgg ttttcaacag cactcaaacg gtatgctcgc aggatggaaa ttttcaaatt      780
tcaaggatga agttttggt gaatattttc atgtaaatga tgcggatatg aatcttgcga      840
ttctacctaa agacatgcca ttagaaaatg ctgttatgat aacagatatg atgactactg      900
gatttcatgg agcagaactt gcagatattc aaatgggttc aagtgttgtg gtaattggca      960
ttggagctgt tggcttaatg ggaatagcag gtgctaaatt acgtggagca ggtagaataa     1020
ttggagtggg gagcaggccg atttgtgttg aggctgcaaa attttatgga gcaacagata     1080
ttctaaatta taaaaatggt catatagttg atcaagttat gaaattaacg aatggaaaag     1140
gcgttgaccg cgtaattatg gcaggcggtg ttctgaaaac attatcccaa gcagtatcta     1200
tggttaaacc aggaggaata atttctaata taaattatca tggaagtgga gatgctttac     1260
taataccacg tgtagaatgg ggatgtgaaa tggctcacaa gactataaaa ggaggtcttt     1320
gtcctggggg acgtttgaga gcagaaatgt taagagatat ggtagtatat aatcgtgttg     1380
atctaagtaa attagttaca catgtatatc atggatttga tcacatagaa gaagcactgt     1440
tattaatgaa agacaagcca aaagacttaa ttaaagcagt agttatatta taaatggagg     1500
cgctcgttga tctgagcctt gcccctgac gaacggcgt ggatgaaga tactgctctc     1560
aagtgctgaa gcggtagctt agctccccgt ttcgtgctga tcagtctttt tcaacacgta     1620
aaaagcggag gagttttgca attttgttgg ttgtaacgat cctccgttga ttttggcctc     1680
tttctccatg ggcgggctgg gcgtatttga agcggttctc tcttctgccg tta           1733
```

<210> SEQ ID NO 24
<211> LENGTH: 1556
<212> TYPE: DNA
<213> ORGANISM: Artificial Sequence
<220> FEATURE:
<223> OTHER INFORMATION: Synthetic Construct- Example 24: designer
Fructose-Diphosphate-Aldolase DNA construct

<400> SEQUENCE: 24

```
agaaaatctg gcaccacacc atggtagggt gcgagtgacc ccgcgcgact tggaagggtt       60
caaacgaccc cgccgtacga acttttgtcg ggggcgctc ccggatggta gggtgcgagt      120
gaccccgcgc gacttggaag ggttcaaacg accccgccgt acgaactttt gtcgggggc      180
gctcccggat ggccctgatg atgaagtcgt cggccagcct gaaggctgtg tcgctggccg      240
ctctcgccgc gccgtcgttg tgcgcgccgg gcaagtacga tgaggagctg attaagaccg      300
ctggcaccgt tgcctccaag ggccgcggta tcctggccat ggacgagtca acgccacct      360
gcggcaaacg cctggactcc atcggcgtgg agaacaccga ggagaaccgc cgcgcctacc      420
gcgagctgct ggtgaccgcc cccggcctgg gccagtacat ctccggcgct atcctgttcg      480
aggagaccct gtatcagtcc accgcctccg gcaagaagtt cgtcgatgtg atgaaggagc      540
agaacatcgt gcccgcatc aaggtcgaca agggcctggt gccctgtcca acaccaacga      600
tgagctggtg catgggcctg gacggctgga caagcgctgc tgagtactac aaggccggcg      660
```

```
ctcgcttcgc caagtggcgc tcggtcgtct cgatccccca cggcccctcg atcatgctgc      720
cgcgactggc ctacggcctg gcccgctacg ccgccatcgc ccagaacgcc ggtctggtgc      780
ccattgtgga gcccgaggtc ctgctggacg gtgagcacga catcgaccgc tgcctggagg      840
tgcaggaggc catctgggcc gagaccttca agtacatggc cgacaacaag gtcatgttgc      900
agggtatcct gctgaagccc gccatggtca cccccggcgc tgactgcaag aacaaggccg      960
gccccgccaa ggttgccgag tacaccctga agatgctggc cgcgcgtgcc ccccggtcc     1020 ccggcatcat gttcctgtcg ggcggccagt ccagctgga gtcgaccctg aacctgaacg     1080
ccatgaacca gagccccaac ccgtggcacg tgtcgttctc gtacgcccgc gctctgacga     1140
acaccgttct gaagacctgg caggcaagcc cgagaacggt ccaggcgccc aggctcgctg     1200
ctcaagcgcg caaggccaac tcggacgctc agcagggcaa gtacgacgcc accaccgagg     1260
gcaaggaggc tgcccagggc atgtacgaga agggaaaagg ctacgtctac taataaatgg     1320
aggcgctcgt tgatctgagc cttgcccct gacgaacggc ggtggatgga agatactgct      1380
ctcaagtgct gaagcggtag cttagctccc cgtttcgtgc tgatcagtct ttttcaacac     1440
gtaaaaagcg gaggagtttt gcaattttgt tggttgtaac gatcctccgt tgattttggc     1500
ctctttctcc atgggcgggc tgggcgtatt tgaagcggtt ctctcttctg ccgtta         1556
```

<210> SEQ ID NO 25
<211> LENGTH: 1379
<212> TYPE: DNA
<213> ORGANISM: Artificial Sequence
<220> FEATURE:
<223> OTHER INFORMATION: Synthetic Construct- Example 25: designer Triose-Phosphate-Isomerase DNA construct

<400> SEQUENCE: 25

```
agaaaatctg gcaccacacc atggtagggt gcgagtgacc ccgcgcgact ggaagggtt       60 caaacgaccc cgccgtacga acttttgtcg ggggcgctc ccggatggta gggtgcgagt      120
gaccccgcgc gacttggaag ggttcaaacg accccgccgt acgaactttt gtcggggggc     180
gctcccggat ggcagctacc tctctcactg cccctccttc tttctccggt ctccgccgca     240
tttctcccaa gctcgacgct gccgccgtct cctcccacca atccttcttc caccgcgtca     300
attcctctac ccgtctcgtt tcttcctctt cttcttctca tcgctccccc agaggtgttg     360
ttgccatggc tggatccgga agtttttcg ttggaggaaa ctggaagtgt aacgggacta     420
aggactccat cgccaagctt atctccgatc tcaacagtgc aaccttggaa gcagatgtag     480
atgttgttgt gtcacctcca tttgtctaca tcgaccaggt caaatcctcg ttgacagacc     540
gtattgacat atcaggtcag aactcttggg ttgggaaagg tggagccttc actggtgaaa     600
tcagcgtgga acagctcaaa gaccttggct gcaagtgggt cattcttggg cattccgaac     660
ggagacatgt catcggagaa aaagatgagt ttatcgggaa gaaagctgca tatgcattga     720
gtgagggtct tggagtgata gcttgtattg gggaaaagct agaagagagg gaagcaggca     780
agacgtttga tgtttgcttc gcgcaactga aggcgtttgc tgatgctgtg cctagctggg     840
acaatatagt tgttgcatac gagcctgtat gggcaattgg aactggtaaa gttgcatctc     900
ctcagcaagc acaagaagtc catgtagctg tccgcggttg gctaaagaag aatgtctctg     960
aggaagttgc ttccaaaacg agaatcatat atggaggttc tgtcaatgga ggcaacagtg    1020
cagagcttgc caaagaagaa gacattgatg gatttcttgt tggtggtgcc tccttgaagg    1080
gtcctgagtt tgcaaccatt gtgaactcag tcacgtcgaa gaaagttgct gcttgataaa    1140
```

```
tggaggcgct cgttgatctg agccttgccc cctgacgaac ggcggtggat ggaagatact    1200
gctctcaagt gctgaagcgg tagcttagct ccccgtttcg tgctgatcag tcttttcaa    1260 cacgtaaaaa gcggaggagt tttgcaattt tgttggttgt aacgatcctc cgttgatttt    1320
ggcctctttc tccatgggcg ggctgggcgt atttgaagcg gttctctctt ctgccgtta    1379
```

<210> SEQ ID NO 26
<211> LENGTH: 2156
<212> TYPE: DNA
<213> ORGANISM: Artificial Sequence
<220> FEATURE:
<223> OTHER INFORMATION: Synthetic Construct- Example 26: designer
      Phosphofructose-Kinase DNA construct

<400> SEQUENCE: 26

```
agaaaatctg gcaccacacc atggtagggt gcgagtgacc ccgcgcgact tggaagggtt      60
caaacgaccc cgccgtacga acttttgtcg gggggcgctc ccggatggta gggtgcgagt     120
gaccccgcgc gacttggaag ggttcaaacg accccgccgt acgaactttt gtcgggggc     180 gctcccggat ggccgccgtc attgccaagt cctccgtctc cgcggccgtg gctcgcccgg    240
cccgctccag cgtgcgcccc atggccgcgc tgaagcccgc cgtcaaggct gccccgtgg    300 ctgccccggc tcaggccaac cagatggaag cttcgatttc gtttctgggg tcaacaaaac    360
ccaatatttc cttgtttaac ccttcttcaa acgtccttcc tcgtagagat ttccctcttc    420
ctgctttgaa attgaagaaa gtttcagtgc tgcctcgaat cttgcaccag aaacgactca    480
tcagagctca gtgctctgat ggattcaaac cagaggaaga cgatgggttt gtcctagaag    540
acgttcctca cttgaccaaa tttctccctg atttaccgtc atatccaaat ccattgaaag    600
aaagccaagc atatgccatt gttaagcgaa cttttgtcag ttccgaagat gtggttgcgc    660
aaaatattgt agtccagaag ggaagtaagc gaggagtaca ctttaggcga gcagggcctc    720
gagaaagagt gtacttcaga tcagatgaag taaaagcttg catagtgact tgtgggggct    780
tgtgccctgg aatcaatact gttatacggg aaattgtatg tggattgaac aatatgtatg    840
gtgttaataa cattctcggc attcaggag gatatagagg cttttactcc aaaaacacta    900
tgaacctgac acctaaagta gttaacgata ttcataaacg cggtggcact tttcttcaaa    960
cctcaagagg aggacatgat acagcgaaga ttgttgataa tattcaagat agaggaataa    1020
atcaggtata tattattgga ggtggtggga cgcaaaaggg tgcagagaag atatacgagg    1080
aagttgagag gcgtggtctt caagtggcgg tttctggcat tcctaagaca attgataatg    1140
atattgctgt gattgacaaa tcatttggct ttgatacggc ggttgaggaa gcacaacgag    1200
ctattaatgc tgcacatgta gaggtcgaga gcgtggaaaa tggagttggt atcgttaaac    1260
tcatgggcag atacagtggt tttattgcca tgattgcaac tttagcgaat cgtgatgtgg    1320
attgttgctt gattccagag tctccatttt tccttgaagg aaagggtggg ctctttgagt    1380
ttattgaaga acgactcaaa gagaatagc acatggttat tgtgatagct gaaggagctg    1440
gacaggatta tgttgctcaa gcatgcgtg catctgaaac taaagacgcc tcaggaaata    1500
gactcttgct tgatgttggt ctatggttga ctcaacagat aaaggatcac tttacaaatg    1560
ttcggaaaat gatgataaat atgaagtaca tagacccaac gtatatgata agagcaatac    1620
cgagtaacgc atcagacaat gtctattgca ctcttcttgc ccaaagtgca gttcatggag    1680
caatggctgg gtactcaggt ttcactgtag gaccagttaa cagtagacat gcttacatcc    1740
caatttctgt gacggaagtg acaaatacgg tgaagttaac tgataggatg tgggctagac    1800
```

```
tccttgcatc gacaaatcaa ccgagtttct tgactggtga aggagcattg cagaatgtga    1860
tcgacatgga aactcaagaa aagatcgata acatgaagat ctcttctatc taataaatgg    1920
aggcgctcgt tgatctgagc cttgccccct gacgaacggc ggtggatgga agatactgct    1980
ctcaagtgct gaagcggtag cttagctccc cgtttcgtgc tgatcagtct ttttcaacac    2040
gtaaaaagcg gaggagtttt gcaattttgt tggttgtaac gatcctccgt tgattttggc    2100
ctctttctcc atgggcgggc tgggcgtatt tgaagcggtt ctctcttctg ccgtta        2156
```

<210> SEQ ID NO 27
<211> LENGTH: 860
<212> TYPE: DNA
<213> ORGANISM: Artificial Sequence
<220> FEATURE:
<223> OTHER INFORMATION: Synthetic Construct- Example 27: designer
      Nia1-promoter-linked Starch-Synthase-iRNA DNA construct

<400> SEQUENCE: 27

```
agaaaatctg gcaccacacc tatatggtag ggtgcgagtg accccgcgcg acttggagct     60
cgatggcccc gggttgtttg gggcgtccgc ctctcgcgct attctgagct ggagaccgag    120
gcgcatgaaa atgcattcgc ttccatagga cgctgcattg tggcttgaag gttcaaggga    180
agggttcaaa cgaccccgcc gtacgaactt ttgtcggggg gcgctcccgg ccccgggctc    240
ttgtgcgcgc attagggctt cgggtcgcaa gcaagacgat acatgccagc cggctcacca    300
ccgccaccag cggcttgcgg gggtccacct ccaggcccag accttctgc agaaactcct    360 tgcacagcgc cttcccggcg gggcggtcgg cgtcgaagtt ggctggcagc agcgcgtcag    420
tggccgggtt ccactcctca cagtcaatgc cgttcaggat gccgtggaac ttggagcgca    480
gctcggggcg cgcgaaggtg gatctcgccg tcccagcggt agcccttggg cacctcgatg    540
tcgcattcgt gcttgaggcc ctcaatctgg tccttggca ggcactcgta gaacggcagc     600
atgaccgtca cgaagtgtaa atggaggcgc tcgttgatct gagccttgcc ccctgacgaa    660
cggcggtgga tggaagatac tgctctcaag tgctgaagcg gtagcttagc tccccgtttc    720
gtgctgatca gtcttttttca acacgtaaaa agcggaggag ttttgcaatt ttgttggttg    780
taacgatcct ccgttgattt tggcctcttt ctccatgggc gggctgggcg tatttgaagc    840
ggttctctct tctgccgtta                                                860
```

<210> SEQ ID NO 28
<211> LENGTH: 1328
<212> TYPE: DNA
<213> ORGANISM: Artificial Sequence
<220> FEATURE:
<223> OTHER INFORMATION: Synthetic Construct- Example 28: designer
      HydA1-promoter-linked Starch-Synthase-iRNA DNA construct

<400> SEQUENCE: 28

```
agaaaatctg gcaccacacc gagctgtcat gcgttgttcc gttatgtgtc gtcaaacgcc     60
ttcgagcgct gcccggaaca atgcgtacta gtataggagc catgaggcaa gtgaacagaa    120
gcgggctgac tggtcaaggc gcacgatagg gctgacgagc gtgctgacgg ggtgtaccgc    180
cgagtgtccg ctgcattccc gccggattgg gaaatcgcga tggtcgcgca taggcaagct    240
cgcaaatgct gtcagcttat cttacatgaa cacacaaaca ctctcgcagg cactagcctc    300
aaatgaagag cttcatgcgg agggatcgcg tcggcgcggg gctccgcggt gcagccagca    360
caaagcccgt ctcaagggtc gccagcgtga ggcctgcgcc taccgcctac cgcactgcct    420
```

```
gccaagttgc gaaggtggat gaaatggtgt cggtggatga ggagcttact cgtctccgca      480
aggagaacga gctcctgcgc gcccaactgg cgctgtacca gcagaaccag cagccgtccg      540
tgggtgccgc tgccgttgcc ccgcctgctg ccgccacgaa ggtgctggag aagccggcgc      600
cgtaagtaac ctaacggtga gcagcatgca atattttagc gtcgatactc ggaaactata      660
ggagcgcatc agccgaccga tgttcgcgtt gctgtcgcag gcccaaccgt gccaccgccg      720
tggtgtgcaa ggcgcagaag gcggccaggc cgccgctgcc gctgctctgg ccataagtaa      780
cctaacggcg ccggcttctc cagcaccttc gtggcggcag caggcggggc aacggcagcg      840
gcacccacgg acggctgctg gttctgctgg tacagcgcca gttgggcgcg caggagctcg      900
ttctccttgc ggagacgagt aagctcctca tccaccgaca ccatttcatc caccttcgca      960
acttggcagg cagtgcggta ggcggtaggc gcaggcctca cgctggcgac ccttgagacg     1020
ggctttgtgc tggctgcacc gcggagcccc gcgccgagcg catccctccg catgaagctc     1080
ttcattaaat ggaggcgctc gttgatctga gccttgcccc ctgacgaacg gcggtggatg     1140
gaagatactg ctctcaagtg ctgaagcggt agcttagctc cccgtttcgt gctgatcagt     1200
ctttttcaac acgtaaaaag cggaggagtt ttgcaatttt gttggttgta acgatcctcc     1260
gttgattttg gcctctttct ccatgggcgg gctgggcgta tttgaagcgg ttctctcttc     1320
tgccgtta                                                              1328
```

<210> SEQ ID NO 29
<211> LENGTH: 1889
<212> TYPE: DNA
<213> ORGANISM: Artificial Sequence
<220> FEATURE:
<223> OTHER INFORMATION: Synthetic Construct- Example 29: designer
      Amylase DNA construct

<400> SEQUENCE: 29

```
agaaaatctg gcaccacacc atggtagggt gcgagtgacc ccgcgcgact tggaagggtt       60
caaacgaccc cgccgtacga acttttgtcg gggggcgctc ccggatggta gggtgcgagt      120
gaccccgcgc gacttggaag ggttcaaacg accccgccgt acgaactttt gtcgggggc      180 gctcccggct cgagcatatg gccgccgtca ttgccaagtc ctccgtctcc gcggccgtgg      240
ctcgcccggc ccgctccagc gtgcgcccca tggccgcgct gaagcccgcc gtcaaggctg      300 ccccccgtggc tgccccggct caggccaacc agatggcgaa caaacacatg tccctttctc      360
tcttcatcgt cctccttggc ctctcgtgca gcttggcctc cgggcaagtc ctgtttcagg      420
gttttaactg ggagtcgtgg aagcacaatg cgggtggta caacttcctg atgggcaagg      480
tggacgacat cgccgccgct ggcgtcacgc acgtgtggct cccccccggcg tcgcagtccg      540 tcgccgagca agggtacatg ccgggccggc tctacgacct ggacgcctcc aagtacggca      600
acaaggcgca gctcaagtcc ctcatcggcg cgctccacgg caagggcgtc aaggccatcg      660
ccgacatcgt catcaaccac cgcacggcgg agcgcaagga cggccgggc atctactgca      720 tcttcgaggg cggcacccg gacgcgcgcc tcgactgggg ccccacatg atctgccgcg      780 acgaccggcc ctacgccgac ggcaccggca cccggacac cggcgccgac ttcggggccg      840
cgccggacat cgaccacctc aacccgcgcg tccagaagga gctcgtcgag tggctcaact      900
ggctcaggac cgacgtcggc ttcgacggct ggcgcttcga cttcgccaag ggctactccg      960
cggacgtggc caagatctac gtcgaccgct ccgagcccag cttcgccgtc gccgagatat     1020
ggacgtcgct ggcgtacggc ggggacggca agccgaacct caaccaggac ccgcaccggc     1080
```

| | |
|---|---:|
| aggagctggt gaactgggtg aacaaggtgg gcggctccgg ccccgccacc acgttcgact | 1140 |
| tcaccaccaa gggcatcctc aacgtggccg tggagggcga gctgtggcgc ctgcgcggca | 1200 |
| ccgacggcaa ggcgccgggc atgatcgggt ggtggccggc caaggcggtg accttcgtcg | 1260 |
| acaaccacga caccggctcc acgcagcaca tgtggccctt ccttccgac agggtcatgc | 1320 |
| agggatatgc ctacatcctc acgcacccag ggaccccatg catcttctac gatcatttct | 1380 |
| tcgactgggg cttgaaggag gagatcgatc gtctggtgtc aatcaggacc cgacagggga | 1440 |
| tacacagtga gagcaagctg cagatcatgg aggccgacgc cgacctttac cttgccgaga | 1500 |
| tcgacggcaa ggtcatcgtc aagctcgggc caagatacga tgtcggacac ctcattcctg | 1560 |
| aaggcttcaa ggtggtcgcg catggcaatg actatgccgt atgggagaaa gtataaggct | 1620 |
| gctgccccgg ctgctgctaa tctagataaa tggaggcgct cgttgatctg agccttgccc | 1680 |
| cctgacgaac ggcggtggat ggaagatact gctctcaagt gctgaagcgg tagcttagct | 1740 |
| ccccgtttcg tgctgatcag tctttttcaa cacgtaaaaa gcggaggagt tttgcaattt | 1800 |
| tgttggttgt aacgatcctc cgttgatttt ggcctctttc tccatgggcg ggctgggcgt | 1860 |
| atttgaagcg gttctctctt ctgccgtta | 1889 |

<210> SEQ ID NO 30
<211> LENGTH: 3089
<212> TYPE: DNA
<213> ORGANISM: Artificial Sequence
<220> FEATURE:
<223> OTHER INFORMATION: Synthetic Construct- Example 30: designer
      Starch-Phosphorylase DNA construct

<400> SEQUENCE: 30

| | |
|---|---:|
| agaaaatctg gcaccacacc atggtagggt gcgagtgacc ccgcgcgact tggaagggtt | 60 |
| caaacgaccc cgccgtacga acttttgtcg gggggcgctc ccggatggta gggtgcgagt | 120 |
| gaccccgcgc gacttggaag ggttcaaacg accccgccgt acgaactttt gtcgggggc | 180 |
| gctcccggat ggccgccgtc attgccaagt cctccgtctc cgcggccgtg gctcgcccgg | 240 |
| cccgctccag cgtgcgcccc atggccgcgc tgaagcccgc cgtcaaggct gccccgtgg | 300 |
| ctgccccggc tcaggccaac cagatggcgg atgcgaaagc aaacggaaag aatgaggcgg | 360 |
| ccaaactggc gaaaattccg gcggctgcga atccattggc taatgaacca tcggcgattg | 420 |
| catcaaatat aagttaccac gtgcagtaca gtcctcattt ctcgccgact aagttcgagc | 480 |
| cggagcaagc tttctttgcc acggcggagg ttgtccgcga tcgtcttatt caacaatgga | 540 |
| atgagacata ccaccatttt aataaagttg atccgaagca acatactac ctatcaatgg | 600 |
| aatttcttca aggaaggact ttgactaatg caattggcag tttggacatt cagaatgcat | 660 |
| atgctgatgc tttaaataat ttggggcatg tccttgagga gatagctgaa caggaaaaag | 720 |
| atgctgcact aggaaatggt gggctgggca ggctagcttc atgcttctta gactccatgg | 780 |
| caacattgaa tttgcctgca tggggttatg gttttgagata ccggtatggg ctgttcaagc | 840 |
| agaagatcac caagcagggt caagaagaag ttgctgaaga ttggcttgag aaatttagtc | 900 |
| cttgggaagt tgtcaggcat gatgtggtat ttccggtcag attttttggg agtgttatgg | 960 |
| ttaatccaaa tggaacgaga aaatggggttg ggggtgaagt tgtccaagcc gtagcttatg | 1020 |
| atataccaat tccagggtac aaaaccaaga acactatcag tcttcgtctc tgggacgcta | 1080 |
| aagctagcgc tgaggatttc aatttatttc agtttaatga tggacaatac gaatctgctg | 1140 |
| cacagcttca ttctcgagct caacagattt gtgctgtgct ctaccccggg gattctactg | 1200 |

```
aagaagggaa gcttttaagg ctgaaacaac aattctttct ctgcagtgct tcacttcagg   1260
atatgattct tagattcaag gagaggaaaa gtggaaggca gtggtctgaa tttcccagca   1320
aggtagctgt acaactgaat gatactcatc caacacttgc aattccagag ttgatgcgat   1380
tgctaatgga tgaggaagga cttggatggg atgaagcatg ggatataaca acaaggactg   1440
ttgcttatac caatcacaca gtacttcctg aagcacttga gaagtggtca caagcagtaa   1500
tgtggaagct tcttcctcgc catatggaaa taattgaaga gattgacaag agattcattg   1560
caatggtccg ctccacaagg agtgaccttg agagtaagat tcccagcatg tgcatcttgg   1620
ataataatcc caaaaagccg gttgttagga tggcaaactt atgtgtagta tctgcgcata   1680
cggtaaatgg tgttgctcag ttgcacagtg atatcttaaa ggccgacttg ttcgctgact   1740
atgtttctct atggccaaac aaactccaaa ataaaactaa tggcattact cctcgtcgat   1800
ggctccggtt ttgcaatcct gagctcagca aaattatcac aaaatggtta aaaaccgatc   1860
agtgggttac gaaccttgac ctgcttgtag gtcttcgtca gtttgctgac aacacagaac   1920
tccaagctga atgggaatct gctaagatgg ccagtaagaa acatttggca gactacatat   1980
ggcgagtaac cggtgtaacg attgatccta atagcttatt tgacatacaa gtcaagcgca   2040
ttcatgaata caagagacaa ctgctaaata ttttgggcgc aatctacaga tacaagaagt   2100
tgaaggagat gagccctcag gagcggaaga aaactactcc acgcaccatt atgtttggag   2160
ggaaagcatt tgcaacatat acaaacgcaa aaagaatagt aaagttggtt aatgatgttg   2220
gtgaagtcgt caacaccgat cctgaggtca atagttattt gaaggtggta tttgttccaa   2280
attacaatgt ctctgttgcg gagttgctta ttccaggaag tgagctatct cagcatatta   2340
gcacagcagg catggaggca agtggcacaa gcaacatgaa attttctcta aatggttgcc   2400
tcattatagg aacattggat ggagctaatg tggaaatcag gcaggagata ggagaggaga   2460
atttctttct ctttggtgca ggagcagacc aagtccctaa gctgcggaag gaaagagaag   2520
atggattgtt caaccagat cctcggtttg aagaggccaa gcaatttata agaagtggag   2580
catttggaag ctatgactac aacccgcttc ttgattccct ggaggggaac actggttatg   2640
gtcgtggtga ttattttcta gttggttatg acttccaag ttacttagag gctcaggaca   2700
gagttgacca agcttacaag gaccggaaga agtggctgaa gatgtctata ttaagtacag   2760
ctggcagtgg gaaattcagc agtgatcgca caattgcaca gtatgctaag gaaatctgga   2820
acataacaga atgccgtaca tcatgataaa tggaggcgct cgttgatctg agccttgccc   2880
cctgacgaac ggcggtggat ggaagatact gctctcaagt gctgaagcgg tagcttagct   2940
ccccgtttcg tgctgatcag tcttttttcaa cacgtaaaaa gcggaggagt tttgcaattt   3000
tgttggttgt aacgatcctc cgttgatttt ggcctctttc tccatgggcg ggctgggcgt   3060
atttgaagcg gttctctctt ctgccgtta                                    3089
```

<210> SEQ ID NO 31
<211> LENGTH: 1949
<212> TYPE: DNA
<213> ORGANISM: Artificial Sequence
<220> FEATURE:
<223> OTHER INFORMATION: Synthetic Construct- Example 31: designer
      Hexose-Kinase DNA construct

<400> SEQUENCE: 31

```
agaaaatctg gcaccacacc atggtagggt gcgagtgacc ccgcgcgact tggaagggtt     60
caaacgaccc cgccgtacga acttttgtcg gggggcgctc ccggatggta gggtgcgagt    120
```

```
gaccccgcgc gacttggaag ggttcaaacg accccgccgt acgaactttt gtcgggggc    180
gctcccggat ggccgccgtc attgccaagt cctccgtctc cgcggccgtg gctcgcccgg   240
cccgctccag cgtgcgcccc atggccgcgc tgaagcccgc cgtcaaggct gccccgtgg   300
ctgccccggc tcaggccaac cagatggcta acacccccg ccgaaaacct tcccggaagg   360
gatcaatggc tgatatgccg aaggatgtgc ttgaccagct caagacgctg gaagagctct   420
tcacagttga ccaggagaag ctgaagcaga tcgttgagca tttcatcaag gagttacaga   480
agggcctcag tgtcgaaggc ggaaacattc ccatgaacgt gacttgggtt ctgggatttc   540
ccactggcca tgagaaaggt acatttctgg ctctggacat gggggcacc aacctgcgcg    600
tctgcgaaat tgagctctcc gaagagaagg gcgagtttga tgtcacacag tccaagtatc   660
gaatccccga gagctcaag agcggtgaat catcagaact atgggaatat attgccgact    720
gtgtacagca gttcatagaa tactaccatg acggttgcac ggctttgcca gacctgccgc   780
tgggctttac ctttcgtac cctgctactc aagaatatgt tgaccacggt gtcctacaga    840
gatggaccaa gggttttgat attgacggcg tcgagggcaa agacgtcgtc ccaatgttag   900
aagaagcttt ggctaagaag gttaaaaatt cagctctttc cccattttc tttggctata    960
tggtgctaat tactttacag ggtctccca ttaaagttgc cgctctagta aacgacacga    1020
ctggcacact tattgcttcc gcctacactg acccagagat gaaatcggc tgtatcttcg    1080
gcacaggcgt caacgccgcc tacatggaaa atgcgggctc tatccctaaa atagcccact   1140
acaatttacc tcccgacacc ccagtcgcta tcaactgcga atacggcgcc ttcgacaacg   1200
aactcattgt cctcccccga acgcagtatg acgacgtatc ccaactacgt aaaccatact   1260
ccctggactc ctccttccta gccttcatcg aagaagatcc cttcgagaac ctgtcagaaa   1320
cgcgagatct cttcgaacgc accctgggga tctacgcatt gccctcggag ctagaattct   1380
gcagacgcct ggcggaattg atcggcacac gtgccgcacg cctctccgct gcggtgttg    1440
cggccatctg caagaagaaa aatatcaccc attgccatgt cggagcggac gggtcggtgt   1500
tcgagaagta cccgcatttc aaggccaggg gcgccagagc cctgcgggag atccttgact   1560
ggccagatag tgaaccggat cgggttgtga tgagcggagc ggaggatggg tctggcgttg   1620
gtgcggcgct tattgcggct ttgacgcttg agagggttaa acaagcttct tgggaatgga   1680
agtacatcgg aagcggtctg tcttaataaa tggaggcgct cgttgatctg agccttgccc   1740
cctgacgaac ggcggtggat ggaagatact gctctcaagt gctgaagcgg tagcttagct   1800
ccccgtttcg tgctgatcag tctttttcaa cacgtaaaaa gcgaggagt tttgcaattt    1860
tgttggttgt aacgatcctc cgttgatttt ggcctctttc tccatgggcg ggctgggcgt   1920
atttgaagcg gttctctctt ctgccgtta                                     1949
```

<210> SEQ ID NO 32
<211> LENGTH: 2249
<212> TYPE: DNA
<213> ORGANISM: Artificial Sequence
<220> FEATURE:
<223> OTHER INFORMATION: Synthetic Construct- Example 32: designer
      Phosphoglucomutase DNA construct

<400> SEQUENCE: 32

```
agaaaatctg gcaccacacc atggtagggt gcgagtgacc ccgcgcgact tggaagggtt    60
caaacgaccc cgccgtacga actttgtcg ggggcgctc ccggatggta gggtgcgagt     120
gaccccgcgc gacttggaag ggttcaaacg accccgccgt acgaactttt gtcgggggc    180
```

```
gctcccggat ggccgccgtc attgccaagt cctccgtctc cgcggccgtg gctcgcccgg    240
cccgctccag cgtgcgcccc atggccgcgc tgaagcccgc cgtcaaggct gccccgtgg    300
ctgccccggc tcaggccaac cagatgtccg atttctccgt ccagaccatt gccaccacgg   360
ccttcacaga ccaaaagcct ggaacctctg gtctcagaaa gaaagttact gtgtttcaac   420
agcctcacta cactgaaaac ttcattcagg ctattctcga tgccattccg aaggtgccc    480
aaggtgccac tcttgttgta ggaggtgatg gccgtttcta caacgacaag gtcatcaact   540
tgatcgccaa aatcgcctcg gccaacggag tttccaagtt gattttgggt caagacggga   600
ttctttccac tccagcaact tcgcatgtaa tcaggatcag gggtgcaact ggaggaatta   660
ttctcactgc ttcacacaac cccggaggcc ccaaaaacga tttgggtatt aagtacaact   720
tgggaaacgg tgcaccagct ccagaatcgg ttaccaacaa gatctatgat gtctccaagg   780
aattgacttc gtacaagctc attgatttac ccgacattga tttgtccaaa acccagaccg   840
tgcaattggg ccctcttgaa gtggaaatca ttgactccac ctctgattac gtagccatgt   900
tgaaggatat ctttgacttc cccttgatca agtcgttcct cgagactgcc actaaggagc   960
agggattcaa ggttttattt gattcgctca atggtgtcac tggcccctac ggctacaaga  1020
tcttcgttga agaattagga ttgcctctta actcaatcca aaattaccac ccattgcctg  1080
actttggtgg tttacaccca gatccaaact tgacctatgc tcatactttg gtcgagaggg  1140
tcgataagga gaatattgcc tttggtgctg catctgatgg tgacggtgac agaaacatga  1200
tctacggtgc tggtaccttt gtttcgcctg gtgactctgt agccatcatc tcggaatacg  1260
ccgattccat cccttacttc aagaagcaag gtgtctacgg tttggccaga tccatgccta  1320
cctctggagc catcgatttg gtagcaaagg ctaaaggatt gaatgtttac gaagtgccaa  1380
ccggttggaa gttcttctgc aaccttttcg acgctgacaa gttgagtatc tgtggtgaag  1440
agtcgtttgg aacaggctcc aaccacatca gagaaaagga cggcctttgg gctgtagttg  1500
cctggttgaa cgtgctagca gattacaacg tcaagaatcc agaatccaag acatctattt  1560
ctgtagtgca gaactcgttt tggaagaaat acggaagaac tttcttcact agatatgact  1620
acgaaaacgt atcgtctgaa ggtgctgccg agctcatcaa cttgttgtct tctattgttg  1680
actctaagaa accaggaagt agcttagctg atggctacgt cgtcaaggaa gctgctaact  1740
tctcgtacac cgatttggac ggctctgttt cgtccaacca aggtttgttc atcaagtttg  1800
aaagcggctt gagattcata gtaagattgt ctggtactgg atcatccggt gctacagtca  1860
gattatatct cgaaaagcac tctgccgacg aatccaccta tggcttaggc gtagaccagt  1920
acttagttga tgacatcaag tttgtcttgg acttgttgaa gttcaagcag ttcttgggaa  1980
aggatgaacc agatgttcgt acctagtaaa tggaggcgct cgttgatctg agccttgccc  2040
cctgacgaac ggcggtggat ggaagatact gctctcaagt gctgaagcgg tagcttagct  2100
ccccgtttcg tgctgatcag tcttttttcaa cacgtaaaaa gcggaggagt tttgcaattt  2160
tgttggttgt aacgatcctc cgttgatttt ggcctctttc tccatgggcg ggctgggcgt  2220
atttgaagcg gttctctctt ctgccgtta                                    2249
```

<210> SEQ ID NO 33
<211> LENGTH: 2231
<212> TYPE: DNA
<213> ORGANISM: Artificial Sequence
<220> FEATURE:
<223> OTHER INFORMATION: Synthetic Construct- Example 33: designer
      Glucosephosphate-Isomerase DNA construct

<400> SEQUENCE: 33

```
agaaaatctg gcaccacacc atggtagggt gcgagtgacc ccgcgcgact tggaagggtt    60
caaacgaccc cgccgtacga acttttgtcg gggggcgctc ccggatggta gggtgcgagt   120
gaccccgcgc gacttggaag ggttcaaacg accccgccgt acgaactttt gtcgggggc    180
gctcccggat ggccgccgtc attgccaagt cctccgtctc cgcggccgtg gctcgcccgg   240
cccgctccag cgtgcgcccc atggccgcgc tgaagcccgc cgtcaaggct gccccgtgg    300
ctgccccggc tcaggccaac cagatgtcca ataactcatt cactaacttc aaactggcca   360
ctgaattgcc agcctggtct aagttgcaaa aaatttatga atctcaaggt aagactttgt   420
ctgtcaagca agaattccaa aaagatgcca agcgttttga aaaattgaac aagactttca   480
ccaactatga tggttccaaa atcttgttcg actactcaaa gaacttggtc aacgatgaaa   540
tcattgctgc attgattgaa ctggccaagg aggctaacgt caccggtttg agagatgcta   600
tgttcaaagg tgaacacatc aactccactg aagatcgtgc tgtctaccac gtcgcattga   660
gaaacagagc taacaagcca atgtacgttg atggtgtcaa cgttgctcca gaagtcgact   720
ctgtcttgaa gcacatgaag gagttctctg aacaagttcg ttctggtgaa tggaagggtt   780
ataccggtaa gaagatcacc gatgttgtta acatcggtat tggtggttcc gatttgggtc   840
cagtcatggt cactgaggct ttgaagcact acgctggtgt cttggatgtc cacttcgttt   900
ccaacattga cggtactcac attgctgaaa ccttgaaggt tgttgaccca gaaactactt   960
tgtttttgat tgcttccaag actttcacta ccgctgaaac tatcactaac gctaacactg  1020
ccaagaactg gttcttgtcg aagacaggta atgatccatc tcacattgct aagcatttcg  1080
ctgctttgtc cactaacgaa accgaagttg ccaagttcgg tattgacacc aaaaacatgt  1140
ttggtttcga aagttgggtc ggtggtcgtt actctgtctg gtcggctatt ggtttgtctg  1200
ttgccttgta cattggctat gacaactttg aggctttctt gaagggtgct gaagccgtcg  1260
acaaccactt cacccaaacc ccattggaag acaacattcc attgttgggt ggtttgttgt  1320
ctgtctggta caacaacttc tttggtgctc aaacccattt ggttgctcca ttcgaccaat  1380
acttgcacag attcccagcc tacttgcaac aattgtcaat ggaatctaac ggtaagtctg  1440
ttaccagagg taacgtgttt actgactact ctactggttc tatcttgttt ggtgaaccag  1500
ctaccaacgc tcaacactct ttcttccaat tggttcacca aggtaccaag ttgattccat  1560
ctgatttcat cttagctgct caatctcata acccaattga gaacaaatta catcaaaaga  1620
tgttggcttc aaacttcttt gctcaagctg aagctttaat ggttggtaag gatgaagaac  1680
aagttaaggc tgaaggtgcc actggtggtt tggtcccaca caaggtcttc tcaggtaaca  1740
gaccaactac ctctatcttg gctcaaaaga ttactccagc tactttgggt gctttgattg  1800
cctactacga acatgttact ttcactgaag gtgccatttg gaatatcaac tctttcgacc  1860
aatgggggtgt tgaattgggt aaagtcttgg ctaaagtcat cggcaaggaa ttggacaact  1920
cctccaccat ttctacccac gatgcttcta ccaacggttt aatcaatcaa ttcaaggaat  1980
ggatgtgata aatggaggcg ctcgttgatc tgagccttgc cccctgacga acggcggtgg  2040
atggaagata ctgctctcaa gtgctgaagc ggtagcttag ctccccgttt cgtgctgatc  2100
agtcttttc aacacgtaaa aagcggagga gttttgcaat tttgttggtt gtaacgatcc   2160
tccgttgatt ttggcctctt tctccatggg cgggctgggc gtatttgaag cggttctctc  2220
ttctgccgtt a                                                       2231
```

```
<210> SEQ ID NO 34
<211> LENGTH: 1709
<212> TYPE: DNA
<213> ORGANISM: Artificial Sequence
<220> FEATURE:
<223> OTHER INFORMATION: Synthetic Construct- Example 34: designer
      oxyphotobacterial Butanol Dehydrogenase DNA construct

<400> SEQUENCE: 34
agaaaatctg gcaccacacc atccaaactc gccacccgca aaccaatggc atggccgagc      60
gctgcaacgg tcgcattgcc aagattctgc gtgctgagcg ctttgtctcc gctgctgatc     120
tgcaagagac gctcacgcga tacctctggg cgtgcaatca ccgcattccc caacgcgctt     180
tgggccacat gaccccccatc gagagactcc gaacgtggca aatggaggga ccagagttgt    240
tcagttcaca ggtagataat gtcgcgggtc ttgatagtta gcaataaata cagtttcaga     300
atatctgtaa tacaaaaact gtatcgagac aagaaaaaag tagcaaaatt tacaaatgtt     360
catgattcat ctggctaaat tggatgttca actgacccat tgaagacaag ggcaacaacc     420
atggagaatt ttagatttaa tgcatataca gagatgcttt ttggaaaggg acaaatagag     480
aagcttccag aggttttaaa aagatatggt aaaaatatat tacttgcata tggtggtgga     540
agtataaaaa agaatggact ctatgatact atccaaaagc tattgaaaga ttttaatatt     600
gttgaattaa gtggtattga accaaatcca agaattgaaa ctgtaagacg tggagttgaa     660
cttttgcagaa aaaataaagt agatgttatt ttagctgttg gtgagggag tacaatagac    720
tgctcaaagg ttatagggggc aggttattat tatgctggag atgcatggga ccttgtaaaa   780
aatccagcta aaataggtga ggttttacca atagtgacag ttttaacaat ggcagctact    840
ggttctgaaa tgaatagaaa tgctgttatt tcaaagatgg atacaaatga aaagcttgga    900
acaggatcac ctaagatgat ccctcaaact tctattttag atccagaata tttgtataca    960
ttgccagcaa ttcaaacagc tgcaggttgt gctgatatta tgtcacacat atttgaacaa   1020
tattttaata aaactacaga tgcttttgta caagataaat ttgcggaagg tttgttgcaa   1080
acttgtataa aatattgccc tgttgctttta aaggaaccaa agaattatga agctagagca   1140
aatataatgt gggctagttc aatggctctt aacggacttt taggaagtgg gaaagctgga   1200
gcttggactt gtcatccaat agaacatgaa ttaagtgcat tttatgatat aactcatgga   1260
gtaggtcttg caattttaac tccaagttgg atgagatata tcttaagtga tgtaacagtt   1320
gataagtttg ttaacgtatg gcatttagaa caaaagaag ataaatttgc tcttgcaaat    1380
gaagcaatag atgcaacaga aaaattctt aaagcttgtg gtattccaat gactttaact   1440
gaacttggaa tagataaagc aaactttgaa aagatggcaa aagctgcagt agaacatggt   1500
gctttagaat atgcatatgt ttcattaaat gccgaggatg tatataaaat tttagaaatg   1560
tccctttaat aaggctgaga tcttcttcag tgcattgtag ttgaatgaag ggttaggggg   1620
gaaatgcccc cctattttt gtctagccat cctgccacgt ttgacagggt agcaatttcg   1680
acacgatagg gttctctctt ctgccgtta                                       1709

<210> SEQ ID NO 35
<211> LENGTH: 1967
<212> TYPE: DNA
<213> ORGANISM: Artificial Sequence
<220> FEATURE:
<223> OTHER INFORMATION: Synthetic Construct- Example 35: designer
      oxyphotobacterial Butyraldehyde Dehydrogenase DNA construct

<400> SEQUENCE: 35
```

```
agaaaatctg gcaccacacc atccaaactc gccacccgca aaccaatggc atggccgagc    60
gctgcaacgg tcgcattgcc aagattctgc gtgctgagcg ctttgtctcc gctgctgatc   120
tgcaagagac gctcacgcga tacctctggg cgtgcaatca ccgcattccc aacgcgctt    180
tgggccacat gaccccatc gagagactcc gaacgtggca atggaggga ccagagttgt    240
tcagttcaca ggtagataat gtcgcgggtc ttgatagtta gcaataaata cagtttcaga   300
atatctgtaa tacaaaaact gtatcgagac aagaaaaaag tagcaaaatt tacaaatgtt   360
catgattcat ctggctaaat tggatgttca actgacccat tgaagacaag ggcaacaacc   420
atgattaaag acacgctagt ttctataaca aagatttaa aattaaaaac aaatgttgaa    480
aatgccaatc taagaactca aaggatgat tcttcatgtt tcggagttt cgaaaatgtt    540
gaaaatgcta aagcaatgc cgtacacgca caaagatat tatcccttca ttatacaaaa    600
gaacaaagag aaaaaatcat aactgagata agaaaggccg cattagaaaa taagagatt    660
ctagctacaa tgattcttga agaaacacat atgggaagat atgaagataa aatattaaag   720
catgaattag tagctaaata cactcctggg acagaagatt taactactac tgcttggtca   780
ggagataacg ggcttacagt tgtagaaatg tctccatatg gcgttatagg tgcaataact   840
ccttctacga atccaactga aactgtaata tgtaatagta taggcatgat agctgctgga   900
aatactgtgg tatttaacgg acatccaggc gctaaaaaat gtgttgcttt tgctgtcgaa   960
atgataaata aagctattat ttcatgtggt ggtcctgaga atttagtaac aactataaaa  1020
aatccaacta tggactctct agatgcaatt attaagcacc cttcaataaa actactttgc  1080
ggaactggag ggccaggaat ggtaaaaaacc ctcttaaatt ctggtaagaa agctataggt  1140
gctggtgctg gaaatccacc agttattgta gatgatactg ctgatataga aaaggctggt  1200
aagagtatca ttgaaggctg ttcttttgat aataatttac cttgtattgc agaaaaagaa  1260
gtatttgttt ttgagaacgt tgcagatgat ttaatatcta acatgctaaa aaataatgct  1320
gtaattataa atgaagatca agtatcaaag ttaatagatt tagtattaca aaaaaataat  1380
gaaactcaag aatactctat aaataagaaa tgggtcggaa aagatgcaaa attattctta  1440
gatgaaaatag atgttgagtc tccttcaagt gttaaatgca taatctgcga agtaagtgca  1500
aggcatccat ttgttatgac agaactcatg atgccaatat taccaattgt aagagttaaa  1560
gatatagatg aagctattga atatgcaaaa atagcagaac aaaatagaaa acatagtgcc  1620
tatatttatt caaaaaatat agacaaccta aataggtttg aaagagaaat cgatactact  1680
atctttgtaa agaatgctaa atcttttgcc ggtgttggtt atgaagcaga aggctttaca  1740
actttcacta ttgctggatc cactggtgaa ggaataactt ctgcaagaaa ttttacaaga  1800
caaagaagat gtgtactcgc cggttaataa ggctgagatc ttcttcagtg cattgtagtt  1860
gaatgaaggg ttagggggga aatgccccc tatttttgt ctagccatcc tgccacgttt   1920
gacagggtag caatttcgac acgatagggt tctctcttct gccgtta                 1967
```

<210> SEQ ID NO 36
<211> LENGTH: 1602
<212> TYPE: DNA
<213> ORGANISM: Artificial Sequence
<220> FEATURE:
<223> OTHER INFORMATION: Synthetic Construct- Example 36: designer
    oxyphotobacterial Butyryl-CoA Dehydrogenase DNA construct

<400> SEQUENCE: 36

```
agaaaatctg gcaccacacc tgatctgcaa gagacgctca cgcgatacct ctgggcgtgc    60
```

```
aatcaccgca ttccccaacg cgctttgggc cacatgaccc ccatcgagag actccgaacg    120
tggcaaatgg agggaccaga gttgttcagt tcacaggtag ataatgtcgc gggtcttgat    180
agttagcaat aaatacagtt tcagaatatc tgtaatacaa aaactgtatc gagacaagaa    240
aaaagtagca aaatttacaa atgttcatga ttcatctggc taaattggat gttcaactga    300
cccattgaag acaagggcaa caaccatgaa tttccaatta actagagaac aacaattagt    360
acaacaaatg gttagagaat cgcagtaaaa tgaagttaag ccaatagctg ctgaaatcga    420
cgaaacagaa agattcccta tggaaaacgt tgaaaaaatg gctaagctta aaatgatggg    480
tatcccattt tctaaagaat tggtggagc aggcggagag gttctttcat atataatagc    540
tgtggaagaa ttatcaaaag tttgtggtac tacaggagtt attctttcag cgcatacatc    600
attatgtgca tcagtaatta atgaaaatgg aactaacgaa caaagagcaa atatttacc     660 tgatctttgc agcggtaaaa agatcggtgc tttcggatta actgaaccag gtgctggtac    720
agatgctgca ggacaacaaa caactgctgt attagaaggg gatcattatg tattaaatgg    780
ttcaaaaatc ttcataacaa atggtggagt tgctgaaact ttcataatat ttgctatgac    840
agataagagt caaggaacaa aaggaatttc tgcattcata gtagaaaagt cattcccagg    900
attctcaata ggaaaattag aaaataagat ggggatcaga gcatcttcaa ctactgagtt    960
agttatggaa aactgcatag taccaaaaga aaacctactt agcaaagaag gtaagggatt    1020
tggtatagca atgaaaactc ttgatggagg aagaattggt atagctgctc aagctttagg    1080
tattgcagaa ggagcttttg aagaagctgt taactatatg aaagaaagaa aacaatttgg    1140
taaaccatta tcagcattcc aaggattaca atggtatata gctgaaatgg atgttaaaat    1200
ccaagctgct aaatacttag tatacctagc tgcaacaaag aagcaagctg gtgagcctta    1260
ctcagtagat gctgcaagag ctaaattatt tgctgcagat gttgcaatgg aagttacaac    1320
taaagcagtt caaatctttg gtggatatgg ttacactaaa gaatacccag tagaaagaat    1380
gatgagagat gctaaaatat gcgaaatcta cgaaggaact tcagaagttc aaaagatggt    1440
tatcgcagga agcatttaaa gataaggctg agatcttctt cagtgcattg tagttgaatg    1500
aagggttagg ggggaaatgc ccccctattt tttgtctagc catcctgcca cgtttgacag    1560
ggtagcaatt tcgacacgat agggttctct cttctgccgt ta                      1602
```

<210> SEQ ID NO 37
<211> LENGTH: 1248
<212> TYPE: DNA
<213> ORGANISM: Artificial Sequence
<220> FEATURE:
<223> OTHER INFORMATION: Synthetic Construct- Example 37: designer oxyphotobacterial Crotonase DNA construct

<400> SEQUENCE: 37

```
agaaaatctg gcaccacacc tgatctgcaa gagacgctca cgcgatacct ctgggcgtgc     60
aatcaccgca ttccccaacg cgctttgggc cacatgaccc ccatcgagag actccgaacg    120
tggcaaatgg agggaccaga gttgttcagt tcacaggtag ataatgtcgc gggtcttgat    180
agttagcaat aaatacagtt tcagaatatc tgtaatacaa aaactgtatc gagacaagaa    240
aaaagtagca aaatttacaa atgttcatga ttcatctggc taaattggat gttcaactga    300
cccattgaag acaagggcaa caaccatgga attaaaaaat gttattcttg aaaaagaagg    360
gcatttagct attgttacaa tcaatagacc aaaggcatta aatgcattga attcagaaac    420
actaaaagat ttaaatgttg ttttagatga tttagaagca gacaacaatg tgtatgcagt    480
```

```
tatagttact ggtgctggtg agaaatcttt tgttgctgga gcagatattt cagaaatgaa    540
agatcttaat gaagaacaag gtaaagaatt tggtattta ggaaataatg tcttcagaag     600
attagaaaaa ttggataagc cagttatcgc agctatatca ggatttgctc ttggtggtgg    660
atgtgaactt gctatgtcat gtgacataag aatagcttca gttaaagcta aatttggtca    720
accagaagca ggacttggaa taactccagg atttggtgga actcaaagat tagcaagaat    780
agttggacca ggaaaagcta aagaattaat ttatacttgt gaccttataa atgcagaaga    840
agcttataga ataggcttag ttaataaagt agttgaatta gaaaaattga tggaagaagc    900
aaaagcaatg gctaacaaga ttgcagctaa tgctccaaaa gcagttgcat attgtaaaga    960
tgctatagac agaggaatgc aagttgatat agatgcagct atattaatag aagcagaaga   1020
ctttgggaag tgctttgcaa cagaagatca aacagaagga atgactgcgt tcttagaaag   1080
aagagcagaa aagaattttc aaaataaata aggctgagat cttcttcagt gcattgtagt   1140
tgaatgaagg gttagggggg aaatgccccc ctatttttg tctagccatc ctgccacgtt    1200
tgacagggta gcaatttcga cacgataggg ttctctcttc tgccgtta               1248

<210> SEQ ID NO 38
<211> LENGTH: 1311
<212> TYPE: DNA
<213> ORGANISM: Artificial Sequence
<220> FEATURE:
<223> OTHER INFORMATION: Synthetic Construct- Example 38: designer
      oxyphotobacterial 3-Hydroxybutyryl-CoA Dehydrogenase DNA construct

<400> SEQUENCE: 38
agaaaatctg gcaccacacc tgatctgcaa gagacgctca cgcgatacct ctgggcgtgc     60
aatcaccgca ttccccaacg cgctttgggc cacatgaccc ccatcgagag actccgaacg    120
tggcaaatgg agggaccaga gttgttcagt tcacaggtag ataatgtcgc gggtcttgat    180
agttagcaat aaatacagtt tcagaatatc tgtaatacaa aaactgtatc gagacaagaa    240
aaaagtagca aatttacaa atgttcatga ttcatctggc taaattggat gttcaactga     300
cccattgaag acaagggcaa caaccatgaa aaagattttt gtacttggag caggaactat    360
gggtgctggt atcgttcaag cattcgctca aaaaggttgt gaggtaattg taagagacat    420
aaaggaagaa tttgttgaca gaggaatagc tggaatcact aaaggattag aaaagcaagt    480
tgctaaagga aaaatgtctg aagaagataa agaagctata ctttcaagaa tttcaggaac    540
aactgatatg aagttagctg ctgactgtga tttagtagtt gaagctgcaa tcgaaaacat    600
gaaaattaag aaggaaatct ttgctgagtt agatggaatt tgtaagccag aagcgatttt    660
agcttcaaac acttcatctt tatcaattac tgaagttgct tcagctacaa agagacctga    720
taaagttatc ggaatgcatt tctttaatcc agctccagta atgaagcttg ttgaaattat    780
taaaggaata gctacttctc aagaaacttt tgatgctgtt aaggaattat cagttgctat    840
tggaaaagaa ccagtagaag ttgcagaagc tccaggattc gttgtaaacg gaatcttaat    900
cccaatgatt aacgaagctt cattcatcct tcaagaagga atagcttcag ttgaagatat    960
tgatacagct atgaaatatg gtgctaacca tccaatggga ccttagctt taggagatct   1020 tattggatta gatgttgct tagctatcat ggatgttta ttcactgaaa caggtgataa    1080
caagtacaga gctagcagca tattaagaaa atatgttaga gctggatggc ttggaagaaa   1140
atcaggaaaa ggattctatg attattctaa ataaggctga gatcttcttc agtgcattgt   1200
agttgaatga agggttaggg gggaaatgcc ccctattt ttgtctagcc atcctgccac    1260
```

```
gtttgacagg gtagcaattt cgacacgata gggttctctc ttctgccgtt a           1311
```

<210> SEQ ID NO 39
<211> LENGTH: 1665
<212> TYPE: DNA
<213> ORGANISM: Artificial Sequence
<220> FEATURE:
<223> OTHER INFORMATION: Synthetic Construct- Example 39: designer
    oxyphotobacterial Thiolase DNA construct

<400> SEQUENCE: 39

```
agaaaatctg gcaccacacc tgatctgcaa gagacgctca cgcgatacct ctgggcgtgc    60
aatcaccgca ttccccaacg cgctttgggc cacatgaccc ccatcgagag actccgaacg   120
tggcaaatgg agggaccaga gttgttcagt tcacaggtag ataatgtcgc gggtcttgat   180
agttagcaat aaatacagtt tcagaatatc tgtaatacaa aaactgtatc gagacaagaa   240
aaaagtagca aaatttacaa atgttcatga ttcatctggc taaattggat gttcaactga   300
cccattgaag acaagggcaa caaccatggg caaagaaagt agttttagct gtgcatgtcg   360
tacagccatc ggaacaatgg gtggatctct tagcacaatt cctgcagtag atttaggtgc   420
tatcgttatc aaagaggctc ttaaccgcgc aggtgttaaa cctgaagatg ttgatcacgt   480
atacatggga tgcgttattc aggcaggaca gggacagaac gttgctcgtc aggcttctat   540
caaggctggt cttcctgtag aagtacctgc agttacaact aacgttgtat gtggttcagg   600
tcttaactgt gttaaccagg cagctcagat gatcatggct ggagatgctg atatcgttgt   660
tgccggtggt atggaaaaca tgtcacttgc accatttgca cttcctaatg gccgttacgg   720
atatcgtatg atgtggccaa gccagagcca gggtggtctt gtagacacta tggttaagga   780
tgctctcttgg gatgctttca atgattatca tatgatccag acagcagaca acatctgcac   840
agagtggggt cttacacgtg aagagctcga tgagtttgca gctaagagcc agaacaaggc   900
ttgtgcagca atcgaagctg gcgcattcaa ggatgagatc gttcctgtag agatcaagaa   960
gaagaaagag acagttatct tcgatacaga tgaaggccca agacagggtg ttacacctga  1020
atctcttttca aagcttcgtc ctatcaacaa ggatggattc gttacagctg gtaacgcttc  1080
aggtatcaac gacggtgctg cagcactcgt agttatgtct gaagagaagg ctaaggagct  1140
cggcgttaag cctatggcta cattcgtagc tggagcactt gctggtgttc gtcctgaagt  1200
tatgggtatc ggtcctgtag cagctactca gaaggctatg aagaaggctg tatcgagaa  1260
cgtatctgag ttcgatatca tcgaggctaa cgaagcattc gcagctcagt ctgtagcagt  1320
tggtaaggat cttggaatcg acgtccacaa gcagctcaat cctaacgtgt gtgctatcgc  1380
tcttggacac ccagttggag cttcaggtgc tcgtatcctt gttacacttc ttcacgagat  1440
gcagaagaaa gacgctaaga agggtcttgc tacactttgc atcggtggcg gtatgggatg  1500
cgctactatc gttgagaagt acgaataagg ctgagatctt cttcagtgca ttgtagttga  1560
atgaagggtt agggggggaaa tgcccccta tttttttgtct agccatcctg ccacgtttga  1620
cagggtagca atttcgacac gatagggttc tctcttctgc cgtta                 1665
```

<210> SEQ ID NO 40
<211> LENGTH: 4071
<212> TYPE: DNA
<213> ORGANISM: Artificial Sequence
<220> FEATURE:
<223> OTHER INFORMATION: Synthetic Construct- Example 40: designer
    oxyphotobacterial Pyruvate-Ferredoxin Oxidoreductase DNA construct

<400> SEQUENCE: 40

```
agaaaatctg gcaccacacc tgatctgcaa gagacgctca cgcgatacct ctgggcgtgc      60
aatcaccgca ttccccaacg cgctttgggc cacatgaccc ccatcgagag actccgaacg     120
tggcaaatgg agggaccaga gttgttcagt tcacaggtag ataatgtcgc gggtcttgat     180
agttagcaat aaatacagtt tcagaatatc tgtaatacaa aaactgtatc gagacaagaa     240
aaaagtagca aaatttacaa atgttcatga ttcatctggc taaattggat gttcaactga     300
cccattgaag acaagggcaa caaccatggc gcagaggtgc aaggagcccg tcgacggaac     360
gacagccacg acgcacgtgg cctacttcat gagcgacagc gcgttcatct tccccatcac     420
gcccagctcg gtcatgtccg aggtcgccca cgagtggtcc atgaacggcc gcaagaacgc     480
cttcggccag cccacgatgg tccgccagat gcagagcgag gctgggtctg ccggcgccct     540
gcacggcgcg ctcagcgagg gagcgctggc gacgacgttc acgagcagcc agggcctgct     600
gctcatgatc cccaacatgt acaagatcgc cggcgagctc ctgccctgcg tcatgcacat     660
cgccgcccgc accgtcgcca ccgaggccct ctctatcttc ggcgaccaca cggatgtcta     720
cgcggtgagg tcgacggggt tcgcgttcct gtgctccgcg accgtccagg agtgcatcca     780
catgtccgcc gccgcgcacg ccgccaccct gtcccagcga gtcccgttcg cccacttctt     840
cgacggcttc cgcacgtccc acgagatcca gaagatcgac ttcccctcgg acgccgacct     900
gctggcctgc atgaactttg acgacgtccg caggttccgt ggccgctcgc tgtgctgcga     960
gcgcccgctg ctgcgcggga cggcgcagaa ccccgacgtc ttcatgcagg cgtccgagtc    1020
gaacctggcg acgctggcca gggtccccgc ggccatcgac gaggcgctgg ctcgtgtgaa    1080
caaggtgttc gggaccaact acaggaccta cgagtactat ggccaccccg aggccacgga    1140
cgtgatcgtg gccatgggaa gcggcaccga agtggccatc tcgactgcca acttcctcaa    1200
ctcgcgcgac gcgaactcga gggtcggcgt cgtgagggtg cggctgttcc ggccgtttgt    1260
gtcggcggcg tttgtggctg cgctgcccaa gaccgtcaag aggatctgcg ttctggaccg    1320
cgggagggac gggcaggcgg ccgcggaccc cctgcaccag gacgtcctgt cggcgctggg    1380
tctggcagcg cccgggaggg ttcaggtgtg cgtgggaggc gtgtacggtc tgtcgtccaa    1440
ggacttcaac cccgaccacg tgatcgccgt gtacaggaac ctcgcgtcgg cgagccccaa    1500
gaacaggttc agcgtcggca tcgtcgacga cgtgacgcac aacagcctgg acatgggaga    1560
gcacgtggac gcgctgccgc aggggacgaa gcagtgcctg ctgtgggggca tcggcggaga    1620 cgggaccatc ggggcgaaca agacggccat caagctgatc gcggaccaca cggagctgca    1680
cgcgcagggg tactttgcgt acgacgccaa caaggccggc ggcctgacag tctcgcacct    1740
gcggttcggc ccgacgcggt tcgaggcgcc gtacctggtg aacgacagca actacgtggc    1800
gtgccacaac ttctcgtacg tgcacaggtt caacctgctg tcgtcgctgc gcaccggggg    1860
cacgttcgtg ctcaactgcc cgtgccggac cgtggaggag ctggacacgg cactcccggt    1920
gcgcctgagg cgcgagatcg ccaggcggca ggccaagttc tatgtgatcg acgcgaccaa    1980
gatcgccaag gacaacggga tgggcccgtt catcaacatg gtcctccagg ccgtgttctt    2040
ctatctgtcc cacgtgctcg atgtgaacga ggcagtggca ctcctgaaga agagcatcca    2100
gaagatgtac gcgcgcaagg gcgaggaggt tgtcaggaag aacgtggcat cggtcgacgc    2160
gtcgctggat cccaaggcgt tgctgcacat cgagtacccc gcagacaggt ggcttgcgct    2220
ggccgacgag cacgtgcccc gcatgggtct gctcactgtc cccgagcgcc tgcagaagtt    2280
caacgccgag ctgtacgagc cgaccctcgc gtacgatggg gagagcatcc cggtcagcag    2340
```

```
gttccctcgc ggcggcgaga cgccgacggg cacgactcag ctgggcaagc gtggcatcgc    2400
cgagagcgtg ccgcactgga accacgagaa gtgcgtgcag tgcaaccagt gctcgttcgt    2460
gtgcccgcac gccgtcatcc ggtcgtacca gatcagcgag gaggagatga agaacgcccc    2520
tgccggcttc gacactctta agtcgcgcaa gcccgggtat cgtttccgca tcaacgtcag    2580
cgccctggac tgcactggct gcagcgtgtg cgtggagcag tgcccagtca agtgcctgga    2640
gatgaagcct ctcgagtccg agttcgagat gcagaaggac gccatcaggt tcgtccgcga    2700
gatggtcgcg cccaagcccg agctgggaga ccgcaagact cccgtcggca tcgcgtctca    2760
cacgccgctg ttcgagttcc cgggagcctg cgccgggtgc ggtgagaccc cgctggtgcg    2820
cctcgtgacg cagatgttcg gtgagcgcat ggtcatcgcc gcggccactg ggtgcaactc    2880
gatctgggga cgtcgttcc cgaacgtgcc gtacacaacc aacgcccgcg gggagggccc    2940
cgcgtggcac aactcgctgt cgaggacgc ggcggagctc gggtatggca ttacgtgtgc    3000
gtatcgccag cgccgcgagc gcctcatcgg catcgtgcgg agcgtcgtcg acgatgcggg    3060
atccgtgcag ggtctgtctg ctgagctgaa ggctctgctg gtcgagtggc tcgcgcacgt    3120
cagggacttc gagaagaccc cgagctccg cgacaggatg aaccccctga tcgacgcaat    3180
cccagcgaac gcggactgca gggttctgga gctcaggag aagcacaacc gcgagctgat    3240
cgcgcgcacg agtttctgga tcctcggtgg cgacgggtgg gcgtacgaca tcggcttcgg    3300
tggactggac cacgtgatcg ccaacaacga ggacgtcaac atccttgttc tcgacacgga    3360
ggtctactcc aacactggtg gccagcgctc caagtcgacg ccgctcggcg cccgcgccaa    3420
gtacgctgtg ctgggcaagg acactgggaa gaaggacctg ggccgcatcg cgatgaccta    3480
cgagaccgcg tacgtggcca gcatcgcgca gggagccaac cagcagcagt gcatggacgc    3540
gctgagggag gccgaggcct accagggccc ctcgatcgtc attgcgtaca ctccgtgcat    3600
ggagcaccag atggtccgcg ggatgaagga gagccagaag aaccagaagc tggctgtgga    3660
gacgggctac tggctgctgt accgcttcaa ccccgacctc atccacgagg caagaaccc    3720 cttcacccctc gactcgaagc ctccctcgaa gcctcccaag gagttcctgg acacgcaggg    3780
ccgtttcatt actctgcagc gcgagcaccc cgagcaggcc cacctccttc acgaggcact    3840
cacccgctct ctggccaccc gcttcgtgcg ctaccagcgc ctcgtgcagc tgtacgagcc    3900 cgctgccct gccgcagctc ctgccacgca ttaaggctga gatcttcttc agtgcattgt    3960
agttgaatga agggttaggg gggaaatgcc cctatttt ttgtctagcc atcctgccac    4020
gtttgacagg gtagcaattt cgacacgata gggttctctc ttctgccgtt a            4071
```

<210> SEQ ID NO 41
<211> LENGTH: 1806
<212> TYPE: DNA
<213> ORGANISM: Artificial Sequence
<220> FEATURE:
<223> OTHER INFORMATION: Synthetic Construct- Example 41: designer
      oxyphotobacterial Pyruvate Kinase DNA construct

<400> SEQUENCE: 41

```
agaaaatctg gcaccacacc tgatctgcaa gagacgctca cgcgatacct ctgggcgtgc      60
aatcaccgca ttccccaacg cgctttgggc cacatgaccc ccatcgagag actccgaacg     120
tggcaaatgg agggaccaga gttgttcagt tcacaggtag ataatgtcgc gggtcttgat     180
agttagcaat aaatacagtt tcagaatatc tgtaatacaa aaactgtatc gagacaagaa     240
aaaagtagca aaatttacaa atgttcatga ttcatctggc taaattggat gttcaactga     300
```

```
cccattgaag acaagggcaa caaccgtgtt cactaaaatt gtagctacat tggggccttc    360
gactgataga ctgccggata taacggccct gttgagcaag gttcacgcg tgcggataaa    420
tatgtctcac gcatcgccat cggaggtaga ggcccgcgtg aacgccgtga ggaagtatga    480
ggagaccagc gggaggtata tagccattat agcggatcta aggggcccca gcgtcaggac    540
cggccttatg cgccctctac agataacggc gggcgcccgc gtctccttta aattagccga    600
gaaggggac ggcttcgtac ctgtgccgcg gcgtgagttc ttcgaagtaa tcgaggaggg    660
agacgaggtt cttatgttag acggaaaact cgtcttgagg ataatcagcg cagcgcagac    720
ctcggccgag gccgagtcgt tatcctccgg cgtcatatcc agcaataagg caatagtggt    780
caaaggcaag gaatatcata tagagcagcc tgtggaggaa gacataaggg cgcttcagac    840
gctctctcgg ttcagagacg acgtagacta cgtggccctc agccttgtga gagacggagc    900
agacgtgagg aaaatgagga gcgtcgtcga ggaggctggg ctcacctccg gcataatggc    960
caaaatagag acgaagagcg cagtagataa aatcgaggag ataatcaatg cggccgacta   1020
catagttata gcgagaggcg atctggcgct gcactacgga ctggagtaca ttcctaaagt   1080
acagaggctc ttggtggaga gatctctctc ggcaggaagg cccgtggcgg tggccacgca   1140
gcttttggac tctatgcaga ccaacacgac gcccactagg gcggaggtca acgacgtgta   1200
cacaacggcg agtctcggag tggactctct gtggctgacc aacgagactg cgagcggaga   1260
gcacccgtta gaggcagtgg attggctgag gaggatagtg tcgcaggtcg agttcggag    1320
acttaaggct gcgtcgccgg ccgacgcacg cgataggttc gccaaagccg tggtagatat   1380
ggccgaggac atgggagggg aaatcgcagt atactcaatg acgggaactc tggcgaagag   1440
aatagctaaa tttaggccga tgacgacagt ctacgtcgga gtcaacgaga ggaggctcgc   1500
gaggatgttg gagctccgcg aggatgttgg agctcatatg gggcctagag cctgtggtcg   1560
tgccggcgca tacttacgag gagggcctcg agaggctcct ctccagattc tccgacaaag   1620
tcttgatagc cacgtatggg ctcagaggcg gcacacatac tattaataag gctgagatct   1680
tcttcagtgc attgtagttg aatgaagggt taggggggaa atgccccct atttttgtc    1740
tagccatcct gccacgtttg acagggtagc aatttcgaca cgatagggtt ctctcttctg   1800
ccgtta                                                              1806

<210> SEQ ID NO 42
<211> LENGTH: 1696
<212> TYPE: DNA
<213> ORGANISM: Artificial Sequence
<220> FEATURE:
<223> OTHER INFORMATION: Synthetic Construct- Example 42: designer
      oxyphotobacterial Enolase DNA construct

<400> SEQUENCE: 42
agaaaatctg gcaccacacc tgaccccat cgagagactc cgaacgtggc aaatggaggg     60
accagagttg ttcagttcac aggtagataa tgtcgcgggt cttgatagtt agcaataaat    120
acagtttcag aatatctgta atacaaaaac tgtatcgaga caagaaaaaa gtagcaaaat    180
ttacaaatgt tcatgattca tctggctaaa ttggatgttc aactgaccca ttgaagacaa    240
gggcaacaac cttattttt cttcaagtta agaatgcgt tcattccagg ataaacggca     300
atgctgccaa gctcttcttc aattctcaag agctgattgt attttgctac tctgtctgtt    360
cttgacggtg cacctgtctt tatctgacca gcatttactg caacaacaag gtcagcaatt    420
gttgtatctt cagtctcacc tgatctgtgg gatacaactg cagtgtagcc tgctctattt    480
```

```
gccatttcaa tagcttctaa agtttctgta agtgttccta tctgattaag cttaatcaat      540
attgagtttg caacgccaag ttctattccc tttgcaagcc tctttgtgtt tgtaacaaac      600
aaatcatcac ccacaagctg aatcttcttg ccaagtgctt cagttagcat cttccagcct      660
tcccagtcct cttctgcaac accgtcttca attgatacaa ttgggtactt ttcaacaagt      720
tttacccaga attctaccat ttcttctttt gttctaactt taccttctct ttcgaaatga      780
tactttccat cttcttcatt gtagagctca gatgttgcag ggtcaagcgc aattgcaata      840
tccttaccag gagtataacc agcttttttca attgcttcga caattacttc caatggctct      900
tcgttagact tcaagtttgg tgcaaatcca ccttcatcac ccactgttgt gttgtatcct      960
cttgccttca atacatttct taattgatgg aatgtctcag cacacatcct gagtgcttcg     1020
ctaaaagatt ttgcaccaac tggcattatc ataaactctt gtaggtcaac agagttgtca     1080
gcatgctttc caccgttcaa atattcatc attggcacag gtaaatactt tgcattgaca      1140
ccaccaatgt attggtacag tggaagacca agtgcgtttg ccgctgcctt cgcaactgcc     1200
aaagatacac ccaaaattgc atttgcacca agcttgctct tgttctctgt cccatcaagc     1260
tcaatcataa gcctgtcaat ctcaacttgg ttaagagcgt tcattccaat tatttctggc     1320
gcaataacct cgtttacatt ttcgactgct ttgagaaccc cttttcccat atatcttttt     1380
ttatcaccgt ctctgagttc aacagcctcg aacatacctg ttgacgcacc tgatggaaca     1440
gcagctctac ctacaaattc atcatttaca acaacttcta cttcaacagt tgggtttcct     1500
cttgaatcca gaatttctct tgcttttaca gctgtaattg aaagatcaac cttcattaag     1560
gctgagatct tcttcagtgc attgtagttg aatgaagggt taggggggaa atgccccct      1620 atttttttgtc tagccatcct gccacgtttg acagggtagc aatttcgaca cgatagggtt     1680
ctctcttctg ccgtta                                                      1696
```

<210> SEQ ID NO 43
<211> LENGTH: 2029
<212> TYPE: DNA
<213> ORGANISM: Artificial Sequence
<220> FEATURE:
<223> OTHER INFORMATION: Synthetic Construct- Example 43: designer
      oxyphotobacterial Phosphoglycerate-Mutase DNA construct

<400> SEQUENCE: 43

```
agaaaatctg gcaccacacc tgaccccat cgagagactc cgaacgtggc aaatggaggg       60
accagagttg ttcagttcac aggtagataa tgtcgcgggt cttgatagtt agcaataaat      120
acagtttcag aatatctgta atacaaaaac tgtatcgaga caagaaaaaa gtagcaaaat      180
ttacaaatgt tcatgattca tctggctaaa ttggatgttc aactgaccca ttgaagacaa      240
gggcaacaac cctacgccgg cgcctgcttc tcctcctgcc ggcagcactt ctccaaaggg      300
tgcacgttcg cttctcttgt aatcagggtc tggccggtca tctcggccgg tttcgggatg      360
cccagcaggt gcaggatggt gggggccaca tcccgcaggc tgccgtcccg cagcgcaatg      420
ccggcggtat cccgcccgat caggatgaac ggcaccgggc tggtggtgtg ggccgtatga      480
ggctgtccct cttcgtccac catctcatcc gcattgccgt ggtctgccgt tatcaggagc      540
gtgccgtcct tttccaggac ggcccgcgcc acctttccaa ggcagcggtc gattgtttct      600
atggccttta ccgttgcctt catgtcgccg gtatgcccga ccatgtcggg attggcgtaa      660
ttcattatga ttcgtcgta cttgcccgag gccagccgct ccagaaaggt gccggtgacc      720
tcgttggcgc tcatttcggg cttcaggtcg taggtggcca cccgcgggga gggcaccagg      780
```

-continued

```
atcctgtctt cgccggggta tggcttttct aagccgccgt tgaagaagaa ggtcacatgg    840
gcgtactttt ccgtttcggc caggcggagc tgggtcatgc cgtgcctgct taaaacctcg    900
cccagggtat tgcgcagctc ctgcggctga acgccaccg gcgccttaat ggtcttgtcg     960
taaagggtca tgcaggtaaa atgcacggca gggtagccct gctttctggc aaacccggtg   1020
aaatcctcgt ccacaaaggc cctggtaatc tggcgggccc ggtccggccg gaagttaaag   1080
aaaataacgg cgtcgccctt cattattttg gcggccggcc cacccgaccc gtttaccacg   1140
acggtgggct ggataaactc gtcggtttca tcccttccgt accccaggtc aaccgcctcc   1200
agcgggcttg ttgcctgaat gccctcgcct aaaaccattg cgttgtacgc ccgctcggtg   1260
cggtcccagc ggcggtctct gtccatggcg taatagcgcc ccattaccgt tgccaccgcc   1320
ccaaagccca gttcgcccag cttcttcctt aactgctcga agtattcttt tgcgttggcc   1380
ggcggcacgt cgcgcccgtc caggaaggca tggacaaaga cgttgcgcat gttctcgcgg   1440
gcggccaggt ccaggagggc gaaaggtgg ctgatatggc tgtgcactcc gccgtccgat    1500
aaaagcccca tcaggtgaag ggccttatta ttctccctgg cgtatctcac cgcctccagc   1560
aggacttcgt tcttgaaaaa ggtcccgtcc ttgatggcgc ggcttattct ggtaagctcc   1620
tggtacacca ccctgccggc gcctatgttc aagtgtccca cctcggaatt gcccatctgg   1680
ccctcgggaa gccccacgtc ctcgccggaa cagctcaggg cacagtgggg gtaaccggcc   1740
agaaagctct tgaaattcgg tgtgctggcc agggctatgg cattgccccg gacattggaa   1800
ctgaggcccc agccgtccag aaccaccagc accaggggcc tgccgccggc ataccggccg   1860
cagggcgttg cagctacgtc ttccttcaat aaggctgaga tcttcttcag tgcattgtag   1920
ttgaatgaag ggttaggggg gaaatgcccc cctattttt gtctagccat cctgccacgt    1980
ttgacagggt agcaatttcg acacgatagg gttctctctt ctgccgtta                2029
```

<210> SEQ ID NO 44
<211> LENGTH: 1687
<212> TYPE: DNA
<213> ORGANISM: Artificial Sequence
<220> FEATURE:
<223> OTHER INFORMATION: Synthetic Construct- Example 44: designer oxyphotobacterial Phosphoglycerate Kinase DNA construct

<400> SEQUENCE: 44

```
agaaaatctg gcaccacacc tgaccccat cgagagactc cgaacgtggc aaatggaggg     60
accagagttg ttcagttcac aggtagataa tgtcgcgggt cttgatagtt agcaataaat   120
acagtttcag aatatctgta atacaaaaac tgtatcgaga caagaaaaaa gtagcaaat    180 ttacaaatgt tcatgattca tctggctaaa ttggatgttc aactgaccca ttgaagacaa   240
gggcaacaac cttatttatc gagcagcgcc cttactcccg gcagttgctt cccttccaga   300
aactccaggg aagcgccgcc gccggttgag atatgggtca ttttgccggc tacgccggcc   360
ttcttggccg ccgccgccgt gtcaccgccg ccgattacgg tgacgcgtt taattcggcc    420 agcgtccggg ctattgcttc ggtgcccctg gcaaaaggat ccatttcaaa aacgcccatt   480
ggtccgttcc agaccacggt cctggccgcc ctgagggctt cggtgaaaag tctgatggac   540
tcgggcccta tatccagggc catccactcc gcgggattt gatcgaccgg caccgtcctt    600
tgctcctggc cgggcgccgg ccccggcgcc accaccacat ccaccggcag gaggagcttt   660
acttccctgc ttctggcttc tgcaatcagc ttcctgccca ggtcaatctt gtcggcctcc   720
agcagggact taccgacgct gtaccttgt gccttcagaa aggtattggc catcccgccg    780
```

| | |
|---|---|
| ccaatgataa ccgtatcgac tttggtcagc aggttgaaaa ttactcccag cttgtcggaa | 840 |
| actttcgagc cgcccacgac ggctgcaaaa gggcgctccg ggctggtcag cagcctgccc | 900 |
| agtatttcca gctctttttc catcagcagg cctgccacgg ccggcaaaaa cccggcaacg | 960 |
| ccctcggtgg aggcgtgggc ccggtgtgcg gttccaaacg catcgtttac aaagacatct | 1020 |
| gccagctcag ccagttgccg ggcaaacttc tcgtcgtttt tctcctcctc cgggtggaaa | 1080 |
| cggacgtttt ccagcagcac cacgtccccg tcctgcatct gggcaacggc ggacctggcg | 1140 |
| gcttctccca cgcagtcgcc ggccttaacc accgttttcc ccagcagttc ggaaaggcgc | 1200 |
| ctggcaacgg gatccatttt gtacctctcg tccaccctgc ccttgggccg gcccaggtgc | 1260 |
| gaaaccagaa taaccctggc tttttgtccg ataaggtagt ttatggtggg cacggcctcc | 1320 |
| tttatttaa cgtcatcggc cacccggccg ttttccatcg gcacgttgaa gtccacccgc | 1380 |
| aacaggaccc gcttgccctt tacatctata tcccttaccg ttttttggc cactaaggct | 1440 |
| gagatcttct tcagtgcatt gtagttgaat gaagggttag gggggaaatg cccccctatt | 1500 |
| ttttgtctag ccatcctgcc acgtttgaca gggtagcaat ttcgacacga tagcgtgctg | 1560 |
| tactgttttt tgctcgtcag ggttgggttt tgtcatcgac acccaaggat tggagtcggt | 1620 |
| gctcaataat cgccagttgc tgttgggcag ccgccaattg cgcctgaggt tctctcttct | 1680 |
| gccgtta | 1687 |

<210> SEQ ID NO 45
<211> LENGTH: 1514
<212> TYPE: DNA
<213> ORGANISM: Artificial Sequence
<220> FEATURE:
<223> OTHER INFORMATION: Synthetic Construct- Example: designer oxyphotobacterial Glyceraldehyde-3-Phosphate Dehydrogenase DNA construct

<400> SEQUENCE: 45

| | |
|---|---|
| agaaaatctg gcaccacacc tgatctgcaa gagacgctca cgcgatacct ctgggcgtgc | 60 |
| aatcaccgca ttccccaacg cgctttgggc cacatgaccc ccatcgagag actccgaacg | 120 |
| tggcaaatgg agggaccaga gttgttcagt tcacaggtag ataatgtcgc gggtcttgat | 180 |
| agttagcaat aaatacagtt tcagaatatc tgtaatacaa aaactgtatc gagacaagaa | 240 |
| aaaagtagca aaatttacaa atgttcatga ttcatctggc taaattggat gttcaactga | 300 |
| cccattgaag acaagggcaa caaccaatgg atttgggcgg atcggacgtt tagcattcag | 360 |
| aagaattcaa gatgtagaag gtcttgaagt agttgcagtt aacgacttaa cagatgacga | 420 |
| tatgttagct catttattaa aatacgatac tatgcaaggt cgtttcactg gagaagttga | 480 |
| agttatcgaa ggtggattcc gtgttaacgt aaaagaaatt aaatcattcg atgaccagat | 540 |
| gctgggtaaa ttaccatggg gcgatttaga tatcgacgta gtattagaat gtactggttt | 600 |
| ctatactgat aaagaaaaag cacaagctca catcgatgca ggtgctaaaa agtattaat | 660 |
| ctcagctcca gctaaaggtg atgtaaaaac aatcgtattc aacactaacc atgacgcatt | 720 |
| agacggttca gaaacagttg tttcaggtgc ttcttgtact actaactcat tagcaccagt | 780 |
| tgcaaaagtt ttaagtgatg aattcggttt agttgaaggt ttcatgacta caattcacgc | 840 |
| ttacactggt gaccaaaata cacaagacgc acctcacaga aaaggtgaca acgtcgtgc | 900 |
| acgtgcagca gcagaaaata ttatccctaa ctcaacaggt gctgctaaag ctatcggtaa | 960 |
| agttattcca gaaatcgatg gtaaattaga cggtggagca caacgtgttc cagttgctac | 1020 |
| tgggtcttta actgaattaa ctgtagtatt agacaaacaa gatgtaactg ttgaccaagt | 1080 |

```
taacagtgct atgaaacaag cttcagacga atcattcggt tacactgaag acgaaatcgt    1140
atcttctgat atcgttggta tgacttacgg ttcattattc gatgcgactc aaactcgtgt    1200
tatgactgtt ggagatcgtc aattagttaa agttgcagct tggtacgaca aagagtgggg    1260
taaggctgag atcttcttca gtgcattgta gttgaatgaa gggttagggg ggaaatgccc    1320 ccctatttt tgtctagcca tcctgccacg tttgacaggg tagcaatttc gacacgatag     1380
cgtgctgtac tgttttttgc tcgtcagggt tgggttttgt catcgacacc caaggattgg    1440
agtcggtgct caataatcgc cagttgctgt tgggcagccg ccaattgcgc ctgaggttct    1500
ctcttctgcc gtta                                                      1514

<210> SEQ ID NO 46
<211> LENGTH: 609
<212> TYPE: DNA
<213> ORGANISM: Artificial Sequence
<220> FEATURE:
<223> OTHER INFORMATION: Synthetic Construct- Example 46: designer
      Nial-promoter-controlled Proton-Channel DNA construct

<400> SEQUENCE: 46
agaaaatctg gcaccacacc tatatggtag ggtgcgagtg accccgcgcg acttggagct      60
cgatggcccc gggttgtttg gggcgtccgc ctctcgcgct attctgagct ggagaccgag     120
gcgcatgaaa atgcattcgc ttccatagga cgctgcattg tggcttgaag gttcaaggga    180
agggttcaaa cgaccccgcc gtacgaactt ttgtcggggg gcgctcccgg ccccgggctc    240
ttgtgcgcgc attagggctt cgggtcgcaa gcaagacgat acatggccgg catcggcgcc    300
gtgctgaagg tcctgaccac cggcctgccc gccctgatca gctggatcaa gcgcaagcgc    360
cagcagtaaa tggaggcgct cgttgatctg agccttgccc cctgacgaac ggcggtggat    420
ggaagatact gctctcaagt gctgaagcgg tagcttagct ccccgtttcg tgctgatcag    480 tcttttttcaa cacgtaaaaa gcggaggagt tttgcaattt tgttggttgt aacgatcctc    540
cgttgatttt ggcctctttc tccatgggcg ggctgggcgt atttgaagcg ttctctctt     600 ctgccgtta                                                            609

<210> SEQ ID NO 47
<211> LENGTH: 1360
<212> TYPE: DNA
<213> ORGANISM: Artificial Sequence
<220> FEATURE:
<223> OTHER INFORMATION: Synthetic Construct- Example 47: designer
      nirA-promoter-controlled NAD-dependent
      Glyceraldehyde-3-Phosphate-Dehydrogenase DNA construct

<400> SEQUENCE: 47
agaaaatctg gcaccacacc cttcttgcag aacatgcatg atttacaaaa agttgtagtt     60
tctgttacca attgcgaatc gagaactgcc taatctgccg agtatatgaa cggatttggc    120
aggataggac gactggtgtt gcgggcgcg gtggagaagg gcacggtgga ggtggtggcg    180
gtgaacgatc cgttcatctt cccggacgcg gcgtacgctg cgtacatgct gcagtacgac    240
tcgacgcacg gggcgttccc gggtgaggtg ggcagcgacg gggagcactt ggtggtgaac    300
gggaagaagc tggcgtgctt tgcgatccgc gatccggcgg agatcccgtg gggctcggtc    360
ggcgccgact acgtcgtgga gtccaccggc gtgttcaccg tgaccgagaa ggcgtcgttg    420
cacgtcaagg gcggcgcgaa gaaggtggtt atatcggcgc cgtcgaagga tgcgcccatg    480
tttgtgatgg gcgtgaacca tgacgcctac accaaggact tgacggtggt gtcgaatgcg    540
```

```
tcttgcacca ccaacttgtt tggcgccgct ggccaagatc atcgacgagg cgttcggcat      600
cgggatgggc ctcatgagca ccatccacgc ggtgacggcc acgcaaaaga cggtggatgg      660
gccgagctcc aaagactggc gcggtgtcgc ggcgcgttcc agtcgattat cccagcagc       720 accggcgctg cgaaagcggt cggcaaggtg tacccgaagc tgaacggcaa gctgaccggc      780
atggcgttcc gcgtgccggt gcccgacgtg tccgtggtag acttgacagt gaccctgaag      840
aaggagacca actacgagga gatcaaaaag gctgtcaagc aggcgtcgca gagcccgcac      900
tacaagggca tcgtggcgta caccgagcac cccatcgtgt cggccgacct ggtgcacaac      960
ccgtactcgt cggtgttcga tgccgaagcc ggtatcatgc tgtcgcccac gtttgtgaaa     1020
ctggtcagct ggtaatagtg atcccggccg ctactaaagc ctgatttgtc ttgatagctg     1080
ctcctgcctt tgggcagggg cttttttctg tctgccattc ttgaggatgg cggactcttt     1140
cccttttgct ctacgcccat gaatgcgatc gcagtctccc ctgtccagca cgttggagtg     1200
attggtggtg gccagttagc ttggatgctg gcaccagcag cgcaacagtt ggggatgtcg     1260
ctgcacgttc aaacacccaa tgatcacgac ccagcagtag cgatcgcgga tcaaaccgta     1320
ttagcagcag ttgctgacgc ggttctctct tctgccgtta                           1360

<210> SEQ ID NO 48
<211> LENGTH: 1621
<212> TYPE: DNA
<213> ORGANISM: Artificial Sequence
<220> FEATURE:
<223> OTHER INFORMATION: Synthetic Construct- Example 48: designer
      nirA-promoter-controlled Phosphoglycerate-Kinase DNA construct

<400> SEQUENCE: 48
agaaaatctg gcaccacacc cttcttgcag aacatgcatg atttacaaaa agttgtagtt       60
tctgttacca attgcgaatc gagaactgcc taatctgccg agtatatgtc atttgtcttc      120
gagcgcgacg acacccggca gctgttttcc ttccataaac tcgagcgaag cgccgccgcc      180
ggtggagata tgatccattt tgtcggccaa gccgaatttc tcaaccgccg ccgccgaatc      240
cccgccgccg atgaccgaat aggtgtcggg cgcttccgcc agtgcttcgg cgatcgcttt      300
tgtcccatgg gcgaacgctt ccatttcaaa gacgcccatc gggccgttcc agacaacgag      360
cttcgattga cgaatgacat cgcggtacaa ttcgcgcgtt tcgggccgga tgtcaagcgc      420
ctcccaatcg ctcggaatgg cgtcgatggc gacgactttc gtgttggcgt cgttcgcaaa      480
ccggtcggcg acgaccacgt ccaccggcat ataaaaacgg acgccttttt ctttcgcctt      540
ttccataaac gatttggcga gttcgatttt gtcctcctca agcagcgact tgccgacgtc      600
atggccgagc gctttgacga acgtatacgc cagtccgccg ccgatgatca agttgtcgac      660
tttttcaagc aaattgtcga tgacgccgat tttgtctttc actttcgcgc cgccgatgat      720
cgccgtaaac gggcggtccg gattcgagag cgctttgccg agcacttcga gttcttttc       780 catcaaaaac ccgccaccg caggcaagta atgggcgatg ccttccgtcg acgcatgagc      840
gcggtgggcg cgccgaacg catcgttgac atacagatcc gcgagctccg caaacgcttt      900
ggccagctct ggatcgtttt tctcttcgcc agggtaaaaa cggacgttct caagcaagag      960
cacgtcgcct tcgttcaaac ggtcgaccgc cgctttcacc tcatcgccga ccgcttcatt     1020
cgttttggcg accggccgtt caagcagctc gccgagccgc ttcgcaacgg catccaaacg     1080
caattcttcg accactttc ctttcgggcg gccgaggtgg ctcgccaaaa tgactttcgc      1140
cccgtgctcg atcaaatagc ggatcgtcgg gagtgcggcg cgaatgcgcg tgtcatcggt     1200
```

```
gatggcgcct tgctccatcg gaacgttgaa atcgacgcgg caaaagacgc gctttcccct   1260
cacctcaacg tcgcggatcg tcttcttgtt cattaatagt gatcccggcc gctactaaag   1320
cctgatttgt cttgatagct gctcctgcct ttgggcaggg gcttttttct gtctgccatt   1380
cttgaggatg gcggactctt tccctttgc tctacgccca tgaatgcgat cgcagtctcc    1440
cctgtccagc acgttggagt gattggtggt ggccagttag cttggatgct ggcaccagca   1500
gcgcaacagt tggggatgtc gctgcacgtt caaacaccca atgatcacga cccagcagta   1560
gcgatcgcgg atcaaaccgt attagcagca gttgctgacg cggttctctc ttctgccgtt   1620
a                                                                  1621

<210> SEQ ID NO 49
<211> LENGTH: 1990
<212> TYPE: DNA
<213> ORGANISM: Artificial Sequence
<220> FEATURE:
<223> OTHER INFORMATION: Synthetic Construct- Example 49: designer
      nirA-promoter-controlled Phosphoglycerate-Mutase DNA construct

<400> SEQUENCE: 49
agaaaatctg gcaccacacc cttcttgcag aacatgcatg atttacaaaa agttgtagtt     60
tctgttacca attgcgaatc gagaactgcc taatctgccg agtatatgct cgagcattta    120
tttaataata agcgagcttc ccttcatctc tgaaggtttt tctaacccta agatgtctaa    180
gattgttgga gcaatgtctg ctaagattcc atcatctctt aatttaacat tgccatatcc    240
cacaagatac aaaggcacct tatttgttgt atgagctgta tgaggctcac ctgtctcata    300
atcaatcatc tgttcacagt tgccatggtc agcagtaata ataaccactc caccctttc    360 taaaaccttg ttaacaactt ttccaataca ctcatctaca gcctcaactg cctttattgc    420
agcctctaaa acgcctgtgt gccctaccat gtcaccattt gcatagttac atattatcac    480
atcatattca tctcttttcaa ttctctcaag taaagcttct gttacctcgt atgcactcat    540
ctcaggttta agatcatatg ttgcaacctt tggtgatggt accaatacccc tgtcttctcc   600 gacatttggt acttccacac cgccgttgaa gaaaaaggtg acatgagcat acttttctgt    660
ctcagcaatt cgaagttgtt ttaaccctaa cttgctaaaa tactctccca aagtgtttgt    720
caggttctct ggtttgaatg caacatggca atttttattt gtcacatcat actgagtcat    780
gcatacaaag aacacttcga atatcctttt tttccttttca aaaccgtcaa attcaacatc   840
acaaaacgct cttgtaagct gtcttgctct gtcaggtctg aagttaaaga aaataatact    900
gtcatgttca tttattgttg cgacaggttt tccattttca agcacaacag tcggaattac    960
aaactcatca gtgttacctt ttttatacga cttttcaacc gcctctaatc ctgagcttgc   1020
atactcgcct tcaccaaaga ccattgcatt atatgccttt tcaactcttt cccatctttt   1080
gtctctgtcc attgcatagt atctgcccat cactgttgca atcttaccac aaccaatttc   1140
ttttatcttc tgttcaagct cttcaatgta aattttttgcg ctcgaaggtg gaacatctcg  1200
cccatccaaa aagcaatgaa catatacttt ttcaagattg tgcctctttg caagttttaa   1260
aagtgcgtaa agatgtgtgt tgtggctgtg aacaccacca tctgataaaa gtcccatcag   1320
atgaagagaa gagttatatt ttttgcaatt ctctattgcc atcaaaaact cttctttttc    1380
aaaaaaatca ccgtctttaa ttgactttgt tattcttgta aattcttggt aaacaattct   1440
tcctgcaccc aggttcagat gtccaacttc agaattcccc atttgtcctt cgggaagacc    1500
aacatccata ccactgctac caatcagggt atatgggtaa ttcttttcgt aatagtcaag   1560
```

-continued

```
gttaggggtc ttacccaaag caacagcgtt tccctcttgc tttgggttat aaccccaacc      1620
gtccatgata atcaacacaa caggttttt cattaatcta gataatagtg atcccggccg      1680
ctactaaagc ctgatttgtc ttgatagctg ctcctgcctt tgggcagggg cttttttctg      1740
tctgccattc ttgaggatgg cggactcttt cccttttgct ctacgcccat gaatgcgatc      1800
gcagtctccc ctgtccagca cgttggagtg attggtggtg gccagttagc ttggatgctg      1860
gcaccagcag cgcaacagtt ggggatgtcg ctgcacgttc aaacacccaa tgatcacgac      1920
ccagcagtag cgatcgcgga tcaaaccgta ttagcagcag ttgctgacgc ggttctctct      1980
tctgccgtta                                                            1990
```

<210> SEQ ID NO 50
<211> LENGTH: 1765
<212> TYPE: DNA
<213> ORGANISM: Artificial Sequence
<220> FEATURE:
<223> OTHER INFORMATION: Synthetic Construct- Example 50: designer nirA-promoter-controlled Enolase DNA construct

<400> SEQUENCE: 50

```
agaaaatctg gcaccacacc cttcttgcag aacatgcatg atttacaaaa agttgtagtt        60
tctgttacca attgcgaatc gagaactgcc taatctgccg agtatatgct cgagcatatg       120
ctaaataaac ccgtcgtttc cattgaagaa attaccgcta gagaaatttt agactctcgt       180
ggccgtccta ccattgaagc agaagtctta ctggaaacag gggctttcgg tattgcccag       240
gttcccagtg gcgcgtcaac tggtagcttc gaggcccacg aattacggga tgatgacccc       300
aaccgctacg gtggtaaagg cgttctcaaa gcggttagta acgttataga cgaaattgcc       360
cctaaaatta tcggaatgga tgggttagat caaactgcga tcgatcacac catgattgag       420
ttagacggtt ctactaataa aaaagaatta ggggccaatg ctatccttgc cgtttcctta       480
gccactgcaa aagctgccgc cgatgaatta gccctttcccc tgtaccgtta tttaggggt       540 cccttggcca atgtcttacc cgtccccatg atgaacgtga ttaacggggg ttctcacgcg       600
gataataacg tagacttcca ggagtttatg attatgccag tgggtgcgga ctctttaaa       660 gaagctttga ggtggggggc cgaagtgttt gcttccctca gtaaagttct aaaagagcgt       720
aaattgctct ctggggtagg agacgagggg ggatacgccc cgaacctggg atcgaaccag       780
gaagccttag atttgctcat agaagccatt gaaaaggcgg ggtataagcc aggggaacag       840
gtggctttag cgatggatgt ggcttcaagt gagtttata aggatggcga atatatttat       900
gatggttctc cccattcccc tcaagaattt atcgattatt taggtaaatt agtggatcaa       960
tatcctatta tttccattga agatggctta caagaagatg actgggatag ctggaaaagt      1020
ttgaccgata cgttaggatc tcgcattcag ttagttgggg acgatctttt tgtcacgaac      1080
cccactcgtc tgcaaaaagg cattgatatg ggtgtgggta atagtattct cattaaactc      1140
aatcaaattg gtagtttaac ggaaacgtta gatacgattg ctttagcgac tcgtcatcaa      1200
tatagttccg ttatttccca tcgttccgga gaaaccgaag acactaccat tgcagactta      1260
gccgtagcta cacgcgctgg acaaatcaaa accggttctc tgtgtcgtag tgaacgggta      1320
gccaaatata accgactatt acgtattgaa gaagaattag gcgatcgcgc agtttatgct      1380
gcaaaagtgg gtttaggccc tcaataaggc tgctgccccg gctgctgcta atctagataa      1440
tagtgatccc ggccgctact aaagcctgat ttgtcttgat agctgctcct gcctttgggc      1500
aggggctttt ttctgtctgc cattcttgag gatggcggac tctttccctt ttgctctacg      1560
```

```
cccatgaatg cgatcgcagt ctccctgtc cagcacgttg gagtgattgg tggtggccag    1620
ttagcttgga tgctggcacc agcagcgcaa cagttgggga tgtcgctgca cgttcaaaca    1680
cccaatgatc acgacccagc agtagcgatc gcggatcaaa ccgtattagc agcagttgct    1740
gacgcggttc tctcttctgc cgtta                                          1765

<210> SEQ ID NO 51
<211> LENGTH: 1888
<212> TYPE: DNA
<213> ORGANISM: Artificial Sequence
<220> FEATURE:
<223> OTHER INFORMATION: Synthetic Construct- Example 51: designer
      nirA-promoter-controlled Pyruvate-Kinase DNA construct

<400> SEQUENCE: 51
agaaaatctg gcaccacacc cttcttgcag aacatgcatg atttacaaaa agttgtagtt      60
tctgttacca attgcgaatc gagaactgcc taatctgccg agtatatgct cgagcatatg     120 ttaaaaaga cgaaaatcgt tgcacgcag gtccgtcca cagagaaacc gggcgtaatt       180
gatgcactga ttgccaatgg catgaactgc gcacgcttca atttctccca tggtgaccac    240
gaagaacatc ttggccgtat caatatggtt cgtgaagctg ccaagaaggc tggcaaggtt    300
atctctttaa tcctcgatac caaaggtccg gaaatgcgtc tgggcgagtt caaagatggc    360
aaagttatgc tcgaaaaggg caacaagttc actttgacct atgacgatga accgggtgat    420
gaaactcatg tttccgtaaa ccacaaaggt ctttacacgg aagttaagcc gggcgacacc    480
ctgctcctct ccgatggcct cgtagctctc aaagttgatg aaatcaaggg caaggatatc    540
gttacgacga ttcagaacag cggtaagatg agcacgcgca agcgcgtagc tgctccgggc    600
gtaccccttg gtctgcctcc tatctccgaa caggatgcta aggacatcat ctttggctgc    660
gaacaggata tggatttcgt agctgcttcc ttcatccagc gtccggatga tgttatcgcc    720
atccgcaagc tcatcgaaga gcacaatggc cacatggaaa ttctgccgaa gatcgaaaac    780
ctcgaaggtg ttaagaactt cgatgcaatc ctggaagttt ccgacggcat catggttgcc    840
cgtggtgacc tgggcgtaga agttccggca gaagatgtgc cccttattca gaaggaaatc    900
atccgcaagt gcaacgctgc tggcaagccg gttatcgttg ctacgcagat gctcgactcc    960
atggaacgca acccgcgtcc gacccgtgca gaagtttctg acgttggtaa cgccatcctc    1020
gatggtacgg atgccatcat gctgtccggc gaaacggctt ccggtgacta tccggtagaa    1080
gcagttgcca cgatgaaccg cattgcacag cgcatggaaa gctcccttga atacaaggaa    1140
ctctatgtag aacgtggtct gcagcacatg gaatcccgta cgcgtgctat cgctcatgct    1200
acggttcaga tggcttatga gctcgatgct ccggctatta tcacgccgac cgaatccggt    1260
tacacgacga aggtcgtttc caagtatcgt ccgaaggctg ctatcgtagc ttacacgccg    1320
agcgaaaaag ttctgcgtca gctgaacctg cgttggggcg tatatccggt actcggcacc    1380
cagtggagcg atgtggatga atgatcagc aatgcaacgg ctgctgctgt taaggaagac    1440
ctcgtacagc gcggcgacct caccatcatc acctccggtg tgaagatgga atcccgtacg    1500
cgtgctatcg ctcatgctac ggacatctaa ggctgctgcc ccggctgctg ctaatctaga    1560
taatagtgat cccggccgct actaaagcct gatttgtctt gatagctgct cctgcctttg    1620
ggcaggggct ttttctgtc tgccattctt gaggatggcg gactctttcc cttttgctct    1680
acgcccatga atgcgatcgc agtctcccct gtccagcacg ttgagtgat tggtggtggc     1740 cagttagctt ggatgctggc accagcagcg caacagttgg ggatgtcgct gcacgttcaa    1800
```

```
acacccaatg atcacgaccc agcagtagcg atcgcggatc aaaccgtatt agcagcagtt    1860
gctgacgcgg ttctctcttc tgccgtta                                       1888

<210> SEQ ID NO 52
<211> LENGTH: 2188
<212> TYPE: DNA
<213> ORGANISM: Artificial Sequence
<220> FEATURE:
<223> OTHER INFORMATION: Synthetic Construct- Example 52: designer
      nirA-promoter-controlled Pyruvate-Decarboxylase DNA construct

<400> SEQUENCE: 52
agaaaatctg gcaccacacc cttcttgcag aacatgcatg atttacaaaa agttgtagtt      60
tctgttacca attgcgaatc gagaactgcc taatctgccg agtatatgct cgagcatatg     120
gtatcaacct acccagaatc agaggttact ctaggaaggt acctctttga gcgactccac     180
caattgaaag tggacaccat tttcggcttg ccgggtgact tcaacctttc cttattggac     240
aaagtgtatg aagttccgga tatgaggtgg gctggaaatg ccaacgaatt gaatgctgcc     300
tatgctgccg atggttactc cagaataaag ggattgtctt gcttggtcac aactttggt      360 gttggtgaat tgtctgcttt aaacggagtt ggtggtgcct atgctgaaca cgtaggactt     420
ctacatgtcg ttggagttcc atccatatcg tcacaggcta aacagttgtt gctccaccat     480
accttgggta atggtgactt cactgttttt cacagaatgt ccaatagcat ttctcaaact     540
acagcatttc tctcagatat ctctattgca ccaggtcaaa tagatagatg catcagagaa     600
gcatatgttc atcagagacc agtttatgtt ggtttaccgg caaatatggt tgatctcaag     660
gttccttcta gtctcttaga aactccaatt gatttgaaat tgaaacaaaa tgatcctgaa     720
gctcaggaag aagttgttga aacagtcctg aagttggtgt cccaagctac aaaccccatt     780
atcttggtag acgcttgtgc cctcagacac aattgcaaag aggaagtcaa acaattggtt     840
gatgccacta ttttcaagt ctttacaact ccaatgggta aatctggtat ctccgaatct     900
catccaagat ttggcggtgt ctatgtcggg acaatgtcga gtcctcaagt caaaaaagcc     960
gttgaaaatg ccgatcttat actatctgtt ggttcgttgt tatcggactt caatacaggt    1020
tcattttcat actcctacaa gacgaagaat gttgttgaat tccactctga ctatatgaaa    1080
atcagacagg ccaccttccc aggagttcaa atgaaagaag ccttgcaaca gttgataaaa    1140
agggtctctt cttacatcaa tccaagctac attcctactc gagttcctaa aaggaaacag    1200
ccattgaaag ctccatcaga agctcctttg acccaagaat atttgtggtc taaagtatcc    1260
ggctggttta gagagggtga tattatcgta accgaaactg gtacatctgc tttcggaatt    1320
attcaatccc attttcccag caacactatc ggtatatccc aagtcttgtg gggctcaatt    1380
ggtttcacag taggtgcaac agttggtgct gccatggcag cccaggaaat cgaccctagc    1440
aggagagtaa ttttgttcgt cggtgatggt tcattgcagt tgacggttca ggaaatctct    1500
acgttgtgta atgggattg taacaatact tatctttacg tgttgaacaa tgatggttac    1560
actatagaaa ggttgatcca cggcaaaagt gccagctaca acgatataca gccttggaac    1620
catttatcct tgcttcgctt attcaatgct aagaaatacc aaaatgtcag agtatcgact    1680
gctggagaat tggactcttt gttctctgat aagaaatttg cttctccaga taggataaga    1740
atgattgagg tgatgttatc gagattggat gcaccagcaa atcttgttgc tcaagcaaag    1800
ttgtctgaac gggtaaacct tgaaaattga ggctgctgcc ccggctgctg ctaatctaga    1860
taatagtgat cccggccgct actaaagcct gatttgtctt gatagctgct cctgcctttg    1920
```

```
ggcaggggct tttttctgtc tgccattctt gaggatggcg gactctttcc cttttgctct    1980
acgcccatga atgcgatcgc agtctcccct gtccagcacg ttggagtgat tggtggtggc    2040
cagttagctt ggatgctggc accagcagcg caacagttgg ggatgtcgct gcacgttcaa    2100
acacccaatg atcacgaccc agcagtagcg atcgcggatc aaaccgtatt agcagcagtt    2160
gctgacgcgg ttctctcttc tgccgtta                                       2188
```

<210> SEQ ID NO 53
<211> LENGTH: 1510
<212> TYPE: DNA
<213> ORGANISM: Artificial Sequence
<220> FEATURE:
<223> OTHER INFORMATION: Synthetic Construct- Example 53: designer
      nirA-promoter-controlled NAD(P)H-dependent Alcohol-Dehydrogenase
      DNA construct

<400> SEQUENCE: 53

```
agaaaatctg gcaccacacc cttcttgcag aacatgcatg atttacaaaa agttgtagtt      60
tctgttacca attgcgaatc gagaactgcc taatctgccg agtatatgtt agctacctct     120
gtgccagaaa cccaaaaggg tgttattttc tatgagaatg gtggtaaatt ggaatacaag     180
gacattccag ttccaaagcc aaagccaaat gaaatcttga tcaacgtcaa gtactccggt     240
gtgtgtcata ccgatttgca cgcatggaag ggtgactggc cattgccaac caagttgcca     300
ttggtcggtg gtcacgaagg tgctggtgtc gttgttgcta tgggtgaaaa cgtcaagggc     360
tggaacattg gtgactttgc gggtatcaaa tggttgaacg ttcttgtat gtcctgtgaa      420 tactgtgaat tgtccaatga atccaactgt ccagatgctg acttgtctgg ttacacccac     480
gatggttctt ccaacaata ccgtaccgca gatgctgttc aagctgccag aattccaaag     540
ggtaccgatt tggctgaagt tgctccaacc ctatgtgccg gtgttactgt ttacaaggct     600
ttgaaaagtg ctaacttgaa ggctggtgac tgggttgcca tctctggtgc tgctggtggt     660
ctaggttctc tagctgtcca atacgccaag gccatgggtt acagagtcgt tggtatcgac     720
ggtggtgaag aaaagggtaa gttggtcaag caattgggtg gtgaagcctt tgttgatttc     780
accaaaacca aggacatggt tgctgaaatc caagaaatca ccaacggtgg tccacacggt     840
gtcattaacg tctctgtttc tgaagctgcc atgaacgctt ccactcaatt cgtcagacca     900
actggtactg tcgtattggt cggtttgcca gctggtgccg tcatcaagtc cgaagtcttc     960
tcccacgtcg ttaagtctat taacatcaag ggttcttacg tcggtaacag agctgacacc    1020
agagaagcta tcaacttctt cgctaacggt cacgtccact ctccaatcaa ggttgttggt    1080
ttgtccgaac taccaaaggt ttacgaattg atggaacaag gtaagatttt gggtagatac    1140
gttgttgaca cctccaacta gggctgctgc cccggctgct gctaatagtg atcccggccg    1200
ctactaaagc ctgatttgtc ttgatagctg ctcctgcctt tgggcagggg cttttttctg    1260
tctgccattc ttgaggatgg cggactcttt ccctttgct ctacgcccat gaatgcgatc     1320
gcagtctccc ctgtccagca cgttggagtg attggtggtg gccagttagc ttggatgctg    1380
gcaccagcag cgcaacagtt ggggatgtcg ctgcacgttc aaacacccaa tgatcacgac    1440
ccagcagtag cgatcgcgga tcaaaccgta ttagcagcag ttgctgacgc ggttctctct    1500
tctgccgtta                                                           1510
```

<210> SEQ ID NO 54
<211> LENGTH: 56
<212> TYPE: PRT

```
<213> ORGANISM: Artificial Sequence
<220> FEATURE:
<223> OTHER INFORMATION: Synthetic Construct- Example 54: designer
      selected Hyd1 transit peptide

<400> SEQUENCE: 54

Met Ser Ala Leu Val Leu Lys Pro Cys Ala Ala Val Ser Ile Arg Gly
1               5                   10                  15

Ser Ser Cys Arg Ala Arg Gln Val Ala Pro Arg Ala Pro Leu Ala Ala
            20                  25                  30

Ser Thr Val Arg Val Ala Leu Ala Thr Leu Glu Ala Pro Ala Arg Arg
        35                  40                  45

Leu Gly Asn Val Ala Cys Ala Ala
    50                  55

<210> SEQ ID NO 55
<211> LENGTH: 45
<212> TYPE: PRT
<213> ORGANISM: Artificial Sequence
<220> FEATURE:
<223> OTHER INFORMATION: Synthetic Construct- Example 55: designer
      selected RbcS2 transit peptide

<400> SEQUENCE: 55

Met Ala Ala Val Ile Ala Lys Ser Ser Val Ser Ala Ala Val Ala Arg
1               5                   10                  15

Pro Ala Arg Ser Ser Val Arg Pro Met Ala Ala Leu Lys Pro Ala Val
            20                  25                  30

Lys Ala Ala Pro Val Ala Ala Pro Ala Gln Ala Asn Gln
        35                  40                  45

<210> SEQ ID NO 56
<211> LENGTH: 7
<212> TYPE: PRT
<213> ORGANISM: Artificial Sequence
<220> FEATURE:
<223> OTHER INFORMATION: Synthetic Construct- Example 56: designer
      selected ferredoxin transit peptide

<400> SEQUENCE: 56

Met Ala Met Ala Met Arg Ser
1               5

<210> SEQ ID NO 57
<211> LENGTH: 33
<212> TYPE: PRT
<213> ORGANISM: Artificial Sequence
<220> FEATURE:
<223> OTHER INFORMATION: Synthetic Construct- Example 57: designer
      selected CF0CF1 subunit-delta transit peptide

<400> SEQUENCE: 57

Met Leu Ala Ala Lys Ser Ile Ala Gly Pro Arg Ala Phe Lys Ala Ser
1               5                   10                  15

Ala Val Arg Ala Ala Pro Lys Ala Gly Arg Arg Thr Val Val Val Met
            20                  25                  30

Ala
```